(12) United States Patent
Allison et al.

(10) Patent No.: US 7,550,492 B2
(45) Date of Patent: Jun. 23, 2009

(54) BENZO[1,2,5]THIADIAZOLE COMPOUNDS

(75) Inventors: Brett Allison, Del Mar, CA (US); Laura C. McAfee, King of Prussia, PA (US); Victor K. Phuong, San Diego, CA (US); Michael H. Rabinowitz, San Diego, CA (US); Nigel P. Shankley, Solana Beach, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/775,535

(22) Filed: Jul. 10, 2007

(65) Prior Publication Data

US 2007/0276016 A1 Nov. 29, 2007

Related U.S. Application Data

(63) Continuation of application No. 10/811,292, filed on Mar. 26, 2004, now Pat. No. 7,241,759.

(60) Provisional application No. 60/458,638, filed on Mar. 28, 2003.

(51) Int. Cl.
*A61K 31/433* (2006.01)
(52) U.S. Cl. ...................................... 514/362
(58) Field of Classification Search .............. 514/231.5, 514/254.03, 322, 361, 362
See application file for complete search history.

(56) References Cited

U.S. PATENT DOCUMENTS 5,534,530 A 7/1996 Frehel et al.
6,239,131 B1 5/2001 Shinozaki et al.

FOREIGN PATENT DOCUMENTS

| EP | 0620221 A1 | 10/1994 |
|---|---|---|
| WO | WO 00/78145 A1 | 12/2000 |
| WO | WO 02/42248 A2 | 5/2002 |
| WO | WO 02/090353 A1 | 11/2002 |
| WO | WO 2004/013087 | 2/2004 |

OTHER PUBLICATIONS

Black, J.W. and S.B. Kalindjian Pharmacol. Toxicol. 2002 vol. 91 pp. 275-281.
De Tullio, P. et al., Exp. Opin. Invest. Drugs 2000 vol. 9(1) pp. 129-146.
Herranz, R. Med. Res. Rev. 2003 vol. 23(5) pp. 559-605.
McDonald, I.M. Exp. Opin. Ther. Patents 2001 vol. 11(3) pp. 445-462.
Mikhailitsyn et al Meditsinskaya Parazitologiya I Parazitarne Bolexni 1991 vol. 6 pp. 52-53.
Mikhailitsyn et al Meditsinskaya Parazitologiya I Parazitarne Bolexni 1991 vol. 2 pp. 36-38.
Morton, M.F. et al., Br. J. Pharmacol. 2003 vol. 140(1) pp. 218-224.
Petrov et al Meditsinskaya Parazitologiya I Parazitarnye Bolexni 1996 vol. 4 pp. 40-42.
Revel, L. and F. Makovec Drugs Future 1998 vol. 23(7) pp. 751-766.
Tracy, H.J. and R.A. Gregory Nature (London) 1964 vol. 204 pp. 935-938.
Varnavas, A. et al., Eur. J. Med. Chem. 2004 vol. 39 pp. 85-97.
Varnavas, A. et al., Bioorg. Med. Chem. 2003 vol. 11 pp. 741-751.
Varnavas, A. et al., Il Farmaco 2001 vol. 56 pp. 555-564.

*Primary Examiner*—Taofiq A Solola
(74) *Attorney, Agent, or Firm*—Samuel Kais

(57) ABSTRACT

Certain amidophenyl-sulfanylamino-benzo[1,2,5]thiadiazole compounds are CCK2 modulators useful in the treatment of CCK2 mediated diseases.

2 Claims, No Drawings

BENZO[1,2,5]THIADIAZOLE COMPOUNDS

RELATED APPLICATIONS

This application is a continuation of parent application Ser. No. 10/811,292, which claims the benefit of priority of U.S. provisional application No. 60/458,638, filed Mar. 28, 2003. The complete disclosures of the aforementioned related U.S. patent applications are hereby incorporated by reference for all purposes.

FIELD OF THE INVENTION

There is provided by the present invention compounds that are CCK2 receptor modulators. More particularly, there is provided by the present invention benzo[1,2,5]thiadiazoles that are CCK2 receptor modulators useful for the treatment of disease states mediated by CCK2 receptor activity.

BACKGROUND OF THE INVENTION

This invention relates to gastrin and cholecystokinin (CCK) receptor ligands. The invention also relates to methods for preparing such ligands and to compounds that are useful intermediates in such methods. The invention further relates to pharmaceutical compositions comprising such ligands and methods for preparing such pharmaceutical compositions.

The gastrins and cholecystokinins are structurally related neuropeptides that exist in gastrointestinal tissue, gastrinomas and, in the case of the cholecystokinins, the central nervous system (J. H. Walsh, Gastrointestinal Hormones, L. R. Johnson, ed., Raven Press, New York, 1994, p. 1).

Several forms of gastrin are found including 34-, 17- and 14-amino acid species with the minimum active fragment being the C-terminal tetrapeptide (TrpMetAspPhe-NH2), which is reported in the literature to have full pharmacological activity (H. J. Tracy and R. A. Gregory, Nature (London), 1964, 204:935-938). Much effort has been devoted to the synthesis of analogs of this tetrapeptide (and the N-protected derivative Boc-TrpMetAspPhe-NH-2) in an attempt to elucidate the relationship between structure and activity.

Natural cholecystokinin is a 33 amino acid peptide (CCK-33, the C-terminal 5 amino acids of which are identical to those of gastrin. Also found naturally is the C-terminal octapeptide (CCK-8) of CCK-33. A review of CCK receptors, ligands and the activities thereof may be found in P. de Tullio et al, (Exp. Opin. Invest. Drugs, 2000, 9(1): 129-146).

Gastrin and cholecystokinin are key regulators of gastrointestinal function. In addition, cholecystokinin is a neurotransmitter in the brain. Gastrin is one of the three primary stimulants of gastric acid secretion. In addition to the acute stimulation of gastric acid, gastrin has a trophic effect on the gastrointestinal mucosa and is implicated as a trophic hormone of several adenocarcinomas, including pancreatic, colorectal, esophageal and small cell lung.

Cholecystokinin stimulates intestinal motility, gallbladder contraction and pancreatic enzyme secretion, and is known to have trophic actions on the pancreas thus increasing, inter alia, pancreatic enzyme production. Cholecystokinin also inhibits gastric emptying and has various effect in the central nervous system, including regulation of appetite and pain.

Gastrin acts on CCK2 (otherwise known as gastrin/CCK-B receptors) whereas cholecystokinin acts on both CCK2 and CCK1 receptors (otherwise known as cholecystokinin/CCK-A receptors). Compounds that bind to cholecystokinin and/or gastrin receptors are important because of their potential pharmaceutical use as antagonists of the natural peptides or mimetics of the natural peptides acting as partial or full agonists at the cholecystokinin and/or gastrin receptors. A selective gastrin receptor antagonist has not yet been marketed. However, several are currently undergoing clinical evaluation. JB95008 (gastrazole) is being developed by The James Black Foundation and Johnson & Johnson for the potential treatment of advanced pancreatic cancer (pancreatic adenocarcinoma), and is currently in Phase II clinical trails. ML Laboratories and Panos are developing L-365,260 (Colycade), which is in Phase II clinical trials for pain. Other potential indications included eating disorders and cancer. YF-476 (formerly YM-220), under join development by Yamanouchi and Ferring Research Institute, is in Phase I clinical trials for gastro-esophageal reflux disease (GERD). In Phase I trials, Zeria Pharmaceutical is investigating Z-360, an orally available 1,5-benzodiazepine derivative (WO-09825911), as a potential treatment for gastroduodenal ulcers and reflux esophagitis. CR 2945 (itriglumide), an orally active anthranilic acid derivative, has been investigated by Rotta in Phase I trials of anxiety disorders, cancer (particularly colon cancer) and peptic ulcer.

Gastrimmune, Aphton Corporation's anti-gastrin vaccine, which works by chemical neutralization of the hormone, is undergoing late stage clinical trials for cancer indications, in particular, pancreatic and gastric tumors.

In addition to those indications described above, gastrin (CCK2) antagonists have been proposed for the following gastrin-related disorders: gastrointestinal ulcers, Barrett's esophagus, antral G cell hyperplasia, pernicious anaemia, Zollinger-Ellison syndrome and other conditions in which lower gastrin activity or lower acid secretions is desirable.

Cholecystokinin (CCK1) receptors have been shown to mediate cholecystokinin-stimulated gallbladder contraction, pancreatic enzyme secretion, satiety, gastric emptying inhibition and regulation of peristalsis, indicating a key role in the integrated physiological gastrointestinal response to a meal. In addition, there is evidence that cholecystokinin receptors mediate a mitogenic action of cholecystokinin on some adenocarcinomas. Consequently, selective cholecystokinin receptor antagonists, for example, devazepide (Merck), lorglumide (Rotta), 2-NAP (JBF), dexloxiglumide (Rotta) and lintitript (Sanofi) have been examined in the clinic for potential applications in, inter alia, irritable bowel syndrome, chronic constipation, non-ulcer dyspepsia, acute and chronic pancreatitis, biliary disease and pancreatic cancer. Additional roles of cholecystokinin receptors include the regulation or appetite and metabolism, indicating potential therapeutic applications in the treatment of disorders such as obesity and anorexia nervosa. Other possible uses are in the potentiation of opiate (for example morphine) analgesia and in the treatment of cancers, especially of the pancreas. Moreover, ligands for cholecystokinin/gastrin receptors in the brain have been claimed to possess anxiolytic activity, and gastrin receptor antagonists would be expected to act as neurological agents towards the relief of anxiety and related neuroses and psychoses.

SUMMARY OF THE INVENTION

The invention features a compound of formula (I):

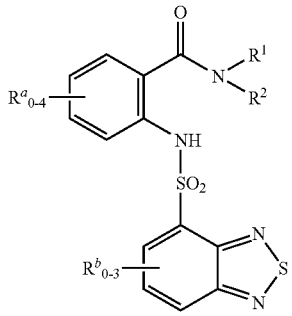

wherein

R$^1$ and R$^2$ are each independently selected from the group consisting of a) H, C$_{1-7}$alkyl, C$_{2-7}$alkenyl, C$_{2-7}$alkynyl, C$_{3-7}$cycloalkyl, C$_{3-7}$cycloalkenyl, benzo-fusedC$_{4-7}$cycloalkyl where the point of attachment is a carbon atom adjacent to the ring junction, C$_{3-7}$cycloalkylC$_{1-7}$alkyl, b) naphthyl-(CR$^s{}_2$)—, benzoylC$_{0-3}$alkyl-(CR$^s{}_2$)—, phenyl, said phenyl optionally fused at two adjacent carbon atoms to R$^f$, phenyl-(CR$^s{}_2$)—, said phenyl optionally fused at two adjacent carbon atoms to R$^f$, R$^f$ is a linear 3- to 5-membered hydrocarbon moiety having 0 to 1 unsaturated bonds and having 0, 1 or 2 carbon members which is a carbonyl, c) Ar$^6$—(CR$^s{}_2$)—, where Ar$^6$ is a 6-membered heteroaryl having carbon as a point of attachment, having 1 or 2 heteroatom members which are —N═ and optionally benzo fused, d) Ar$^5$—(CR$^s{}_2$)—, where Ar$^5$ is a 5-membered heteroaryl having carbon as a point of attachment, having 1 heteroatom member selected from the group consisting of O, S, >NH or >NC$_{1-4}$alkyl, having 0 or 1 additional heteroatom member which is —N═ and optionally benzo fused, e) Ar$^{6-6}$—(CR$^s{}_2$)—, where Ar$^{6-6}$ is phenyl having the point of attachment and fused to a 6-membered heteroaryl having 1 or 2 heteroatom members which are —N═, f) Ar$^{6-5}$—(CR$^s{}_2$)—, where Ar$^{6-5}$ is phenyl having the point of attachment and fused to a 5-membered heteroaryl having 1 heteroatom member selected from the group consisting of O, S, >NH or >NC$_{1-4}$alkyl and having 0 or 1 additional heteroatom member which is —N═, g) C$_{1-4}$alkylO— and HSC$_{1-4}$alkyl, where R$^1$ and R$^2$ are not simultaneously H and, except in positions where R$^s$ is indicated, each of a) to g) is substituted with 0, 1, 2, or 3 of R$^q$, R$^q$ is independently selected from the group consisting of C$_{1-4}$alkyl, hydroxy, fluoro, chloro, bromo, iodo, trifluoromethyl, aminoC$_{1-4}$alkyl, C$_{1-4}$alkylaminoC$_{1-4}$alkyl, diC$_{1-4}$alkylaminoC$_{1-4}$alkyl, HO—C$_{1-4}$alkyl, C$_{1-4}$alkylO—C$_{1-4}$alkyl, HS—C$_{1-4}$alkyl, C$_{1-4}$alkylS—C$_{1-4}$alkyl, C$_{1-4}$alkoxy and C$_{1-4}$alkylS—, R$^s$ is independently selected from the group consisting of hydrogen, C$_{1-4}$alkyl, trifluoromethyl, aminoC$_{1-4}$alkyl, C$_{1-4}$alkylaminoC$_{1-4}$alkyl, diC$_{1-4}$alkylaminoC$_{1-4}$alkyl, HO—C$_{1-4}$alkyl, HS—C$_{1-4}$alkyl, C$_{1-4}$alkylS—C$_{1-4}$alkyl and phenyl;

or, alternatively.

R$^1$ and R$^2$ may be taken together with the nitrogen to which they are attached and are selected from the group consisting of i) 10-Oxa-4-aza-tricyclo[5.2.1.0$^{2,6}$]dec-4-yl, optionally mono- or di-substituted with R$^p$, R$^p$ is independently selected from the group consisting of hydroxy, C$_{1-4}$alkyl, hydroxyC$_{1-4}$alkyl, phenyl, mono-, di- or tri-halo substituted phenyl and hydroxyphenyl, ii) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl, optionally having one carbon member which forms a bridge and having 0, 1 or 2 substituents R$^p$, iii) a benzo fused 4-7 membered heterocyclic ring said heterocyclic ring having 0 or 1 additional heteroatom members separated from the nitrogen of attachment by at least one carbon member and selected from O, S, —N═, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents R$^p$, iv) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N═, >NH or >NR$^p$, having 0, 1 or 2 unsaturated bonds, having 0, 1 or 2 carbon members which is a carbonyl and having 0, 1 or 2 substituents R$^p$;

v) 8-oxo-1,5,6,8-tetrahydro-2H,4H-1,5-methano-pyrido[1,2-a][1,5]diazocin-3-yl, optionally having 0, 1 or 2 substituents R$^p$;

R$^a$ is, independently, selected from the group consisting of —C$_{1-6}$alkyl, —C$_{2-6}$alkenyl, —C$_{3-6}$cycloalkyl, —Ophenyl, —Obenzyl, —SH, —SC$_{1-6}$alkyl, —OH, —OC$_{1-6}$alkyl, —OC$_{3-6}$cycloalkyl, —Ophenyl, —Obenzyl, —SH, —SC$_{1-6}$alkyl, —SC$_{3-6}$cycloalkyl, —Sphenyl, —Sbenzyl, —CN, —NO$_2$, —N(R$^y$)R$^z$ (wherein R$^y$ and R$^z$ are independently selected from H, C$_{1-4}$alkyl or C$_{1-6}$cycloalkylC$_{1-4}$alkyl), —(C═O)C$_{1-4}$alkyl, —SCF$_3$, halo, —CF$_3$, —OCF$_3$, and —COOC$_{1-4}$alkyl, or, alternatively, two adjacent R$^a$, may be taken together with the carbons of attachment to form a fused ring and selected from the group consisting of phenyl, pyridyl and pyrimidinyl;

R$^b$ is, independently, selected from the group consisting of —C$_{1-4}$alkyl and halogen;

and enantiomers, diastereomers, hydrates, solvates and pharmaceutically acceptable salts, esters and amides thereof.

The invention also features pharmaceutical compositions containing such compounds and methods of using such compositions in the treatment or prevention of disease states mediated by CCK2 receptor activity.

DETAILED DESCRIPTION

Preferably, $R^1$ and $R^2$ are, independently, selected from the group consisting of hydrogen, a) $C_{1-7}$alkyl, ethenyl, propenyl, butenyl, ethynyl, propynyl, cyclobutyl, cyclopentyl, cyclohexyl, cycloheptyl, cyclopentenyl, cyclohexenyl, indan-1-yl, 1,2,3,4-tetrahydro-naphthalen-1-yl, 6,7,8,9-tetrahydro-5H-benzocyclohepten-5-yl, cyclobutyl$C_{1-4}$alkyl, cyclopentyl$C_{1-4}$alkyl, cyclohexyl$C_{1-4}$alkyl, cycloheptyl$C_{1-4}$alkyl, b) phenyl, 6,7,8,9-tetrahydro-5H-benzocyclohepten-1,2,3 or 4-yl, optionally 5,6,7,8 or 9 oxo substituted, 5,6,7,8-tetrahydro-naphthalen-1,2,3 or 4-yl, optionally 5,6,7 or 8 oxo substituted, benzyl, 6,7,8,9-tetrahydro-5H-benzocyclohepten-1,2,3 or 4-ylmethyl, optionally 5,6,7,8, or 9 oxo substituted, 5,6,7,8-tetrahydro-naphthalen-1,2,3 or 4-ylmethyl, optionally 5,6,7 or 8 oxo substituted, 1-phenyleth-1-yl, benzhydryl, naphthylmethyl, benzoylmethyl, 1-benzoyleth-1-yl, c) pyridylmethyl, pyrazinylmethyl, pyrimidinylmethyl, pyridazinylmethyl, quinolin-2,3 or 4-ylmethyl, isoquinolin-1,3 or 4-ylmethyl, quinazolin-2 or 4-ylmethyl, quinoxalin-2 or 3-ylmethyl, d) furanylmethyl, thiophenylmethyl, 1-(H or $C_{1-4}$alkyl) pyrrolylmethyl, oxazolylmethyl, thiazolylmethyl, pyrazolylmethyl, imidazolylmethyl, isoxazolylmethyl, isothiazolylmethyl, benzofuran-2 or 3-ylmethyl, benzothiopen-2 or 3-ylmethyl, 1-(H or $C_{1-4}$alky)-1H-indol-2 or 3-ylmethyl, 1-(H or $C_{1-4}$alkyl)-1H-benzimidazol-2-ylmethyl, benzooxazol-2-ylmethyl, benzothiazol-2-ylmethyl, e) quinolin-5,6,7 or 8-ylmethyl, isoquinolin-5,6,7 or 8-ylmethyl, quinazolin-5,6,7 or 8-ylmethyl, quinoxalin-5,6,7 or 8-ylmethyl, f) benzofuran-4,5,6 or 7-ylmethyl, benzothiophen-4,5,6 or ylmethyl, 1-(H or $C_{1-4}$alky)-1H-indol-4,5,6 or 7-ylmethyl, 1-(H or $C_{1-4}$alkyl)-1H-benzimidazol-4,5,6 or 7-ylmethyl, benzooxazol-4,5,6 or 7-ylmethyl, benzothiazol-4,5,6 or 7-ylmethyl, g) $C_{1-4}$alkylO— and HS$C_{1-4}$alkyl, where each of a) to g) is substituted with 0, 1, 2, or 3 of $R^q$.

Most preferably, $R^1$ $R^2$ are, independently, selected from the group consisting of hydrogen, methyl, ethyl, butyl, hexyl, phenyl, 6,7,8,9-tetrahydro-5H-benzocyclohepten-2-yl, optionally 5,6,7,8 or 9 oxo substituted, benzyl 1-phenyleth-1-yl, furanylmethyl, benzoylethyl, 1-benzoyleth-1yl, methylO—, cyclohexyl, cyclohexylmethyl, pyridylethyl, naphthylmethyl, 1,2,3,4-tetrahydro-naphthalen-1-yl, benzhydryl, where each member is substituted with 0, 1, 2, or 3 of $R^q$.

Specific $R^1$ and $R^2$ are, independently, selected from the group consisting of hydrogen, methyl, ethyl, butyl, phenyl, benzyl, 2-bromobenzyl, 2-chlorobenzyl, 4-chlorobenzyl, 2,4-dichlorobenzyl, 3,4-dichlorobenzyl, 2,6-dichlorobenzyl, 2,4,6-trichlorobenzyl, 2-fluorobenzyl, 4-fluorobenzyl, 2,4,-difluorobenzyl, 2,6-difluorobenzyl, 2,4,6-trifluorobenzyl, 2-chloro-4-fluorobenzyl, 2-fluoro-4-bromobenzyl, 2-fluoro-4-chlorobenzyl, 2-methylbenzyl, 2-methylsulfanylbenzyl, 2-trifluoromethylbenzyl, 1-phenyleth-1-yl, 1-phenylprop-1-yl, 1-(4-bromophenyl)eth-1-yl, 1-(4-fluorophenyl)eth-1-yl, 1-2,4-dibromophenyl)eth-1-yl, 1-(2,4-dichlorophenyl)eth-1-yl, 1-(3,4-dichlorophenyl)eth-1-yl, 1-(2,4-difluorophenyl) eth-1-yl, 1-(3,4-methylphenyl)eth-1-yl, 1-methyl-1-phenyleth-1-yl, 1-phenyl-2-dimethylaminoeth-1yl, 1-benzoyleth-1-yl, cyclohexyl, 1-cyclohexyleth-1-yl, furan-2-ylmethyl, naphth-1-ylmethyl, methoxy, methylSethyl, 6-methyl-6-hydroxyhept-2yl, pyrid-2-ylethyl, 1,2,3,4-tetrahydro-naphthalen-1-yl, 1-phenyl-2-hydroxyeth-1-yl, benzhydryl, 4-hydroxymethylpiperidin-1-yl, 1-phenyl-2-yl-2-phenyleth-1-yl and 9-oxo-6,7,8,9-tetrahydro-5H-benzocyclohepten-2yl.

It is preferred that one of $R^1$ and $R^2$ is H or $C_{1-4}$alkyl where the other is not H or $C_{1-4}$alkyl. It is also preferred that one of $R^1$ and $R^2$ is H, methyl or ethyl.

In another preferred embodiment, at least one of $R^1$ and $R^2$ are selected from the groups consisting of

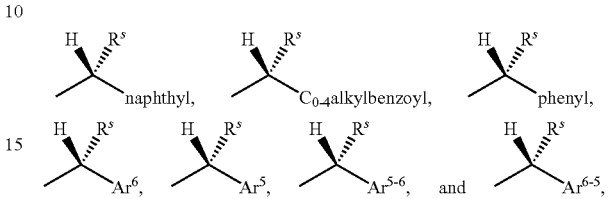

where $R^s$ is not hydrogen, said phenyl is optionally fused at two adjacent carbon atoms to $R^f$ and, except in positions where $R^s$ is indicated, each member is substituted with 0, 1, 2, or 3 of $R^q$.

Preferably, $R^f$ is selected from the group consisting of —$CH_2CH_2CH_2$—, —$CH_2CH_2CH_2CH_2$—, —$CH_2CH_2CH_2CH_2CH_2$— and —(C=O)$CH_2CH_2CH_2$—.

Preferably, $R^s$ is selected from the group consisting of hydrogen, methyl, ethyl, propyl, trifluoromethyl, aminomethyl, methylaminomethyl, dimethylaminomethyl, hydroxymethyl, methoxymethyl, thiomethyl, methylthiomethyl and phenyl.

Most preferably, $R^s$ is selected from the group consisting of H, methyl, ethyl, hydroxymethyl and dimethylaminomethyl.

Preferably, $R^q$ is selected from the group consisting of methyl, ethyl, propyl, t-butyl, hydroxy, fluoro, chloro, bromo, iodo, trifluoromethyl, aminomethyl, methylaminomethyl, dimethylaminomethyl, hydroxymethyl, methoxymethyl, thiomethyl, methylthiomethyl, methoxy, ethoxy, methylmercapto and ethylmercapto.

Most preferably, $R^q$ is selected from the group consisting of methyl, hydroxy, fluoro, chloro, bromo, iodo and trifluoromethyl.

Preferably, $R^1$ and $R^2$ taken together with the nitrogen to which they are attached are selected from the group consisting of i) 10-Oxa-4-aza-tricyclo[5.2.1.0$^{2,6}$]dec-4yl, ii) 2-pyrrolin-1-yl, 3-pyrrolin-1-yl, pyrrolidin-1-yl, 2-imidazolin-1-yl, 3-(H or $R^p$)imidazolidin-1-yl, piperidin-1-yl, morpholin-4yl, thiomorpholin-4-yl, 3-(H or $R^p$)piperazin-1-yl, azepan-1-yl, thiazolidin-3-yl, oxazolidin-3-yl, 2,5-dihydro-pyrrol-1-yl, azetidin-1-yl, where each member of ii) in each ring has 0 or 1 unsaturated bond and has 0, 1 or 2 carbon members which is a carbonyl, iii) 3,4-dihydro-2H-quinolin-1yl, 3,4-dihydro-2H-quinolin-2-yl, 2,3-dihydro-indol-1-yl, 1,3-dihydro-isoindol-2-yl, 1-oxo-1,3-dihydro-isoindol-2yl, tetrahydro-benzo[b, c or d]azepin-1-yl, where each member of iii) in each ring has 0 or 1 unsaturated bond and has 0, 1 or 2 carbon members which are a carbonyl, iv) decahydro-quinolin-1-yl, octahydro-isoquinolin-2-yl, octahydro-[1 or 2]pyrindin-1 or 2-yl, octahydro-indol-1-yl, octahydro-isoindol2-yl, hexahydro-cyclopenta[b]pyrrol-1-yl, hexahydro-cyclopenta[c]pyrrol-2yl, (5,6,7 or 8-H or $R^p$)-decahydro-[1,5, or 1,6 or 1,7 or 1,8]naphthyridin-1-yl, (5,6,7 or 8-H or $R^p$)-decahydro-[2,5 or 2,6 or 2,7 or 2,8]naphthyridin-2-yl, 1-H or $R^p$-octahydro-pyrrolo[2,3-c]pyridin-6-yl, 2-H or $R^p$-octahydro-pyrrolo[3,4-c]pyridin-5-yl, 1-H or R$^p$-octahydro-pyrrolo[3,2-c]pyridin-5-yl, 1-H or R$^p$-octahydro-pyrrolo[2,3,-b]pyridin-7-yl, 6-H or R$^p$-octahydro-pyrrolo[3,4-b]pyridin-1-yl, 1-H or R$^p$-octahydro-pyrrolo[3,2-b]pyridin-4-yl, 5-H or R$^p$-octahydro-pyrrolo[3,4-c]pyridin-2-yl, 6-H or R$^p$-octahydro-pyrrolo[2,3-c]pyridin-1-yl, 1-H or R$^p$-octahydro-pyrrolo[3,4-b]pyridin-6-yl, 7-H or R$^p$-octahydro-pyrrolo[2,3-b]pyridin-1-yl, octahydro-1,5-methano-pyrido[1,2-a][1,5]diazocin-3-yl, where each member of iv) in each ring has 0, 1 or 2 carbon members which is a carbonyl, each ring of attachment has 0 or 1 unsaturated bonds and each secondary ring has 0, 1 or 2 unsaturated bonds.

v) 8-oxo-1,5,6,8-tetrahydro-2H,4H-1,5-methano-pyrido[1,2-a][1,5]diazocin-3-yl, where each member of i), ii), iii), iv) or v) is further substituted with 0, 1 or 2 of R$^p$.

Most preferably, R$^1$ and R$^2$ taken together with the nitrogen to which they are attached are selected from the group consisting of 10-Oxa-4-aza-tricyclo[5.2.1.0$^{2.6}$]dec-4-yl, 2-pyrrolin-1-yl, 3-pyrrolin-1-yl, 3-pyrrolin-1-yl, pyrrolidin-1-yl, 2-imidazolin-1yl, imidazolidin-1-yl, piperidin-1-yl, morpholin-4-yl, thiomorpholin-4-yl, piperazin-1-yl, azepan-1-yl, thiazolidin-3-yl, oxazolidin-3yl, 2,5-dihydro-pyrrol-1yl, 8-oxo-1,5,6,8-tetrahydro-2H,4H-1,5-methano-pyrido[1,2-a][1,5]diazocin-3-yl, azetidin-1-yl, octahydro-quinolin-1-yl, 3,4-dihydro-2H-quinolin-1-yl, 3,4-dihydro-2H-quinolin-2yl, where each member is further substituted with 0, 1 or 2 of R$^p$.

Specific R$^1$ and R$^2$ taken together with the nitrogen to which they are attached are selected from the group consisting of 1-methyl-10-Oxa-4-aza-tricyclo[5.2.1.0$^{2.6}$]dec-4-yl, azetidin-1-yl, pyrrolin-1-yl, 2-hydroxymethylpyrrolin-1-yl, 2,4-dimethyl-3-ethylpyrrolidin-1-yl, piperidin-1-yl, 2-methylpiperidin-1-yl, 4-hydroxymethylpiperidin-1-yl, 4-phenylpiperidin-1-yl, azepan-1-yl, 4-(2-hydroxyphenyl)piperazin-1-yl, morpholin-4-yl, octahydro-isoquinolin-2-yl, decahydro-quinolin-1-yl, thiazolidin-3-yl, 2,5-dimethyl-2,5-dihydro-pyrrol-1yl, 8-oxo-1,5,6,8-tetrahydro-2H,4H-1,5-methano-pyrido[1,2-a][1,5]diazocin-3-yl and 3,4-dihydro-2H-quinolin-2-yl.

Preferably, R$^p$ is selected from the group consisting of hydroxy, methyl, ethyl, propyl, hydroxymethyl, hydroxyethyl, phenyl, p-halophenyl, m-halophenyl, o-halophenyl, phenyl and p-hydoxphenyl.

Most preferably, R$^p$ is selected from the group consisting of hydroxy, methyl, ethyl, hydroxymethyl, hydroxyethyl, phenyl, mono-fluorosubstituted phenyl and mono-chlorosubstituted phenyl.

Preferably, R$^a$ is selected from the group consisting of methyl, ethyl, propyl, ethenyl, propenyl, cyclopropyl, cyclobutyl, phenyl, furanyl, thienyl, pyrrol-1-yl, benzyl, methoxy, ethoxy, propoxy, cyclopropoxy, cyclobutoxy, cyclopentoxy, phenoxy, benzoxy, —SH, —Smethyl, —Sethyl, —S-t-butyl, —Scyclopropyl, —Sphenyl, —Sbenzyl, nitro, cyano, amino, dimethylamino, (cyclohexylmethyl) amino, acetyl, —SCF$_3$, I, F, Cl, Br, trifluoromethyl, —OCF$_3$ and carboxymethyl.

Preferably, there is one R$^a$. More preferably, there is one R$^a$ positioned on the ring para to the amide substituent.

Preferably, where two adjacent R$^a$ are taken together with the carbons of attachment to form a fused ring, the fused ring is benzo.

Most preferably, R$^a$ is selected from the group consisting of nitro, F, Cl, Br, fused benzo, I, CF$_3$, methoxy, ethoxy, propoxy, i-propoxy, ethenyl, cyclopentoxy, 2-propenyl, phenyl, furanyl, thienyl, amino, pyrrol-1-yl, dimethylamino, (cyclohexylmethyl)amino, —SCH$_3$, —Sethyl, —S-t-butyl, —Sbenzyl, —SCF$_3$, i-propyl and methyl.

Preferably, R$^b$ is absent or selected from the group consisting of methyl, ethyl, I, F, Cl and Br.

Most preferably, R$^b$ is absent.

Pharmaceutically acceptable salts include amino addition salts that are pharmacologically effective. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. See example, S. M. Berge, et al., "Pharmaceutical Salts," J. Pharm. Sci., 1977, 66; 1-19, which is incorporated herein by reference.

Preferred compounds, where R$^1$ and R$^2$ taken together with the nitrogen to which they are attached form a heterocyclic ring structure, as defined in groups i)-v) above, are made according to the synthetic methods outlined in Schemes A and B and are selected from the group consisting of:

| EX | Compound |
|---|---|
| 1 | Benzo[1,2,5]thiadiazole-4-sulfonic acid [5-chloro-2-(piperidine-1-carbonyl)-phenyl]-amide |
| 2 | Benzo[1,2,5]thiadiazole-4-sulfonic acid [5-nitro-2-(piperidine-1-carbonyl)-phenyl]-amide |
| 3 | Benzo[1,2,5]thiadiazole-4-sulfonic acid [4-bromo-2-(piperidine-1-carbonyl)-phenyl]-amide |
| 4 | Benzo[1,2,5]thiadiazole-4-sulfonic acid [3-(piperidine-1-carbonyl)-naphthalen-2-yl]-amide |
| 5 | Benzo[1,2,5]thiadiazole-4-sulfonic acid [5-bromo-2-(piperidine-1-carbonyl)-phenyl]-amide |
| 6 | Benzo[1,2,5]thiadiazole-4-sulfonic acid [5-iodo-2-(piperidine-1-carbonyl)-phenyl]-amide |
| 10 | Benzo[1,2,5]thiadiazole-4-sulfonic acid [5-methoxy-2-(piperidine-1-carbonyl)-phenyl]-amide |
| 11 | Benzo[1,2,5]thiadiazole-4-sulfonic acid [5-ethoxy-2-(piperidine-1-carbonyl)-phenyl]-amide |
| 12 | Benzo[1,2,5]thiadiazole-4-sulfonic acid [2-(piperidine-1-carbonyl)-5-propoxy-phenyl]-amide |
| 13 | Benzo[1,2,5]thiadiazole-4-sulfonic acid [5-isopropoxy-2-(piperidine-1-carbonyl)-phenyl]-amide |
| 14 | Benzo[1,2,5]thiadiazole-4-sulfonic acid [5-cyclopentyloxy-2-(piperidine-1-carbonyl)-phenyl]-amide |
| 15 | Benzo[1,2,5]thiadiazole-4-sulfonic acid [2-(piperidine-1-carbonyl)-5-vinyl-phenyl]-amide |
| 16 | Benzo[1,2,5]thiadiazole-4-sulfonic acid [5-allyl-2-(piperidine-1-carbonyl)-phenyl]-amide |
| 17 | Benzo[1,2,5]thiadiazole-4-sulfonic acid [5-ethyl-2-(piperidine-1-carbonyl)-phenyl]-amide |
| 18 | Benzo[1,2,5]thiadiazole-4-sulfonic acid [2-(piperidine-1-carbonyl)-5-propyl-phenyl]-amide |
| 19 | Benzo[1,2,5]thiadiazole-4-sulfonic acid [4-(piperidine-1-carbonyl)-biphenyl-3-yl]-amide |
| 20 | Benzo[1,2,5]thiadiazole-4-sulfonic acid [5-furan-2-yl-2-(piperidine-1-carbonyl)-phenyl]-amide |
| 21 | Benzo[1,2,5]thiadiazole-4-sulfonic acid [5-furan-3-yl-2-(piperidine-1-carbonyl)-phenyl]-amide |
| 22 | Benzo[1,2,5]thiadiazole-4-sulfonic acid [2-(piperidine-1-carbonyl)-5-thiophen-2-yl-phenyl]-amide |
| 23 | Benzo[1,2,5]thiadiazole-4-sulfonic acid [2-(piperidine-1-carbonyl)-5-thiophen-3-yl-phenyl]-amide |
| 24 | Benzo[1,2,5]thiadiazole-4-sulfonic acid [5-amino-2-(piperidine-1-carbonyl)-phenyl]-amide |
| 25 | Benzo[1,2,5]thiadiazole-4-sulfonic acid [2-(piperidine-1-carbonyl)-5-pyrrol-1-yl-phenyl]-amide |
| 26 | Benzo[1,2,5]thiadiazole-4-sulfonic acid [5-dimethylamino-2-(piperidine-1-carbonyl)-phenyl]-amide |
| 27 | Benzo[1,2,5]thiadiazole-4-sulfonic acid [5-cyclohexylmethyl-amino)-2-(piperidine-1-carbonyl)-phenyl]-amide |
| 28 | Benzo[1,2,5]thiadiazole-4-sulfonic acid [5-methylsulfanyl-2-(piperidine-1-carbonyl)-phenyl]-amide |
| 29 | Benzo[1,2,5]thiadiazole-4-sulfonic acid [5-ethylsulfanyl-2-(piperidine-1-carbonyl)-phenyl]-amide |

-continued

| EX | Compound |
|---|---|
| 30 | Benzo[1,2,5]thiadiazole-4-sulfonic acid [5-isobutylsulfanyl-2-(piperidine-1-carbonyl)-phenyl]-amide |
| 31 | Benzo[1,2,5]thiadiazole-4-sulfonic acid [5-benzylsulfanyl-2-(piperidine-1-carbonyl)-phenyl]-amide |
| 32 | Benzo[1,2,5]thiadiazole-4-sulfonic acid [2-(piperidine-1-carbonyl)-5-trifluoromethyl-phenyl]-amide |
| 33 | Benzo[1,2,5]thiadiazole-4-sulfonic acid [5-fluoro-2-(piperidine-1-carbonyl)-phenyl]-amide |
| 34 | Benzo[1,2,5]thiadiazole-4-sulfonic acid [3-chloro-2-(piperidine-1-carbonyl)-phenyl]-amide |
| 35 | Benzo[1,2,5]thiadiazole-4-sulfonic acid [4,5-dibromo-2-(piperidine-1-carbonyl)-phenyl]-amide |
| 36 | Benzo[1,2,5]thiadiazole-4-sulfonic acid [4,5-dichloro-2-(piperidine-1-carbonyl)-phenyl]-amide |
| 37 | Benzo[1,2,5]thiadiazole-4-sulfonic acid [5-isopropyl-2-(piperidine-1-carbonyl)-phenyl]-amide |
| 44 | Benzo[1,2,5]thiadiazole-4-sulfonic acid [5-methyl-2-(piperidine-1-carbonyl)-phenyl]-amide |
| 54 | Benzo[1,2,5]thiadiazole-4-sulfonic acid [5-chloro-2-(1-methyl-10-oxa-4-aza-tricyclo[5.2.1.0$^{2.6}$]decane-4-carbonyl)-phenyl]-amide |
| 60 | Benzo[1,2,5]thiadiazole-4-sulfonic acid [5-chloro-2-(pyrrolidine-1-carbonyl)-phenyl]-amide |
| 62 | Benzo[1,2,5]thiadiazole-4-sulfonic acid [5-chloro-2-(4-hydroxymethyl-piperidine-1-carbonyl)-phenyl]-amide |
| 63 | Benzo[1,2,5]thiadiazole-4-sulfonic acid {5-chloro-2-[4-(2-hydroxy-phenyl)-piperazine-1-carbonyl]-phenyl}-amide |
| 64 | Benzo[1,2,5]thiadiazole-4-sulfonic acid [5-chloro-2-(2-hydroxymethyl-pyrrolidine-1-carbonyl)-phenyl]-amide |
| 66 | Benzo[1,2,5]thiadiazole-4-sulfonic acid [5-chloro-2-(2,5-dimethyl-2,5-dihydro-pyrrole-1-carbonyl)-phenyl]-amide |
| 68 | Benzo[1,2,5]thiadiazole-4-sulfonic acid [2-(azepane-1-carbonyl)-5-chloro-phenyl]-amide |
| 70 | Benzo[1,2,5]thiadiazole-4-sulfonic acid [5-chloro-2-(2-methyl-piperidine-1-carbonyl)-phenyl]-amide |
| 71 | Benzo[1,2,5]thiadiazole-4-sulfonic acid [5-chloro-2-(octahydro-isoquinoline-2-carbonyl)-phenyl]-amide |
| 72 | Benzo[1,2,5]thiadiazole-4-sulfonic acid [5-chloro-2-(3-ethyl-2,4-dimethyl-pyrrolidine-1-carbonyl)-phenyl]-amide |
| 73 | Benzo[1,2,5]thiadiazole-4-sulfonic acid [5-chloro-2-(4-phenyl-piperidine-1-carbonyl)-phenyl]-amide |
| 75 | Benzo[1,2,5]thiadiazole-4-sulfonic acid [5-chloro-2-(octahydro-quinoline-1-carbonyl)-phenyl]-amide |
| 78 | Benzo[1,2,5]thiadiazole-4-sulfonic acid [2-azetidine-1-carbonyl)-5-chloro-phenyl]-amide |
| 79 | Benzo[1,2,5]thiadiazole-4-sulfonic acid [5-chloro-2-(thiazolidine-3-carbonyl)-phenyl]-amide |
| 80 | Benzo[1,2,5]thiadiazole-4-sulfonic acid [5-chloro-2-(1,2,3,4-tetrahydro-naphthalene-2-carbonyl)-phenyl]-amide |
| 89 | Benzo[1,2,5]thiadiazole-4-sulfonic acid [5-chloro-2-(8-oxo-1,5,6,8-tetrahydro-2H,4H-1,5-methano-pyrido[1,2-a][1,5]diazocine-3-carbonyl)-phenyl]-amide |
| 90 | Benzo[1,2,5]thiadiazole-4-sulfonic acid [5-chloro-2-(2,5-dimethyl-pyrrolidine-1-carbonyl)-phenyl]-amide |
| 91 | Benzo[1,2,5]thiadiazole-4-sulfonic acid [5-chloro-2-(morpholine-4-carbonyl)-phenyl]-amide |
| 137 | Benzo[1,2,5]thiadiazole-4-sulfonic acid [5-bromo-2-(morpholine-4-carbonyl)-phenyl]-amide |
| 138 | Benzo[1,2,5]thiadiazole-4-sulfonic acid [5-iodo-2-(morpholine-4-carbonyl)-phenyl]-amide |
| 139 | Benzo[1,2,5]thiadiazole-4-sulfonic acid [5-methyl-2-(morpholine-4-carbonyl)-phenyl]-amide |
| 140 | 7-Methyl-benzo[1,2,5]thiadiazole-4-sulfonic acid [5-bromo-2-(piperidine-1-carbonyl)-phenyl]-amide |
| 177 | 5-Methyl-benzo[1,2,5]thiadiazole-4-sulfonic acid [5-bromo-2-(piperidine-1-carbonyl)-phenyl]-amide |
| 178 | 7-Bromo-benzo[1,2,5]thiadiazole-4-sulfonic acid [5-bromo-2-(piperidine-1-carbonyl)-phenyl]-amide |
| 182 | Benzo[1,2,5]thiadiazole-4-sulfonic acid [5-chloro-2-(1,3,4,5-tetrahydro-benzo[c]azepine-2-carbonyl)-phenyl]-amide |
| 7 | 2-(Benzo[1,2,5]thiadiazole-4-sulfonylamino)-N-benzyl-4-chloro-N-methyl-benzamide |
| 8 | 2-(Benzo[1,2,5]thiadiazole-4-sulfonylamino)-N-benzyl-4-bromo-N-methyl-benzamide |
| 9 | 2-(Benzo[1,2,5]thiadiazole-4-sulfonylamino)-N-benzyl-4-iodo-N-methyl-benzamide |
| 38 | 3-(Benzo[1,2,5]thiadiazole-4-sulfonylamino)-naphthalene-2-carboxylic acid (4-fluoro-benzyl)-methylamide |
| 39 | (R)-2-(Benzo[1,2,5]thiadiazole-4-sulfonylamino)-N-[1-(2,4-difluoro-phenyl)-ethyl]-4-trifluoromethylbenzamide |
| 40 | (R)-2-(Benzo[1,2,5]thiadiazole-4-sulfonylamino)-N-[1-(2,4-difluorophenyl)-ethyl]-4-fluorobenzamide |
| 41 | (R)-2-(Benzo[1,2,5]thiadiazole-4-sulfonylamino)-N-[1-(2,4-difluoro-phenyl)-ethyl]-benzamide |
| 42 | (R)-2-(Benzo[1,2,5]thiadiazole-4-sulfonylamino)-N-[1-(2,4-dichlorophenyl)-ethyl]-4-methylbenzamide |
| 43 | (R)-2-(Benzo[1,2,5]thiadiazole-4-sulfonylamino)-5-chloro-N-[1-(2,4-dichloro-phenyl)-ethyl]-benzamide |
| 45 | 2-(Benzo[1,2,5]thiadiazole-4-sulfonylamino)-4-chloro-N-(2-chloro-benzyl)-benzamide |
| 46 | 2-(Benzo[1,2,5]thiadiazole-4-sulfonylamino)-N-benzyl-4-chloro-N-(5-hydroxy-1,5-dimethylhexyl)benzamide |
| 47 | 2-(Benzo[1,2,5]thiadiazole-4-sulfonylamino)-4-chloro-N-(2-methylsulfanyl-benzyl)benzamide |
| 48 | 2-(Benzo[1,2,5]thiadiazole-4-sulfonylamino)-4-chloro-N-(2-dimethylamino-1-phenyl-ethyl)-N-methylbenzamide TFA salt |
| 49 | 2-(Benzo[1,2,5]thiadiazole-4-sulfonylamino)-N-benzyl-4-chloro-N-ethyl-benzamide |
| 50 | N-Benzhydryl-2-(benzo[1,2,5]thiadiazole-4-sulfonylamino)-4-chloro-N-methyl-benzamide |
| 51 | (S) 2-(Benzo[1,2,5]thiadiazole-4-sulfonylamino)-4-chloro-N-methyl-N-(1-phenyl-ethyl)-benzamide |
| 52 | (R) 2-(Benzo[1,2,5]thiadiazole-4-sulfonylamino)-4-chloro-N-methyl-N-(1-phenyl-ethyl)-benzamide |
| 53 | (R) 2-(Benzo[1,2,5]thiadiazole-4-sulfonylamino)-4-chloro-N-(1-phenyl-ethyl)-benzamide |
| 55 | 2-(Benzo[1,2,5]thiadiazole-4-sulfonylamino)-N-(4-bromo-2-fluoro-benzyl)-4-chloro-benzamide |
| 56 | (R) 2-(Benzo[1,2,5]thiadiazole-4-sulfonylamino)-N-[1-(4-bromo-phenyl)-ethyl]-4-chloro-benzamide |
| 57 | (R) 2-(Benzo[1,2,5]thiadiazole-4-sulfonylamino)-4-chloro-N-(1-p-tolyl-ethyl)-benzamide |
| 58 | 2-(Benzo[1,2,5]thiadiazole-4-sulfonylamino)-4-chloro-N-methyl-N-phenyl-benzamide |
| 59 | 2-(Benzo[1,2,5]thiadiazole-4-sulfonylamino)-N-butyl-4-chloro-benzamide |
| 61 | 2-(Benzo[1,2,5]thiadiazole-4-sulfonylamino)-4-chloro-N-[1-(4-fluoro-phenyl)-ethyl]-benzamide |
| 65 | 2-(Benzo[1,2,5]thiadiazole-4-sulfonylamino)-4-chloro-N,N-diethyl-benzamide |
| 67 | 2-(Benzo[1,2,5]thiadiazole-4-sulfonylamino)-4-chloro-N-furan-2-ylmethyl-N-methyl-benzamide |
| 69 | 2-(Benzo[1,2,5]thiadiazole-4-sulfonylamino)-4-chloro-N-methyl-N-naphthalen-1-ylmethyl-benzamide |
| 74 | 2-(Benzo[1,2,5]thiadiazole-4-sulfonylamino)-4-chloro-N-cyclohexyl-N-methyl-benzamide |
| 76 | (R)-2-(Benzo[1,2,5]thiadiazole-4-sulfonylamino)-4-chloro-N-(1-cyclohexyl-ethyl)-benzamide |
| 77 | 2-(Benzo[1,2,5]thiadiazole-4-sulfonylamino)-4-chloro-N-(9-oxo-6,7,8,9-tetrahydro-5H-benzocyclohepten-2-yl)-benzamide |
| 81 | 2-(Benzo[1,2,5]thiadiazole-4-sulfonylamino)-4-chloro-N-(2,4-difluoro-benzyl)-benzamide |
| 82 | 2-(Benzo[1,2,5]thiadiazole-4-sulfonylamino)-4-chloro-N-(2-fluoro-benzyl)-benzamide |
| 83 | 2-(Benzo[1,2,5]thiadiazole-4-sulfonylamino)-4-chloro-N-(2,4-dichloro-benzyl)-benzamide |
| 84 | 2-(Benzo[1,2,5]thiadiazole-4-sulfonylamino)-4-chloro-N-(3,4-dichloro-benzyl)-benzamide |
| 85 | 2-(Benzo[1,2,5]thiadiazole-4-sulfonylamino)-4-chloro-N-(4-chloro-benzyl)-benzamide |
| 86 | 2-(Benzo[1,2,5]thiadiazole-4-sulfonylamino)-4-chloro-N-(4-fluoro-benzyl)-benzamide |
| 87 | 2-(Benzo[1,2,5]thiadiazole-4-sulfonylamino)-4-chloro-N-(1,2,3,4-tetrahydro-naphthalen-1-yl)-benzamide |
| 88 | 2-(Benzo[1,2,5]thiadiazole-4-sulfonylamino)-4-chloro-N-[1-(3,4-dichloro-phenyl)-ethyl]-benzamide |

Still further preferred compounds, where $R^1$ and $R^2$ are each independently selected from groups a)-g), as defined above, are made according to the synthetic methods outlines in Schemes A and B and are selected from the group consisting of:

| EX | Compound |
|---|---|
| 92 | 2-(Benzo[1,2,5]thiadiazole-4-sulfonylamino)-4-chloro-N-(4-chloro-2-fluoro-benzyl)-benzamide |
| 93 | 2-(Benzo[1,2,5]thiadiazole-4-sulfonylamino)-4-chloro-N-(2-chloro-4-fluoro-benzyl)-benzamide |
| 94 | 2-(Benzo[1,2,5]thiadiazole-4-sulfonylamino)-4-chloro-N-(2-trifluoromethyl-benzyl)-benzamide |
| 95 | (S)-2-(Benzo[1,2,5]thiadiazole-4-sulfonylamino)-4-chloro-N-(2-hydroxy-1-phenyl-ethyl)-benzamide |
| 96 | 2-(Benzo[1,2,5]thiadiazole-4-sulfonylamino)-N-(4-bromo-benzyl)-4-chloro-benzamide |
| 97 | 2-(Benzo[1,2,5]thiadiazole-4-sulfonylamino)-4-chloro-N-(1-phenyl-propyl)-benzamide |
| 98 | 2-(Benzo[1,2,5]thiadiazole-4-sulfonylamino)-4-chloro-N-(2-methyl-benzyl)-benzamide |
| 99 | 2-(Benzo[1,2,5]thiadiazole-4-sulfonylamino)-N-(2-bromo-benzyl)-4-chloro-benzamide |
| 100 | (R)-2-(Benzo[1,2,5]thiadiazole-4-sulfonylamino)-4-iodo-N-methyl-N-(1-phenyl-ethyl)-benzamide |
| 101 | (R)-2-(Benzo[1,2,5]thiadiazole-4-sulfonylamino)-4-bromo-N-methyl-N-(1-phenyl-ethyl)-benzamide |
| 102 | 2-(Benzo[1,2,5]thiadiazole-4-sulfonylamino)-4-bromo-N-(2,4-dichloro-benzyl)-benzamide |
| 103 | 2-(Benzo[1,2,5]thiadiazole-4-sulfonylamino)-N-(2,4-dichloro-benzyl)-4-iodo-N-methyl-benzamide |
| 104 | 2-(Benzo[1,2,5]thiadiazole-4-sulfonylamino)-N-(2,4-difluoro-benzyl)-4-iodo-N-methyl-benzamide |
| 105 | 2-(Benzo[1,2,5]thiadiazole-4-sulfonylamino)-N-[1-(4-fluoro-phenyl)-ethyl]-4-iodo-N-methyl-benzamide |
| 106 | 2-(Benzo[1,2,5]thiadiazole-4-sulfonylamino)-N-(2-chloro-4-fluoro)-benzyl)-4-iodo-N-methyl-benzamide |
| 107 | 2-(Benzo[1,2,5]thiadiazole-4-sulfonylamino)-4-chloro-N-(2,4-dichloro-benzyl)-N-methyl-benzamide |
| 108 | 2-(Benzo[1,2,5]thiadiazole-4-sulfonylamino)-4-chloro-N-(2-chloro-4-fluoro-benzyl)-N-methyl-benzamide |
| 109 | 2-(Benzo[1,2,5]thiadiazole-4-sulfonylamino)-4-chloro-N-(2,4-difluoro-benzyl)-N-methyl-benzamide |
| 110 | 2-(Benzo[1,2,5]thiadiazole-4-sulfonylamino)-4-bromo-N-(2-chloro-4-fluoro-benzyl)-N-methyl-benzamide |
| 111 | 2-(Benzo[1,2,5]thiadiazole-4-sulfonylamino)-4-bromo-N-(2,4-difluoro-benzyl)-N-methyl-benzamide |
| 112 | 2-(Benzo[1,2,5]thiadiazole-4-sulfonylamino)-4-bromo-N-[1-(4-fluoro-phenyl)-ethyl]-N-methyl-benzamide |
| 113 | 2-(Benzo[1,2,5]thiadiazole-4-sulfonylamino)-4-bromo-N-(2,4-dichloro-benzyl)-N-methyl-benzamide |
| 114 | 2-(Benzo[1,2,5]thiadiazole-4-sulfonylamino)-N-(2,4-dichloro-benzyl)-4-iodo-benzamide |
| 115 | (R)-2-(Benzo[1,2,5]thiadiazole-4-sulfonylamino)-4-iodo-N-(1-phenyl-ethyl)-benzamide |
| 116 | (R)-2-(Benzo[1,2,5]thiadiazole-4-sulfonylamino)-4-bromo-N-(1-phenyl-ethyl)-benzamide |
| 117 | 2-(Benzo[1,2,5]thiadiazole-4-sulfonylamino)-4-bromo-N-methoxy)-N-methyl-benzamide |
| 118 | (R)-2-(Benzo[1,2,5]thiadiazole-4-sulfonylamino)-5-chloro-N-methyl-N-(1-phenyl-ethyl)-benzamide |
| 119 | 2-(Benzo[1,2,5]thiadiazole-4-sulfonylamino)-N-(2,4-dichloro-benzyl)-benzamide |
| 120 | 2-(Benzo[1,2,5]thiadiazole-4-sulfonylamino)-N-(2,4-dichloro-benzyl)-4-methyl-benzamide |
| 121 | 2-(Benzo[1,2,5]thiadiazole-4-sulfonylamino)-5-chloro-N-(2,4-dicholro-benzyl)-benzamide |
| 122 | 2-(Benzo[1,2,5]thiadiazole-4-sulfonylamino)-N-(2,4-dichloro-benzyl)-N-methyl-benzamide |
| 123 | 2-(Benzo[1,2,5]thiadiazole-4-sulfonylamino)-N-(2,4-dichloro-benzyl)-4,N-dimethyl-benzamide |
| 124 | 2-(Benzo[1,2,5]thiadiazole-4-sulfonylamino)-5-chloro-N-(2,4-dichloro-benzyl)-N-methyl-benzamide |
| 125 | 2-(Benzo[1,2,5]thiadiazole-4-sulfonylamino)-5-chloro-N-(2,4-difluoro-benzyl)-N-methyl-benzamide |
| 126 | 2-(Benzo[1,2,5]thiadiazole-4-sulfonylamino)-N-(2-chloro-4-fluoro-benzyl)-N-methyl-benzamide |
| 127 | 2-(Benzo[1,2,5]thiadiazole-4-sulfonylamino)-N-(2-chloro-4-fluoro-benzyl)-4,N-methyl-benzamide |
| 128 | 2-(Benzo[1,2,5]thiadiazole-4-sulfonylamino)-5-chloro-N-(2-chloro-4-fluoro-benzyl)-N-methyl-benzamide |
| 129 | 2-(Benzo[1,2,5]thiadiazole-4-sulfonylamino)-4-chloro-N-[1-(4-fluoro-phenyl)-ethyl]-N-methyl-benzamide |
| 130 | 2-(Benzo[1,2,5]thiadiazole-4-sulfonylamino)-5-chloro-N-[1-(4-fluoro-phenyl)-ethyl]-N-methyl-benzamide |
| 131 | 2-(Benzo[1,2,5]thiadiazole-4-sulfonylamino)-4-bromo-N-(2,4-difluoro-benzyl)-benzamide |
| 132 | 2-(Benzo[1,2,5]thiadiazole-4-sulfonylamino)-N-(2,4-difluoro-benzyl)-4-iodo-benzamide |
| 133 | 2-(Benzo[1,2,5]thiadiazole-4-sulfonylamino)-N-(2,4-difluoro-benzyl)-4-methyl-benzamide |
| 134 | 2-(Benzo[1,2,5]thiadiazole-4-sulfonylamino)-5-chloro-N-(2,4-difluoro-benzyl)-benzamide |
| 135 | 2-(Benzo[1,2,5]thiadiazole-4-sulfonylamino)-N-benzyl-N-methyl-benzamide |
| 136 | 2-(Benzo[1,2,5]thiadiazole-4-sulfonylamino)-N-benzyl-4,N-dimethyl-benzamide |
| 141 | 2-(Benzo[1,2,5]thiadiazole-4-sulfonylamino)-4-chloro-N-(2,6-difluoro-benzyl)-benzamide |
| 142 | 2-(Benzo[1,2,5]thiadiazole-4-sulfonylamino)-4-chloro-N-(2,6-dichloro-benzyl)-benzamide |
| 143 | 2-(Benzo[1,2,5]thiadiazole-4-sulfonylamino)-4-chloro-N-(2,4,6-trifluoro-benzyl)-benzamide |
| 144 | 2-(Benzo[1,2,5]thiadiazole-4-sulfonylamino)-4-chloro-N-(2,4,6-trichloro-benzyl)-benzamide |
| 145 | 2-(Benzo[1,2,5]thiadiazole-4-sulfonylamino)-4-chloro-N-(1-methyl-1-phenyl-ethyl)-benzamide |
| 146 | (R)-2-(Benzo[1,2,5]thiadiazole-4-sulfonylamino)-4-chloro-N-[1-(2,4-dichloro-phenyl)-ethyl]-benzamide |
| 147 | (R)-2-(Benzo[1,2,5]thiadiazole-4-sulfonylamino)-4-chloro-N-[1-(2,4-difluoro-phenyl)-ethyl]-benzamide |
| 148 | 2-(Benzo[1,2,5]thiadiazole-4-sulfonylamino)-4-bromo-N-(2,6-difluoro-benzyl)-benzamide |
| 149 | 2-(Benzo[1,2,5]thiadiazole-4-sulfonylamino)-4-bromo-N-(2,6-dichloro-benzyl)-benzamide |
| 150 | 2-(Benzo[1,2,5]thiadiazole-4-sulfonylamino)-4-bromo-N-(2,4,6-trifluoro-benzyl)-benzamide |
| 151 | 2-(Benzo[1,2,5]thiadiazole-4-sulfonylamino)-4-bromo-N-(2,4,6-trichloro-benzyl)-benzamide |
| 152 | 2-(Benzo[1,2,5]thiadiazole-4-sulfonylamino)-4-bromo-N-(2-chloro-4-fluoro-benzyl)-benzamide |
| 153 | 2-(Benzo[1,2,5]thiadiazole-4-sulfonylamino)-4-bromo-N-(1-methyl-1-phenyl-ethyl)-benzamide |
| 154 | (R)-2-(Benzo[1,2,5]thiadiazole-4-sulfonylamino)-4-bromo-N-[1-(2,4-dichloro-phenyl)-ethyl]-benzamide |
| 155 | (R)-2-(Benzo[1,2,5]thiadiazole-4-sulfonylamino)-4-bromo-N-[1-(2,4-difluoro-phenyl)-ethyl]-benzamide |
| 156 | 2-(Benzo[1,2,5]thiadiazole-4-sulfonylamino)-4-iodo-N-(2,4,6-trifluoro-benzyl)-benzamide |
| 157 | 2-(Benzo[1,2,5]thiadiazole-4-sulfonylamino)-4-iodo-N-(2,4,6-trichloro-benzyl)-benzamide |
| 158 | 2-(Benzo[1,2,5]thiadiazole-4-sulfonylamino)-N-(2-chloro-4-fluoro-benzyl)-4-iodo-benzamide |
| 159 | (R)-2-(Benzo[1,2,5]thiadiazole-4-sulfonylamino)-N-[1-(2,4-dichlorn-phenyl)-ethyl]-4-iodo-benzamide |
| 160 | (R)-2-(Benzo[1,2,5]thiadiazole-4-sulfonylamino)-N-[1-(2,4-difluoro-phenyl)-ethyl]-4-iodo-benzamide |
| 161 | 2-(Benzo[1,2,5]thiadiazole-4-sulfonylamino)-N-(2,6-dichloro-benzyl)-benzamide |
| 162 | 2-(Benzo[1,2,5]thiadiazole-4-sulfonylamino)-N-(2,4,6-trifluoro-benzyl)-benzamide |
| 163 | 2-(Benzo[1,2,5]thiadiazole-4-sulfonylamino)-N-(2-chloro-4-fluoro-benzyl)-benzamide |
| 164 | 2-(Benzo[1,2,5]thiadiazole-4-sulfonylamino)-4-methyl-N-(2,4,6-trifluoro-benzyl)-benzamide |
| 165 | 2-(Benzo[1,2,5]thiadiazole-4-sulfonylamino)-4-methyl-N-(2,4,6-trichloro-benzyl)-benzamide |
| 166 | 2-(Benzo[1,2,5]thiadiazole-4-sulfonylamino)-N-(2-chloro-4-fluoro-benzyl)-4-methyl-benzamide |
| 167 | (R)-2-(Benzo[1,2,5]thiadiazole-4-sulfonylamino)-N-[1-(2,4-difluoro-phenyl)-ethyl]-4-methyl-benzamide |
| 168 | 2-(Benzo[1,2,5]thiadiazole-4-sulfonylamino)-5-chloro-N-(2-chloro-4-fluoro-benzyl)-benzamide |
| 169 | (R)-2-(Benzo[1,2,5]thiadiazole-4-sulfonylamino)-5-chloro-N-[1-(2,4-difluoro-phenyl)-ethyl]-benzamide |
| 170 | (R)-2-(Benzo[1,2,5]thiadiazole-4-sulfonylamino)-4,N-dimethyl-N-(1-phenyl-ethyl)-benzamide |
| 171 | 2-(Benzo[1,2,5]thiadiazole-4-sulfonylamino)-N-(2,4-difluoro-benzyl)-N-methyl-benzamide |

-continued

| EX | Compound |
|---|---|
| 172 | 2-(Benzo[1,2,5]thiadiazole-4-sulfonylamino)-N-(2,4-difluoro-benzyl)-4,N-dimethyl-benzamide |
| 173 | 2-(Benzo[1,2,5]thiadiazole-4-sulfonylamino)-N-[1-(4-fluoro-phenyl)-ethyl]-N-methyl-benzamide |
| 174 | 2-(Benzo[1,2,5]thiadiazole-4-sulfonylamino)-N-[1-(4-fluoro-phenyl)-ethyl]-4,N-dimethyl-benzamide |
| 175 | 2-(Benzo[1,2,5]thiadiazole-4-sulfonylamino)-N-(2,4-difluoro-benzyl)-benzamide |
| 176 | 2-(Benzo[1,2,5]thiadiazole-4-sulfonylamino)-N-benzyl-5-chloro-N-methyl-benzamide |
| 179 | 2-(Benzo[1,2,5]thiadiazole-4-sulfonylamino)-4-chloro-N-(2-methylsulfanyl-benzyl)-benzamide |
| 180 | 2-(Benzo[1,2,5]thiadiazole-4-sulfonylamino)-4-chloro-N-(4-fluoro-benzyl)-N-methyl-benzamide |
| 181 | 2-(Benzo[1,2,5]thiadiazole-4-sulfonylamino)-4-chloro-N-(4-chloro-benzyl)-N-methyl-benzamide |
| 183 | 2-(Benzo[1,2,5]thiadiazole-4-sulfonylamino)-4-bromo-N-[1-(4-fluoro-phenyl)-ethyl]-benzamide |
| 184 | 2-(Benzo[1,2,5]thiadiazole-4-sulfonylamino)-4-bromo-N-(4-fluoro-benzyl)-N-methyl-benzamide |
| 185 | 2-(Benzo[1,2,5]thiadiazole-4-sulfonylamino)-4-bromo-N-(4-chloro-benzyl)-N-methyl-benzamide |
| 186 | 2-(Benzo[1,2,5]thiadiazole-4-sulfonylamino)-N-(2,6-dichloro-benzyl)-4-iodo-benzamide |
| 187 | 2-(Benzo[1,2,5]thiadiazole-4-sulfonylamino)-N-[1-(4-chloro-phenyl)-ethyl]-4-iodo-benzamide |
| 188 | 2-(Benzo[1,2,5]thiadiazole-4-sulfonylamino)-N-(4-fluoro-benzyl)-4-iodo-N-methyl-benzamide |
| 189 | 2-(Benzo[1,2,5]thiadiazole-4-sulfonylamino)-N-(4-chloro-benzyl)-4-iodo-N-methyl-benzamide |
| 190 | 2-(Benzo[1,2,5]thiadiazole-4-sulfonylamino)-N-[1-(2,4-dichloro-phenyl)-ethyl]-4-trifluoromethyl-benzamide |
| 191 | 2-(Benzo[1,2,5]thiadiazole-4-sulfonylamino)-N-benzyl-N-methyl-4-trifluoromethyl-benzamide |
| 192 | 2-(Benzo[1,2,5]thiadiazole-4-sulfonylamino)-N-(4-fluoro-benzyl)-N-methyl-4-trifluoromethyl-benzamide |
| 193 | 2-(Benzo[1,2,5]thiadiazole-4-sulfonylamino)-N-(4-chloro-benzyl)-N-methyl-4-trifluoromethyl-benzamide |
| 194 | 2-(Benzo[1,2,5]thiadiazole-4-sulfonylamino)-N-[1-(4-fluoro-phenyl)-ethyl]-N-methyl-4-trifluoromethyl-benzamide |
| 195 | (R)-2-(Benzo[1,2,5]thiadiazole-4-sulfonylamino)-N-methyl-N-(1-phenyl-ethyl)-4-trifluoromethyl-benzamide |
| 196 | (R)-2-(Benzo[1,2,5]thiadiazole-4-sulfonylamino)-N-[1-(2,4-dichloro-phenyl)-ethyl]-4-fluoro-benzamide |
| 197 | 2-(Benzo[1,2,5]thiadiazole-4-sulfonylamino)-N-benzyl-4-fluoro-N-methyl-benzamide |
| 198 | 2-(Benzo[1,2,5]thiadiazole-4-sulfonylamino)-4-fluoro-N-[1-(4-fluoro-phenyl)-ethyl]-N-methyl-benzamide |

Although all the compounds of formula I are novel for the uses and in the formulations taught herein, not all compounds of formula I are novel as such. Therefore, broadly, the invention may not include compounds in which:
A) one or both of $R^1$ and $R^2$ is phenyl substituted with 0, 1, 2, or 3 of $R^q$, and
B) $R^1$ and $R^2$ taken together with the nitrogen to which they are attached is a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds and having 0, 1 or 2 substituents $R^p$ and $R^a$ is nonexistent or there is a single $R^a$ at the meta position of benzamide.

More specifically, the invention may not include compounds in which:
A) one or both of $R^1$ and $R^2$ is phenyl substituted with 0, 1, 2, or 3 of halo, and
B) $R^1$ and $R^2$ taken together with the nitrogen to which they are attached is a 4-7 membered heterocyclic ring said heterocyclic ring having 0 or 1 additional heteroatom members separated from the nitrogen of attachment by at least one carbon member and selected from O and having 0, 1 or 2 substituents $R^p$ and $R^a$ is nonexistent or there is a single $R^a$ at the meta position of benzamide.

Even more specifically, the invention may not include compounds in which:
A) one or both of $R^1$ and $R^2$ is phenyl substituted with 1, 2, or 3 of halo, and
B) $R^1$ and $R^2$ taken together with the nitrogen to which they are attached is a 6 membered heterocyclic ring said heterocyclic ring having 0 or 1 additional heteroatom member separated from the nitrogen of attachment by at least one carbon member and selected from O and $R^a$ is nonexistent or there is a single $R^a$ at the meta position of benzamide.

Most specifically, the invention does not include compounds in category B) of the formula:

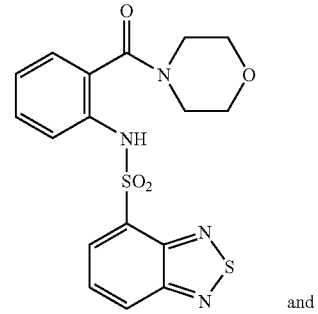

and

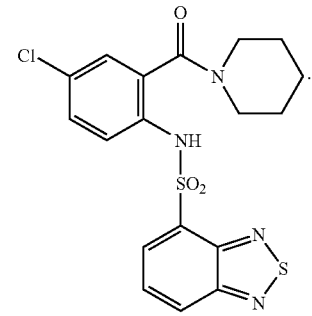

The features and advantages of the invention are apparent to one of ordinary skill in the art. Based on this disclosure, including the summary, detailed description, background, examples and claims, one of ordinary skill in the art will be able to make modifications and adaptations to various conditions and usages. Publications described herein are incorporated by reference in their entirety.

Compounds of the present invention may be produced according to two broadly described reaction schemes. In Scheme A, sulfonylation is the final step of the process and in Scheme B, sulfonylation is the initial step of the process. Persons skilled in the art will recognize that certain compounds are more advantageously produces by one scheme as compared to the other.

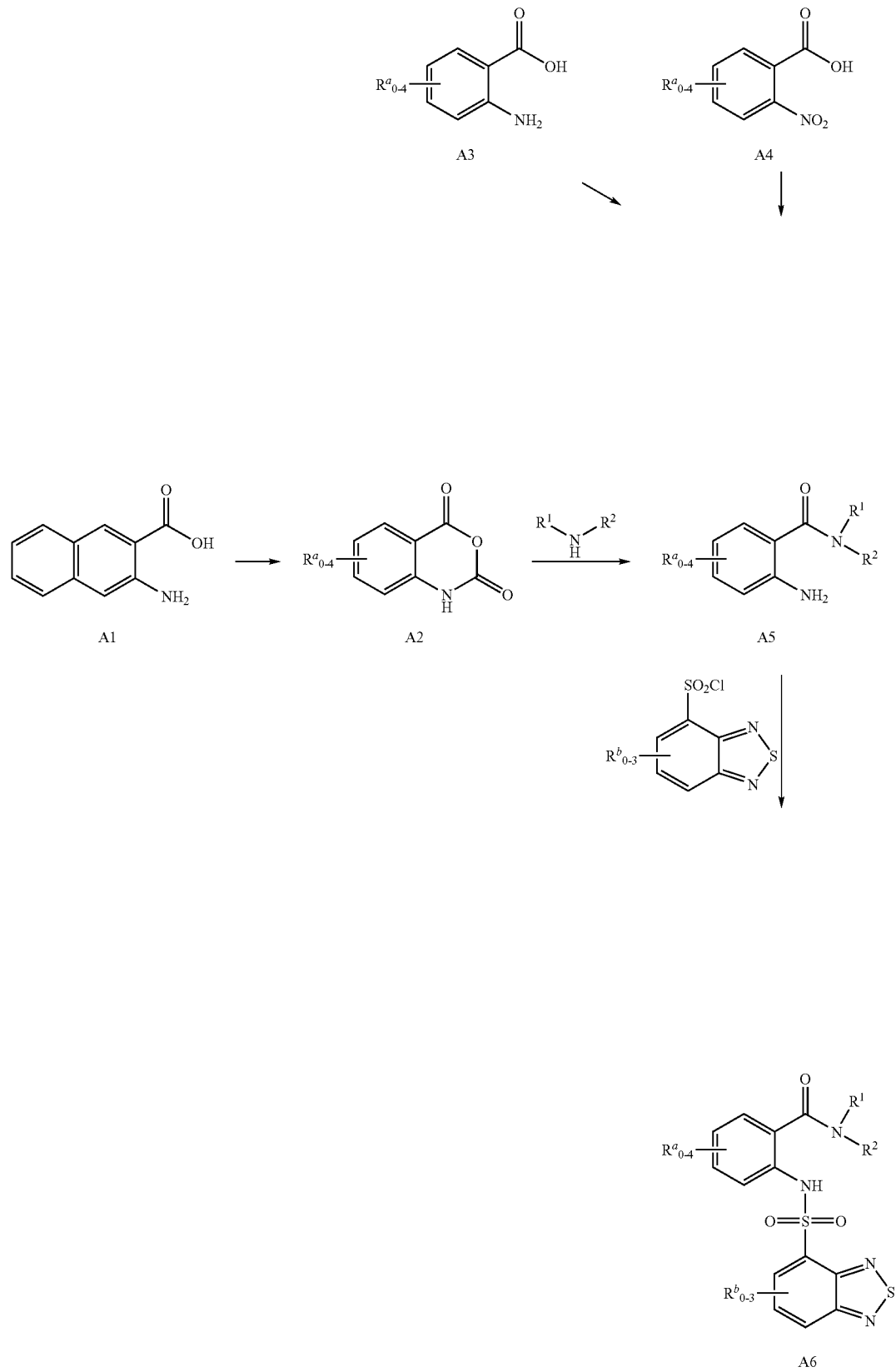

Referring to Scheme A, commercially available aminon-aphthoic acid A1 is reacted with triphosgene and Hünig's base to produce the benzo fused isatoic anhydride species of the genus A2. Various isatoic anhydrides A2 are available commercially. An amine is acylated with the isatoic anhydride A2 to produce a benzamide A5. Benzamide A5 may also be obtained from commercially available anthranilic acid A3 through peptide coupling. Benzamide A5 may additionally be obtained from commercially available nitrobenzoic acid A4 through peptide coupling followed by reduction of the nitro group. Benzamide A5 is sulfonylated with the sulfonyl chloride to produce active compounds A6. Where $R^a$ or $R^b$ is a primary or secondary amine or hydroxy, they can be protected with common protecting groups. In the case of the primary or secondary amine, there can be employed Boc or Cbz. In the case of hydroxy, there can be employed TBS, TES or benzyl. Of course a precursor substituent may be employed in the reaction steps and late transformed into the desired substituent. For example, where A6 is produced with $R^a$ as nitro, the nitro may be reduced to the amine, and the amine may be, for example, alkylated, acylated, diazotized, etc.

Scheme B

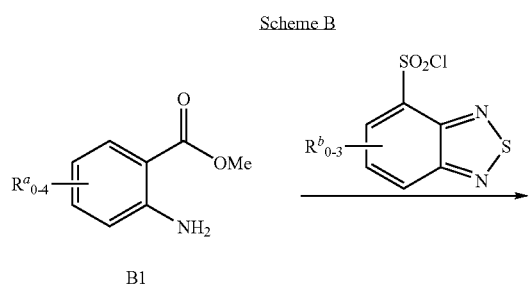

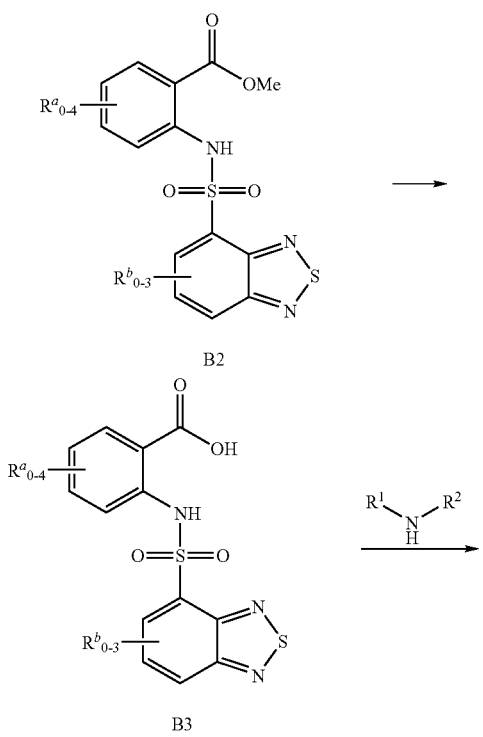

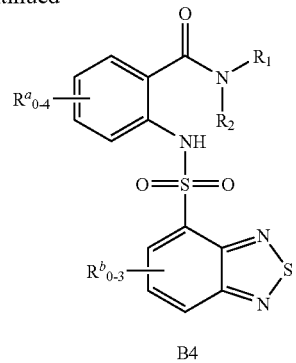

B4

Referring to Scheme B, methyl anthranilate B1 is sulfonylated to sulfonamide B2. The methyl ester is hydrolyzed to the acid B3. Acid B3 undergoes peptide coupling under standard conditions with an amine to produce active compounds B4. Where $R^a$ or $R^b$ is a primary or secondary amine or hydroxy, it can be protected with common protecting groups. In the case of the primary or secondary amine, there can be employed Boc or Cbz. In the case of hydroxy, there can be employed TBS, TES or benzyl. Of course, a precursor substituent may be employed in the reaction steps and later transformed into the desired substituent. For example, where B4 is produced with $R^a$ as nitro, the nitro may be reduced to the amine and the amine may be, for example, alkylated, acylated, diazotized, etc.

The compounds of the present invention are CCK2 modulators and, as disclosed herein, many are demonstrated CCK2 antagonists. As such, the compounds are useful in the treatment of CCK2 mediated disease states. Particularly, the compounds may be used in the treatment or prevention of pancreatic adenocarcinoma, pain, eating disorders, gastro-esophageal reflux disease, gastroduodenal ulcers, reflux esophagitis, anxiety, colon cancer, peptic ulcers, pancreatic tumors, gastric tumors, Barrett's esophagus, antral G cell hyperplasia, pernicious anaemia and Zollinger-Ellison syndrome. Particularly, CCK2 antagonists are now in development for the treatment or prevention of pancreatic adenocarcinoma, pain, gastro-esophageal reflux disease, gastroduodenal ulcers, reflux esophagitis, anxiety, colon cancer, peptic ulcers, pancreatic tumors and gastric tumors.

It is anticipated that the compounds of the invention can be administered by oral or parenteral routes, including intravenous, intramuscular, intraperitoneal, subcutaneous, rectal and topical administration, and inhalation. For oral administration, the compounds of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate and lactose. Corn starch and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the active ingredient is mixed with a solid diluent and soft gelatin capsules wherein the active ingredient is mixed with water or an oil such as peanut oil, liquid paraffin or olive oil. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be with the scope of this invention.

Protocol for Preparative Reversed-Phase HPLC

Gilson®
Column: YMC-Pack ODS-A, 5 μm, 75×30 mm
Flow rate: 10 mL/min
Detection: λ=220 & 254 nm
Gradient (acetonitrile/water, 0.05% trifluoroacetic acid)

| 1) | 0.0 min | 20% acetonitrile/80% water |
| 2) | 20.0 min | 99% acetonitrile/1% water |

Protocol for HPLC (Reversed-Phase)

Hewlett Packard Series 1100
Column: Agilent ZORBAX® C8, 5 μm, 4.6×150 mm
Flow rate: 1 mL/min
Detection: λ=220 & 254 nm
Gradient (acetonitrile/water, 0.05% trifluoroacetic acid)

| 1) | 0.0 min | 1% acetonitrile/99% water |
| 2) | 8.0 min | 99% acetonitrile/1% water |

Mass spectra were obtained on an Agilent series 1100 MSD using electrospray ionization (ESI) in either positive or negative modes as indicated.

NMR spectra were obtained on either a Bruker model DPX400 (400 MHz) or DPX500 (500 MHz) spectrometer. The format at the $^1$H NMR data below is: chemical shift in ppm down field of the tetramethylsilane reference (multiplicity, coupling constant J in Hz, integration).

Example 1

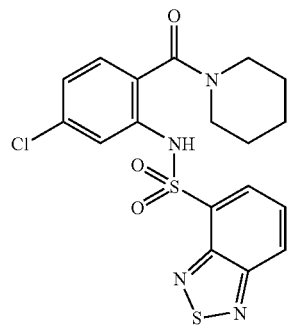

Benzo[1,2,5]thiadiazole-4-sulfonic acid [5-chloro-2-(piperidine-1-carbonyl)-phenyl]-amide A. 2-Amino-4-chlorobenzoic acid piperidine amide. To a solution of 4-chloroisatoic anhydride (3.0 g, 15.2 mmol) in dimethylformamide (DMF) (60 mL) was added piperidine (1.5 mL, 15.2 mmol) followed by 4-dimethylaminopyridine (DMAP) (183 mg, 1.5 mmol). The mixture was allowed to stir at ambient temperature overnight and concentrated in vacuo. The dark brown residue was purified by silica gel chromatography (hexanes/EtOAc) to provide the amide as a white solid (3.01 g, 83%). MS (ESI): m/z 239 [M+H]$^+$, 261 [M+Na]$^+$. $^1$H NMR (400 MHz, CDCl$_3$): (rotameric broadening) 7.00 (d, J=8.2 Hz, 1H), 6.78 (d, J=1.9 Hz, 1H), 6.72 (dd, J=8.2, 1.9 Hz), 5.20-4.10 (bs, 2H), 3.80-3.30 (bs, 4H), 1.73-1.42 (bm, 6H).

B. Benzo[1,2,5]thiadiazole-4-sulfonic acid [5-chloro-2-(piperidine-1-carbonyl)-phenyl]-amide. 2-Amino-4-chlorobenzoic acid piperidine amide (0.059 g, 0.25 mmol) was dissolved in 1,2-dichloroethane (1 mL) and treated with pyridine (0.030 mL, 0.38 mmol) followed by a solution of 4-chlorosulfonyl-2,1,3-benzothiadiazole (61 mg, 0.26 mmol) in a mixture of 1,2-dichloroethane (0.45 mL) and DMF (0.05 mL). The reaction mixture was shaken overnight at ambient temperature. Solid-supported liquid-liquid extraction was performed. A column (~1×3 cm) of Hydromatrix coarse diatomaceous earth was prepared and wetted with 1 N HCl (1.25 mL). The crude reaction mixture was passed through the column. The Hydromatrix was rinsed with dichloromethane (DCM) (1 mL), DMF (1 mL), and then DCM again (1 mL), and the combined washes were concentrated in vacuo. The crude product was redissolved in DMF (~1 mL) and purified by preparative reversed-phase HPLC (acetonitrile/water, 0.05% trifluoroacetic acid (TFA)) to provide the sulfonamide as a solid (31 mg, 28%). HPLC (reversed-phase): R$_T$=9.63 min (single peak). MS (ESI): m/z 437 [M+H]$^+$, 459 [M+Na]$^+$. $^1$H NMR (400 MHz, CDCl$_3$): (rotameric broadening) 9.01 (s, 1H), 8.17 (dd, J=7.0, 1.0 Hz, 1H), 8.13 (dd, J=8.8, 1.0 Hz, 1H), 7.59 (dd, J=8.8, 7.0 Hz, 1H), 7.56 (dd, J=1.5, 0.6 Hz, 1H), 6.89 (abx, J=8.0, 1.5, 0.6 Hz, 2H), 3.70-2.70 (bs, 4H), 1.70-1.30 (bm, 6H).

Example 2

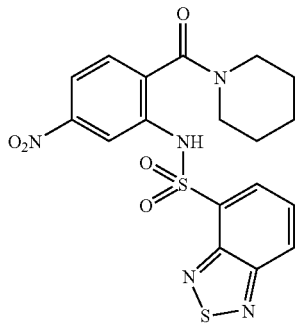

Benzo[1,2,5]thiadiazole-4-sulfonic acid [5-nitro-2-(piperidine-1-carbonyl)-phenyl]-amide A. 2-Amino-4-nitrobenzoic acid piperidine amide. This compound was prepared in analogy to EXAMPLE 1 using 4-nitroisatoic anhydride (2.5 g, 12.0 mmol), piperidine (1.2 mL, 12.0 mmol), and DMAP (0.146 g, 1.2 mmol). The title compound was obtained as a yellow solid (1.86 g, 62%). MS (ESI): m/z 250 [M+H]$^+$, 272 [M+Na]$^+$. $^1$H NMR (400 MHz, CDCl$_3$): (rotameric broadening) 7.63 (dd, J=1.9, 0.2 Hz, 1H), 7.61 (dd, J=8.2, 2.2 Hz, 1H), 7.25 (dd, J=8.2, 0.2 Hz, 1H), 4.49 (bs, 2H), 3.90-3.10 (bm, 4H), 1.75-1.38 (bm, 6H).

B. Benzo[1,2,5]thiadiazole-4-sulfonic acid [5-nitro-2-(piperidine-1-carbonyl)-phenyl]-amide. This compound was prepared in analogy to EXAMPLE 1 using 2-amino-4-nitrobenzoic acid piperidine amide (0.062 g, 0.25 mmol), pyridine (0.030 mL, 0.038 mmol), and 4-chlorosulfonyl-2,1,3-benzothiadiazole (61 mg, 0.26 mmol). The title sulfonamide was obtained as a solid (6 mg, 5%). HPLC (reversed-phase): R$_T$=9.11 min (single peak). MS (ESI): m/z 448 [M+H]$^+$, 470 [M+Na]$^+$. $^1$H NMR (400 MHz, CDCl$_3$): (rotameric broadening) 8.90 (s, 1H), 8.48 (d, J=2.2 Hz, 1H), 8.38 (dd, J=7.0, 1.0 Hz, 1H), 8.27 (dd, J=8.8, 1.0 Hz, 1H), 7.88 (dd, J=8.4, 2.2 Hz, 1H), 7.75 (dd, J=8.8, 7.0 Hz, 1H), 7.25 (d, J=8.4 Hz, 1H), 3.80-3.30 (bm, 2H), 3.30-2.80 (bm, 2H), 1.75-1.40 (bm, 6H).

Example 3

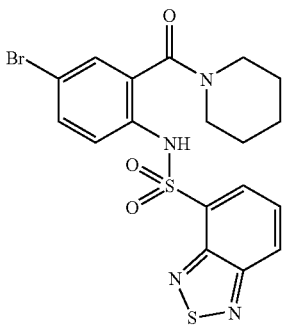

Benzo[1,2,5]thiadiazole-4-sulfonic acid [4-bromo-2-(piperidine-1-carbonyl)-phenyl]-amide A. 2-Amino-5-bromobenzoic acid piperidine amide. To a stirred solution of 5-bromoisatoic anhydride (2.88 g, 11.9 mmol) in DMF (20 mL) was added piperidine (1.20 mL, 11.9 mmol) and DMAP (0.14 g, 1.19 mmol). The reaction mixture was stirred 15 h at ambient temperature, poured into water, and extracted with DCM (4×). The combined organic extracts were washed with 1:1 water/brine (3×), dried (MgSO$_4$), and concentrated. The residue was dissolved in 1:1 Et$_2$O/EtOAc and washed with water (5×) to remove DMF. The organic layer was dried (MgSO$_4$) and concentrated. The residue was triturated with a mixture of Et$_2$O and hexanes and allowed to stand 0° C. overnight. The solid product was collected by suction filtration and air-dried to give the desired amide as a tan solid (1.65 g, 49%). mp=93-95° C. MS (ESI): m/z 283 [M+H]$^+$, 305 [M+Na]$^+$. $^1$H NMR (400 MHz, CDCl$_3$): (rotameric broadening) 7.23 (dd, J=8.6, 2.3 Hz, 1H), 7.18 (d, J=2.3 Hz, 1H), 6.59 (d, J=8.6 Hz, 1H), 4.90-4.00 (bs, 2H), 3.90-2.90 (bm, 4H), 1.90-1.10 (bm, 6H).

B. Benzo[1,2,5]thiadiazole-4-sulfonic acid [4-bromo-2-(piperidine-1-carbonyl)-phenyl]-amide. This compound was prepared in analogy to EXAMPLE 1 using 2-amino-5-bromobenzoic acid piperidine amide (0.071 g, 0.25 mmol), pyridine (0.031 mL, 0.38 mmol), and 4-chlorosulfonyl-2,1,3-benzothiadiazole (61 mg, 0.26 mmol). The title sulfonamide was obtained as a solid (30 mg, 25%). HPLC (reversed-phase): R$_T$=9.67 min (single peak). MS (ESI): m/z 481 [M+H]$^+$, 503 [M+Na]$^+$. $^1$H NMR (400 MHz, CDCl$_3$): (rotameric broadening) 8.67 (s, 1H), 8.23 (dd, J=8.8, 1.1 Hz, 1H), 8.21 (dd, J=7.0, 1.1 Hz, 1H), 7.67 (dd J=8.8, 7.0 Hz, 1H), 7.53 (d, J=8.8 Hz, 1H), 7.40 (dd, J=8.8, 2.3, Hz, 1H), 7.17 (d, J=2.3 Hz, 1H), 3.75-2.65 (bm, 4H), 1.90-1.30 (bm, 6H). Elemental analysis: calculated for C$_{18}$H$_{17}$BrN$_4$O$_3$S$_2$, C, 44.91; H, 3.56; N, 11.64. found C, 44.83; H, 3.39; N, 11.48.

Example 4

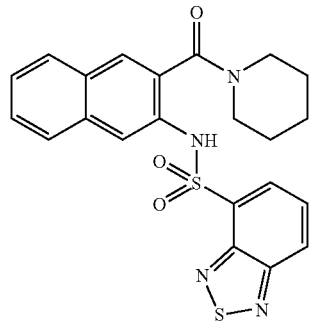

Benzo[1,2,5]thiadiazole-4-sulfonic acid [3-piperidine-1-carbonyl)-naphthalen-2-yl]-amide A. 3-Amino-2-naphthoic acid piperidine amide. To a solution of 3-amino-2-naphthoic acid (0.30 g, 1.6 mmol) in tetrahydrofuran (THF) (40 mL) at ambient temperature was added triphosgene (0.158 g, 0.53 mmol). After stirring 2 h at room temperature, Hünig's base (0.56 mL, 3.2 mmol) was added. The reaction mixture was stirred 1 h, and piperidine (0.64 mL, 6.4 mmol) was added. After 2 h, the mixture was poured into 0.5 M HCl (100 mL) and extracted with DCM (2×50 mL). The combined organic layers were dried (Na$_2$SO$_4$) and concentrated. The crude residue was purified by flash chromatography (hexanes/EtOAc) to afford the title compound as a pale orange solid (263 mg, 65%). MS (ESI): m/z 255 [M+H]$^+$. $^1$H NMR (400 MHz, CDCl$_3$): (rotameric broadening) 7.66 (dd, J=8.1, 1.0 Hz, 1H), 7.57 (s, 1H), 7.54 (dd, J=8.3, 1.0 Hz, 1H), 7.36 (ddd, J=8.1, 8.0, 1.0 Hz, 1H), 7.22 (ddd, J=8.3, 8.0, 1.0 Hz, 1H), 7.00 (s, 1H), 4.60-4.20 (bs, 2H), 3.90-3.20 (bm, 4H), 1.80-1.40 (bm, 6H), B. Benzo[1,2,5]thiadiazole-4-sulfonic acid [3-(piperidine-1-carbonyl)-naphthalen-2-yl]-amide. 3-Amino-2-naphthoic acid piperidine amide (263 mg, 1.03 mmol), 4-chlorosulfonyl-2,1,3-benzothiadiazole (295 mg, 1.24 mmol), and pyridine (0.242 mL, 3 mmol) were added to DCM (10 mL) and allowed to stir at ambient temperature overnight. The reaction mixture was poured into 1 N HCl and extracted twice with DCM. The combined organic extracts were dried (Na$_2$SO$_4$) and concentrated in vacuo. The crude residue was purified by flash chromatography (hexanes/EtOAc) to afford the desired product as a slightly impure orange solid. Trituration and stirring with methanol at ambient temperature overnight provided the tile sulfonamide as a white powder, which was collected by suction filtration and air-dried (308 mg, 66%). MS (ESI): m/z 453 [M+H]$^+$, 475 [M+Na]$^+$. $^1$H NMR (400 MHz, CDCl$_3$): (rotameric broadening) 8.88 (s, 1H), 8.26 (dd, J=7.0, 1.0 Hz, 1H), 8.19 (dd, J=8.8, 1.0 Hz, 1H), 8.04 (s, 1H), 7.76 (d, J=8.2 Hz, 1H), 7.67 (d, J=8.0 Hz, 1H), 7.64 (dd, J=8.8, 7.0 Hz, 1H), 7.49 (arom m, 1H), 7.41 (arom m, 1H), 7.26 (s, 1H), 3.70-2.70 (bm, 4H), 1.80-1.30 (bm, 6H). Elemental analysis: calculated for C$_{22}$H$_{20}$N$_4$O$_3$S$_2$, C, 58.39; H, 4.45; N, 12.38. found C, 58.66; H, 4.57; N, 12.49.

Example 5

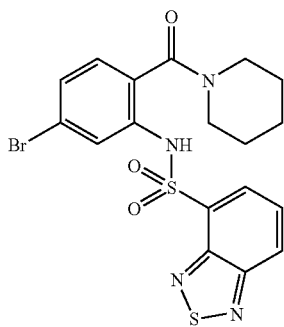

Benzo[1,2,5]thiadiazole-4-sulfonic acid [5-bromo-2-(piperidine-1-carbonyl)-phenyl]-amide A. 4-Bromo-4-nitrobenzoic acid. A mixture of 4-bromo-2-nitrotoluene (5.0 g, 23 mmol), KMnO$_4$ (10.9 g, 69 mmol), and water (250 mL) was heated at reflux overnight in a 1 L round-bottom flask fitted with a reflux condenser. The brown suspended MnO$_2$ was removed by filtration through a pad of Celite®. The filter cake was washed with water. The basic filtrate was acidified to pH~1 with concentrated HCl and extracted with EtOAc (3×300 mL). The combined organic layers were dried (MgSO$_4$) and concentrated in vacuo to provide pure benzoic acid (1.22 g, 22%). $^1$H NMR (400 MHz, CD$_3$OD): 8.07 (d, J=1.9 Hz, 1H), 7.85 (dd, J=8.2, 1.9 Hz, 1H), 7.65 (d, J=8.2 Hz, 1H). MS (ESI): neg. ion m/z 244 [M−H]$^-$.

B. 4-Bromo-2-nitrobenzoic acid piperidine amide. A suspension of 4-bromo-2-nitrobenzoic acid (0.60 g, 2.44 mmol) in thionyl chloride (8 mL) was heated to reflux for 2 h. The reaction mixture became homogeneous. The mixture was cooled and concentrated in vacuo in give 4-bromo-2-nitrobenzoyl chloride as a white solid, which was used immediately in the following reaction $^1$H NMR (400 MHz, CDCl$_3$): 8.20 (d, J=1.9 Hz, 1H), 7.92 (dd, J=8.2, 1.9 Hz, 1H), 7.65 (d, J=8.2 Hz, 1H). To a solution of 4-bromo-2-nitrobenzoyl chloride (2.44 mmol) in DCM (15 mL) at ambient temperature was added piperidine (1.2 mL, 12.2 mmol). The reaction mixture was stirred for 3 h then poured into water and extracted with DCM (2×). The combined organic extracts were washed with brine, dried (MgSO$_4$), and concentrated in vacuo. The residue was purified by flash chromatography (hexanes/EtOAc) to afford the title amide as a white solid (0.52 g, 76%). MS (ESI): m/z 313 [M+H]$^+$. $^1$H NMR (400 MHz, CDCl$_3$): (rotameric broadening) 8.33 (d, J=1.9 Hz, 1H), 7.82 (dd, J=8.1, 1.9 Hz, 1H), 7.27 (d, J=8.1 Hz, 1H), 3.82-3.65 (bm, 2H), 3.16 (t, J=5.6 Hz, 2H), 1.90-1.35 (bm, 6H).

C. 4-Bromo-2-aminobenzoic acid piperidine amide. A solution of 4-bromo-2-nitrobenzoic acid piperidine amide (0.206 g, 0.66 mmol) in 1:1 EtOAc/DCM (10 mL) was treated with solid SnCl$_2$.2 H$_2$O (0.595 g, 2.6 mmol). The mixture was stirred at ambient temperature for 4 h then poured into saturated aqueous NaHCO$_3$ resulting in formation of a gelatinous emulsion. The emulsion was extracted with DCM (2×). The combined organic extracts were dried (MgSO$_4$) and concentrated in vacuo. The residue was purified by flash chromatography (hexanes/EtOAc) to provide the desired aniline as a white solid (0.16 g, 86%). MS (ESI): m/z 283 [M+H]$^+$, 305 [M+Na]$^+$. $^1$H NMR (400 MHz, CDCl$_3$): (rotameric broadening) 6.72 (d, J=8.1 Hz, 1H), 6.67 (d, J=1.8 Hz, 1H), 6.62 (dd, J=8.1, 1.8 Hz, 1H), 4.90-3.90 (bs, 2H), 3.70-3.30 (bm, 4H), 1.75-1.45 (bm, 6H).

D. Benzo[1,2,5]thiadiazole-4-sulfonic acid [5-bromo-2-(piperidine-1-carbonyl)-phenyl]-amide. To a solution of 4-bromo-2-aminobenzoic acid piperidine amide (0.145 g, 0.51 mmol) was added pyridine (0.062 mL, 0.76 mmol) and 4-chlorosulfonyl-2,1,3-benzothiadiazole (0.129 g, 0.55 mmol). The mixture was stirred at ambient temperature for 12 h then poured into 1 N HCl and extracted with DCM (2×). The combined organic extracts were dried (MgSO$_4$) and concentrated in vacuo. The crude residue was purified by flash chromatography (hexanes/EtOAc) to afford the title sulfonamide as an off-white solid (0.18 g, 74%). HPLC (reversed-phase): R$_T$=9.68 min (single peak). MS (ESI): m/z 481/483 [M+H]$^+$, 503 [M+Na]$^+$; neg. ion m/z 479/481 [M−H]$^-$. $^1$H NMR (400 MHz, CDCl$_3$): (rotameric broadening) 8.95 (s, 1H), 8.25 (dd, J=7.0, 1.0 Hz, 1H), 8.21 (dd, J=8.8, 1.0 Hz, 1H), 7.80 (d, J=1.8 Hz, 1H), 7.68 (dd, J=8.8, 7.0 Hz, 1H), 7.14 (dd, J=8.2, 1.8 Hz, 1H), 6.90 (d, J=8.2 Hz, 1H) 3.70-2.70 (bm, 4H), 1.80-1.30 (bm, 6H). Elemental analysis: calculated for $C_{18}H_{17}BrN_4O_3S_2$, C, 44.91; H, 3.56; N 11.64. found C, 44.52; H, 3.23; N, 11.25.

Example 6

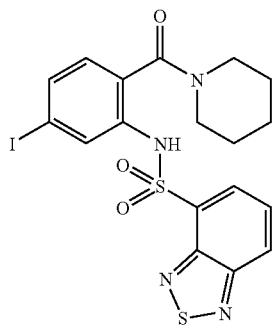

Benzo[1,2,5]thiadiazole-4-sulfonic acid [5-iodo-2-(piperidine-1-carbonyl)-phenyl]-amide A. 4-Iodo-2-nitrobenzoic acid. 4-Iodo-2-nitrotoluene (9.0 g, 34.2 mmol), $KMnO_4$ (22.0 g, 139 mmol) and water (340 mL) were heated at reflux of 5 h. The resulting brown suspension of $MnO_2$ was filtered off through a pad of Celite®, and the filter cake was washed with water. The basic filtrate was acidified with concentrated HCl causing crystallization of the desired acid. The crystals were collected by suction filtration and dried affording 1.86 g of the acid. The mother liquor was extracted with DCM (3×200 mL), and the combined extracts were dried ($Na_2SO_4$) and concentrated in vacuo to afford an additional 0.16 g of the benzoic acid. Total yield=2.02 g (20%). $^1$H NMR (400 MHz, $CD_3OD$): 8.13 (d, J=1.6 Hz, 1H), 8.01 (dd, J=8.1, 1.6 Hz, 1H), 7.50 (d, J=8.1 Hz, 1H).

B. 4-Iodo-2-nitrobenzoic acid piperidine amide. A suspension of 4-iodo-2-nitrobenzoic acid (1.0 g, 3.4 mmol) in thionyl chloride (10 mL) was heated to reflux for 45 min. The reaction mixture became homogeneous. The mixture was cooled and concentrated in vacuo to give 4-iodo-2-nitrobenzoyl chloride as a yellow oil, which was used immediately in the following reaction. $^1$H NMR (500 MHz, $CDCl_3$): 8.38 (d, J=1.6 Hz, 1H), 8.12 (dd, J=8.1, 1.6 Hz, 1H), 7.48 (d, J=8.1 Hz, 1H). To a solution of 4-iodo-2-nitrobenzoyl chloride (3.4 mmol) in DCM (10 mL) at ambient temperature was added piperidine (1.3 mL, 13.1 mmol). The reaction mixture was stirred for 0.5 h then poured into 1 N HCl and extracted with DCM (2×). The combined organic extracts were dried ($Na_2SO_4$), and concentrated in vacuo affording the title amide as a white solid (1.2 g, 98%). MS (ESI): m/z 361 [M+H]$^+$, 383 [M+Na]$^+$. $^1$H NMR (400 MHz, $CDCl_3$): (rotameric broadening) 8.51 (d, J=1.6 Hz, 1H), 8.01 (dd, J=8.0, 1.6 Hz, 1H), 7.12 (d, J=8.0 Hz, 1H), 3.85-3.65 (bm, 2H), 3.16 (t, J=5.6 Hz, 2H), 1.90-1.35 (bm, 6H).

C. 4-Iodo-2-nitrobenzoic acid piperidine amide. A solution of 4-iodo-2-nitrobenzoic acid piperidine amide (0.21 g, 0.58 mmol) in EtOAc (5 mL) was treated with $SnCl_2 \cdot 2 H_2O$ (0.654 g, 2.9 mmol). The mixture was stirred at ambient temperature for 12 h then poured into saturated aqueous $NaHCO_3$ resulting in formation of a gelatinous emulsion. The emulsion was extracted with DCM (5×). The combined organic extracts were dried ($Na_2SO_4$) and concentrated in vacuo affording the aniline as a yellow foam (0.19 g, 100%). MS (ESI): m/z 331 [M+H]$^+$, 353 [M+Na]$^+$. $^1$H NMR (400 MHz, $CDCl_3$): (rotameric broadening) 7.08 (d, J=1.1 Hz, 1H), 7.03 (d, J=8.0 Hz, 1H), 6.77 (dd, J=8.0, 1.1 Hz, 1H), 4.50-4.20 (bs, 2H), 3.80-3.20 (bm, 4H), 1.75-1.45 (bm, 6H).

D. Benzo[1,2,5]thiadiazole-4-sulfonic acid [5-bromo-2-(piperidine-1-carbonyl)-phenyl]-amide. To a solution of 4-iodo-2-aminobenzoic acid piperidine amide (0.19 g, 0.58 mmol) was added pyridine (0.141 mL, 1.74 mmol) and 4-chlorosulfonyl-2,1,3-benzothiadiazole (0.153 g, 0.64 mmol). The mixture was stirred at ambient temperature for 12 h then poured into 1 N HCl and extracted with DCM (2×). The combined organic extracts were dried ($Na_2SO_4$) and concentrated in vacuo. The crude residue was purified by flash chromatography (hexanes/EtOAc) then recrystallization (methanol/DCM) to afford the title sulfonamide as white crystals (0.23 g, 75%). HPLC (reversed-phase): $R_T$=9.79 min (single peak). MS (ESI): m/z 529 [M+H]$^+$, 551 [M+Na]$^+$. $^1$H NMR (400 MHz, $CDCl_3$): (rotameric broadening) 8.90 (s, 1H), 8.27 (dd, J=7.0, 1.0 Hz, 1H), 8.24 (dd, J=8.8, 1.0 Hz, 1H), 8.02 (d, J=1.6 Hz, 1H), 7.71 (dd, J=8.8, 7.0 Hz, 1H), 7.38 (dd, J=8.0, 1.6 Hz, 1H), 6.76 (d, J=8.0 Hz, 1H), 3.70-2.70 (bm, 4H), 1.75-1.30 (bm, 6H). Elemental analysis: calculated for $C_{18}H_{17}IN_4O_3S_2$, C, 40.92; H, 3.24; N, 10.60. found C, 41.04; H, 3.00; N, 10.47.

Example 7

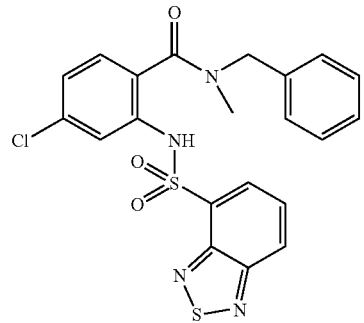

2-(Benzo[1,2,5]thiadiazole-4-sulfonylamino)-N-benzyl-4-N-methyl-benzamide

A. 2-(Benzo[1,2,5]thiadiazole-4-sulfonylamino)-4-chlorobenzoic acid methyl ester. To a solution of methyl 2-amino-4-chlorobenzoate (7.0 g, 37.7 mmol) in DCM (75 mL) at ambient temperature was added 4-chlorosulfonyl-2,1,3-benzothiadiazole (9.45 g, 39.6 mmol), pyridine (9.1 mL, 112 mmol) and DMAP (0.23 g, 1.88 mmol). The mixture was stirred at ambient temperature overnight, poured into 1 N HCl (200 mL), and extracted with DCM (2×100 mL). The combined organic layers were dried ($Na_2SO_4$) and concentrated in vacuo. The crude residue was purified by flash chromatography (hexanes/EtOAc) to afford the title sulfonamide as a tan solid (11.65 g, 80%). MS (ESI): neg. ion m/z 382 [M−H]$^-$. $^1$H NMR (400 MHz, $CDCl_3$): 11.38 (s, 1H)), 8.40 (dd, J=7.2, 1.2 Hz, 1H), 8.24 (dd, J=8.8, 1.2 Hz, 1H), 7.80 (d, J=8.4 Hz, 1H), 7.76 (d, J=2.0 Hz, 1H), 7.74 (dd, J=8.8, 7.2 Hz, 1H) 6.94 (dd, J=8.4, 2.0 Hz, 1H), 3.92 (s, 3H). Elemental analysis: calculated for $C_{14}H_{13}ClN_3O_4S_2$, C, 43.81; H, 2.63; N, 10.95. found C, 44.19; H, 3.00; N, 11.23.

B. 2-(Benzo[1,2,5]thiadiazole-4-sulfonylamino)-4-chlorobenzoic acid. To a stirred suspension of 2-(benzo[1,2,5]

thiadiazole-4-sulfonylamino)-4-chlorobenzoic acid methyl ester (2.0 g, 5.2 mmol) in THF (12 mL) at ambient temperature was added 2 M aqueous LiOH (10 mL). The resulting orange mixture was stirred overnight at ambient temperature then poured into 0.5 M HCl (150 mL) causing precipitation of the desired benzoic acid. After stirring the mixture several minutes to complete precipitation, the product was collected by suction filtration and air-dried to afford the acid as a tan solid (1.87 g, 97%). MS (ESI): neg. ion m/z 368 [M−H]⁻. ¹H NMR (400 MHz, CDCl₃): 11.22 (bs, 1H), 8.43 (dd, J=7.2, 1.0 Hz, 1H), 8.26 (dd, J=8.8, 1.0 Hz, 1H), 7.90 (d, J=8.8 Hz, 1H), 7.80 (d, J=2.0 Hz, 1H), 7.75 (dd, J=8.8, 7.2 Hz, 1H), 6.99 (dd, J=8.8, 2.0 Hz, 1H). Elemental analysis: calculated for $C_{13}H_8ClN_3O_4S_2$, C, 42.22; H, 2.18; N, 11.36. found C, 41.92; H, 2.50; N, 11.38.

C. 2-(Benzo[1,2,5]thiadiazole-4-sulfonylamino)-N-benzyl-4-chloro-N-methyl-benzamide. To a solution of 2-(benzo[1,2,5]thiadiazole-4-sulfonylamino-4-chlorobenzoic acid (18 mg, 0.05 mmol) in a mixture of THF (0.08 mL) and DMF (0.40 mL) at ambient temperature was added pyridine (0.012 mL, 0.15 mmol) followed by O-(7-azabenzotriazol-1yl)-N,N,N',N'-tetramethyluronium hexafluorophosphate (HATU) (0.038 g, 0.1 mmol). The reaction mixture was agitated for 1 h on a shaker. N-methylbenzylamine (0.013 mL, 0.1 mmol) was added. (If the amine had been a salt, then Hünig's base (0.017 mL, 0.1 mmol) would also have been added.) The reaction mixture was agitated for 1 h. TFA (0.050 mL) was added to quench the reaction. The mixture was diluted with DMF (1 mL), and the product amide was obtained by purification of the entire reaction mixture by preparative reversed-phase chromatography (acetonitrile/water, 0.05% TFA). The title amide was obtained as a solid (8 mg, 33%). HPLC (reversed-phase): $R_T$=9.94 min (single peak). MS (ESI): m/z 471 [M−H]⁻. ¹H NMR (400 MHz, CDCl₃): (rotameric broadening) 9.15 (bs, 1H), 8.32 (bd, J=6.8 Hz, 1H), 8.29-8.18 (bm, 1H), 7.79-7.63 (bm, 2H), 7.48-7.26 (bm, 4H), 7.15-6.83 (bm, 2H), 7.02 (bd, J=8.2 Hz, 1H), 4.65-4.37 (bs, 1.3H), 4.37-4.00 (bs, 0.7H), 3.15-2.70 (bs, 1.1H), 2.70-2.35 (bs, 1.9H).

Example 8

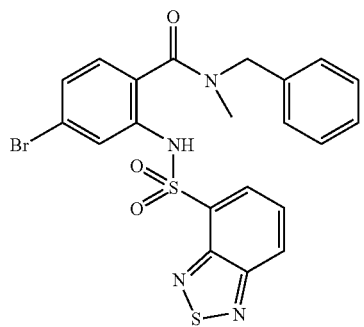

2-(Benzo[1,2,5]thiadiazole-4-sulfonylamino)-N-benzyl-4-bromo-N-methyl-benzamide

A. Methyl 2-amino-4-bromobenzoate. To a stirred solution of 4-bromo-2-nitrobenzoic acid (EXAMPLE 5) (3.81 g, 15 mmol) in DMF (30 mL) at 0° C. was added, 1,8-diazabicycloundecane (DBU) (10.3 mL, 75 mmol) followed by methyl iodide (4.67 mL, 75 mmol). The reaction mixture was stirred 15 min at 0° C. then allowed to warm to room temperature and stir overnight. The mixture was poured into water and extracted with EtOAc (2×). The combined organic extracts were washed with water (2×), dried (MgSO₄), and concentrated in vacuo. The residue was purified by flash chromatography (hexanes/EtOAc) to afford methyl 4-bromo-2-nitrobenzoate as a pale yellow solid (3.52 g, 90%). To a solution of the nitrobenzoate (3.52 g, 13.5 mmol) in 1:1 EtOAc/DCM (30 mL) at ambient temperature was added SnCl₂.2 H₂O (15.27 g, 67 mmol). The reaction mixture was allowed to stir overnight. The solvents were evaporated in vacuo, and the residue was partitioned between saturated aqueous NaHCO₃ and DCM. The layers were separated, and the aqueous layer was further extracted with DCM (2×). The combined organic layers were dried (MgSO₄) and concentrated in vacuo to provide the pure aminobenzoate as a white solid (2.89 g, 93%). ¹H NMR (400 MHz, CDCl₃): 7.70 (d, J=8.6 Hz, 1H), 6.84 (d, J=1.9 Hz, 1H), 6.75 (dd, J=8.6, 1.9 Hz, 1H), 5.78 (bs, 2H) 3.86 (s, 3H).

B. 2-(Benzo[1,2,5]thiadiazole-4-sulfonylamino)-4-bromo-benzoic acid methyl ester. This compound was prepared as described in EXAMPLE 7 using the following reagents: methyl 2-amino-4-bromobenzoate (2.89 g, 12.5 mmol), 4-chlorosulfonyl-2,1,3-benzothiadiazole (3.54 g, 15 mmol), pyridine (2.0 mL, 25 mmol), and DCM (40 mL). The title sulfonamide was obtained as a tan solid (3.95 g, 75%). MS (ESI): neg. ion m/z 426 [M−H]⁻. ¹H NMR (400 MHz, CDCl₃): 11.34 (bs, 1H), 8.40 (dd, J=7.0, 0.9 Hz, 1H), 8.24 (dd, J=8.8, 0.9 Hz, 1H), 7.92 (d, J=1.8 Hz, 1H), 7.74 (dd, J=8.8, 7.0 Hz, 1H), 7.72 (d, J=8.5 Hz, 1H), 7.10 (dd, J=8.5, 1.8 Hz, 1H), 3.92 (s, 3H).

C. 2-(Benzo[1,2,5]thiadiazole-4-sulfonylamino)-4-bromobenzoic acid. This compound was prepared as described in EXAMPLE 7 using the following reagents: 2-(benzo[1,2,5]thiadiazole-4-sulfonylamino)-4-bromobenzoic acid methyl ester (2.95 g, 6.89 mmol), THF (20 mL), and 2 M aqueous LiOH (18 mL). The title acid was obtained as a tan solid (1.87 g, 97%). ¹H NMR (500 MHz, CDCl₃): 11.14 (bs, 1H), 8.42 (dd, J=7.2, 1.1 Hz, 1H), 8.26 (dd, J=8.8, 1.1 Hz, 1H), 7.98 (d, J=1.6 Hz, 1H), 7.82 (d, J=8.5 Hz, 1H), 7.75 (dd, J=8.8, 7.2 Hz, 1H), 7.16 (dd, J=8.5, 1.6 Hz, 1H).

D. 2-(Benzo[1,2,5]thiadiazole-4-sulfonylamino)-N-benzyl-4-bromo-N-methyl-benzamide. This compound was prepared as described in EXAMPLE 7 using the following reagents: 2-(benzo[1,2,5]thiadiazole-4-sulfonylamino)-4-bromobenzoic acid (21 mg, 0.05 mmol), THF (0.08 mL), DMF (0.40 mL), pyridine (0.012 mL, 0.15 mmol), HATU (0.038 g, 0.1 mmol), and N-methylbenzylamine (0.013 mL, 0.1 mmol). The title amide was obtained as a solid (13 mg, 50%). HPLC (reversed-phase): $R_T$=9.91 min (single peak). MS (ESI): m/z 517/519 [M+H]⁺, 539/541 [M+Na]⁺. ¹H NMR (400 MHz, CDCl₃): (rotameric broadening) 9.07 (bs, 1H), 8.32 (bd, J=6.9 Hz, 1H), 8.3-8.2 (bm, 1H), 7.9-7.8 (bm, 1H), 7.8-7.65 (bm, 1H), 7.45-7.25 (bm, 4H), 7.2-7.0 (bm, 2H), 6.95 (bd, J=8.5 Hz, 1H), 4.65-4.4 (bs, 1.3H), 4.4-4.0 (bs, 0.7H), 3.15-2.75 (bs, 1.1H), 2.70-2.35 (bs, 1.9H).

Example 9

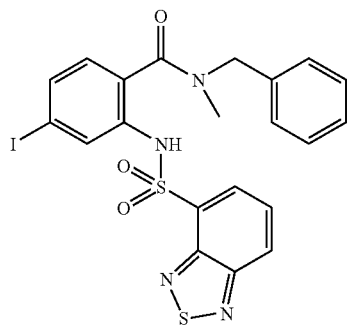

2-(Benzo[1,2,5]thiadiazole-4-sulfonylamino)-N-benzyl-4-iodo-N-methyl-benzamide

A. Methyl 2-amino-4-iodobenzoate. This compound was prepared as described in EXAMPLE 8 using the following reagents: 4-iodo-2-nitrobenzoic acid (see EXAMPLE 6) (2.32 g, 7.9 mmol), DMF (30 mL), DBU (2.4 mL, 16 mmol), and methyl iodide (1.5 mL, 24 mmol). Methyl 4-iodo-2-nitrobenzoate was obtained as a pale yellow solid (2.30 g, 95%). The intermediate nitrobenzoate was then reduce using the following reagents: nitrobenzoate (2.29 g, 7.4 mmol), 1:1 EtOAc/DCM (10 mL), and SnCl$_2$.2 H$_2$O (8.35 g, 37 mmol). The title aminobenzoate was obtained as a yellow solid (1.87 g, 91%). $^1$H NMR (500 MHz, CDCl$_3$): 7.52 (d, J=8.5 Hz, 1H), 7.07 (d, J=1.6 Hz, 1H), 6.96 (dd, J=8.5, 1.6 Hz, 1H), 5.72 (bs, 2H), 3.86 (s, 3H).

B. 2-(Benzo[1,2,5]thiadiazole-4-sulfonylamino)-4-iodobenzoic acid methyl ester. This compound was prepared as described in EXAMPLE 7 using the following reagents: methyl 2-amino-4-iodobenzoate (1.60 g, 5.8 mmol), 4-chlorosulfonyl-2,1,3-benzothiadiazole (1.76 g, 7.51 mmol), pyridine (0.93 mL, 11.5 mmol), and DCM (45 mL). The title sulfonamide was obtained as a tan solid (1.87 g, 68%). MS (ESI): neg. ion m/z 474 [M–H]$^-$. $^1$H NMR (400 MHz, CDCl$_3$): 11.26 (bs, 1H), 8.40 (dd, J=7.0, 1.0 Hz, 1H), 8.24 (dd, J=8.8, 1.0 Hz, 1H), 8.12 (d, J=1.5 Hz, 1H), 7.74 (dd, J=8.8, 7.0 Hz, 1H), 7.53 (d, J=8.5 Hz, 1H), 7.32 (dd, J=8.5, 1.5 Hz, 1H), 3.91 (s, 3H).

C. 2-(Benzo[1,2,5]thiadiazole-4-sulfonylamino)-4-iodobenzoic acid. This compound was prepared as described in EXAMPLE 7 using the following reagents: 2-(benzo[1,2,5]thiadiazole-4-sulfonylamino)-4-iodobenzoic acid methyl ester (1.87 g, 3.93 mmol). THF (20 mL), and 2 M aqueous LiOH (18 mL). The title acid was obtained as a tan solid (1.24 g, 69%). $^1$H NMR (500 MHz, CDCl$_3$): 11.03 (bs, 1H), 8.34 (dd, J=7.2, 1.1 Hz, 1H), 8.19 (dd, J=8.8, 1.1 Hz, 1H), 8.09 (d, J=1.6 Hz, 1H), 7.69 (dd, J=8.8, 7.2 Hz, 1H), 7.56 (d, J=8.5 Hz, 1H), 7.30 (dd, J=8.5, 1.6 Hz, 1H).

D. 2-(Benzo[1,2,5]thiadiazole-4-sulfonylamino)-N-benzyl-4-iodo-N-methyl-benzamide. This compound was prepared as described in EXAMPLE 7 using the following reagents: 2-(benzo[1,2,5]thiadiazole-4-sulfonylamino)-4-iodobenzoic acid (23 mg, 0.05 mmol), THF (0.08 mL), DMF (0.40 mL), pyridine (0.012 mL, 0.15 mmol), HATU (0.038 g, 0.1 mmol), and N-methylbenzylamine (0.013 mL, 0.1 mmol).

The title amide was obtained as a solid (14 mg, 50%). HPLC (reversed-phase): R$_T$=9.97 min (single peak). MS (ESI): m/z 565 [M+H]$^+$, 587 [M+Na]$^+$. $^1$H NMR (400 MHz, CDCl$_3$): (rotameric broadening) 9.02 (bs, 1H), 8.31 (bd, J=6.7 Hz, 1H), 8.3-8.2 (bm, 1H), 8.05-7.95 (bm, 1H), 7.85-7.65 (bm, 1H), 7.45-7.25 (bm, 5H), 7.15-7.0 (bm, 1H), 6.79 (bd, J=8.1 Hz, 1H), 4.6-4.4 (bs, 1.3H), 4.35-4.0 (bs, 0.7H), 3.05-2.75 (bs, 1.1H), 2.65-2.35 (bs, 1.9H).

Example 10

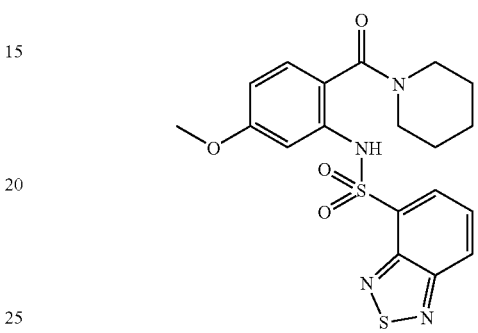

Benzo[1,2,5]thiadiazole-4-sulfonic acid [5-methoxy-2-(piperidine-1-carbonyl)-phenyl]-amide A. (4-Methoxy-2-nitro-phenyl)-piperidin-1-yl-methanone. To a stirred solution of (4-iodo-2-nitro-phenyl-piperidin-1-yl-methanone (100 mg, 0.28 mmol) in methanol (2.0 mL) was added CuI (5.0 g, 0.027 mmol), 1,10-phenanthroline (10 mg, 0.055 mmol), and cesium carbonate (180 mg, 0.55 mmol). The reaction mixture was heated in a sealed tube to 110° C. for 24 h, after which it was cooled to room temperature. The mixture was taken up in DCM (5 mL) and washed with water. The organic layers were dried (Mg$_2$SO$_4$) filtered, and concentrated in vacuo. The resulting oil was purified on silica gel (MPLC, 20% hexanes/80% EtOAc) to provide the ether product (70 mg, 0.26 mmol, 96%). TLC (silica gel, 3:1 EtOAc/hexanes): R$_f$=0.17. MS (ESI): m/z 265 [M+H]$^+$, 287 [M+Na]$^+$.

B. (2-Amino-4-methoxy-phenyl)-piperidin-1-yl-methanone. (4-Methoxy-2-nitro-phenyl)-piperidin-1-yl-methanone (70 mg, 0.27 mmol) was dissolved in 1:1 DCM/EtOAc (10 mL), and SnCl$_2$.2 H$_2$O (300 mg, 1.32 mmol) was added. The mixture was stirred overnight at ambient temperature then concentrated in vacuo. The resulting oil was suspended in DCM and neutralizing by shaking with aqueous NaHCO$_3$. The organic layer was dried (MgSO$_4$), filtered, and concentrated in vacuo to provide the title compound (50 mg, 0.21 mmol, 81%). TLC (silica gel, EtOAc): R$_f$=0.39. MS (ESI): m/z 235 [M+H]$^+$, 257 [M+Na]$^+$.

C. Benzo[1,2,5]thiadiazole-4-sulfonic acid [5-methoxy-2-(piperidine-1-carbonyl)-phenyl]-amide. 4-Chlorosulfonyl-2,1,3-benzothiadiazole (60 mg, 0.26 mmol), was added to a solution of (2-amino-4-methoxy-phenyl)-piperidin-1-yl-methanone (50 mg, 0.21 mmol) and pyridine (0.026 mL, 0.32 mmol) in DCM (3 mL). The mixture was left standing overnight at ambient temperature. Then the volatiles were stripped in vacuo, and the resulting oil was taken up in 8 mL EtOAc and washed with 1 N HCl. The organic layer was dried (MgSO$_4$), filtered, concentrated, and purified on silica gel (MPLC, hexanes/EtOAc) to provide the title compound (40 mg, 0.092 mmol, 43%). TLC (silica gel, EtOAc): $R_f$=0.28. MS (ESI): m/z 433 [M+H]$^+$, 455 [M+Na]$^+$. HPLC (reversed-phase): $R_T$=9.08 min (single peak). $^1$H NMR (400 MHz, CDCl$_3$): (rotameric broadening) 9.34 (s, 1H), 8.23 (dd, J=7.0 Hz, 1.0 Hz, 2H), 7.66 (m, 1H), 7.22 (dd, J=5.5 Hz, 2.5 Hz, 1H), 6.98 (d, J=12 Hz, 1H), 6.53 (dd, J=8.6 Hz, 2.5 Hz, 1H), 3.79 (s, 3H), 3.20-3.10 (bs, 4H), 1.63-1.58 (m, 2H), 1.43 (bs, 4H).

Example 11

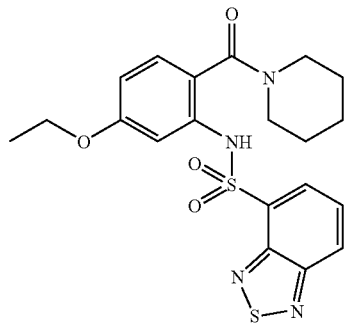

Benzo[1,2,5]thiadiazole-4-sulfonic acid [5-ethoxy-2-(piperidine-1-carbonyl)-phenyl]-amide This compound was prepared as described for the methyl ether analog in EXAMPLE 10 substituting ethanol for methanol in Step A. TLC (silica gel, 3:1 EtOAc/hexanes): $R_f$=0.33. MS (ESI): m/z 447 [M+H]$^+$, 469 [M+Na]$^+$. HPLC (reversed-phase): $R_T$=9.56 min (single peak). $^1$H NMR (400 MHz, CDCl$_3$): (rotameric broadening) 9.34 (s, 1H), 8.23 (dd, J=7.0 Hz, 1.0 Hz, 2H), 7.66 (m, 1H), 7.22 (dd, J=2.5 Hz, 1H), 6.98 (d, J=12 Hz, 1H), 6.53 (dd, J=8.6 Hz, 2.5 Hz, 1H), 4.01 (m, 2H), 3.16 (bs, 4H), 1.63-1.58 (m, 2H), 1.43 (bs, 4H), 1.40 (t, 7 Hz, 3H).

Example 12

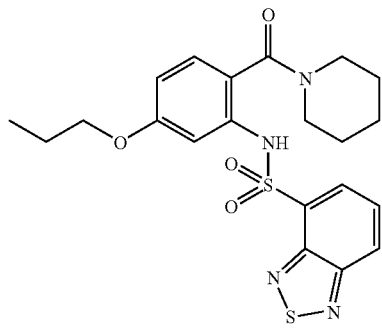

Benzo[1,2,5]thiadiazole-4-sulfonic acid [2-(piperidine-1-carbonyl)-5-propoxy-phenyl]-amide This compound was prepared as described for the methyl ether analog in EXAMPLE 10 substituting n-propanol for methanol in Step A. TLC (silica gel, 3:1 EtOAc/hexanes): $R_f$=0.34. MS (ESI): m/z 461 [M+H]$^+$, 483 [M+Na]$^+$. HPLC (reversed-phase): $R_T$=9.96 min (single peak). $^1$H NMR (400 MHz, CDCl$_3$): (rotameric broadening) 9.34 (s, 1H), 8.23 (dd, J=7.0 Hz, 1.0 Hz, 2H), 7.66 (m, 1H), 7.22 (dd, J=2.5 Hz, 1H), 6.95 (d, J=12 Hz, 1H), 6.52 (dd, J=8.6 Hz, 2.5 Hz, 1H), 3.89 (t, J=6.5 Hz, 2H), 3.16 (bs, 4H), 1.80-1.75 (m, 2H), 1.59-1.57 (m, 2H), 1.42 (bs, 4H), 1.02 (t, 7.5 Hz, 3H).

Example 13

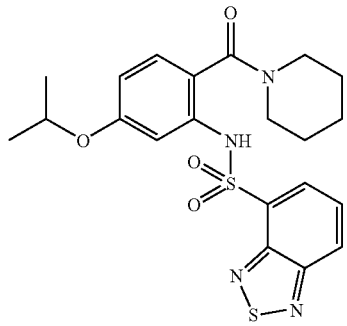

Benzo[1,2,5]thiadiazole-4-sulfonic acid [5-isopropoxy-2-(piperidine-1-carbonyl)-phenyl]-amide This compound was prepared as described for the methyl ether analog in EXAMPLE 10 substituting substituting i-propanol for methanol in Step A. TLC (silica gel, 3:1 EtOAc/hexanes): $R_f$=0.40. MS (ESI): m/z 461 [M+H]$^+$, 483 [M+Na]$^+$. HPLC (reversed-phase): $R_T$=9.86 min (single peak). $^1$H NMR (400 MHz, CDCl$_3$): (rotameric broadening) 9.33 (s, 1H), 8.22 (dd, J=7.0 Hz, 1.0 Hz, 2H), 7.65 (m, 1H), 7.20 (d, J=2.5 Hz, 1H), 6.97 (d, J=12 Hz, 1H), 6.49 (dd, J=8.6 Hz, 2.5 Hz, 1H), 4.56-4.50 (m, 1H), 3.16 (bs, 4H), 1.60-1.58 (m, 2H), 1.42-1.38 (bs, 4H), 1.31 (d, J=6.0 Hz, 6H).

Example 14

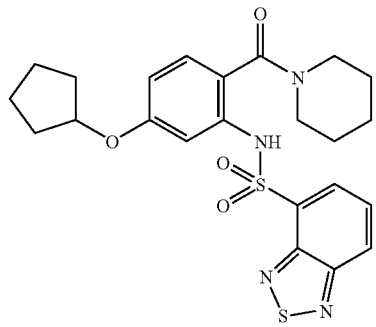

Benzo[1,2,5]thiadiazole-4-sulfonic acid [5-cyclopentyloxy-2-(piperidine-1-carbonyl)-phenyl]-amide This compound was prepared as described for the methyl ether analog in EXAMPLE 10 substituting substituting cyclopentanol for methanol in Step A. TLC (silica gel, 3:1 EtOAc/hexanes): $R_f$=0.37. MS (ESI): m/z 487 [M+H]$^+$, 509 [M+Na]$^+$. HPLC (reversed-phase): $R_T$=10.45 min (single peak). $^1$H NMR (400 MHz, CDCl$_3$): (rotameric broadening)

9.35 (s, 1H), 8.22 (dd, J=7.0 Hz, 1.0 Hz, 2H), 7.66 (m, 1H), 7.18 (dd, J=2.5 Hz, 1H), 6.93 (d, J=12 Hz, 1H), 6.48 (dd, J=8.6 Hz, 2.5 Hz, 1H), 4.73-4.69 (m, 1H), 3.16 (bs, 4H), 2.04 (m, 2H), 1.76 (m, 4H), 1.60 (m, 4H), 1.42 (m, 4H).

Example 15

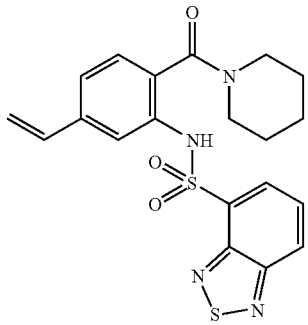

Benzo[1,2,5]thiadiazole-4-sulfonic acid [2-(piperidine-1-carbonyl)-5-vinyl-phenyl]-amide A. 2-Nitro-4-vinylbenzoic acid piperidine amide. To a stirred solution of tetrakis(triphenylphosphine) palladium (0) (6 mg, 0.0054 mmol), 4-bromo-2-nitrobenzoic acid piperidine amide (EXAMPLE 5; 85 mg, 0.27 mmol), and toluene (10 mL), was added tributylvinylstannane (0.087 mL, 0.30 mmol) under a nitrogen atmosphere. The reaction mixture was heated to 115° C. for 12 h after which it was cooled to room temperature. The mixture was taken up in EtOAc (20 mL) and washed with water and aqueous NaHCO$_3$. The organic layers were dried (Mg$_2$SO$_4$), filtered, and concentrated in vacuo. The resulting oil was purified on silica gel (MLPC, hexanes/EtOAc) to afford product (40 mg, 0.15 mmol, 57%). TLC (silica gel, 1:1 EtOAc/hexanes): R$_f$=0.25. MS (ESI): m/z 261 [M+H]$^+$, 283 [M+Na]$^+$.

B. 2-Amino-4-vinylbenzoic acid piperidine amide. A solution of 2-nitro-4-vinylbenzoic acid piperidine amide (40 mg, 0.15 mmol) was dissolved in 1:1 EtOAc/DCM (10 mL), and SnCl$_2$.2 H$_2$O (173 mg, 0.77 mmol) was added. The mixture was stirred overnight at ambient temperature then concentrated in vacuo. The resulting oil was suspended in DCM and neutralized by shaking with aqueous NaHCO$_3$. The organic layer was dried (MgSO$_4$), filtered, and concentrated in vacuo to afford the title compound (30 mg, 0.13 mmol, 86%). TLC (silica gel, EtOAc): R$_f$=0.42. MS (ESI): m/z 231 [M+H]$^+$, 253 [M+Na]$^+$.

C. Benzo[1,2,5]thiadiazole-4-sulfonic acid. [2-(piperidine-1-carbonyl)-5-vinyl-phenyl]-amide. 4-Chlorosulfonyl-2,1,3-benzothiadiazole (37 mg, 0.16 mmol), was added to a solution of (2-amino-4-vinylbenzoic acid piperidine amide (30 mg, 0.13 mmol) and pyridine (0.016 mL, 0.20 mmol) in DCM (3 mL). The mixture was left standing overnight at ambient temperature. Then the volatiles were stripped in vacuo, and the resulting oil was taken up in 8 mL EtOAc and washed with 1 N HCl. The organic layer was dried (MgSO$_4$), filtered, concentrated, and purified on silica gel (MPLC, hexanes/EtOAc) to provide the title compound (20 mg, 0.047 mmol, 36%). TLC (silica gel, 3:1 EtOAc/hexanes): R$_f$=0.47. MS (ESI): m/z 429 [M+H]$^+$, 451 [M+Na]$^+$. HPLC (reversed-phase): R$_T$=9.46 min (single peak). $^1$H NMR (400 MHz, CDCl$_3$): (rotameric broadening) 8.95 (s, 1H), 8.22 (m, 2H), 7.68 (s, 1H) 7.64 (d, J=7 Hz, 1H), 7.08 (d, J=8 Hz, 1H), 7.06 (d, J=14 Hz, 1H), 6.63 (m, 1H), 5.73 (d, J=13 Hz, 1H), 5.29 (d, J=11 Hz, 1H), 3.41-2.90 (bs, 4H), 1.59 (m, 2H), 1.25 (bs, 4H).

Example 16

Benzo[1,2,5]thiadiazole-4-sulfonic acid [5-allyl-2-(piperidine-1-carbonyl)-phenyl]-amide This compound was prepared as described in EXAMPLE 15 substituting allytributylstannane for tributylvinylstannane in Step A. TLC (silica gel, 3:1 EtOAc/hexanes): R$_f$=0.53. MS (ESI): m/z 443 [M+H]$^+$, 465 [M+Na]$^+$. HPLC (reversed-phase): R$_T$=9.63 min (single peak). $^1$H NMR (400 MHz, CDCl$_3$): (rotameric broadening) 8.94 (s, 1H), 8.22 (m, 2H), 7.65 (m, 1H), 7.45 (s, 1H), 6.98 (d, 13 Hz, 1H) 6.85 (d, J=8 Hz, 1H), 5.93-5.79 (m, 1H), 5.06 (m, 2H), 3.32 (d, J=7 Hz, 2H), 3.28-2.96 (bs, 4H), 1.57 (m, 2H), 1.44 (bs, 4H). Elemental analysis: calculated for C$_{21}$H$_{22}$N$_4$O$_3$S$_2$, C, 56.99; H, 5.01; N, 12.66. found C, 56.60; H, 5.40; N, 12.28.

Example 17

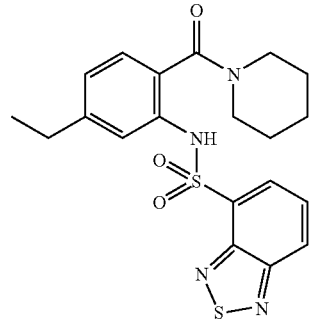

Benzo[1,2,5]thiadiazole-4-sulfonic acid [5-ethyl-2-(piperidine-1-carbonyl)-phenyl]-amide To a stirred solution of 2-nitro-4-vinylbenzoic acid piperidine amide (100 mg, 0.39 mmol) in methanol (15 mL) was added Pd on carbon (10 wt %, 25 mg). The reaction mixture was maintained under ~1 atm H$_2$ and stirred for 12 h. The mixture was filtered through Celite® and concentrated in vacuo to yield (4-ethyl-2-nitro-phenyl)-piperidin-1-yl-methanone, which was subsequently reduced to (2-amino-4-ethyl-phenyl-piperidin-1-yl-methanone with SnCl$_2$.2 H$_2$O as described in EXAMPLE 5. The title compound was prepared from the aniline (90 mg, 0.39 mmol) and 4-chlorosulfonyl-2,1,3-benzothiadiazole (181 mg, 0.78 mmol), and purified as described in EXAMPLE 15. TLC (silica gel, 3:1 EtOAc/hexanes): $R_f$=0.32. MS (ESI): m/z 431 [M+H]$^+$, 453 [M+Na]$^+$. HPLC (reversed-phase): $R_T$=9.52 min (single peak). $^1$H NMR (400 MHz, CDCl$_3$): (rotameric broadening) 8.95 (s, 1H), 8.21 (m, 2H), 7.65 (dd, J=8.8 Hz, 7 Hz, 1H), 7.47 (d, J=1.3 Hz, 1H), 6.95 (d, J=7.8 Hz, 1H) 6.85 (dd, J=7.9 Hz, 1.6 Hz, 1H), 3.14 (bs, 4H), 2.60 (m, 2H), 1.61 (m, 2H), 1.43 (bs, 4H), 1.17 (t, J=7.6 Hz, 3H). Elemental analysis: calculated for $C_{20}H_{22}N_4O_3S_2$, C, 55.79; H, 5.15; N, 13.01. found C, 55.44; H, 5.50; N, 12.62.

Example 18

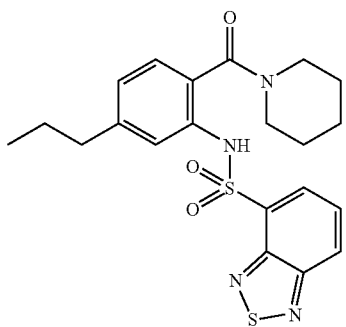

Benzo[1,2,5]thiadiazole-4-sulfonic acid [2-(piperidine-1-carbonyl)-5-propyl-phenyl]-amide This compound was prepared via reduction of 2-allyl-2-nitrobenzoic acid piperidine amide as described in the general procedure of EXAMPLE 17. TLC (silica gel, 3:1 EtOAc/hexanes): $R_f$=0.30. MS (ESI): m/z 445 [M+H]$^+$, 467 [M+Na]$^+$. HPLC (reversed-phase): $R_T$=10.04 min (single peak). $^1$H NMR (400 MHz, CDCl$_3$): (rotameric broadening) 8.94 (s, 1H), 8.21 (m, 2H), 7.65 (dd, J=8.8 Hz, 7 Hz, 1H), 7.47 (d, J=1.3 Hz, 1H), 6.95 (d, J=7.8 Hz, 1H) 6.82 (dd, J=7.9 Hz, 1.6 Hz, 1H), 3.10 (bs, 4H), 2.52 (t, J=7.4 Hz, 2H), 1.61-1.52 (m, 4H), 1.43 (bs, 4H), 0.87 (t, J=7.3 Hz, 3H).

Example 19

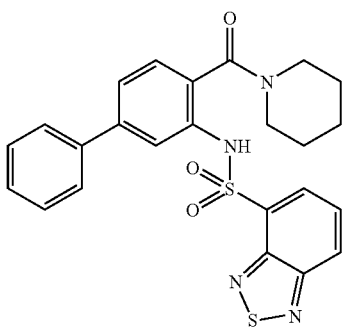

Benzo[1,2,5]thiadiazole-4-sulfonic acid [4-(piperidine-1-carbonyl)-biphenyl-3-yl]-amide A. 3-Nitrobiphenyl-4-carboxylic acid piperidine amide. 4-Bromo-2-nitrobenzoic acid piperidine amide (EXAMPLE 5; 100 mg, 0.32 mmol) and 2 M Na$_2$CO$_3$ (0.32 mL, 0.64 mmol, aqueous) were added to a solution of tetrakis(triphenylphosphine) palladium (0) (15 mg, 0.013 mmol) in ethylene glycol dimethyl ether (8 mL), and the reaction mixture was stirred for 15 min. Phenylboronic acid (39 mg, 0.32 mmol) was added to the mixture, which was then heated to 80° C. for 12 h. The mixture was cooled to room temperature, taken up to 10 mL of DCM, and washed with water and brine. The organic layers were dried (Mg$_2$SO$_4$), filtered, and concentrated in vacuo. The resulting oil was purified on silica gel (MPLC, 85% hexanes/15% EtOAc) to yield product (60 mg, 0.19 mmol). TLC (silica gel, 1:1 EtOAc/hexanes): $R_f$=0.54. MS (ESI): m/z 311 [M+H]$^+$, 333 [M+Na]$^+$.

B. 3-Aminobiphenyl-4-carboxylic acid piperidine amide. 3-Nitrobiphenyl-4-carboxylic acid piperidine amide (60 mg, 0.19 mmol) was dissolved in 1:1 DCM/EtOAc (8 mL), and SnCl$_2$.2 H$_2$O (218 mg, 0.97 mmol) was added. The mixture was stirred overnight at ambient temperature then concentrated in vacuo. The resulting oil was suspended in DCM and neutralized by shaking with aqueous NaHCO$_3$. The organic layer was dried (MgSO$_4$), filtered, and concentrated in vacuo to afford the title compound (53 mg, 0.19 mmol, 98%).

C. Benzo[1,2,5]thiadiazole-4-sulfonic acid [4-(piperidine-1-carbonyl)-biphenyl-3-yl]-amide. 4-Chlorosulfonyl-2,1,3-benzothiadiazole (50 mg, 0.21 mmol) was added to a solution of 3-aminobiphenyl-4-carboxylic acid piperidine amide (60 mg, 0.21 mmol) and pyridine (0.025 mL, 0.32 mmol) in DCM (8 mL). The mixture was left standing overnight at ambient temperature. Then the volatiles were stripped in vacuo, and the resulting oil was taken up in 10 mL EtOAc and washed with 1 N HCl. The organic layer was dried (MgSO$_4$), filtered, concentrated, and purified on silica gel (MPLC, hexanes/EtOAc) to provide the title compound (80 mg, 0.17 mmol, 80%). TLC (silica gel, 1:1 EtOAc/hexanes): $R_f$=0.38. MS (ESI): m/z 479 [M+H]$^+$, 501 [M+Na]$^+$. HPLC (reversed-phase): $R_T$=10.02 min (single peak). $^1$H NMR (400 MHz, CDCl$_3$): (rotameric broadening) 9.00 (s, 1H), 8.22 (m, 2H), 7.89 (d, J=1.61 Hz, 1H) 7.65 (dd, J=8.8 Hz, 7.0 Hz, 1H), 7.52 (m, 2H), 7.44 (m, 2H), 7.37 (m, 1H), 7.25 (m, 1H), 7.11 (d, J=8.0 Hz, 1H), 3.22 (bs, 4H), 1.60 (m, 2H), 1.47 (bs, 4H).

Example 20

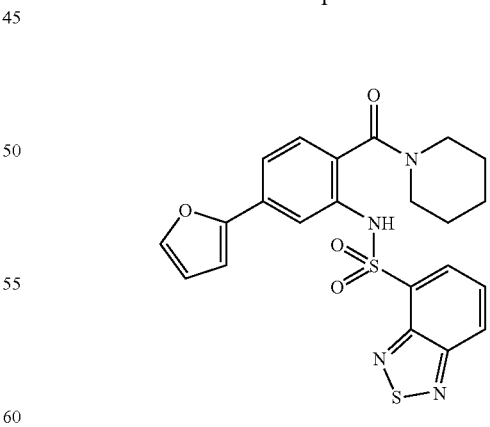

Benzo[1,2,5]thiadiazole-4-sulfonic acid [5-furan-2-yl-2-(piperidine-1-carbonyl)-phenyl]-amide This compound was prepared as described in EXAMPLE 19 substituting 2-furylboronic acid for phenylboronic acid in Step A. MS (ESI): m/z 469 [M+H]+, 491 [M+Na]+. HPLC (reversed-phase): R_T=9.65 min (single peak). $^1$H NMR (400 MHz, CDCl$_3$): (rotameric broadening) 9.01 (s, 1H), 8.26 (d, J=7.0 Hz, 1H), 8.20 (d, J=8.8 Hz, 1H), 7.96 (s, 1H), 7.66 (t, J=7.6 Hz, 1H), 7.49 (s, 1H), 7.32 (d, J=8.0, 1H), 7.05 (d, J=8.0 Hz, 1H), 6.71 (d, J=32 Hz, 1H), 6.48 (s, 1H), 3.14 (bs, 4H), 1.59 (m, 2H), 1.45 (bs, 4H).

Example 21

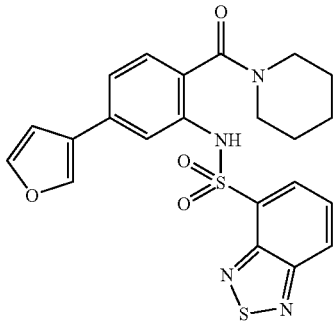

Benzo[1,2,5]thiadiazole-4-sulfonic acid [5-furan-3-yl-2-(piperidine-1-carbonyl)-phenyl]-amide This compound was prepared as described in EXAMPLE 19 substituting 3-furylboronic acid for phenylboronic acid in Step A. MS (ESI): m/z 469 [M+H]+, 491 [M+Na]+. HPLC (reversed-phase): R_T=9.49 min (single peak). $^1$H NMR (400 MHz, CDCl$_3$): (rotameric broadening) 9.01 (s, 1H), 8.22 (m, 2H), 7.78 (d, J=1.6 Hz, 1H), 7.73 (s, 1H), 7.65 (dd, J=8.8 Hz, 1H), 7.48 (t, J=1.8, 1H), 7.14 (dd, J=8.0 Hz, 1.6 Hz, 1H), 7.04 (d, J=8.0, 1H), 6.65 (m, 1H), 3.15 (bs, 4H), 1.59 (m, 2H), 1.44 (bs, 4H).

Example 22

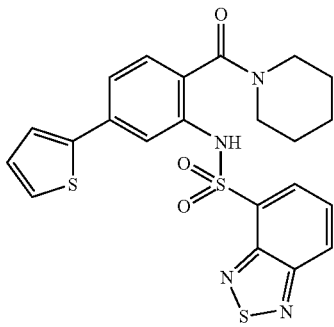

Benzo[1,2,5]thiadiazole-4-sulfonic acid [2-(piperidine-1-carbonyl)-5-thiophen-2-yl-phenyl]-amide This compound was prepared as described in EXAMPLE 19 substituting 2-thienylboronic acid for phenylboronic acid in Step A. TLC (silica gel, 1:1 EtOAc/hexanes): R_f=0.37. MS (ESI): m/z 485 [M+H]+, 507 [M+Na]+. HPLC (reversed-phase): R_T=9.88 min (single peak). $^1$H NMR (400 MHz, CDCl$_3$): (rotameric broadening) 9.03 (s, 1H), 8.28 (d, J=7.0 Hz, 1H), 8.21 (d, J=8.8 Hz, 1H), 7.90 (s, 1H), 7.68 (t, J=8.0 Hz, 1H), 7.32 (m, 1H), 7.24 (m, 1H), 7.08 (m, 2H), 3.20 (bs, 4H), 1.61 (m, 2H), 1.47 (bs, 4H).

Example 23

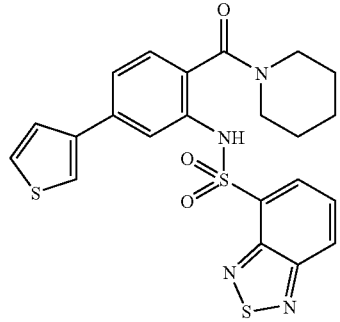

Benzo[1,2,5]thiadiazole-4-sulfonic acid [2-(piperidine-1-carbonyl)-5-thiophen-3-yl-phenyl]-amide This compound was prepared as described in EXAMPLE 19 substituting 3-thienylboronic acid for phenylboronic acid in Step A. TLC (silica gel, 1:1 EtOAc/hexanes): R_f=0.33. MS (ESI): m/z 485 [M+H]+, 507 [M+Na]+. HPLC (reversed-phase): R_T=9.82 min (single peak). $^1$H NMR (400 MHz, CDCl$_3$): (rotameric broadening) 9.01 (s, 1H), 8.23 (d, J=7.0 Hz, 1H), 8.21 (d, J=8.8 Hz, 1H), 7.90 (s, 1H), 7.65 (t, J=8.0 Hz, 1H), 7.47 (s, 1H), 7.39 (m, 1H), 7.32 (m, 1H), 7.25 (m, 1H), 7.07 (d, J=8.0 Hz, 1H), 3.12 (bs, 4H), 1.59 (m, 2H), 1.45 (bs, 4H).

Example 24

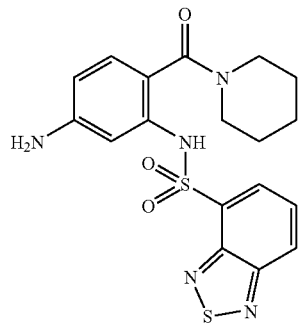

Benzo[1,2,5]thiadiazole-4-sulfonic acid [5-amino-2-(piperidine-1-carbonyl)-phenyl]-amide A solution of benzo[1,2,5]thiadiazole-4-sulfonic acid [5-nitro-2-(piperidine-1-carbonyl)-phenyl]-amide (EXAMPLE 2; 90 mg, 2.0 mmol) was dissolved in 1:1 EtOAc/DCM (10 mL), and SnCl$_2$.2 H$_2$O (2.3 g, 10 mmol) was added. The mixture was stirred overnight at ambient temperature then concentrated in vacuo. The resulting oil was suspended in DCM and neutralized by shaking with aqueous NaHCO$_3$. The organic layer was dried (MgSO$_4$), filtered and concentrated in vacuo to afford the title compound (69 mg, 1.7 mmol, 82%). TLC (silica gel, 3:1 EtOAc/hexanes): $R_f$=0.42. MS (ESI): m/z 418 [M+H]$^+$, 440 [M+Na]$^+$. HPLC (reversed-phase): $R_T$=8.15 min (single peak). $^1$H NMR (400 MHz, CDCl$_3$): (rotameric broadening) 9.80 (s, 1H), 8.40 (m, 2H), (dd, J=8.8 Hz, 1.0 Hz, 1H), 8.15 (dd, J=7.0 Hz, 1.0 Hz, 1H), 7.82 (dd, J=8.8 Hz, 1.0 Hz, 1H), 6.77 (d, J=8.4 Hz, 1H), 6.74 (d, J=2.2 Hz, 1H), 6.19 (dd, J=8.4 Hz, 2.3 Hz, 1H), 5.75 (d, J=2.3 Hz, 2H), 2.96 (bs, 4H), 1.45 (bs, 2H), 1.24 (bs, 4H).

Example 25

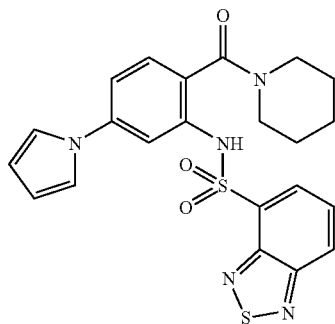

Benzo[1,2,5]thiadiazole-4-sulfonic acid [2-(piperidine-1-carbonyl)-5-pyrrol-1-yl-phenyl]-amide To a stirred solution of benzo[1,2,5]thiadiazole-4-sulfonic acid [5-amino-2-(piperidine-1-carbonyl)-phenyl]-amide (EXAMPLE 24; 25 mg, 0.06 mmol) in glacial acetic acid (3 mL) was added 2,5-dimethoxytetrahydrofuran (8 μL, 0.06 mmol). The reaction mixture was heated to 120° C. for 45 min after which it was cooled to room temperature. The mixture was taken up to 4 mL of DCM and washed with water. The organic layer was removed, dried and purified by preparative reversed-phase HPLC (acetonitrile/water, 0.05% TFA) to afford the title compound (12 mg, 0.02 mmol, 43%). MS (ESI): m/z 468 [M+H]$^+$, 490 [M+Na]$^+$. HPLC (reversed-phase): $R_T$=9.71 min (single peak). $^1$H NMR (400 MHz, CDCl$_3$): (rotameric broadening) 9.15 (s, 1H), 8.26 (dd, J=7.0 Hz, 1.0 Hz, 1H), 8.22 (dd, J=8.8 Hz, 1.0 Hz, 1H), 7.74 (d, J=2.1 Hz, 1H), 7.67 (dd, J=8.8 Hz, 7 Hz, 1H), 7.10 (d, J=8.3 Hz, 1H), 7.05 (m, 3H), 6.35 (t, J=2.2 Hz, 2H), 3.23 (bs, 4H), 1.61 (m, 2H), 1.48 (bs, 4H).

Example 26

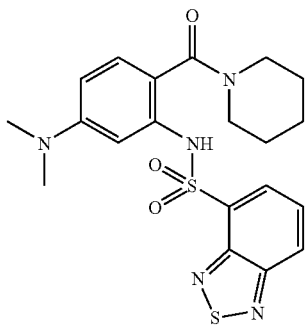

Benzo[1,2,5]thiadiazole-4-sulfonic acid [5-dimethylamino-2-(piperidine-1-carbonyl)-phenyl]-amide To a stirred solution of benzo[1,2,5]thiadiazole-4-sulfonic acid [5-amino-2-(piperidine-1-carbonyl)-phenyl]-amide (EXAMPLE 24; 30 mg, 0.072 mmol) in 2:1 acetonitrile/DCM (6 mL), was added formaldehyde (0.1 mL, 3.6 mmol), sodium cyanoborohydride (68 mg, 1.08 mmol) and acetic acid (12 μL). The reaction mixture was stirred for 3 h at room temperature. 1 M NaOH was added until the solution became basic. The mixture was taken up in DCM (5 mL), and washed with water and brine. The organic layer was removed, dried, and purified by preparative reversed-phase HPLC (acetonitrile/water, 0.05% TFA) to afford the title compound (8 mg, 0.02 mmol, 25%). MS (ESI): m/z 446 [M+H]$^+$, 468 [M+Na]$^+$. HPLC (reversed-phase): $R_T$=9.14 min (single peak). $^1$H NMR (400 MHz, CDCl$_3$): (rotameric broadening) 9.61 (s, 1H), 8.22 (dd, J=7.0 Hz, 1.0 Hz, 1H), 8.18 (dd, J=8.8 Hz, 1.0 Hz, 1H), 7.63 (dd, J=8.8 Hz, 7.0 Hz, 1H), 6.95 (d, J=2.5 Hz, 7 Hz, 1H), 6.90 (d, J=8.7 Hz, 1H), 6.26 (dd, 8.7 Hz, 2.5 Hz, 1H), 3.16 (s, 4H), 2.95 (s, 6H), 1.56 (m, 2H), 1.42 (m, 4H).

Example 27

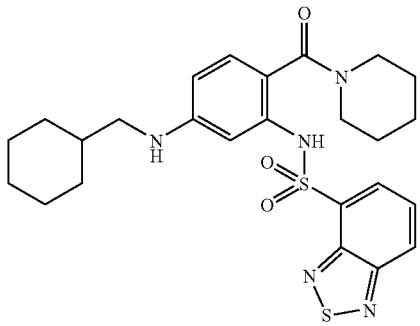

Benzo[1,2,5]thiadiazole-4-sulfonic acid [5-(cyclohexylmethyl-amino)-2-(piperidine-1-carbonyl)-phenyl]-amide To a stirred solution of benzo[1,2,5]thiadiazole-4-sulfonic acid [5-amino-2-(piperidine-1-carbonyl)-phenyl]-amide (EXAMPLE 24; 50 mg, 0.12 mmol) in dichloroethane (4 mL) was added cyclohexanecarboxaldehyde (43 μL, 0.36 mmol), followed by sodium triacetoxyborohydride (50 mg, 0.24 mmol). The reaction mixture was stirred for 12 h at room temperature. 1 M NaOH was added until the solution became basic. The mixture was taken up in 5 mL of DCM and washed with water and aqueous NaHCO$_3$. The organic layer was removed, dried, and purified by preparative reversed-phase HPLC (acetonitrile/water, 0.05% TFA) to afford the title compound (20 mg, 0.04 mmol, 33%). MS (ESI): m/z 514 [M+H]$^+$, 536 [M+Na]$^+$. HPLC (reversed-phase): $R_T$=10.93 min (single peak). $^1$H NMR (400 MHz, CDCl$_3$): (rotameric broadening) 9.36 (s, 1H), 8.20 (dd, J=8.8 Hz, 7.0 Hz, 2H), 7.63 (dd, J=8.8 Hz, 7.0 Hz, 1H), 6.85 (d, J=3.8 Hz, 1H), 6.81 (d, J=2.3 Hz, 1H), 6.15 (dd, J=8.5 Hz, 2.3 Hz, 1H), 3.21 (m, 4H), 2.90 (d, J=6.7 Hz, 2H), 1.74 (m, 6H), 1.57 (m, 2H), 1.46 (m, 4H), 1.22 (m, 3H), 0.96 (m, 2H).

Example 28

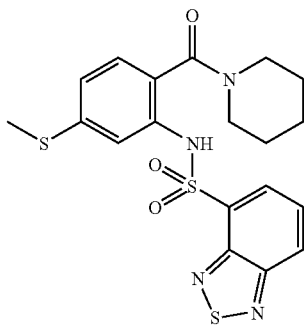

Benzo[1,2,5]thiadiazole-4-sulfonic acid [5-methylsulfanyl-2-(piperidine-1-carbonyl)-phenyl]-amide A. 4-Mercapto-2-nitrobenzoic acid piperidine amide. Sodium nitrite (278 mg, 4.0 mmol) in water (2 mL) was added dropwise to a stirred solution of water (15 mL), concentrated HCl (1 mL), and 4-amino-2-nitrobenzoic acid piperidine amide (EXAMPLE 2; 1.0 g, 4.0 mmol) in THF (7 mL) at 0° C. The reaction mixture was stirred at 0° C. for 20 min, after which O-ethylxanthic acid was added. The mixture was stirred at 0° C. for 15 min, gradually heated to 60° C., then cooled to room temperature and stirred for 2 h. 1,4-Dioxane (15 mL) and concentrated aqueous NH$_4$OH (15 mL) were added, and the mixture was stirred at room temperature for 2 h. 1 N HCl was added until the solution was neutral to pH paper. The reaction mixture was taken up to 40 mL DCM and washed with water. The organic layer was dried (MgSO$_4$), filtered, concentrated, and purified on silica gel (MPLC, hexanes/EtOAc) to provide the title compound (210 mg, 0.89 mmol, 22%). TLC (silica gel, EtOAc): R$_f$=0.37. MS (ESI): m/z 267 [M+H]$^+$, 289 [M+Na]$^+$.

B. 4-Methylthio-2-nitrobenzoic acid piperidine amide. To a stirred solution of 4-mercapto-2-nitrobenzoic acid piperidine amide (50 mg, 0.19 mmol) and sodium hydride (5 mg, 0.21 mmol) in DMF (4 mL), was added iodomethane (0.013 mL, 0.21 mmol). The reaction mixture was stirred at room temperature for 1 h then taken up in 10 mL of EtOAc and washed with water. The organic layer was dried (MgSO$_4$), filtered, and concentrated in vacuo to afford the title compound (35 mg, 0.12 mmol, 67%). TLC (silica gel, EtOAc): R$_f$=0.53.

C. 2-Amino-4-methylthiobenzoic acid piperidine amide. 4-Methylthio-2-nitrobenzoic acid piperidine amide (35 mg, 0.13 mmol) was dissolved in 1:1 DCM/EtOAc (6 mL), and SnCl$_2$.2 H$_2$O (141 mg, 0.62 mmol) was added. The mixture was stirred overnight at ambient temperature then concentrated in vacuo. The resulting oil was suspended in DCM and neutralized by shaking with aqueous NaHCO$_3$. The organic layer was dried (MgSO$_4$), filtered, and concentrated in vacuo to afford the title compound (30 mg, 0.12 mmol, 98%). TLC (silica gel, EtOAc): R$_f$=0.48.

D. Benzo[1,2,5]thiadiazole-4-sulfonic acid [5-methylsulfanyl-2-(piperidine-1-carbonyl)-phenyl]-amide. 4-Chlorosulfonyl-2,1,3-benzothiadiazole (45 mg, 0.19 mmol) was added to a solution of 2-amino-4-methylthiobenzoic acid piperidine amide (40 mg, 0.16 mmol) and pyridine (0.019 mL, 0.24 mmol) in DCM (5 mL). The mixture was left standing overnight at ambient temperature. Then the volatiles were stripped in vacuo, and the resulting oil was taken up in 10 mL EtOAc and washed with 1 N HCl. The organic layer was dried (MgSO$_4$), filtered, concentrated, and purified on silica gel (MPLC, hexanes/EtOAc) to provide the title compound (30 mg, 0.067 mmol, 42%). TLC (silica gel, EtOAc): R$_f$=0.54. MS (ESI): m/z 449 [M+H]$^+$, 471 [M+Na]$^+$. HPLC (reversed-phase): R$_T$=9.42 min (single peak). $^1$H NMR (400 MHz, CDCl$_3$): (rotameric broadening) 9.13 (s, 1H), 8.22 (m, 2H), 7.66 (dd, J=8.8 Hz, 7.0 Hz, 1H), 7.50 (d, J=1.8 Hz, 1H), 6.94 (d, J=8.2 Hz, 1H), 6.85 (dd, J=8.2 Hz, 1H), 3.17 (bs, 4H), 2.45 (s, 3H), 1.61 (m, 2H), 1.43 (bs, 4H).

Example 29

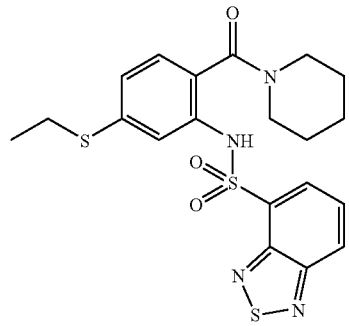

Benzo[1,2,5]thiadiazole-4-sulfonic acid [5-ethylsulfanyl-2-(piperidine-1-carbonyl)-phenyl]-amide This compound was prepared as described in EXAMPLE 28 substituting iodoethane for iodomethane in Step B. TLC (silica gel, 3:1 EtOAc/hexanes): R$_f$=0.25. MS (ESI): m/z 463 [M+H]$^+$, 485 [M+Na]$^+$. HPLC (reversed-phase): R$_T$=9.66 min (single peak). $^1$H NMR (400 MHz, CDCl$_3$): (rotameric broadening) 9.09 (s, 1H), 8.22 (m, 2H), 7.66 (dd, J=8.8 Hz, 7.0 Hz, 1H), 7.54 (d, J=1.7 Hz, 1H), 6.93 (d, J=8.0 Hz, 1H), 6.88 (dd, J=8.1 Hz, 1.8 Hz, 1H), 3.16 (bs, 4H), 2.97 (m, 2H), 1.59 (m, 2H), 1.43 (bs, 4H), 1.34 (t, J=7.4 Hz, 3H).

Example 30

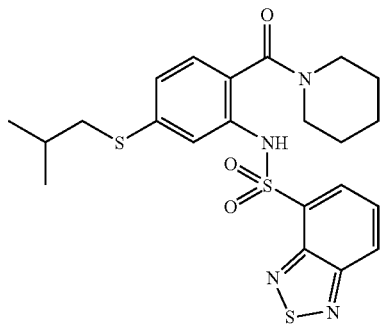

Benzo[1,2,5]thiadiazole-4-sulfonic acid [5-isobutylsulfanyl-2-(piperidine-1-carbonyl)-phenyl]-amide This compound was prepared as described in EXAMPLE 28 substituting isobutyliodide for iodomethane in Step B. MS (ESI): m/z 491 [M+H]+, 513 [M+Na]+. HPLC (reversed-phase): R$_T$=10.40 min (single peak). $^1$H NMR (400 MHz, CDCl$_3$): (rotameric broadening) 9.09 (s, 1H), 8.23 (s, 1H), 8.21 (d, J=2.8 Hz, 1H), 7.66 (dd, J=8.8 Hz, 7.0 Hz, 1H), 7.54 (d, J=1.6 Hz, 1H), 6.89 (m, 2H), 3.16 (bs, 4H), 2.78 (d, J=6.8 Hz, 2H), 1.88 (m, 2H), 1.43 (bs, 4H), 1.04 (d, J=6.7 Hz, 6H).

Example 31

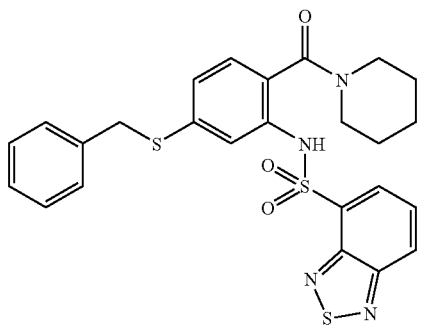

Benzo[1,2,5]thiadiazole-4-sulfonic acid [5-benzyl-sulfanyl-2-(piperidine-1-carbonyl)-phenyl]-amide This compound was prepared as described in EXAMPLE 28 substituting benzylbromide for iodomethane in Step B. TLC (silica gel, 3:1 EtOAc/hexanes): R$_f$=0.32. MS (ESI): m/z 525 [M+H]+, 547 [M+Na]+. HPLC (reversed-phase): R$_T$=10.24 min (single peak). $^1$H NMR (400 MHz, CDCl$_3$): (rotameric broadening) 9.05 (s, 1H), 8.19 (dd, J=8.8 Hz, 1.0 Hz, 1H), 8.09 (dd, J=7.0 Hz, 1.0 Hz, 1H), 7.59 (m, 2H), 7.35-7.28 (m, 5H), 6.91-6.86 (m, 2H), 4.21 (s, 2H), 3.15 (bs, 4H), 1.59 (m, 2H), 1.37 (m, 4H).

Example 32

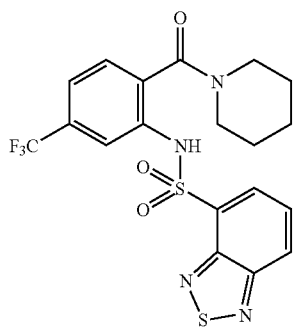

Benzo[1,2,5]thiadiazole-4-sulfonic acid [2-(piperidine-1-carbonyl)-5-trifluoromethyl-phenyl]-amide A. 2-Nitro-4-trifluoromethylbenzoic acid piperidine amide. To a solution of 2-nitro-4-trifluoromethylbenzoic acid (1.1 g, 4.7 mmol) in acetonitrile (20 mL) was added piperidine (0.42 mL, 4.3 mmol) followed by 1-(3-dimethylaminopropyl-3-ethylcarbodiimide hydrochloride (EDC) (0.98 g, 5.1 mmol) and DMF (2 mL). The mixture was stirred at ambient temperature overnight, then was diluted with EtOAc and washed repeatedly with 1 N aqueous NaOH then brine. The organic layer was dried (Na$_2$SO$_4$), filtered, and purified on silica gel (MPLC, hexanes/EtOAc) to provide the amide as a white solid (0.19 g, 0.63 mmol, 13%). TLC (silica gel, 1:1 EtOAc/hexanes): R$_f$=0.60. MS (ESI): m/z 303 [M+H]+, 325 [M+Na]+.

B. 2-Amino-4-trifluoromethylbenzoic acid piperidine amide. 2-Nitro-4-trifluoromethylbenzoic acid piperidine amide (0.19 g, 0.63 mmol) was dissolved in 2:5 DCM/EtOAc (7 mL), and SnCl$_2$.2 H$_2$O (0.71 g, 3.15 mmol) was added. The mixture was stirred overnight at ambient temperature then concentrated in vacuo. The resulting oil was suspended in DCM and neutralized by shaking with aqueous NaHCO$_3$. The organic layer was dried (MgSO$_4$), filtered, concentrated and purified on silica gel (MPLC, EtOAc/hexanes 20% to 70%) to provide the title compound as a white solid (130 mg, 0.48 mmol, 76%). TLC (silica gel, 1:1 EtOAc/hexanes): R$_f$=0.65. MS (ESI): m/z 273 [M+H]+, 295 [M+Na]+.

C. Benzo[1,2,5]thiadiazole-4-sulfonic acid [2-(piperidine-1-carbonyl)-5-trifluoromethyl-phenyl]-amide. 4-Chlorosulfonyl-2,1,3-benzothiadiazole (0.063 g, 0.27 mmol) was added to a solution of 2-amino-4-trifluoromethylbenzoic acid piperidine amide (0.070 mg, 0.26 mmol) and pyridine (0.030 mL, 0.36 mmol) in DCM (1.5 mL). The mixture was left standing overnight at ambient temperature. Then the volatiles were stripped in vacuo, and the resulting oil was taken up in EtOAc (10 mL) and washed with 1 N HCl. The organic layer was removed, dried and purified by preparative reversed-phase HPLC (acetonitrile/water, 0.05% TFA) to afford the title compound as a white foam (46 mg, 0.098 mmol, 36%). MS (ESI): m/z 471 [M+H]+, 493 [M+Na]+. $^1$H NMR (400 MHz, CDCl$_3$): (rotameric broadening) 8.86 (bs, 1H), 8.28 (dd, J=7.0, 1.0 Hz, 1H), 8.24 (dd J=8.8 Hz, 1.0 Hz, 1H), 7.93 (s, 1H), 7.70 (dd, J=8.8, 7.0 Hz, 1H), 7.30 (m, 1H), 7.18 (d, J=8.0 Hz, 1H) 3.49-3.44 (bs, 2H), 3.02-2.96 (bs, 2H) 1.62 (bs, 2H), 1.53-1.25 (bs, 4H). Elemental analysis: calculated for C$_{19}$H$_{17}$F$_3$N$_4$O$_3$S$_2$, C, 48.50; H, 3.64; N, 11.91. found C, 48.69; H, 3.43; N, 11.93.

Example 33

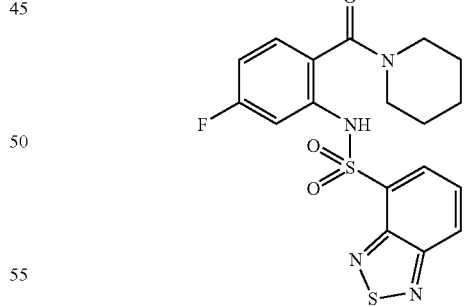

Benzo[1,2,5]thiadiazole-4-sulfonic acid [5-fluoro-2-(piperidine-1-carbonyl)-phenyl]-amide This compound was prepared as described for the trifluoromethyl analog in EXAMPLE 32 substituting 2-nitro-4-fluoromethylbenzoic acid for 2-nitro-4-trifluoromethylbenzoic acid piperidine in Step A. HPLC (reversed-phase): R$_T$=9.30 min (single peak). MS (ESI): m/z 421 [M+H]+, 443 [M+Na]+. $^1$H NMR (400 MHz, CDCl$_3$): (rotameric broadening) 9.18 (bs, 1H), 8.29 (dd, J=7.0, 1.0 Hz, 1H), 8.23 (dd J=8.8, 1.0 Hz, 1H), 7.70 (dd, J=8.8, 7.0 Hz, 1H), 7.41 (dd, J=10.8, 2.5 Hz, 1H) 7.05 (dd, J=8.6, 6.1 Hz, 1H), 6.71 (dd, J=8.6, 7.0, 2.5 Hz, 1H), 3.26-3.22 (bs, 4H), 1.62-1.57 (m, 2H), 1.47 (bs, 4H). Elemental analysis: calculated for $C_{18}H_{17}FN_4O_3S_2$, C, 51.42; H, 4.08; N, 13.32. found C, 51.12; H, 4.01; N, 13.17.

Example 34

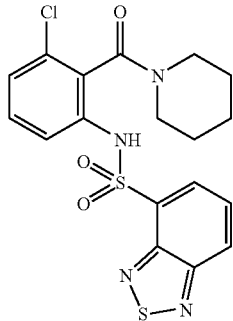

Benzo[1,2,5]thiadiazole-4-sulfonic acid [3-chloro-2-(piperidine-1-carbonyl)-phenyl]-amide To a solution of 2-amino-6-chlorobenzoic acid (1.2 g, 7.0 mmol) in acetonitrile (17 mL) was added piperidine (0.63 mL, 6.3 mmol) followed by EDC (1.46 g, 7.6 mmol) and DMF (21 mL). The mixture was stirred at ambient temperature overnight. An additional 20 mol % piperidine and EDC was added, and the reaction mixture was stirred 3 h. The mixture was diluted with EtOAc and washed repeatedly with 1 N NaOH then brine. The organic layer was dried ($Na_2SO_4$), filtered, and purified on silica gel (MPLC, hexanes/EtOAc, 15% to 70%) to provide amino-6-chlorobenzoic acid piperidine amide as a white solid (0.21 g), which was used directly in the next reaction. The title compound was prepared from amino-6-chlorobenzoic acid piperidine amide (60. mg, 0.25 mmol), 4-chlorosulfonyl-2,1,3-benzothiadiazole (61 mg, 0.26 mmol) and pyridine (0.031 mL, 0.38 mmol), and purified as described in EXAMPLE 32. HPLC (reversed-phase): $R_T$=9.15 min (single peak). MS (ESI): m/z 437/439 [M+H]$^+$, 459/461 [M+Na]$^+$. $^1$H NMR (400 MHz, CDCl$_3$): 8.24 (dd, J=3.3, 1.0 Hz, 1H), 8.23 (dd, J=1.6, 1.0 Hz, 1H), 7.71 (s, 1H), 7.68 (dd, J=8.7, 7.2 Hz, 1H), 7.31 (dd, J=8.1, 1.0 Hz, 1H), 7.16 (dd, J=8.1, 8.1 Hz, 1H), 7.10 (dd, J=8.1, 1.0 Hz, 1H), 3.67 (m, 1H), 3.54 (m, 1H), 3.16 (m, 1H), 3.02 (m, 1H), 1.65 (m, 5H), 1.48 (m, 1H).

Example 35

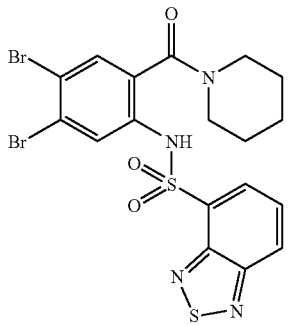

Benzo[1,2,5]thiadiazole-4-sulfonic acid [4,5-di-bromo-2-(piperidine-1-carbonyl)-phenyl]-amide A. [5-Nitro-2-(piperidine-1-carbonyl)-phenyl]-carbamic acid tert-butyl ester. To a solution of 2-amino-4-nitrobenzoic acid piperidine amide (EXAMPLE 2; 0.73 g, 2.9 mmol) in dry DMF (5 mL) was added triethylamine (TEA) (0.40 mL, 2.9 mmol) followed by di-t-butyldicarbonate (0.70 g, 3.2 mmol). After 24 h, an additional 0.45 g di-t-butyldicarbonate was added, and the mixture was heated gently at 50° C. The reaction was monitored by TLC. Volatiles were removed in vacuo, and the resulting oil was purified on silica gel (MPLC, hexanes/EtOAc 10% to 70%) to afford the desired Boc-protected aniline (0.35 g, 1.0 mmol, 34%). MS (ESI): pos. ion m/z 372 [M+H]$^+$, neg. ion m/z 348 [M–H]$^-$. $^1$ NMR (400 MHz, CDCl$_3$): 9.08 (s, 1H), 7.91 (s, 1H), 7.86 (dd, J=8.2, 2.3 Hz, 1H), 3.73 (bm, 2H), 3.33 (bm, 2H), 1.62 (bm, 3H), 1.57 (bm, 3H), 1.53 (s, 9H).

B. [5-Amino-2-(piperidine-1-carbonyl)-phenyl]-carbamic acid tert-butyl ester. A solution of [5-nitro-2-(piperidine-1-carbonyl)-phenyl]-carbamic acid tert-butyl ester (0.16 g, 0.46 mmol) in ethanol (8 mL), containing 1,4-cyclohexadiene (0.64 mL, 6.8 mmol) and Pd on carbon (10 wt %, 0.022 g) was refluxed overnight. The cooled suspension was filtered through Celite®, and concentrated in vacuo. The crude product was purified on silica gel (MPLC, hexanes/EtOAc 10% to 50%) to provide the aniline as a solid (0.050 g, 0.16 mmol, 34%). MS (ESI): pos. ion m/z 320 [M+H]$^+$, 342 [M+Na]$^+$, 661 [2M+Na]$^+$. $^1$H NMR (400 MHz, CDCl$_3$): 8.52 (bs, 1H), 7.62 (bs, 1H), 6.99 (d, J=8.2 Hz, 1H), 6.29 (bd, J=8.0 Hz, 1H), 3.55 (m, 4H), 1.68 (m, 3H), 1.61 (m, 3H), 1.49 (s, 9H).

C. [4,5-Dibromo-2-(piperidine-1-carbonyl)-phenyl]-carbamic acid tert-butyl ester. An oven dried round-bottom flask was purged with nitrogen and charged with CuBr$_2$ (0.040 g, 0.18 mmol) and anhydrous acetonitrile (0.5 mL). t-Butylnitrite (90%), 0.028 mL, 0.24 mmol) was added via syringe, and the reaction mixture was cooled in ice with stirring. [5-Amino-2-(piperidine-1-carbonyl)-phenyl]-carbamic acid tert-butyl ester (0.040 g, 0.13 mmol) was added in small portions over 5 min. The reaction mixture was allowed to warm slowly to ambient temperature over 6.5 h then was partitioned between water and EtOAc. The aqueous layer was extracted with EtOAc (2×), and the combined organic layers were washed with brine and dried (Na$_2$SO$_4$). The crude product was purified on silica gel (MLPC, hexanes/EtOAc 10% to 30%) to provide the dibromo arene as an oil (0.016 g, 0.035 mmol, 30%). MS (ESI): neg. ion m/z 459/461/463 [M–H]$^-$. $^1$H NMR (400 MHz, CDCl$_3$): 8.55 (s, 1H), 7.88 (bs, 1H), 7.38 (s, 1H), 3.56 (bs, 4H), 1.70 (m, 3H), 1.60 (m, 3H), 1.49 (s, 9H).

D. Benzo[1,2,5]thiadiazole-4-sulfonic acid [4,5-dibromo-2-(piperidine-1-carbonyl)-phenyl]-amide. [4,5-Dibromo-2-(piperidine-1-carbonyl)-phenyl]-carbamic acid tert-butyl ester (0.015 g, 0.032 mmol) was dissolved in TFA (2 mL) and allowed to stand at ambient temperature for 1 h. The TFA was removed in vacuo, and the resulting oil was taken up in DCM and washed with 5% aqueous NaHCO$_3$. The organic layer was dried (MgSO$_4$), filtered, and concentrated to give the aniline as a crude oil, which was used directly without purification. The aniline was coupled with 4-chlorosulfonyl-2,1,3-benzothiadiazole (0.010 g, 0.039 mmol), and product was purified, as described in EXAMPLE 32 to provide Benzo[1,2,5]thiadiazole-4-sulfonic acid [4,5-dibromo-2-(piperidine-1-carbonyl)-phenyl]-amide. (0.0034 g, 0.0061 mmol), 20%, two steps). HPLC (reversed-phase): $R_T$=10.15 min (single peak). MS (ESI): m/z ~561 [M+H]$^+$, ~582 [M+Na]$^+$. $^1$H NMR (400 MHz, CDCl$_3$): (rotameric broadening) 8.81 (s, 1H), 8.27 (dd, J=4.1, 1.0 Hz, 1H), 8.25 (dd, J=6.0, 1.0 Hz, 1H), 7.95 (s, 1H), 7.71 (dd, J=8.8, 7.0 Hz, 1H), 7.28 (s, 1H), 3.3-2.8 (bs, 4H), 1.72 (m, 3H), 1.47 (m, 3H).

Example 36

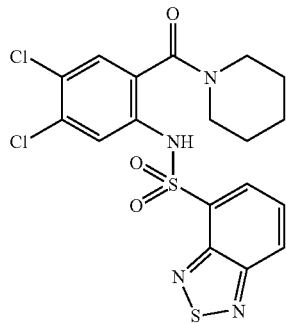

Benzo[1,2,5]thiadiazole-4-sulfonic acid [4,5-dichloro-2-(piperidine-1-carbonyl)-phenyl]-amide A. 1-Bromo-4,5-dichloro-2-nitro-benzene. 4-Bromo-1,2-dichlorobenzene (10.5 g, 46.3 mmol) was added to 25 mL concentrated sulfuric acid at 0° C. A 1:1 mixture of 70% nitric acid and concentrated sulfuric acid (20 mL) was added dropwise over 40 min. The reaction mixture was allowed to warm to ambient temperature with stirring over 0.5 h, then was poured onto cracked ice. The resulting mixture was filtered through paper, and the collected solids were washed with water (5×) and then dried at 45° C. under reduced pressure for 30 min to provide 10.7 g of an 88:12 mixture of desired nitroarene to starting material. Recrystalization from absolute ethanol provided 4.76 g of long yellow needles corresponding to a 20:1 mixture of product to starting material. The mother liquor was concentrated and recrystallized twice to provide an additional 1.18 g of product (17:1 mixture with recovered starting material). TLC (silica gel, 1:1 hexanes/EtOAc): $R_f$=0.45. $^1$H NMR (400 MHz, CDCl$_3$): 7.95 (s, 1H), 7.80 (s, 1H).

B. 4,5-Dichloro-2-nitrobenzoic acid methyl ester. Bistriphenyl-phosphinepalladium dichloride (0.039 g, 0.055 mmol) was added to an oven-dried two-neck 25 mL flask fitted with a reflux condenser and a rubber septum and flushed with nitrogen. The flask was repeatedly evacuated and filled with CO (1 atm). A solution of 1-bromo-4,5-dichloro-2-nitrobenzene (1.00 g, 3.69 mmol) in TEA (0.64 mL, 4.6 mmol) and methanol (0.5 mL) was added via syringe, and the reaction mixture was stirred at 60° C. under 1 atm CO for 18 h. The flask was charged with fresh catalyst (0.04 g) and methanol (0.3 mL), and the reaction mixture was allowed to continue stirring an additional 6 h. The mixture was cooled and filtered, and the filtrate was concentrated and purified on silica gel (MPLC, hexanes/EtOAc 3% to 10%) to provide the methyl ester as a yellow oil (0.324 g, 1.30 mmol, 35%). TLC (silica gel, 9:1 hexanes/EtOAc): $R_f$=0.31. $^1$H NMR (400 MHz, CDCl$_3$): 8.03 (s, 1H), 7.84 (s, 1H), 3.93 (s, 3H).

C. 4,5-Dichloro-2-nitrobenzoic acid piperidine amide. A solution of 4,5-dichloro-2-nitrobenzoic acid methyl ester (0.29 g, 1.16 mmol) in 1:1 THF/methanol (4 mL) was stirred as 1 N aqueous LiOH (2 mL) was added. After 1 h, the mixture was acidified with 1 N HCl and extracted with EtOAc (3×). The combined organic layers were washed with brine, dried (MgSO$_4$), filtered, and concentrated to provide crude 4,5-dichloro-2-nitrobenzoic acid as a light yellow solid (0.26 g, 0.90 mmol, 77%). The acid was refluxed in 4 mL thionyl chloride for 2 h, and the crude reaction mixture was concentrated in vacuo. Residual thionyl chloride was removed by the repeated addition and in vacuo stripping of DCM. The acid chloride was placed under high vacuum for 10 min, and then taken up in dry DCM (5 mL). The mixture was cooled in an ice bath. Piperidine (0.46 g, 5.4 mmol, 0.53 mL) was added, and the reaction mixture was allowed to stand at 0° C. overnight. The mixture was diluted with DCM, washed with 1 N HCl (2×), 5% aqueous NaHCO$_3$ and brine, and dried (MgSO$_4$). Filtration and concentration provided 0.32 g of the desired amide, which could not be separated from an impurity (10%) that corresponded to the product of displacement of a chlorine by an additional equivalent of piperidine. HPLC (reversed-phase): $R_T$=9.35 min (90%), 10.58 (10%). MS (ESI): m/z 303 [M+H]$^+$, minor m/z 352 [M+Na]$^+$.

D. Benzo[1,2,5]thiadiazole-4-sulfonic acid [4,5-dichloro-2-(piperidine-1-carbonyl)-phenyl]-amide. 4,5-dichloro-2-nitrobenzoic acid piperidine amide (0.30 g, 0.98 mmol) was reduced with SnCl$_2$.2 H$_2$O (0.88 g, 3.9 mmol), and the product was purified, as described in EXAMPLE 32 to afford 2-amino-4,5-dichlorobenzoic acid piperidine amide (0.19 g, 0.69 mmol, 70%). The aniline was coupled with 4-chlorosulfonyl-2,1,3-benzothiadiazole (0.18 g, 0.77 mmol), and the product was purified, as described in EXAMPLE 32 to provide the title compound as a light yellow solid (0.115 g, 0.244 mmol, 25%, two steps), mp=178-179° C. MS (ESI): m/z ~471 [M+H]$^+$, ~493 [M+Na]$^+$. $^1$H NMR (400 MHz, DMSO-d$_6$): (rotameric broadening) 10.12 (bs, 1H), 8.41 (dd, J=8.8, 1.0 Hz, 1H), 8.17 (dd, J=8.8, 1.0 Hz, 1H), 7.83 (dd, J=8.8, 7.0 Hz, 1H), 7.53 (s, 1H), 7.46 (s, 1H), 3.35 (bs, 2H), 2.88 (bs, 2H) 1.49 (m, 3H), 1.38-1.31 (m, 3H). Elemental analysis: calculated for $C_{18}H_{16}Cl_2N_4O_3S_2$, C, 45.86; H, 3.42; N, 11.89; S, 13.60; Cl, 15.04. found C, 46.10; H, 3.22; N, 11.77; S, 13.74; Cl, 14.94.

Example 37

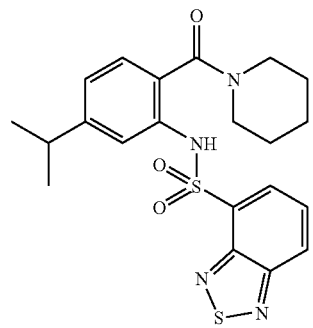

Benzo[1,2,5]thiadiazole-4-sulfonic acid [5-isopropyl-2-(piperidine-1-carbonyl)-phenyl]-amide A. 4-Isopropyl-2-nitrobenzoic acid. A solution of 2-nitro-p-cymene (5.00 g, 27.9 mmol) in dry DMF (30 mL) was heated to 140-150° C. in the presence of DMF-dimethyl acetal (9.98 g, 83.7 mmol) for 16 h. The volatiles were removed in vacuo. The crude enamine was taken up in 60 mL THF, and 50 mL water was added followed by NaIO$_4$ (17.9 g, 83.7 mmol). The deep red solution turned into a yellow slurry within 5 min. After 1 h, the reaction mixture was filtered, and the filtrate was extracted with EtOAc (3×), washed with 5% NaHCO$_3$ (3×) and brine, and dried (MgSO$_4$). Filtration and concentration afforded the crude aldehyde, which was used without further purification. The aldehyde was dissolved in t-butanol (60 mL), and a pH 4.0 acetate buffer (30 mL) was added followed by 2-methyl-2-butene (2.9 g, 41.8 mmol, 4.4 mL). A solution of sodium chlorite (3.0 g, 33.5 mmol) in water (30 mL) was added dropwise over 5 min to the vigorously stirred reaction mixture. After 0.5 h, 100 mL 1 N HCl was added to the reaction mixture, which was then extracted with EtOAc (4×). The combined organic layers were extracted with 1 N aqueous NaOH (5×30 mL). The basic extracts were combined, acidified with 225 mL 1 N HCl to pH 1, and extracted with EtOAc (5×). The combined organic extracts were washed with brine, dried (MgSO$_4$), mixed with decolorizing carbon, and filtered through Celite®. Concentration provided 4-isopropyl-2-nitrobenzoic acid as an off-white solid (2.13 g, 10.5 mmol, 38%, three steps). $^1$H NMR (400 MHz, CDCl$_3$): 8.44 (bs, 1H), 7.77 (d, J=8.0 Hz, 1H), 7.56 (d, J=1.5 Hz, 1H), 7.45 (dd, J=8.0, 1.5 Hz, 1H), 2.96 (m, 1H), 1.22 (d, J=6.8 Hz, 6H).

B. 4-Isopropyl-2-nitrobenzoic acid piperidine amide. 4-Isopropyl-2-nitrobenzoic acid (3.05 g, 15.1 mmol) was dissolved in 20 mL thionyl chloride and refluxed for 40 min. The thionyl chloride was distilled off. Residual thionyl chloride was stripped from the resulting oil using DCM as described in EXAMPLE 36 step C. The crude acid chloride was taken up in fresh DCM (45 mL), and piperidine (7.7 g, 91 mL) was added. After 24 h, the volatiles were removed in vacuo, and the residue was taken up in EtOAc. The resulting solution was washed with 1 N HCl (3×), 5% aqueous NaHCO$_3$ and brine, and dried (MgSO$_4$). Filtration and concentration, followed by purification on silica gel (MPLC, hexanes/EtOAc 10% to 50%) provided the amide as a light yellow solid (3.43 g, 12.4 mmol, 82%). MS (ESI): m/z 277 [M+H]$^+$, 553 [2M+Na]$^+$, 575 [2M+Na]$^+$. $^1$H NMR (400 MHz, CDCl$_3$): 8.03 (d, J=1.7 Hz, 1H) 7.55 (ddd, J=7.8, 1.7, 0.4 Hz, 1H) 7.30 (d, J=7.8 Hz, 1H), 3.77 (bm, 2H), 3.18 (t, J=5.6 Hz, 2H), 3.00 (m, 1H), 1.42 (m, 3H) 1.52 (bm, 3H), 1.31 (d, J=6.8 Hz, 6H).

C. Benzo[1,2,5]thiadiazole-4-sulfonic acid [5-isopropyl-2-(piperidine-1-carbonyl)-phenyl]-amide. 4-Isopropyl-2-nitrobenzoic acid piperidine amide (3.43 g, 12.4 mmol) was reduced with SnCl$_2$.2 H$_2$O (11.2 g, 49.6 mmol), and the product was purified, as described in EXAMPLE 32. The resulting aniline (0.217 g, 0.882 mmol) was coupled with 4-chlorosulfonyl-2,1,3-benzothiadiazole (0.248 g, 1.06 mmol) and pyridine (0.105 g, 1.32 mmol), and the product was purified, as described in EXAMPLE 32 to provide benzo[1,2,5]thiadiazole-4-sulfonic acid [5-isopropyl-2-(piperidine-1-carbonyl)-phenyl]-amide (45%, two steps). mp=125-127° C. MS (ESI): m/z 445 [M+H]$^+$, 467 [M+Na]$^+$, 911 (2M+Na$^+$). $^1$H NMR (400 MHz, CDCl$_3$): (rotameric broadening) 8.22 (dd, J=7.0, 1.0 Hz, 1H), 8.20 (dd, J=8.0, 1.0 Hz, 1H), 7.65 (dd, J=8.8, 1.0 Hz, 1H), 7.49 (dd, J=1.5 Hz, 1H), 6.96 (d, J=7.9 Hz, 1H), 6.87 (dd, J=7.9, 1.5 Hz, 1H), 3.38 (bs, 4H), 2.84 (m, 1H), 1.57 (m, 3H), 1.44 (m, 3H) 1.18 (d, J=6.9 Hz, 6H). Elemental analysis: calculated for C$_{21}$H$_{24}$N$_4$O$_3$S$_2$, C, 56.74; H, 5.44; N, 12.60; S, 14.42. found C, 56.95; H, 5.78; N, 12.64; S, 14.38.

Example 38

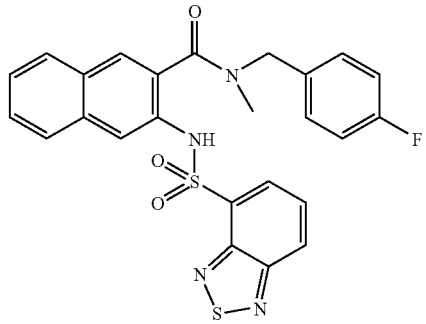

3-(Benzo[1,2,5]thiadiazole-4-sulfonylamino)-naphthalene-2-carboxylic acid (4-fluoro-benzyl)-methylamide A. 3-Amino-naphthalene-2-carboxylic acid methyl ester. To a solution of 1H-naphtho[2,3-d][1,3]oxazine-2,4-dione (4.99 g, 23.4 mmol) in dry DMF (25 mL) was added dry methanol (9.5 mL, 234 mmol) and DMAP (0.28 g, 2.34 mmol). After 16 h, the reaction mixture was partitioned between EtOAc and water, and the organic layer was washed with water (3×) and dried (MgSO$_4$). Purification on silica gel (MPLC, hexanes/EtOAc) provided the methyl ester as a yellow solid (2.12 g, 10.6 mmol, 45%). HPLC (reversed-phase): R$_T$=8.59 min). $^1$H NMR (400 MHz, CDCl$_3$): 8.50 (s, 1H), 7.71 (d, J=8.3 Hz, 1H) 7.53 (d, J=8.3 Hz, 1H) 7.40 (m, 1H), 7.19 (m, 1H), 6.98 (m, 1H), 5.7 (bs, 2H), 3.97 (s, 3H).

B. 3-(Benzo[1,2,5]thiadiazole-4-sulfonylamino)-naphthalene-2-carboxylic acid methyl ester. Benzo[1,2,5]thiadiazole-4-sulfonyl chloride (2.62 g, 11.1 mmol) was added to solution of 3-aminonaphthalene-2-carboxylic acid methyl ester (1.5 g, 7.5 mmol) and pyridine (1.21 mL, 15 mmol) in DCM (20 mL). After 16 h, the reaction mixture was washed with 1 N HCl and dried (MgSO$_4$). Purification on silica gel (MPLC, hexanes/EtOAc) provided the title compound as a yellow solid (1.91 g, 4.86 mmol, 65%). MS (ESI): neg. ion m/z 398 [M−H]$^-$. HPLC (reversed-phase): R$_T$=9.97 min). $^1$H NMR (500 MHz, CDCl$_3$): 8.43 (s, 1H), 8.40 (dd, J=7.1, 1.0 Hz, 1H) 8.15 (dd, J=8.8, 1.0 Hz, 1H), 8.07 (s, 1H), 7.72 (bd, J=9.2 Hz, 2H), 7.64 (dd, J=8.8, 7.7 Hz, 1H), 7.52 (m, 1H), 7.38 (m, 1H), 3.97 (s, 3H).

C. 3-(Benzo[1,2,5]thiadiazole-4-sulfonylamino)-naphthalene-2-carboxylic acid. 3-(Benzo[1,2,5]thiadiazole-4-sulfonylamino)-naphthalene-2-carboxylic acid methyl ester (1.91 g, 4.78 mmol) was dissolved in 3:1 THF/water (10 mL). Lithium hydroxide monohydrate (2 g, 50 mmol) was added, and the reaction mixture was stirred at ambient temperature for 16 h. The mixture was acidified with 1 N HCl, and the resulting precipitate was collected via filtration and washed with water. Drying in air provided the title acid as a tan solid (1.63 g, 4.23 mmol, 89%). MS (ESI): neg. ion m/z 384 [M−H]$^-$. $^1$H NMR (400 MHz, CDCl$_3$): 10.97 (s, 1H), 8.61 (s, 1H), 8.43 (dd, J=7.1, 1.0 Hz, 1H) 8.17 (dd, J=8.8, 1.0 Hz, 1H), 8.13 (s, 1H), 7.77 (dd, J=15.8, 8.2 Hz, 2H), 7.67 (dd, J=8.8, 7.7 Hz, 1H), 7.56 (m, 1H), 7.42 (m, 1H).

D. 3-(Benzo[1,2,5]thiadiazole-4-sulfonylamino)-naphthalene-2-carboxylic acid (4-fluoro-benzyl)-methylamide. 3-(Benzo[1,2,5]thiadiazole-4-sulfonylamino)-naphthalene-2-carboxylic acid was coupled with (4-fluorobenzyl)methylamine as described in EXAMPLE 7 to provide the title compound. MS (ESI): m/z 507 [M+H]$^+$, 529 [M+Na]$^+$. HPLC (reversed-phase): $R_T$=9.82 min). $^1$H NMR (400 MHz, CDCl$_3$) (rotameric mixture): 8.93 (s, 1H), 8.31 (m, 1H), 8.18 (m, 1H), 7.98 (m, 1H), 7.73 (m, 1H), 7.62 (m, 2H), 7.54 (m, 1H), 7.46 (m, 1H), 7.33 (m, 3H), 7.09 (m, 2H), 4.58 (m, 2H), 2.55 (bs, 3H).

Example 39

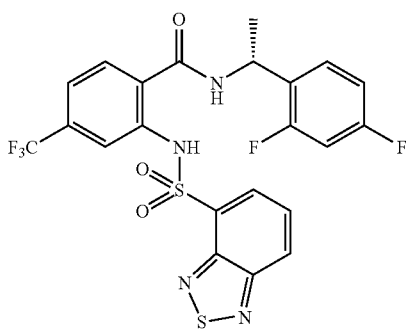

(R)-2-(Benzo[1,2,5]thiadiazole-4-sulfonylamino)-N-[1-(2,4-difluoro-phenyl)-ethyl]-4-trifluoromethyl-benzamide A. S—(S)-2-Methyl-propane-2-sulfinic acid 2,4-difluoro-benzylideneamide. A suspension of 2,4-difluorobenzaldehyde (0.61 g, 4.3 mmol), (S)-tert-butanesulfinamide (0.47 g, 3.9 mmol), and powdered anhydrous CuSO$_4$ (1.24 g, 7.8 mmol) was stirred in DCM (8 mL) overnight. The reaction mixture was filtered, and the filter cake was washed with DCM. The filtrate was concentrated in vacuo to give the crude N-sulfinyl imine as a viscous yellow oil. Purification by flash chromatography (EtOAc/hexanes) provided 0.81 g (84%) of the N-sulfinyl imine as a pale yellow viscous oil. $^1$H NMR (400 MHz, CDCl$_3$): 8.83 (s, 1H), 8.02 (m, 1H), 6.98 (m, 1H), 6.90 (m, 1H), 1.27 (s, 9H).

B. S—(S)-2-Methyl-propane-2-sulfinic acid 1-(R)-[1-2,4-difluoro-phenyl)-ethyl]-amide. To a stirred solution of the above N-sulfinyl imine (0.77 g, 3.1 mmol) in DCM (20 mL) at −50° C., was added a solution of methyl magnesium bromide (3.0 M in Et$_2$O) (2.1 mL, 6.3 mmol). The reaction mixture was stirred at −50° C. for 1 h then allowed to warm to room temperature slowly overnight. The reaction was quenched by the addition of a saturated aqueous NH$_4$Cl, and the mixture was poured into water, and extracted with DCM (3×). The combined organic layers were dried (Na$_2$SO$_4$) and concentrated in vacuo. Purification by flash chromatography (EtOAc/hexanes) provided the title compound as a mixture of diastereomers: ratio S—(S), 1-(R) to S—(S), 1-(S)=95:5 ($^1$H NMR); 90% de. Combined yield for both diastereomers, 0.80 g (99%) of a colorless viscous oil. Major diastereomer: $^1$H NMR (400 MHz, CDCl$_3$): 7.32 (m, 1H), 6.87 (m, 1H), 6.80 (m, 1H), 4.82 (dq, J=6.8, 4.5 Hz, 1H), 3.32 (d, J=4.1 Hz, 1H), 1.56 (d, J=6.8 Hz, 3H), 1.19 (s, 9H).

C. (R)-1-(2,4-Difluoro-phenyl)-ethylamine hydrochloride. To a stirred solution of the above sulfinamide (90% de) (0.80 g, 3.06 mmol) in methanol (7 mL) at ambient temperature, was added 2 mL of a saturated solution of HCl (g) in methanol. After several minutes, precipitated amine hydrochloride was visible. The reaction mixture was allowed to stir for 2 h at ambient temperature. The heterogeneous mixture was concentrated in vacuo until approximately 2 mL of methanol remained, and then the amine hydrochloride was fully precipitated by the addition of Et$_2$O (10 mL). The white solid HCl salt was collected by suction filtration, washed with Et$_2$O, and dried in vacuo. Yield=573 mg (97%), fine white crystals (99% ee). Enantiomeric purity was determined by HPLC on the benzamide derivative of the amine. Chiralcel AS column, 90:10 hexanes/isopropyl alcohol with 0.1% diethylamine, 0.7 mL/min. R enantiomer, $t_r$=18.1 min. S enantiomer, $t_r$=21.0 min. $[\alpha]_D^{20}$=−3.7° (H$_2$O, c=4.37 g/100 mL). $^1$H NMR (400 MHz, methanol-d$_4$): 7.57 (m, 1H), 7.12 (m, 1 H), 7.09 (m, 1H), 4.72 (q, J=7.0 Hz, 1H), 1.65 (d, J=6.8 Hz, 3H).

D. 2-Amino-4-trifluoromethylbenzoic acid methyl ester. To a stirred solution of 2-nitro-4-trifluoromethylbenzoic acid (6.0 g, 25 mmol) in dry DMF (30 mL) at 0° C. was added DBU (35 mL, 25 mmol) followed in 15 min by iodomethane (16 mL, 25 mmol). The reaction mixture was allowed to warm to ambient temperature and stir overnight, then was partitioned between water and EtOAc. The organic layer was washed with water and dried (MgSO$_4$), and the resulting crude product was purified on silica gel (MPLC, hexanes/EtOAc) to provide the methyl ester as a yellow oil (5.7 g, 91%). This material was immediately dissolved in 3:1 EtOAc/DCM (50 mL), and SnCl$_2$.2 H$_2$O (26 g, 110 mmol) was added with stirring. The mixture was held at ambient temperature for 16 h, then 5% aqueous NaHCO$_3$ was added cautiously. The aqueous phase was extracted with DCM (3×), and the combined organic layers were dried (MgSO$_4$). Filtration and concentration provided the aniline as a light yellow solid (4.5 g, 21 mmol, 84% for two steps). HPLC (reversed-phase): $R_T$=9.38 min. $^1$H NMR (400 MHz, CDCl$_3$): 7.95 (d, J=8.3 Hz, 1H), 6.91 (s, 1H), 6.85 (d, J=8.6, 1.3 Hz, 1H), 6.2-5.5 (bs, 2H), 3.90 (s, 3H).

E. 2-(Benzo[1,2,5]thiadiazole-4-sulfonylamino)-4-trifluoromethylbenzoic acid methyl ester. 2-Amino-4-trifluoromethylbenzoic acid methyl ester (1.5 g, 6.8 mmol) was coupled with benzo[1,2,5]thiadiazole-4-sulfonyl chloride (2.4 g, 10 mmol), and the product was purified, as described in EXAMPLE 38 to provide the title compound (0.8 g, 28%). MS (ESI): neg. ion m/z 416 [M−H]$^-$. HPLC (reversed-phase): $R_T$=10.03 min). $^1$H NMR (500 MHz, CDCl$_3$): 11.33 (s, 1H), 8.40 (dd, J=7.1, 1.0 Hz, 1H), 8.23 (dd, J=8.8, 1.0 Hz, 1H), 8.04 (s, 1H), 7.98 (d, J=8.2 Hz, 1H), 7.72 (dd, J=8.8, 7.1 Hz, 1H), 7.18 (m, 1H), 3.96 (s, 3H).

F. 2-(Benzo[1,2,5]thiadiazole-4-sulfonylamino)-4-trifluoromethylbenzoic acid. 2-(Benzo[1,2,5]thiadiazole-4-sulfonylamino)-4-trifluoromethylbenzoic acid methyl ester (0.8 g, 2 mmol) was hydrolyzed with lithium hydroxide monohydrate (0.8 g, 2 mmol), and the product was purified, as described in EXAMPLE 38 to provide the carboxylic acid as a tan solid (0.75 g, 1.9 mmol, quant.). MS (ESI): neg. ion m/z 402 [M−H]$^-$. $^1$H NMR (500 MHz, CDCl$_3$): 11.29 (s, 1H), 8.42 (dd, J=7.1, 1.0 Hz, 1H), 8.24 (dd, J=8.8, 1.0 Hz, 1H), 8.07 (d, J=8.2 Hz, 1H), 8.05 (s, 1H), 7.73 (dd, J=8.8, 7.1, Hz, 1H), 7.22 (m, 1H).

G. (R)-2-(Benzo[1,2,5]thiadiazole-4-sulfonylamino)-N-[1-(2,4-difluorophenyl)-ethyl]-4-trifluoromethylbenzamide. 2-(Benzo[1,2,5]thiadiazole-4-sulfonylamino)-4-trifluoromethylbenzoic acid was couple with (R) 1-(2,4-difluorophenyl)-ethylamine, and the product was purified, as described in EXAMPLE 7 to provide the title compound. MS (ESI): m/z 543 [M+H]+, 565 [M+Na]+. HPLC (reversed-phase): $R_T$=10.20 min). $^1$H NMR (400 MHz, CDCl$_3$): 11.40 (s, 1H), 8.36 (dd, J=7.1, 1.0 Hz, 1H), 8.20 (dd, J=8.8, 1.0 Hz, 1H), 8.00 (m, 1H), 7.70 (dd, J=8.8, 7.1 Hz, 1H), 7.42 (d, J=8.2 Hz, 1H), 7.33 (ddd, J=8.5, 8.5, 6.2 Hz, 1H), 7.21 (dd, J=8.1, 1.0 Hz, 1H), 6.90 (m, 1H), 6.85 (m, 1H), 6.46 (bd, J=8.1 Hz, 1H), 5.35 (m, 1H), 1.58 (d, J=6.9 Hz, 3H).

Example 40

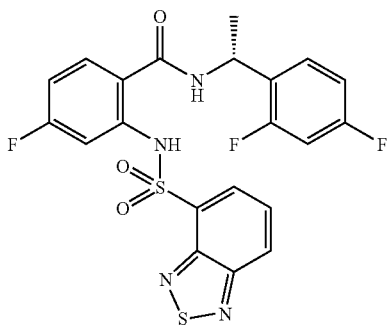

(R)-2-(Benzo[1,2,5]thiadiazole-4-sulfonylamino)-N-[1-(2,4-difluorophenyl)-ethyl]-4-fluorobenzamide A. 2-Amino-4-fluorobenzoic acid methyl ester. 2-Amino-4fluorobenzoic acid (5.0 g, 32 mmol) was dissolved in DCM (50 mL) and cooled to 0° C. Hünig's base (11 ml, 64 mmol) was added followed by triphosgene (3.8 g, 13 mmol). The reaction mixture was stirred for 5 min then allowed to warm to ambient temperature over 45 min. Water was added to the mixture, which was then extracted with DCM (3×), and the combined organic layers were dried (MgSO$_4$). Filtration and concentration provided 7-fluoro-1H-benzo[d][1,3]oxazine-2,4-dione as a tan solid (3.94 g, 21.8 mmol, 68%), which was taken on directly to the next step. To a solution of 7-fluoro-1H-benzo[d][1,3]oxazine-2,4-dione (3.94 g, 21.8 mmol) in DMF (20 mL) was added dry methanol (8.8 mL, 220 mmol) and DMAP (0.27 g, 2.2 mmol). The mixture was allowed to stand overnight, and was then partitioned between EtOAc and water. The organic layer was washed with water (3×) and dried (MgSO$_4$). Filtration and purification on silica gel (MLPC, hexanes/EtOAc) provided the title methyl ester as a white solid (1.89 g, 11.1 mmol, 51%). HPLC (reversed-phase): $R_T$=8.66 min). $^1$H NMR (400 MHz, CDCl$_3$): 7.87 (m, 1H), 6.37 (m, 2H), 3.86 (s, 3H).

B. 2-(Benzo[1,2,5]thiadiazole-4-sulfonylamino)-4-fluorobenzoic acid methyl ester. 2-Amino-4-fluorobenzoic acid methyl ester (1.89 g, 11.2 mmol) was coupled with benzo[1,2,5]thiadiazole-4-sulfonyl chloride (4.0 g, 17 mmol), and the product was purified, as described in EXAMPLE 38 to provide the title compound (1.34 g, 3.65 mmol, 33%). MS (ESI): neg. ion m/z 366 [M–H]−. HPLC (reversed-phase): $R_T$=9.52 min). $^1$H NMR (400 MHz, CDCl$_3$): 11.50 (s, 1H), 8.40 (dd, J=7.1, 1.0 Hz, 1H), 8.23 (dd, J=8.8, 1.0 Hz, 1H), 7.89 (dd, J=8.8, 6.4 Hz, 1H), 7.72 (dd, J=8.8, 7.1, Hz, 1H), 7.47 (dd, J=11.0, 2.5 Hz, 1H), 6.65 (m, 1H), 3.92 (s, 3H).

C. 2-(Benzo[1,2,5]thiadiazole-4-sulfonylamino)-4-fluorobenzoic acid. 2-(Benzo[1,2,5]thiadiazole-4-sulfonylamino)-4-fluorobenzoic acid methyl ester (1.34 g, 3.65 mmol) was hydrolyzed with lithium hydroxide monohydrate (1.53 g, 36.5 mmol), and the product was purified, as described in EXAMPLE 38 to provide the title carboxylic acid as a tan solid (1.04 g, 2.94 mmol, 81%). MS (ESI): neg. ion m/z 352 [M–H]−. $^1$H NMR (400 MHz, CDCl$_3$): 11.31 (s, 1H), 8.42 (dd, J=7.1, 1.0 Hz, 1H), 8.25 (dd, J=8.8, 1.0 Hz, 1H), 8.03 (dd, J=8.8, 6.4 Hz, 1H), 7.74 (dd, J=8.8, 7.1, Hz, 1H), 7.52 (dd, J=11.0, 2.4 Hz, 1H), 6.72 (m, 1H).

D. (R)-2-(Benzo[1,2,5]thiadiazole-4-sulfonylamino)-N-[1-(2,4-difluorophenyl)-ethyl]-4-fluorobenzamide. 2-(Benzo[1,2,5]thiadiazole-4-sulfonylamino)-4-fluorobenzoic acid was coupled with (R) 1-(2,4-difluorophenyl)-ethylamine (see EXAMPLE 39), and the product was purified, as described in EXAMPLE 7 to provide the title compound. MS (ESI): m/z 493 [M+H]+, 515 [M+Na]+. HPLC (reversed-phase): $R_T$=9.84 min). $^1$H NMR (400 MHz, CDCl$_3$) 11.73 (s, 1H), 8.35 (dd, J=7.1, 1.0 Hz, 1H), 8.19 (dd, J=8.8, 1.0 Hz, 1H), 7.69 (dd, J=8.8, 7.0 Hz, 1H), 7.46 (dd, J=11, 2.5 Hz, 1H), 7.32 (m, 2H), 6.92 (m, 1H), 6.84 (m, 1H), 6.66 (m, 1H), 6.34 (bd, J=7.6 Hz, 1H), 5.36 (m, 1H), 1.57 (d, J=6.8 Hz, 3H).

Example 41

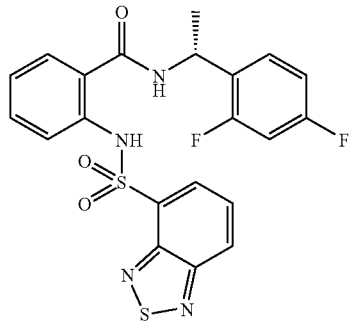

(R)-2-(Benzo[1,2,5]thiadiazole-4-sulfonylamino)-N-[1-(2,4-difluoro-phenyl)-ethyl]-benzamide A. 2-(Benzo[1,2,5]thiadiazole-4-sulfonylamino)benzoic acid methyl ester. Methyl 2-aminobenzoate (2.5 g, 16 mmol) was coupled with benzo[1,2,5]thiadiazole-4-sulfonyl chloride (2.44 g, 6.99 mmol), and the product was purified, as described in EXAMPLE 38 to provide the title compound (1.34 g, 3.65 mmol, 42%). TLC (silica gel, 2:3 EtOAc/hexanes): $R_f$=0.41. $^1$H NMR (400 MHz, CDCl$_3$): 11.27 (s, 1H), 8.37 (dd, J=7.1, 1.0 Hz, 1H), 8.19 (dd, J=8.8, 1.0 Hz, 1H), 7.85 (dd, J=7.9, 1.5 Hz, 1H), 7.71 (m, 1H), 7.68 (dd, J=8.8, 7.0 Hz, 1H), 7.38 (m, 1H), 6.96 (m, 1H), 3.91 (s, 3H).

B. 2-(Benzo[1,2,5]thiadiazole-4-sulfonylamino)benzoic acid. 2-(Benzo[1,2,5]thiadiazole-4-sulfonylamino)benzoic acid methyl ester (2.44 g, 6.98 mmol) was hydrolyzed with lithium hydroxide monohydrate (2.93 g, 69.8 mmol), and the product was purified, as described in EXAMPLE 38 to give the title carboxylic acid as a solid (2.13 g, 6.36 mmol, 91%), $^1$H NMR (500 MHz, CDCl$_3$): 11.11 (s, 1H), 8.39 (dd, J=7.1, 1.0 Hz, 1H), 8.22 (dd, J=8.8, 1.0 Hz, 1H), 7.99 (dd, J=7.9, 1.5 Hz, 1H), 7.77 (dd, J=8.5, 0.6 Hz, 1H), 7.70 (dd, J=8.8, 7.0 Hz, 1H), 7.46 (m, 1H), 7.05 (m, 1H).

D. (R)-2-(Benzo[1,2,5]thiadiazole-4-sulfonylamino)-N-[1-(2,4-difluorophenyl-ethyl]benzamide. 2-(Benzo[1,2,5]thiadiazole-4-sulfonylamino)benzoic acid was coupled with (R) 1-(2,4-difluorophenyl)-ethylamine (see EXAMPLE 39), and the product was purified, as described in EXAMPLE 7 to provide the title compound. MS (ESI): neg. ion m/z 473 [M–H]⁻. HPLC (reversed-phase): $R_T$=9.64 min). $^1$H NMR (400 MHz, CDCl$_3$): 11.38 (s, 1H), 8.32 (dd, J=7.1, 1.0 Hz, 1H), 8.16 (dd, J=8.8, 1.0 Hz, 1H), 7.68 (m, 1H), 7.65 (dd, J=8.8, 7.0 Hz, 1H), 7.30 (m, 3H), 6.98 (m, 1H), 6.88 (m, 1H), 6.85 (m, 1H), 6.40 (bd, J=7.6 Hz, 1H), 5.32 (m, 1H), 1.54 (d, J=6.8 Hz, 3H).

Example 42

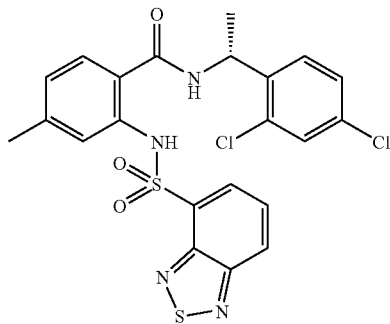

(R)-2-(Benzo[1,2,5]thiadiazole-4-sulfonylamino)-N-[1-(2,4-difluorophenyl)-ethyl]-4-methylbenzamide A. S—(S)-2-Methyl-propane-2-sulfinic acid 2,4-dichlorobenzylideneamide. A suspension of 2,4-dichlorobenzaldehyde (0.75 g, 4.3 mmol), (S)-tert-butanesulfinamide (0.47 g, 3.9 mmol), and powdered anhydrous CuSO$_4$ (1.24 g, 7.8 mmol) in DCM (8 mL) was stirred overnight. The reaction mixture was filtered, and the filter cake was washed with DCM. The filtrate was concentrated in vacuo to give the crude N-sulfinyl imine as white solid. Purification by flash chromatography (EtOAc/hexanes) provided 0.97 g (90%) of the N-sulfinyl imine as a white solid. $^1$H NMR (400 MHz, CDCl$_3$): 8.98 (s, 1H), 8.01 (d, J=8.5 Hz, 1H), 7.48 (d, J=2.1 Hz, 1H), 7.34 (m, 1H), 1.27 (s, 9H).

B. S—(S)-2-Methyl-propane-2-sulfinic acid 1-(R)-[1-2,4-dichloro-phenyl)-ethyl]-amide. To a stirred solution of the above N-sulfinyl imine (0.97 g, 3.5 mmol) in DCM (20 mL) at –50° C. was added a solution of methyl magnesium bromide (3.0 M in Et$_2$O) (2.3 mL, 6.9 mmol). The reaction mixture was stirred at –50° C. for 1 h then allowed to warm to room temperature slowly overnight. The reaction was quenched by the addition of a saturated aqueous NH$_4$Cl, and the mixture was poured into water and extracted with DCM (3×). The combined organic layers were dried (Na$_2$SO$_4$) and concentrated in vacuo. Purification by flash chromatography (EtOAc/hexanes) provided the title compound as a mixture of diastereomers: ratio S—(S), 1-(R) to S—(S), 1-(S)=88:12 ($^1$H NMR); 76% de. Combined yield for both diastereomers, 1.02 g (99%), colorless solid. Major diastereomer: $^1$H NMR (400 MHz, CDCl$_3$): 7.43-7.35 (m, 2H), 7.24 (m, 1H), 5.01 (dq, J=6.7, 4.0 Hz, 1H), 3.39 (d, J=3.7 Hz, 1H), 1.53 (d, J=6.7 Hz, 3H), 1.21 (s, 9H).

C. (R)-1-(2,4-Difluoro-phenyl)-ethylamine hydrochloride. To a stirred solution of the above sulfinamide (76% de) (1.02 g, 3.47 mmol) in 7:4 methanol/DCM (11 mL) at ambient temperature was added 2 mL of a saturated solution of HCl (g) in methanol. After several minutes, precipitated amine hydrochloride was visible. The reaction mixture was allowed to stir for 2 h at ambient temperature. The heterogeneous mixture was concentrated in vacuo until approximately 2 mL of methanol remained, and then the amine hydrochloride was fully precipitated by the addition of Et$_2$O (10 mL). The white solid HCl salt was collected by suction filtration, washed with Et$_2$O, and dried in vacuo. Yield=722 mg (92%), fine white crystals (76% ee). $^1$H NMR (400 MHz, methanol-d$_4$): 7.62 (d, J=2.2 Hz, 1H), 7.57 (d, J=8.4 Hz, 1H), 7.50 (dd, J=8.4, 2.2 Hz, 1H), 1.62 (d, J=6.8 Hz, 3H).

D. 2-(Benzo[1,2,5]thiadiazole-4-sulfonylamino)-4-methylbenzoic acid methyl ester. 2-Amino-4-methyl-benzoic acid methyl ester (1.09 g, 6.60 mmol) was coupled with benzo[1,2,5]thiadiazole-4-sulfonyl chloride (2.32 g, 9.90 mmol), and the product was purified, as described in EXAMPLE 38 to provide the title compound (1.22 g, 3.36 mmol, 53%). $^1$H NMR (500 MHz, CDCl$_3$): 11.28 (s, 1H), 8.36 (dd, J=7.1, 1.0 Hz, 1H), 8.19 (dd, J=8.8, 1.0 Hz, 1H), 7.73 (d, J=8.1 Hz, 1H), 7.68 (dd, J=8.8, 7.1 Hz, 1H), 7.51 (bs, 1H), 6.77 (dd, J=8.1, 0.9 Hz, 1H), 3.89 (s, 3H), 2.28 (s, 3H).

E. 2-(Benzo[1,2,5]thiadiazole-4-sulfonylamino)-4-methylbenzoic acid. 2-(Benzo[1,2,5]thiadiazole-4-sulfonylamino)-4-methylbenzoic acid methyl ester (1.22 g, 3.36 mmol) was hydrolyzed with lithium hydroxide monohydrate (1.41 g, 33.6 mmol), and the product was purified, as described in EXAMPLE 38 to give the title carboxylic acid as a solid (0.89 g, 2.5 mmol, 74%). $^1$H NMR (500 MHz, CDCl$_3$);

F. (R)-2-(Benzo[1,2,5]thiadiazole-4-sulfonylamino)-N-[1-(2,4-dichlorophenyl)-ethyl]-4-methylbenzamide. 2-(Benzo[1,2,5]thiadiazole-4-sulfonylamino)-4-methylbenzoic acid was couple with (R) 1-(2,4-dichlorophenyl)-ethylamine, and the product was purified, as described in EXAMPLE 7 to provide the title compound. MS (ESI): neg. ion m/z 519/521 [M–H]⁻. HPLC (reversed-phase): $R_T$=10.41 min). $^1$H NMR (400 MHz, CDCl$_3$): 11.46 (s, 1H), 8.30 (dd, J=7.1 Hz, 1H), 8.17 (d, J=8.8 Hz, 1H), 7.66 (dd, J=8.8, 7.1 Hz, 1H), 7.51 (s, 1H), 7.42 (s, 1H), 7.24 (m, 3H), 6.79 (d, J=8.0 Hz, 1H), 6.34 (bd, J=7.4 Hz, 1H), 5.38 (m, 1H), 2.28 (s, 3H), 1.53 (d, J=6.8 Hz, 3H).

Example 43

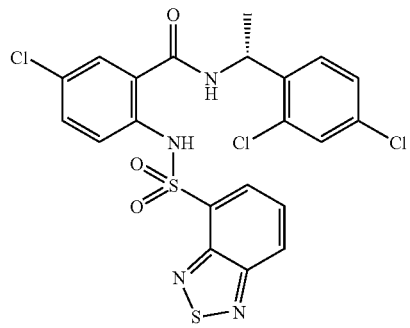

(R)-2-(Benzo[1,2,5]thiadiazole-4-sulfonylamino)-5-chloro-N-[1-(2,4-dichloro-phenyl)-ethyl]-benzamide A. 2-(Benzo[1,2,5]thiadiazole-4-sulfonylamino)-5-chlorobenzoic acid methyl ester. Methyl 2-amino-5-chlorobenzoate (2.0 g, 11 mmol) was coupled with benzo[1,2,5]thiadiazole-4-sulfonyl chloride (3.0 g, 13 mmol), and the product was purified, as described in EXAMPLE 38 to provide the title compound (1.95 g, 5.08 mmol, 47%). $^1$H NMR (500 MHz, CDCl$_3$): 11.15 (s, 1H), 8.34 (dd, J=7.1, 1.0 Hz, 1H), 8.22 (dd, J=8.8, 1.0 Hz, 1H), 7.82 (d, J=2.5 Hz, 1H), 7.71 (m, 1H), 7.69 (m, 1H), 7.34 (dd, J=9.0, 2.5 Hz, 1H), 3.91 (s, 3 H.

B. 2-(Benzo[1,2,5]thiadiazole-4-sulfonylamino)-5-chlorobenzoic acid. 2-(Benzo[1,2,5]thiadiazole-4-sulfonylamino)-5-chlorobenzoic acid methyl ester (2.23 g, 5.81 mmol) was hydrolyzed with lithium hydroxide monohydrate (2.44 g, 58.1 mmol), and the product was purified, as described in EXAMPLE 38 to give the title carboxylic acid as a solid (1.7 g, 4.6 mmol, 79%), $^1$H NMR (500 MHz, CDCl$_3$): 11.15 (s, 1H), 8.36 (dd, J=7.1, 1.0 Hz, 1H), 8.23 (dd, J=8.8, 1.0 Hz, 1H), 7.90 (d, J=2.5 Hz, 1H), 7.72 (m, 1H), 7.70 (m, 1H), 7.37 (dd, J=9.0, 2.5 Hz, 1H).

C. (R)-2-(Benzo[1,2,5]thiadiazole-4-sulfonylamino)-5-chloro-N-[1-(2,4-dichloro-phenyl)-ethyl]-benzamide.
2-(Benzo[1,2,5]thiadiazole-4-sulfonylamino)-5-chlorobenzoic acid was coupled with (R) 1-(2,4-dichlorophenyl)-ethylamine (see EXAMPLE 42), and the product was purified, as described in EXAMPLE 7 to provide the title compound. MS (ESI): neg. ion m/z 539/541/543 [M−H]$^−$. HPLC (reversed-phase): R$_T$=10.67 min). $^1$H NMR (500 MHz, CDCl$_3$): 11.11 (s, 1H), 8.29 (dd, J=7.1, 1.0 Hz, 1H), 8.17 (d, J=8.8, 1.0 Hz, 1H), 7.68 (m, 1H), 7.66 (m, 1H), 7.43 (dd, J=1.5, 0.5 Hz, 1H), 7.29 (m, 2H), 7.25 (m, 2H), 6.32 (bd, J=7.4 Hz, 1H), 5.36 (m, 1H), 1.54 (d, J=6.8 Hz, 3H).

Example 44

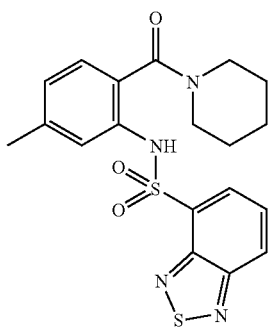

Benzo[1,2,5]thiadiazole-4-sulfonic acid [5-methyl-2-(piperidine-1-carbonyl)-phenyl]-amide The title compound was prepared according to the procedure in EXAMPLE 34, substituting 2-amino-4-methylbenzoic acid for 2-amino-6-chlorobenzoic acid. MS (ESI): m/z 417 [M+H]$^+$, 439 [M+Na]$^+$. $^1$H NMR (400 MHz, CDCl$_3$): (rotameric mixture): 8.95 (bs, 1H), 8.22 (m, 1H), 8.19 (m, 1H), 7.66 (dd, J=8.4, 7.0 Hz, 1H), 7.46 (s, 1H), 6.93 (d, J=7.8 Hz, 1H), 6.83 (d, J=7.8 Hz, 1H), 3.12 (bm, 4H), 2.30 (s, 3H), 1.58 (m, 2H), 1.42 (m, 4H). Elemental analysis: calculated for C$_{19}$H$_{20}$N$_4$O$_3$S$_2$, C, 54.79; H, 4.84; N, 13.45. found C, 54.50; H, 5.10; N, 13.66.

Example 45

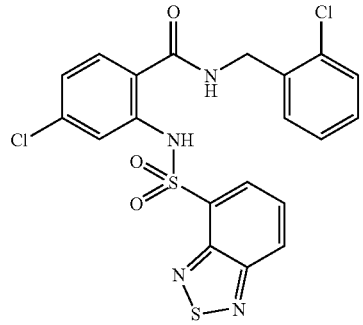

Benzo[1,2,5]thiadiazole-4-sulfonylamino)-4-chloro-N-(2-chloro-benzyl)-benzamide

This compound was prepared using the general procedure described in EXAMPLE 7. MS (ESI): neg. ion m/z 491/493/495 [M−H]$^−$. HPLC (reversed-phase): R$_T$=10.14 min. $^1$H NMR (400 MHz, CDCl$_3$): 11.61 (bs, 1H), 8.37 (m, 1H), 8.20 (m, 1H), 7.70 (m, 2H), 7.45 (M, 1H), 7.37 (m, 1H), 7.32 (m, 2H), 7.27 (m, 1H), 6.92 (bd, J=8.4 Hz, 1H), 6.47 (m, 1H), 4.65 (m, 2H).

Example 46

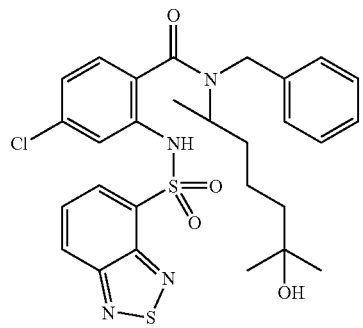

2-(Benzo[1,2,5]thiadiazole-4-sulfonylamino)-N-benzyl-4-chloro-N-(5-hydroxy-1,5-dimethylhexyl) benzamide This compound was prepared using the general procedure described in EXAMPLE 7.

MS (ESI): neg. ion m/z 585/587 [M−H]$^−$. HPLC (reversed-phase): R$_T$=10.00 min. $^1$H NMR (400 MHz, CDCl$_3$): (rotameric broadening) 8.86 (bs, 1H), 8.37 (m, 1H), 8.25 (m, 1H), 7.70 (m, 2H), 7.32 (m, 4H), 7.24 (m, 1H), 6.99 (m, 1H), 6.94 (m, 1H), 4.83 (m, 1H), 4.55 (m, 2H), 3.93 (m, 1H), 2.00 (m, 6H), 1.21 (m, 9H).

Example 47

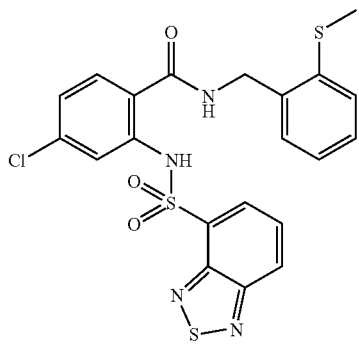

2-(Benzo[1,2,5]thiadiazole-4-sulfonylamino)-4-chloro-N-(2-methylsulfanyl-benzyl)benzamide This compound was prepared using the general procedure described in EXAMPLE 7. MS (ESI): neg. ion m/z 503/505 [M−H]⁻. HPLC (reversed-phase): $R_T$=10.10 min. ¹H NMR (400 MHz, CDCl₃): 11.64 (bs, 1H), 8.36 (m, 1H), 8.19 (m, 1H), 7.70 (m, 2H), 7.34 (m, 2H), 7.21 (m, 3H), 6.90 (m, 1H), 6.45 (m, 1H), 4.58 (m, 2H), 2.51 (s, 3H).

Example 48

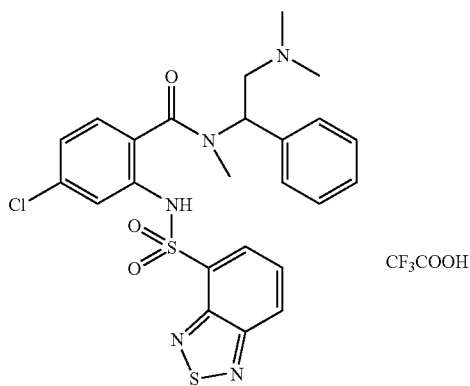

CF₃COOH 2-(Benzo[1,2,5]thiadiazole-4-sulfonylamino)-4-chloro-N-(2-dimethylamino-1-phenyl-ethyl)-N-methylbenzamide TFA salt This compound was prepared using the general procedure described in EXAMPLE 7. MS (ESI): neg. ion m/z 528/530 [M−H]⁻. HPLC (reversed-phase): $R_T$=7.75 min.

Example 49

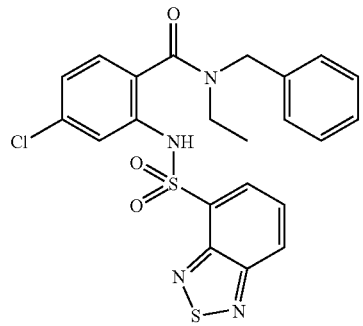

2-(Benzo[1,2,5]thiadiazole-4-sulfonylamino)-N-benzyl-4-chloro-N-ethyl-benzamide

This compound was prepared using the general procedure described in EXAMPLE 7. MS (ESI): neg. ion m/z 485/487 [M−H]⁻. HPLC (reversed-phase): $R_T$=10.16 min. ¹H NMR (400 MHz, CDCl₃): (rotameric broadening) 8.90 (m, 1H), 8.36 (m, 1H), 8.24 (m, 1H), 7.73 (m, 1H), 7.61 (m, 1H), 7.38 (m, 4H), 7.07 (m, 2H), 6.96 (m, 1H), 4.66 and 4.34 (m, 2H), 3.47 (m, 1H), 2.97 (m, 1H), 1.05 and 0.92 (m, 3H).

Example 50

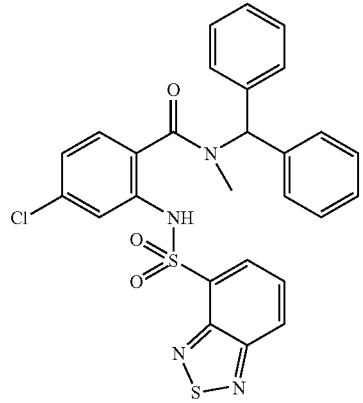

N-(Benzhydryl-2-(benzo[1,2,5]thiadiazole-4-sulfonylamino)-4-chloro-N-methyl-benzamide This compound was prepared using the general procedure described in EXAMPLE 7. MS (ESI): neg. ion m/z 547/549 [M−H]⁻. HPLC (reversed-phase): $R_T$=10.72 min. ¹H NMR (400 MHz, CDCl₃): (rotameric broadening) 9.2-9.0 (m, 1H), 8.40 (bd, J=7.0 Hz, 1H), 8.26 (bd, J=8.5 Hz, 1H), 7.74 (m, 1H), 7.60 (m, 1H), 7.37 (m, 7H), 7.2-6.9 (m, 5H), 6.14 (bs, 1H), 2.8 and 2.6 (m, 3H).

Example 51

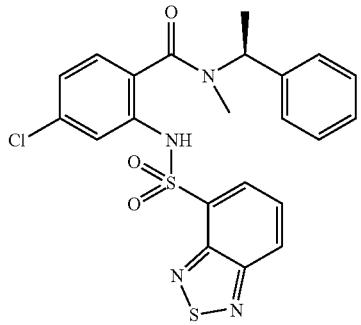

(S)2-(Benzo[1,2,5]thiadiazole-4-sulfonylamino)-4-chloro-N-methyl-N-(1-phenyl-ethyl)-benzamide This compound was prepared using the general procedure described in EXAMPLE 7. MS (ESI): neg. ion m/z 485/487 [M−H]⁻. HPLC (reversed-phase): $R_T$=10.12 min. $^1$H NMR (400 MHz, CDCl$_3$): (rotameric broadening) 9.12 (bs, 1H), 8.38 (dd, J=7.0, 0.8 Hz, 1H), 8.24 (bd, J=8.8 Hz, 1H), 7.73 (m, 1H), 7.61 (d, J=2.0 Hz, 1H), 7.41 (m, 4H), 7.33 (m, 1H), 7.05 (m, 1H), 6.96 (d, J=2.0 Hz, 0.5H), 6.94 (d, J=2.0 Hz, 0.5H), 6.1 (m, 1H), 2.4 (m, 3H), 1.7 (m, 3H).

Example 52

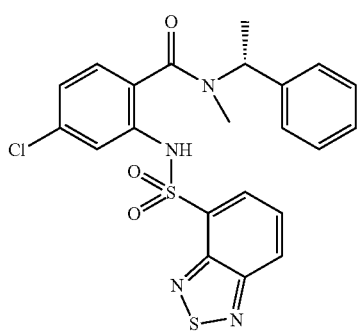

(R)2-(Benzo[1,2,5]thiadiazole-4-sulfonylamino)-4-chloro-N-methyl-N-(1-phenyl-ethyl)-benzamide This compound was prepared using the general procedure described in EXAMPLE 7. MS (ESI): neg. ion m/z 485/487 [M−H]⁻. HPLC (reversed-phase): $R_T$=10.12 min. $^1$H NMR (400 MHz, CDCl$_3$): (rotameric broadening) 9.12 (bs, 1H), 8.38 (dd, J=7.0, 0.8 Hz, 1H), 8.24 (bd, J=8.8 Hz, 1H), 7.73 (m, 1H), 7.61 (d, J=2.0 Hz, 1H), 7.41 (m, 4H), 7.33 (m, 1H), 7.05 (m, 1H), 6.96 (d, J=2.0 Hz, 0.5H), 6.94 (d, J=2.0 Hz, 0.5H), 6.1 (m, 1H), 2.4 (m, 3H), 1.7 (m, 3H).

Example 53

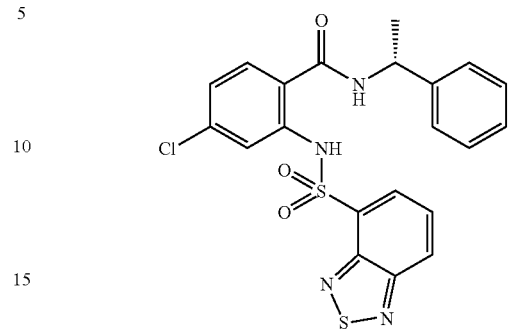

(R)2-(Benzo[1,2,5]thiadiazole-4-sulfonylamino)-4-chloro-N-methyl-N-(1-phenyl-ethyl)-benzamide This compound was prepared using the general procedure described in EXAMPLE 7. MS (ESI): neg. ion m/z 471/473 [M−H]⁻. HPLC (reversed-phase): $R_T$=10.10 min. $^1$H NMR (400 MHz, CDCl$_3$): 11.7 (bs, 1H), 8.35 (dd, J=7.0, 1.0 Hz, 1H), 8.20 (dd J=8.8, 1.0 Hz, 1H), 7.72 (d, J=2.0 Hz, 1H), 7.70 (dd, J=10.8, 2.5 Hz, 1H), 7.34 (m, 5H), 7.23 (d, J=8.5 Hz, 1H), 6.91 (dd, J=8.4, 2.0 Hz, 1H), 6.15 (bd, J=7.6 Hz, 1H), 5.27 (m, 1H), 1.57 (d, J=6.9 Hz, 3H).

Example 54

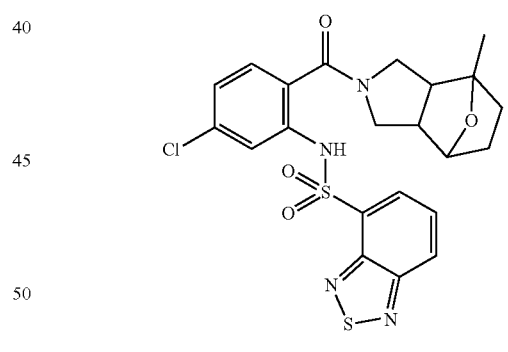

Benzo[1,2,5]thiadiazole-4-sulfonic acid [5-chloro-2-(1-methyl-10-oxa-4-aza-tricyclo[5.2.1.0$^{2,6}$]decane-4-carbonyl)-phenyl]-amide This compound was prepared using the general procedure described in EXAMPLE 7. MS (ESI): neg. ion m/z 503/505 [M−H]⁻. HPLC (reversed-phase): $R_T$=9.29 min. $^1$H NMR (400 MHz, CDCl$_3$): 9.51 (bs, 1H), 8.29 (d, J=7.0 Hz, 1H), 8.22 (d J=8.8 Hz, 1H), 7.70 (dd, J=10.8, 2.5 Hz, 1H), 7.67 (d, J=2.0 Hz, 1H), 7.08 (d, J=6.6 Hz, 1H), 7.00 (m, 1H), 4.3-3.7 (m, 3H), 3.4-3.0 (m, 3H), 2.5-2.2 (m, 3H), 1.84 (m, 1H), 1.54 (bs, 3H), 1.26 (1H).

Example 55

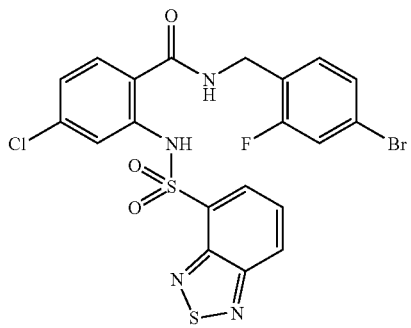

2-(Benzo[1,2,5]thiadiazole-4-sulfonylamino)-N-(4-bromo-2-fluoro-benzyl)-4-chloro-benzamide This compound was prepared using the general procedure described in EXAMPLE 7. MS (ESI): neg. ion m/z 553/555/557 [M−H]⁻. HPLC (reversed-phase): $R_T$=10.37 min. $^1$H NMR (400 MHz, CDCl$_3$): 11.6 (bs, 1H), 8.36 (d, J=7.0 Hz, 1H), 8.21 (dd J=8.8, 0.8 Hz, 1H), 7.73 (d, J=2.0 Hz, 1H), 7.71 (dd, J=7.2, 2.5 Hz, 1H), 7.33 (m, 2H), 7.29 (m, 1H), 7.22 (d, J=8.5 Hz, 1H), 6.92 (dd, J=8.4, 2.0 Hz, 1H), 6.33 (m, 1H), 4.55 (d, J=5.9 Hz, 2H).

Example 56

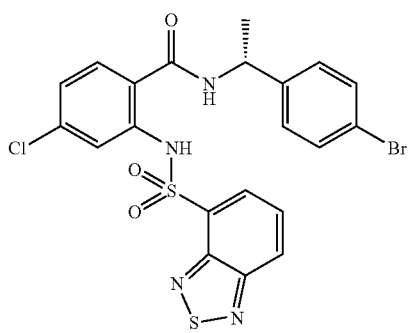

(R)2-(Benzo[1,2,5]thiadiazole-4-sulfonylamino)-N-[1-(4-bromo-phenyl)-ethyl]-4-chloro-benzamide This compound was prepared using the general procedure described in EXAMPLE 7. MS (ESI): neg. ion m/z 549/551/553 [M−H]⁻. HPLC (reversed-phase): $R_T$=10.48 min. $^1$H NMR (400 MHz, CDCl$_3$): 11.62 (bs, 1H), 8.36 (dd, J=7.2, 0.8 Hz, 1H), 8.21 (dd J=8.8, 0.8 Hz, 1H), 7.73 (d, J=2.0 Hz, 1H), 7.71 (dd, J=7.2, 2.5 Hz, 1H), 7.50 (d, J=7.5 Hz, 2H), 7.22 (m, 3H), 6.92 (dd, J=8.4, 2.0 Hz, 1H), 6.12 (bd, J=7.4 Hz, 1H), 5.22 (m, 1H), 1.55 (d, J=5.3 Hz, 3H).

Example 57

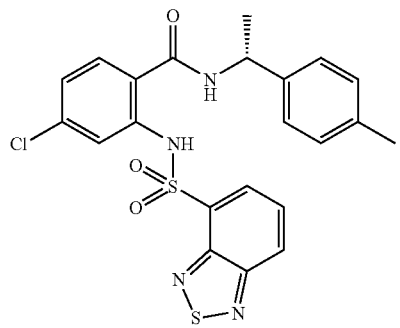

(R)2-(Benzo[1,2,5]thiadiazole-4-sulfonylamino)-4-chloro-N-(1p-tolyl-ethyl)-benzamide This compound was prepared using the general procedure described in EXAMPLE 7. MS (ESI): neg. ion m/z 485/487 [M−H]⁻. HPLC (reversed-phase): $R_T$=10.36 min. $^1$H NMR (400 MHz, CDCl$_3$): 11.68 (bs, 1H), 8.36 (dd, J=7.2, 0.8 Hz, 1H), 8.20 (dd J=8.8, 0.8 Hz, 1H), 7.74 (d, J=2.0 Hz, 1H), 7.70 (dd, J=7.2, 2.5 Hz, 1H), 7.21 (m, 4H), 6.90 (dd, J=8.4, 2.0 Hz, 1H), 6.09 (bd, J=6.3 Hz, 1H), 5.22 (m, 1H), 2.37 (s, 3H), 1.56 (d, J=5.3 Hz, 3H).

Example 58

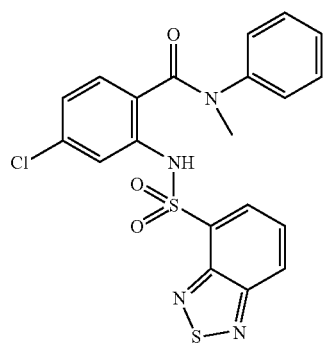

2-(Benzo[1,2,5]thiadiazole-4-sulfonylamino)-4-chloro-N-methyl-N-phenyl-benzamide This compound was prepared using the general procedure described in EXAMPLE 7. MS (ESI): m/z 459 [M+H]⁺, 481 [M+Na]⁺. HPLC (reversed-phase): $R_T$=9.92 min (single peak). $^1$H NMR (400 MHz, CDCl$_3$): (rotameric broadening) 9.83 (s, 1H), 8.37 (dd, J=7.0, 1.0 Hz, 1H), 8.26 (dd, J=8.8, 1.0

Hz, 1H), 7.75 (dd, J=8.8, 7.0, 1H), 7.65 (d, J=8.8, 7.0 Hz, 1H), 7.07-7.04 (m, 3H), 6.55 (m, 2H), 6.30 (d, J=7.0 Hz, 2H), 3.37 (s, 3H).

Example 59

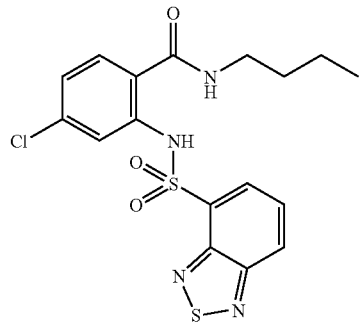

2-(Benzo[1,2,5]thiadiazole-4-sulfonylamino)-N-butyl-4-chloro-benzamide

This compound was prepared using the general procedure described in EXAMPLE 7. MS (ESI): neg. ion m/z 423/425 [M−H]−. HPLC (reversed-phase): $R_T$=9.95 min (single peak). $^1$H NMR (400 MHz, CDCl$_3$): (rotameric broadening) 11.61 (s, 1H), 8.35 (dd, J=7.0, 1.0 Hz, 1H), 8.21 (dd, J=8.8, 1.0 Hz, 1H), 7.73 (dd, J=8.8, 7.0, 1H), 7.70 (d, J=8.8, 7.0 Hz, 1H), 7.20 (d, J=11.2 Hz, 1H), 6.93 (dd, J=8.4, 2.0 Hz, 1H), 6.30 (d, J=7.0 Hz, 2H), 5.89 (s, 1H), 3.36 (m, 2H), 1.54 (m, 2H), 1.38 (m, 2H), 0.97 (t, J=7.3 Hz, 3H).

Example 60

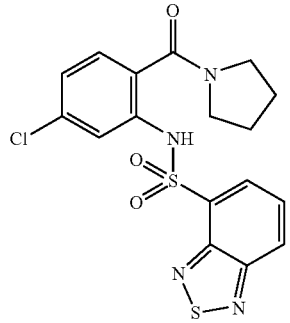

Benzo[1,2,5]thiadiazole-4-sulfonic acid [5-chloro-2-(pyrrolidine-1-carbonyl)-phenyl]-amide This compound was prepared using the general procedure described in EXAMPLE 7. MS (ESI): m/z 421 [M−H]−. HPLC (reversed-phase): $R_T$=9.15 min (single peak). $^1$H NMR (400 MHz, CDCl$_3$): (rotameric broadening) 9.81 (s, 1H), 8.31 (dd, J=7.0, 1.0 Hz, 1H), 8.24 (dd, J=8.8, 1.0 Hz, 1H), 7.71 (dd, J=8.8, 7.0, 1H), 7.66 (d, J=8.8, 7.0 Hz, 1H), 7.14 (d, J=11.2 Hz, 1H), 6.98 (dd, J=8.4, 2.0 Hz, 1H), 3.47 (m, 2H), 3.12 (m, 2H), 1.90 (m, 2H), 1.65 (m, 2H).

Example 61

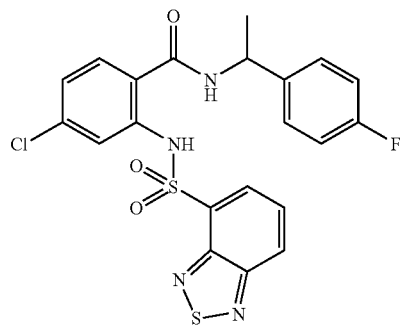

2-(Benzo[1,2,5]thiadiazole-4-sulfonylamino)-4-chloro-N-[1-(4-fluoro-phenyl)-ethyl]-benzamide This compound was prepared using the general procedure described in EXAMPLE 7. MS (ESI): neg. ion m/z 489 [M−H]−. HPLC (reversed-phase): $R_T$=9.95 min (single peak). $^1$H NMR (400 MHz, CDCl$_3$): (rotameric broadening) 11.63 (s, 1H), 8.37 (dd, J=7.0, 1.0 Hz, 1H), 8.21 (dd, J=8.8, 1.0 Hz, 1H), 7.74-7.69 (m, 2H), 7.33-7.21 (m, 3H), 7.09-7.04 (m, 2H), 6.93 (dd, J=8.4, 2.0 Hz, 1H), 6.09 (d, J=7.8 Hz, 1H), 5.25 (t, J=7.0 Hz, 1H), 1.55 (m, 3H). Elemental analysis: calculated for $C_{21}H_{16}ClFN_4O_3S_2$, C, 51.37; H, 3.28; N, 11.41. found C, 51.78; H, 3.40; N, 11.14.

Example 62

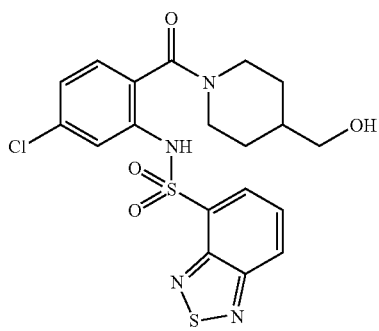

Benzo[1,2,5]thiadiazole-4-sulfonic acid [5-chloro-2-(4-hydroxymethyl-piperidine-1-carbonyl)-phenyl]-amide This compound was prepared using the general procedure described in EXAMPLE 7. MS (ESI): m/z 465 [M−H]−. HPLC (reversed-phase): $R_T$=7.99 min (single peak). $^1$H NMR (400 MHz, CDCl$_3$): (rotameric broadening) 9.00 (s, 1H), 8.28 (dd, J=7.0, 1.0 Hz, 1H), 8.24 (dd, J=8.8, 1.0 Hz, 1H), 7.71 (dd, J=8.8, 7.0 Hz, 1H), 7.65 (m, 1H), 7.00 (m, 2H), 3.51 (d, J=5.9 Hz, 2H), 2.55 (t, J=13.6 Hz, 2H), 1.72 (bs, 3H), 1.54 (bs, 2H), 1.11 (bs, 2H). Elemental analysis: calculated for $C_{19}H_{19}ClN_4O_3S_2$, C, 48.87; H, 4.10; N, 12.00. found C, 48.62; H, 3.90; N, 11.81.

Example 63

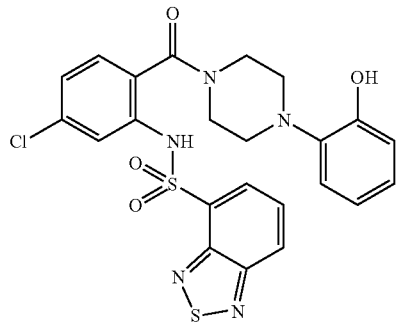

Benzo[1,2,5]thiadiazole-4-sulfonic acid {5-chloro-2-[4-(2-hydroxy-phenyl)-piperazine-1-carbonyl]-phenyl}-amide This compound was prepared using the general procedure described in EXAMPLE 7. MS (ESI): m/z 528 [M−H]$^-$. HPLC (reversed-phase): $R_T$=8.36 min (single peak). $^1$H NMR (400 MHz, CDCl$_3$): (rotameric broadening) 8.84 (s, 1H), 8.34 (dd, J=7.0, 1.0 Hz, 1H), 8.30 (dd, J=8.8, 1.0 Hz, 1H), 7.76 (dd, J=8.8, 7.0 Hz, 1H), 7.48 (d, J=1.8 Hz, 1H), 7.23-7.13 (m, 2H), 7.11-7.08 (m, 2H), 7.02 (dd, J=8.1, 1.3 Hz, 1H), 6.97-6.93 (m, 1H), 3.77 (bs, 4H), 3.10 (bs, 4H).

Example 64

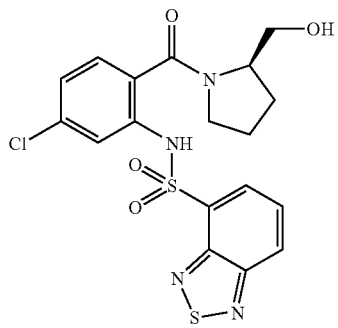

Benzo[1,2,5]thiadiazole-4-sulfonic acid [5-chloro-2-(2-hydroxymethyl-pyrrolidine-1-carbonyl)-phenyl]-amide This compound was prepared using the general procedure described in EXAMPLE 7. MS (ESI): m/z 451 [M−H]$^-$. HPLC (reversed-phase): $R_T$=8.40 min (single peak). $^1$H NMR (500 MHz, CDCl$_3$): (rotameric broadening) 9.46 (s, 1H), 8.33 (dd, J=11.7, 7.0 Hz, 1H), 8.25 (dd, J=8.8, 4.4 Hz, 1H), 7.14 (d, J=8.3 Hz, 1H), 7.01 (dd, J=8.3, 1.8 Hz, 1H), 4.23 (s, 1H), 4.07 (d, J=12.1 Hz, 1H), 3.70 (m, 1H), 3.39 (m, 1H), 3.19 (m, 1H), 2.15 (m, 1H), 1.87 (m, 1H), 1.78 (m, 1H), 1.56 (m, 1H).

Example 65

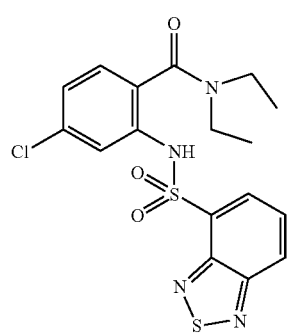

2-(Benzo[1,2,5]thiadiazole-4-sulfonylamino)-4-chloro-N,N-diethyl-benzamide

This compound was prepared using the general procedure described in EXAMPLE 7. MS (ESI): m/z 423 [M−H]$^-$. HPLC (reversed-phase): $R_T$=9.43 min (single peak). $^1$H NMR (400 MHz, CDCl$_3$): (rotameric broadening) 8.87 (s, 1H), 8.32 (dd, J=7.0, 1.0 Hz, 1H), 8.23 (dd, J=8.8, 1.0 Hz, 1H), 7.72 (dd, J=8.8, 7.0 Hz, 1H), 7.48 (d, J=1.8 Hz, 1H), 7.04-6.98 (m, 2H), 3.25 (bs, 4H), 1.05 (bs, 6H).

Example 66

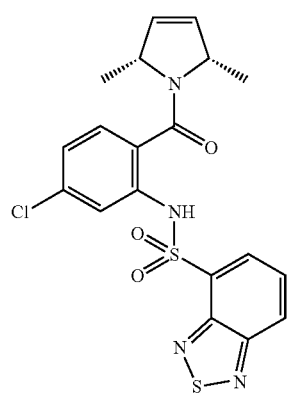

Benzo[1,2,5]thiadiazole-4-sulfonic acid [5-chloro-2-(2,5-dimethyl-2,5-dihydro-pyrrole-1-carbonyl)-phenyl]-amide This compound was prepared using the general procedure described in EXAMPLE 7. MS (ESI): m/z 447 [M−H]$^-$. HPLC (reversed-phase): $R_T$=10.00 min (single peak). $^1$H NMR (400 MHz, CDCl₃): (rotameric broadening) 9.75 (s, 1H), 8.33 (dd, J=7.0, 1.0 Hz, 1H), 8.20 (dd, J=8.8, 1.0 Hz, 1H), 7.78 (d, J=2.0 Hz, 1H), 7.69 (dd, J=8.8, 7.0 Hz, 1H), 7.23 (dd, J=8.3 Hz, 1H), 6.97 (dd, J=8.2, 2.0 Hz, 1H), 5.70 (d, J=6.4 Hz, 1H), 5.42 (d, J=4.6 Hz, 1H), 4.97 (m, 1H), 4.60 (m, 1H), 1.40 (d, J=6.4 Hz, 3H), 0.11 (d, J=6.4 Hz, 3H).

Example 67

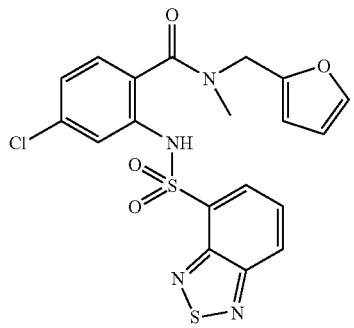

2-(Benzo[1,2,5]thiadiazole-4-sulfonylamino)-4-chloro-N-furan-2-ylmethyl-N-methyl-benzamide This compound was prepared using the general procedure described in EXAMPLE 7. MS (ESI): m/z 461 [M−H]⁻. HPLC (reversed-phase): R$_T$=9.58 min (single peak). ¹H NMR (500 MHz, CDCl₃): (rotameric broadening) 8.97 (s, 1H), 8.30 (dd, J=7.0, 1.0 Hz, 1H), 8.23 (d, J=8.8 Hz, 1H), 7.71 (t, J=7.6 Hz, 1H), 7.67 (s, 1H), 7.43 (s, 1H), 7.04 (s, 2H), 6.37 (s, 2H), 4.57 (s, 1H), 4.06 (s, 1H), 2.86-2.61 (m, 3H).

Example 68

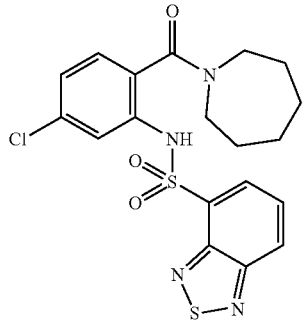

Benzo[1,2,5]thiadiazole-4-sulfonic acid [2-(azepane-1-carbonyl)-5-chloro-phenyl]-amide This compound was prepared using the general procedure described in EXAMPLE 7. MS (ESI): m/z 449 [M−H]⁻. HPLC (reversed-phase): R$_T$=9.79 min (single peak). ¹H NMR (400 MHz, CDCl₃): (rotameric broadening) 8.85 (s, 1H), 8.30 (dd, J=7.0, 1.0 Hz, 1H), 8.24 (d, J=8.8 Hz, 1H), 7.71 (dd, J=8.8, 7.0 Hz, 1H), 7.64 (s, 1H), 7.01 (s, 2H), 3.47 (s, 2H), 2.99 (s, 2H), 1.75 (s, 2H), 1.57 (s, 2H), 1.49 (s, 4H).

Example 69

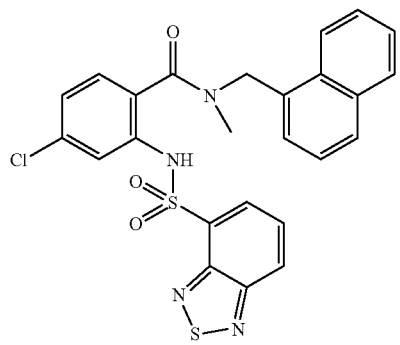

2-(Benzo[1,2,5]thiadiazole-4-sulfonylamino)-4-chloro-N-methyl-N-naphthalen-1-ylmethyl-benzamide This compound was prepared using the general procedure described in EXAMPLE 7. MS (ESI): m/z 521 [M−H]⁻. HPLC (reversed-phase): R$_T$=10.45 min (single peak). ¹H NMR (400 MHz, CDCl₃): (rotameric broadening) 8.97 (s, 1H), 8.25 (m, 2H), 8.05 (s, 1H), 7.87 (m, 3H), 7.58-7.42 (m, 5H), 7.04 (m, 2H), 5.01 (s, 2H), 2.38 (s, 3H).

Example 70

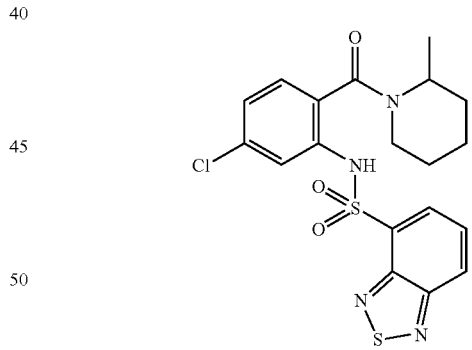

Benzo[1,2,5]thiadiazole-4-sulfonic acid [5-chloro-2-(2-methyl-piperidine-1-carbonyl)-phenyl]-amide This compound was prepared using the general procedure described in EXAMPLE 7. MS (ESI): m/z 449 [M−H]⁻. HPLC (reversed-phase): R$_T$=9.88 min (single peak). ¹H NMR (500 MHz, CDCl₃): (rotameric broadening) 8.89 (s, 1H), 8.33 (d, J=7.0 Hz, 1H), 8.24 (d, J=8.8 Hz, 1H), 7.72 (dd, J=8.8, 7.0 Hz, 1H), 7.62 (s, 1H), 7.00 (m, 2H), 4.45 (s, 1H), 3.49 (s, 1H), 2.89 (m, 1H), 1.64-1.54 (m, 5H), 1.26 (s, 1H), 1.16 (s, 3H).

Example 71

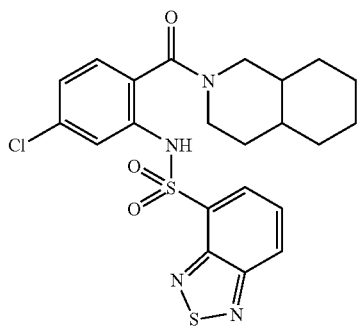

Benzo[1,2,5]thiadiazole-4-sulfonic acid [5-chloro-2-(octahydro-isoquinoline-2-carbonyl)-phenyl]-amide This compound was prepared using the general procedure described in EXAMPLE 7. MS (ESI): m/z 489 [M−H]$^-$. HPLC (reversed-phase): R$_T$=10.67 min (single peak). $^1$H NMR (400 MHz, CDCl$_3$): (rotameric broadening) 8.85 (s, 1H), 8.29 (dd, J=7.0, 1.0 Hz, 1H), 8.25 (dd, J=8.8, 1.0 Hz, 1H), 7.71 (m, 1H), 7.61 (s, 1H), 7.01 (m, 2H), 3.09 (bs, 4H), 1.85-1.38 (m, 12H).

Example 72

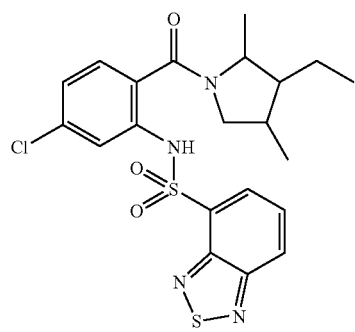

Benzo[1,2,5]thiadiazole-4-sulfonic acid [5-chloro-2-(3-ethyl-(2,4-dimethyl-pyrrolidine-1carbonyl)-phenyl]-amide This compound was prepared using the general procedure described in EXAMPLE 7. MS (ESI): m/z 477 [M−H]$^-$. HPLC (reversed-phase): R$_T$=10.76 min (single peak). $^1$H NMR (500 MHz, CDCl$_3$): (rotameric broadening) 10.10 (s, 1H), 8.33 (dd, J=7.0, 1.0 Hz, 1H), 8.22 (dd, J=8.8, 1.0 Hz, 1H), 7.72 (dd, J=9.9, 7.1 Hz, 1H), 7.65 (s, 1H), 7.12 (d, J=8.3 Hz, 1H), 6.96 (dd, J=8.3, 2.0 Hz, 1H), 3.83 (m, 1H), 3.14 (m, 1H), 3.00 (m, 1H), 1.83 (bs, 2H), 1.45-1.25 (m, 5H), 1.02-0.92 (m, 6H).

Example 73

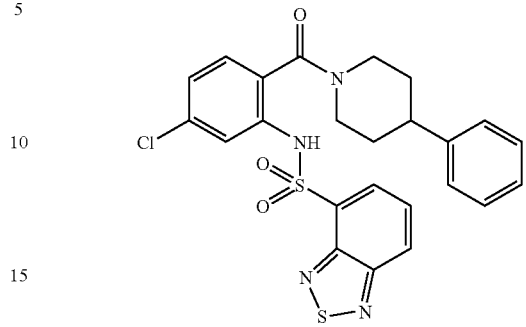

Benzo[1,2,5]thiadiazole-4-sulfonic acid [5-chloro-2-(4-phenyl-piperidine-1-carbonyl)-phenyl]-amide This compound was prepared using the general procedure described in EXAMPLE 7. MS (ESI): m/z 511 [M−H]$^-$. HPLC (reversed-phase): R$_T$=10.31 min (single peak). $^1$H NMR (500 MHz, CDCl$_3$): (rotameric broadening) 9.02 (s, 1H), 8.30 (dd, J=7.0, 1.0 Hz, 1H), 8.24 (dd, J=8.8 Hz, 1H), 7.71 (dd, J=9.9, 7.1 Hz, 1H), 7.66 (d, J=1.74 Hz, 1H), 7.33 (t, J=7.4 Hz, 2H), 7.23 (m, 1H), 7.20 (m, 2H), 7.03 (m, 2H), 2.72-2.67 (m, 2H), 1.86 (bs, 2H), 1.59 (bs, 4H).

Example 74

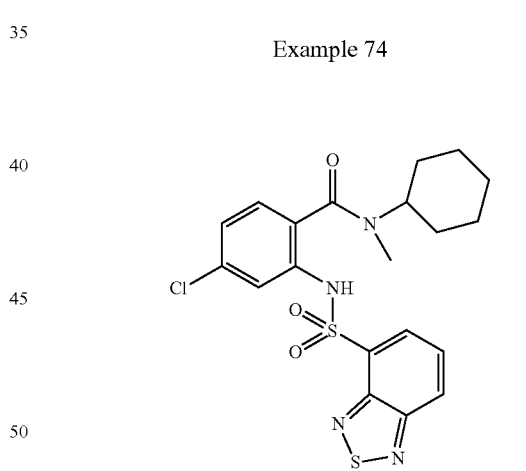

2-(Benzo[1,2,5]thiadiazole-4-sulfonylamino)-4-chloro-N-methyl-N-benzamide

This compound was prepared using the general procedure described in EXAMPLE 7. MS (ESI): m/z 463 [M−H]$^-$. HPLC (reversed-phase): R$_T$=10.23 min (single peak). $^1$H NMR (400 MHz, CDCl$_3$): (rotameric broadening) 9.00 (s, 1H), 8.33 (d, J=7.0 Hz, 1H), 8.24 (dd, J=8.8, 1.0 Hz, 1H), 7.72 (dd, J=9.9, 7.1 Hz, 1H), 7.63 (d, 1H), 7.01 (s, 2H), 1.58-1.04 (m, 11H).

Example 75

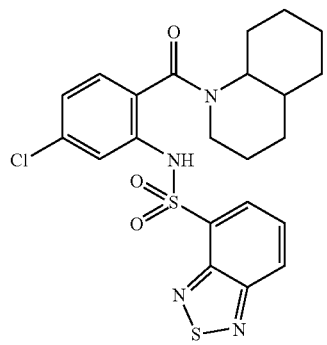

Benzo[1,2,5]thiadiazole-4-sulfonic acid [5-chloro-2-(octahydro-quinoline-1-carbonyl)-phenyl]-amide This compound was prepared using the general procedure described in EXAMPLE 7. MS (ESI): m/z 489 [M–H]$^-$. HPLC (reversed-phase): R$_T$=10.72 min (single peak). $^1$H NMR (500 MHz, CDCl$_3$): (rotameric broadening) 9.08 (s, 1H), 8.33 (d, J=6.7 Hz, 1H), 8.24 (d, J=8.7 Hz, 1H), 7.71 (m, 1H), 7.60 (s, 1H), 7.05-6.97 (m, 2H), 3.30 (m, 2H), 2.19 (m, 1H), 1.80-1.09 (m, 13H).

Example 76

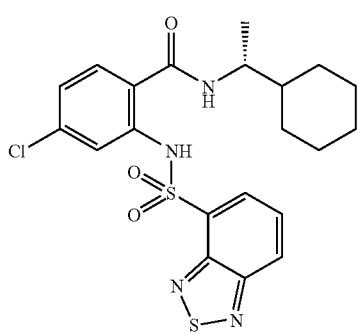

(R)-2-(Benzo[1,2,5]thiadiazole-4-sulfonylamino)-4-chloro-N-(1-cyclohexyl-ethyl)-benzamide This compound was prepared using the general procedure described in EXAMPLE 7. MS (ESI): m/z 477 [M–H]$^-$. HPLC (reversed-phase): R$_T$=10.91 min (single peak). $^1$H NMR (500 MHz, CDCl$_3$): (rotameric broadening) 11.73 (s, 1H), 8.37 (dd, J=7.0, 1.0 Hz, 1H), 8.22 (dd, J=8.8, 1.0 Hz, 1H), 7.74 (dd, J=9.9, 7.1 Hz, 1H), 7.71 (d, J=1.74 Hz, 1H), 7.21 (d, J=8.4 Hz, 1H), 6.93 (dd, J=8.4, 2.0, 1H), 5.75 (d, J=8.5 Hz, 1H), 4.00 (m, 1H), 1.78-1.67 (m, 5H), 1.54 (s, 2H), 1.42 (m, 1H), 1.22-1.14 (m, 4H), 1.01 (m, 2H).

Example 77

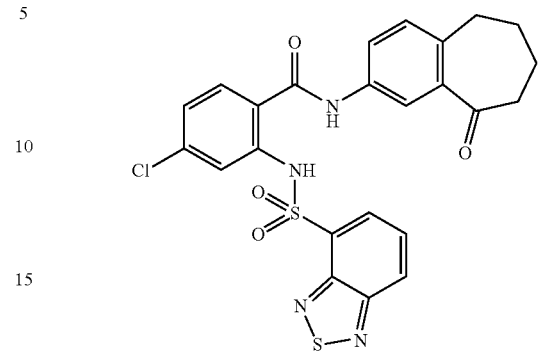

2-(Benzo[1,2,5]thiadiazole-4-sulfonylamino)-4-chloro-N-(9-oxo-6,7,8,9-tetrahydro-5H-benzocyclohepten-2-yl)-benzamide This compound was prepared using the general procedure described in EXAMPLE 7. MS (ESI): m/z 525 [M–H]$^-$. HPLC (reversed-phase): R$_T$=9.99 min (single peak). $^1$H NMR (400 MHz, CDCl$_3$): (rotameric broadening) 11.04 (s, 1H), 8.33 (dd, J=7.0, 1.0 Hz, 1H), 8.19 (dd, J=8.8, 1.0 Hz, 1H), 7.99 (dd, J=9.9, 7.1 Hz, 1H), 7.81 (d, J=1.74 Hz, 1H), 7.69 (dd, J=6.8, 9.0 Hz, 1H), 7.52 (d, J=2.4 Hz, 1H), 7.37 (d, J=8.4 Hz, 1H), 7.31 (d, J=8.0 Hz, 1H), 7.04 (dd, J=8.4, 2.0 Hz, 1H), 2.97 (t, J=6.4 Hz, 2H), 2.76 (t, J=5.8 Hz, 2H), 1.94-1.85 (m, 4H).

Example 78

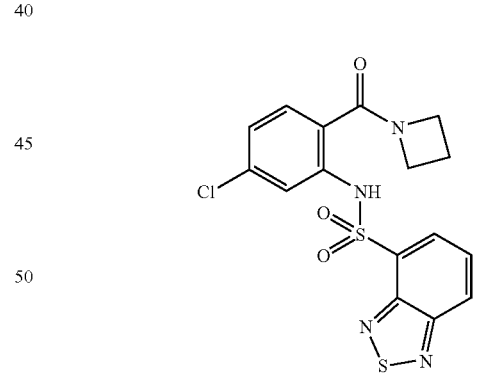

Benzo[1,2,5]thiadiazole-4-sulfonic acid [2-(azetidine-1-carbonyl)-5-chloro-phenyl]-amide This compound was prepared using the general procedure described in EXAMPLE 7. MS (ESI): m/z 407 [M–H]$^-$. HPLC (reversed-phase): R$_T$=9.12 min (single peak). $^1$H NMR (500 MHz, CDCl$_3$): (rotameric broadening) 10.97 (s, 1H), 8.34 (dd, J=7.0, 1.0 Hz, 1H), 8.24 (dd, J=8.8, 1.0 Hz, 1H), 7.72 (dd, J=9.9, 7.1 Hz, 2H), 7.10 (d, J=1.7 Hz, 1H), 6.93 (dd, J=6.8, 9.0 Hz, 1H), 4.04 (m, 4H), 2.27 (m, 2H).

Example 79

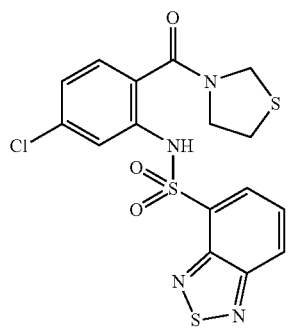

Benzo[1,2,5]thiadiazole-4-sulfonic acid [5-chloro-2-(thiazolidine-3-carbonyl)-phenyl]-amide This compound was prepared using the general procedure described in EXAMPLE 7. MS (ESI): m/z 441 [M+H]$^+$, 463 [M+Na]$^+$. HPLC (reversed-phase): R$_T$=9.24 min (single peak). $^1$H NMR (400 MHz, CDCl$_3$): (rotameric broadening) 9.52 (s, 1H), 8.31 (d, J=7.0, 1H), 8.26 (d, J=8.8 Hz, 1H), 7.72 (m, 2H), 7.13 (d, J=8.3 Hz, 1H), 7.01 (dd, J=1.8, 8.3 Hz, 1H), 4.56 (bs, 1H), 4.21 (bs, 1H), 3.68 (bs, 2H), 2.84 (bs, 2H).

Example 80

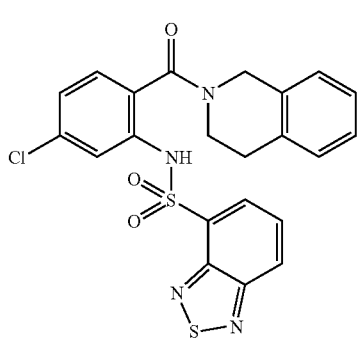

Benzo[1,2,5]thiadiazole-4-sulfonic acid [5-chloro-2-(1,2,3,4-tetrahydro-naphthalene-2-carbonyl)-phenyl]-amide This compound was prepared using the general procedure described in EXAMPLE 7. MS (ESI): m/z 485 [M+H]$^+$. HPLC (reversed-phase): R$_T$=9.93 min (single peak). $^1$H NMR (400 MHz, CDCl$_3$): (rotameric broadening) 9.24 (s, 1H), 8.28 (d, J=7.0 Hz, 1H), 8.15 (s, 1H), 7.74 (s, 1H), 7.66 (s, 1H), 7.25-6.99 (m, 6H), 4.49 (m, 2H), 3.56 (m, 2H), 2.70 (m, 2H).

Example 81

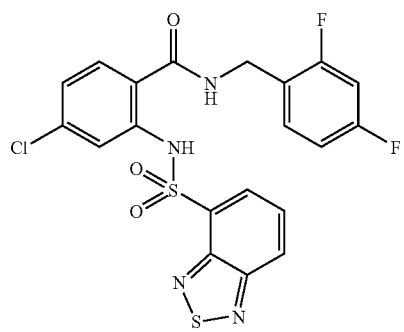

2-(Benzo[1,2,5]thiadiazole-4-sulfonylamino)-4-chloro-N-(2,4-difluoro-benzyl)-benzamide This compound was prepared using the general procedure described in EXAMPLE 7. MS (ESI): m/z 495 [M+H]$^+$. HPLC (reversed-phase): R$_T$=10.02 min (single peak). $^1$H NMR (400 MHz, CDCl$_3$): (rotameric broadening) 11.60 (s, 1H), 8.36 (d, J=7.0 Hz, 1H), 8.21 (d, J=8.8 Hz, 1H), 7.71 (m, 2H), 7.44 (m, 1H), 7.21 (m, 1H), 6.93-6.82 (m, 3H), 6.31 (bs, 1H), 4.56 (d, J=5.8 Hz, 2H).

Example 82

2-(Benzo[1,2,5]thiadiazole-4-sulfonylamino)-4-chloro-N-(2-fluoro-benzyl)-benzamide This compound was prepared using the general procedure described in EXAMPLE 7. MS (ESI): m/z 477 [M+H]$^+$. HPLC (reversed-phase): R$_T$=9.95 min (single peak). $^1$H NMR (400 MHz, CDCl$_3$): (rotameric broadening) 11.63 (s, 1H), 8.36 (dd, J=7.0, 1.0 Hz, 1H), 8.20 (dd, J=8.8, 1.0 Hz, 1H), 7.75-7.68 (m, 2H), 7.48 (m, 1H), 7.43 (m, 1H), 7.18 (m, 2H), 7.09 (m, 1H), 6.91 (dd, J=8.4, 2.0 Hz, 1H), 6.33 (s, 1H), 4.61 (d, J=5.8 Hz, 2H).

Example 83

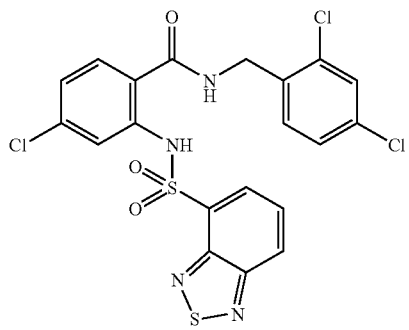

2-(Benzo[1,2,5]thiadiazole-4-sulfonylamino)-4-chloro-N-(2,4-dichloro-benzyl)-benzamide This compound was prepared using the general procedure described in EXAMPLE 7. MS (ESI): m/z 525/527/529 [M−H]⁻. HPLC (reversed-phase): $R_T$=10.57 min (single peak). $^1$H NMR (400 MHz, CDCl$_3$): (rotameric broadening) 11.56 (s, 1H), 8.36 (d, J=7.0, 1.0 Hz, 1H), 8.21 (dd, J=8.8, 1.0 Hz, 1H), 7.75-7.69 (m, 2H), 7.46-7.43 (m, 2H), 7.30 (m, 2H), 6.93 (dd, J=8.4, 2.0 Hz, 1H), 6.42 (m, 1H), 4.61 (d, J=5.8 Hz, 2H).

Example 84

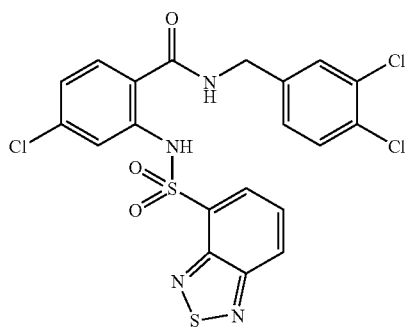

2-(Benzo[1,2,5]thiadiazole-4-sulfonylamino)-4-chloro-N-(3,4-dichloro-benzyl)-benzamide This compound was prepared using the general procedure described in EXAMPLE 7. MS (ESI): m/z 525/527/529 [M−H]⁻. HPLC (reversed-phase): $R_T$=10.51 min (single peak). $^1$H NMR (500 MHz, CDCl$_3$): (rotameric broadening) 11.58 (s, 1H), 8.36 (dd, J=7.0, 1.0 Hz, 1H), 8.21 (dd, J=8.8, 1.0 Hz, 1H), 7.75-7.70 (m, 2H), 7.44-7.40 (m, 2H), 7.24 (m, 1H), 7.17 (dd, J=8.4, 2.0 Hz, 1H), 6.94 (dd, J=8.4, 2.0 Hz, 1H), 6.29 (s, 1H), 4.52 (d, J=5.8 Hz, 2H).

Example 85

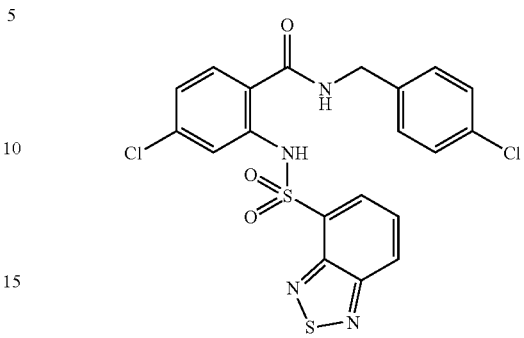

2-(Benzo[1,2,5]thiadiazole-4-sulfonylamino)-4-chloro-N-(4-chloro-benzyl)-benzamide This compound was prepared using the general procedure described in EXAMPLE 7. MS (ESI): m/z 491/493 [M−H]⁻. HPLC (reversed-phase): $R_T$=10.23 min (single peak). $^1$H NMR (500 MHz, CDCl$_3$): (rotameric broadening) 11.60 (s, 1H), 8.37 (dd, J=7.0, 1.0 Hz, 1H), 8.23 (dd, J=8.8, 1.0 Hz, 1H), 7.75-7.70 (m, 2H), 7.35 7.33 (m, 2H), 7.24 (m, 3H), 6.92 (dd, J=8.4, 2.0 Hz, 1H), 6.23 (s, 1H), 4.52 (d, J=5.8 Hz, 2H).

Example 86

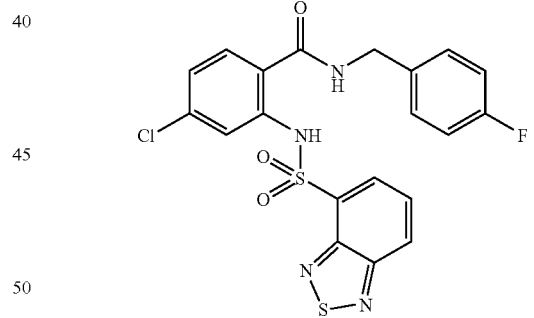

2-(Benzo[1,2,5]thiadiazole-4-sulfonylamino)-4-chloro-N-(4-fluoro-benzyl)-benzamide This compound was prepared using the general procedure described in EXAMPLE 7. MS (ESI): m/z 477 [M+H]⁺. HPLC (reversed-phase): $R_T$=9.94 min (single peak). $^1$H NMR (500 MHz, CDCl$_3$): (rotameric broadening) 11.62 (s, 1H), 8.37 (dd, J=7.0, 1.0 Hz, 1H), 8.23 (dd, J=8.8, 1.0 Hz, 1H), 7.74-7.71 (m, 2H), 7.30-7.27 (m, 2H), 7.22 (m, 1H), 7.06 (t, J=8.6 Hz, 2H), 6.92 (dd, J=8.4, 2.0 Hz, 1H), 6.23 (s, 1H), 4.52 (d, J=5.8 Hz, 2H).

Example 87

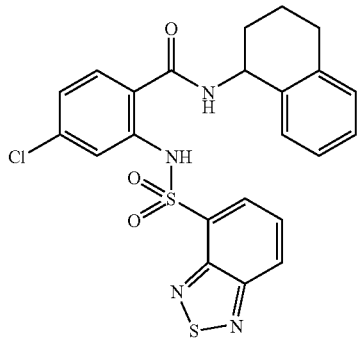

2-(Benzo[1,2,5]thiadiazole-4-sulfonylamino)-4-chloro-N-(1,2,3,4-tetrahydro-naphthalen-1-yl)-benzamide This compound was prepared using the general procedure described in EXAMPLE 7. MS (ESI): m/z 497 [M−H]⁻. HPLC (reversed-phase): $R_T$=10.54 min (single peak). $^1$H NMR (500 MHz, CDCl$_3$): (rotameric broadening) 11.79 (s, 1H), 8.40 (dd, J=7.0, 1.0 Hz, 1H), 8.24 (dd, J=8.8, 1.0 Hz, 1H), 7.76-7.71 (m, 2H), 7.21-7.13 (m, 5H), 6.90 (dd, J=8.5, 2.0 Hz, 1H), 6.17 (d, J=8.1 Hz, 1H), 5.30 (m, 1H), 2.86-2.80 (m, 2H), 2.13-2.09 (m, 1H), 1.90-1.80 (m, 3H).

Example 88

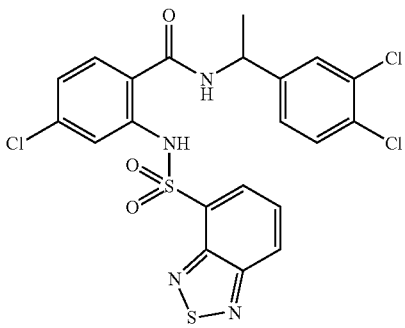

2-(Benzo[1,2,5]thiadiazole-4-sulfonylamino)-4-chloro-N-[1-(3,4-dichloro-phenyl)-ethyl]-benzamide This compound was prepared using the general procedure described in EXAMPLE 7. MS (ESI): m/z 539/541/543 [M−H]⁻. HPLC (reversed-phase): $R_T$=10.59 min (single peak). $^1$H NMR (500 MHz, CDCl$_3$): (rotameric broadening) 11.51 (s, 1H), 8.35 (dd, J=7.0, 1.0 Hz, 1H), 8.20 (dd, J=8.8, 1.0 Hz, 1H), 7.75 (d, J=2.0 Hz, 1H), 7.70 (dd, J=8.8, 7.0 Hz, 1H), 7.44 (m, 1H), 7.29-7.23 (m, 3H), 6.95 (dd, J=8.5, 2.0 Hz, 1H), 6.39 (d, J=8.1 Hz, 1H), 5.50 (t, J=7.2 Hz, 1H), 1.58 (m, 4H).

Example 89

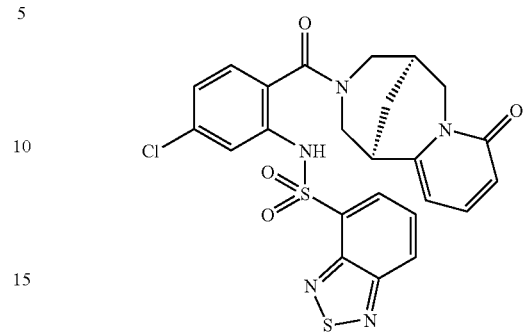

Benzo[1,2,5]thiadiazole-4-sulfonic acid [5-chloro-2-(8-oxo-1,5,6,8-tetrahydro-2H,4H-1,5-methano-pyrido[1,2-a][1,5]diazocine-3-carbonyl)-phenyl]-amide This compound was prepared using the general procedure described in EXAMPLE 7. MS (ESI): m/z 540/542 [M−H]⁻. HPLC (reversed-phase): $R_T$=7.73 min (single peak). $^1$H NMR (500 MHz, CDCl$_3$): (rotameric broadening) 8.37 (bs, 1H), 8.26 (m, 2H), 7.72 (dd, J=8.8, 1.0 Hz, 1H), 7.47 (d, J=1.8 Hz, 1H), 7.35 (m, 1H), 7.22 (m, 1H), 6.86 (bs, 1H), 6.59 (d, J=9.0 Hz, 1H), 6.06 (bs, 1H), 4.20 (d, J=15.5 Hz, 1H), 3.85 (d, J=13.5 Hz, 1H), 3.06 (bs, 1H), 2.94 (d, J=12.7 Hz, 2H), 2.55 (bs, 1H), 2.07 (d, J=13.4 Hz, 1H), 2.00 (d, J=13.3 Hz, 1H).

Example 90

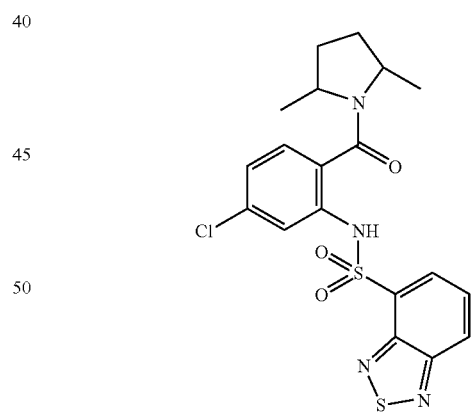

Benzo[1,2,5]thiadiazole-4-sulfonic acid [5-chloro-2-(2,5-dimethyl-pyrrolidine-1-carbonyl)-phenyl]-amide This compound was prepared using the general procedure described in EXAMPLE 7. MS (ESI): m/z 451 [M+H]⁺. HPLC (reversed-phase): $R_T$=9.84 min (single peak). $^1$H NMR (500 MHz, CDCl$_3$): (rotameric broadening) 9.07 (s, 1H), 8.34 (dd, J=7.0, 1.0 Hz, 1H), 8.24 (dd, J=8.8, 1.0 Hz, 1H), 7.72 (dd, J=8.8, 7.0 Hz, 1H), 7.61 (d, J=2.0 Hz, 1H), 7.16 (d, J=8.2 Hz, 1H), 7.00 (dd, J=8.5, 2.0 Hz, 1H), 4.00 (bs, 2H), 1.85 (bs, 4H), 1.12 (bs, 6H).

Example 91

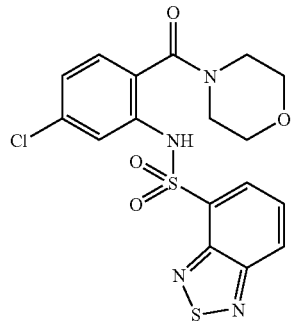

Benzo[1,2,5]thiadiazole-4-sulfonic acid [5-chloro-2-(morpholine-4-carbonyl)-phenyl]-amide This compound was prepared using the general procedure described in EXAMPLE 7. MS (ESI): m/z 439 [M+H]$^+$. HPLC (reversed-phase): R$_T$=8.49 min (single peak). $^1$H NMR (500 MHz, CDCl$_3$): (rotameric broadening) 9.04 (s, 1H), 8.32 (dd, J=7.0, 1.0 Hz, 1H), 8.26 (dd, J=8.8, 1.0 Hz, 1H), 7.73 (dd, J=8.8, 7.0 Hz, 1H), 7.63 (s, 1H), 7.01 (m, 1H), 3.49 (m, 8H).

Example 92

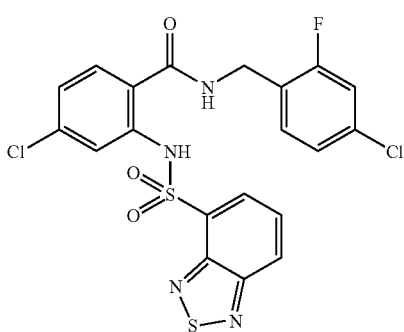

2-(Benzo[1,2,5]thiadiazole-4-sulfonylamino)-4-chloro-N-(4-chloro-2-fluoro-benzyl)-benzamide This compound was prepared using the general procedure described in EXAMPLE 7. MS (ESI): m/z 509/511 [M−H]$^-$. HPLC (reversed-phase): R$_T$=10.31 min (single peak). $^1$H NMR (500 MHz, CDCl$_3$): (rotameric broadening) 11.56 (s, 1H), 8.36 (dd, J=7.0, 1.0 Hz, 1H), 8.21 (dd, J=8.8, 1.0 Hz, 1H), 7.74-7.69 (m, 2H), 7.39 (t, J=8.2 Hz, 1H), 7.21-7.12 (m, 3H), 6.93 (dd, J=8.4, 2.0 Hz, 1H), 6.31 (s, 1H), 4.57 (d, J=6.0 Hz, 2H).

Example 93

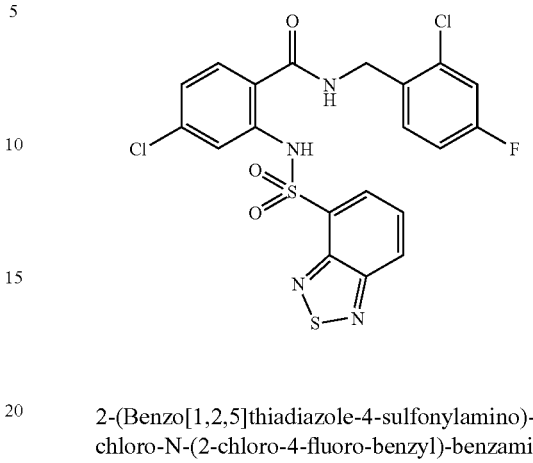

2-(Benzo[1,2,5]thiadiazole-4-sulfonylamino)-4-chloro-N-(2-chloro-4-fluoro-benzyl)-benzamide This compound was prepared using the general procedure described in EXAMPLE 7. MS (ESI): m/z 509/511 [M−H]$^-$. HPLC (reversed-phase): R$_T$=10.24 min (single peak). $^1$H NMR (500 MHz, CDCl$_3$): (rotameric broadening) 11.57 (s, 1H), 8.36 (dd, J=7.0, 1.0 Hz, 1H), 8.21 (dd, J=8.8, 1.0 Hz, 1H), 7.73-7.69 (m, 2H), 7.51 (m, 1H), 7.18 (m, 1H), 7.16 (m, 1H), 7.03 (m, 1H), 6.93 (dd, J=8.4, 2.0 Hz, 1H), 6.41 (s, 1H), 4.61 (d, J=6.0 Hz, 2H).

Example 94

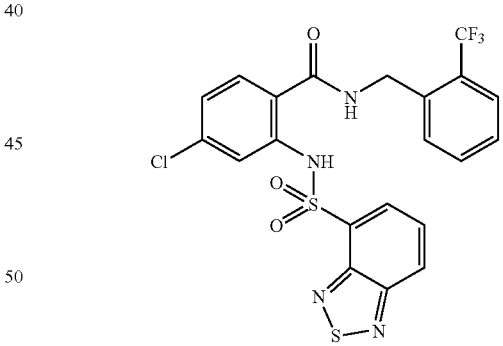

2-(Benzo[1,2,5]thiadiazole-4-sulfonylamino)-4-chloro-N-(2-trifluoromethyl-benzyl)-benzamide This compound was prepared using the general procedure described in EXAMPLE 7. HPLC (reversed-phase): R$_T$=10.27 min (single peak). MS (ESI): neg. ion m/z 525 [M−H]$^-$. $^1$H NMR (400 MHz, CDCl$_3$): (rotameric broadening) 11.62 (s, 1H), 8.37 (dd, J=7.0, 1.0 Hz, 1H), 8.22 (dd, J=8.8, 1.0 Hz, 1H), 7.75-7.66 (m, 4H), 7.61 (app t, J=7.3 Hz, 1H), 7.49 (app t, J=7.6 Hz, 1H), 7.19 (d, J=8.5 Hz, 1H), 6.92 (dd, J=8.4, 2.0 Hz, 1H), 6.29 (bm, 1H), 4.75 (d, J=6.0 Hz, 1H).

Example 95

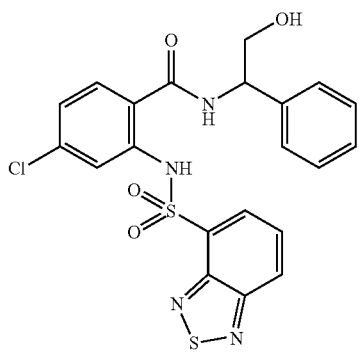

(S)-2-(Benzo[1,2,5]thiadiazole-4-sulfonylamino)-4-chloro-N-(2-hydroxy-1-phenyl-ethyl)-benzamide This compound was prepared using the general procedure described in EXAMPLE 7. HPLC (reversed-phase): $R_T$=9.13 min (single peak). MS (ESI): neg. ion m/z 487 [M–H]⁻. $^1$H NMR (500 MHz, CDCl$_3$): (rotameric broadening) 11.59 (s, 1H), 8.35 (dd, J=7.0 Hz, 1H), 8.20 (d, J=8.8 Hz, 1H), 7.76 (d, J=1.6 Hz, 1H), 7.70 (dd, J=8.8, 7.0 Hz, 1H) 7.43-7.34 (m, 4H), 7.31 (d, J=6.9 Hz, 2H), 6.96 (dd, J=8.3, 1.8 Hz, 1H), 6.76 (bd, J=7.2 Hz, 1H), 5.24 (bm, 1H), 3.99 (bm, 2H), 2.01 (bs, 1H).

Example 96

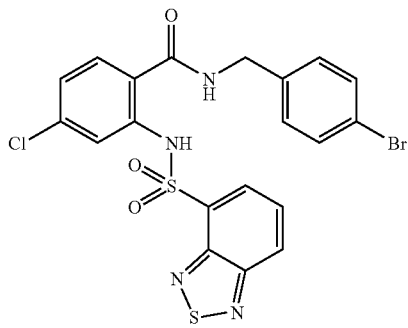

2-(Benzo[1,2,5]thiadiazole-4-sulfonylamino)-N-(4-bromo-benzyl)-4-chloro-benzamide This compound was prepared using the general procedure described in EXAMPLE 7. HPLC (reversed-phase): $R_T$=10.29 min (single peak). MS (ESI): neg. ion m/z 535/537/539 [M–H]⁻. $^1$H NMR (500 MHz, CDCl$_3$): (rotameric broadening) 11.58 (s, 1H), 8.37 (dd, J=7.0, 1.0 Hz, 1H), 8.22 (dd, J=8.8, 1.0 Hz, 1H), 7.75 (d, J=2.0 Hz, 1H), 7.72 (dd, J=8.8, 7.0 Hz, 1H), 7.50 (dd, J=8.4 Hz, 2H), 7.23 (d, J=8.4 Hz, 2H), 7.19 (d, J=8.4 Hz, 1H), 6.92 (dd, J=8.4, 2.0 Hz, 1H), 6.23 (bm, 1H), 4.52 (d, J=5.8 Hz, 2H).

Example 97

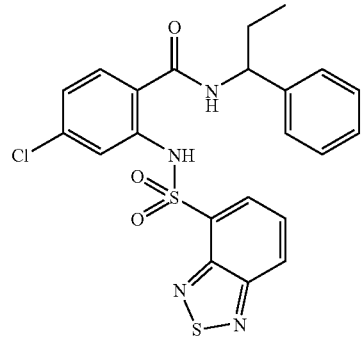

2-(Benzo[1,2,5]thiadiazole-4-sulfonylamino)-4-chloro-N-(1-phenyl-propyl)-benzamide This compound was prepared using the general procedure described in EXAMPLE 7. HPLC (reversed-phase): $R_T$=10.33 min (single peak). MS (ESI): neg. ion m/z 485 [M–H]⁻. $^1$H NMR (400 MHz, CDCl$_3$): (rotameric broadening) 11.66 (bs, 1H), 8.35 (bd, J=7.0 Hz, 1H), 8.18 (bd, J=8.8 Hz, 1H), 7.74 (d, J=2.0 Hz, 1H), 7.69 (dd, J=8.8, 7.0 Hz, 1H), 7.42-7.22 (m, 6H), 6.92 (dd, J=8.4, 2.0 Hz, 1H), 6.12 (bm, 1H), 5.02 (bm, 1H), 1.98-1.78 (m, 2H), 0.92 (t, J=7.3 Hz, 3H).

Example 98

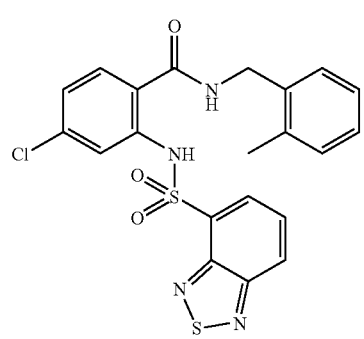

2-(Benzo[1,2,5]thiadiazole-4-sulfonylamino)-4-chloro-N-(2-methyl-benzyl)-benzamide This compound was prepared using the general procedure described in EXAMPLE 7. HPLC (reversed-phase): $R_T$=10.14 min (single peak). MS (ESI): neg. ion m/z 471 [M–H]⁻. $^1$H NMR (400 MHz, CDCl$_3$): (rotameric broadening) 11.70 (bs, 1H), 8.37 (bd, J=7.0 Hz, 1H), 8.23 (bd, J=8.8 Hz, 1H), 7.75 (d, J=2.0 Hz, 1H), 7.72 (dd, J=8.8, 7.0 Hz, 1H), 7.30-7.15 (m, 5H), 6.91 (dd, J=8.4, 2.0 Hz, 1H), 6.03 (bm, 1H), 4.57 (d, J=5.2 Hz, 2H), 2.35 (s, 3H).

Example 99

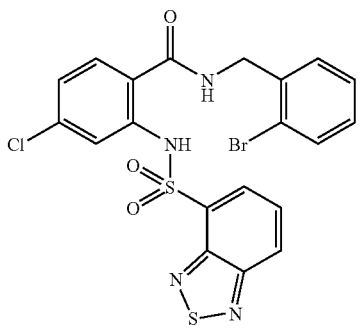

2-(Benzo[1,2,5]thiadiazole-4-sulfonylamino)-N-(2-bromo-benzyl)-4-chloro-benzamide This compound was prepared using the general procedure described in EXAMPLE 7. HPLC (reversed-phase): $R_T$=10.18 min (single peak). MS (ESI): neg. ion m/z 535/537/539 [M−H]⁻. ¹H NMR (400 MHz, CDCl₃): (rotameric broadening) 11.61 (bs, 1H), 8.35 (bd, J=7.0 Hz, 1H), 8.20 (bd, J=8.8 Hz, 1H), 7.74 (d, J=2.0 Hz, 1H), 7.70 (dd, J=8.8, 7.0 Hz, 1H), 7.60 (m, 1H), 7.50 (m, 1H), 7.36 (m, 1H), 7.26-7.18 (m, 2H), 6.93 (dd, J=8.4, 2.0 Hz, 1H), 6.48 (bm, 1H), 4.64 (d, J=5.9 Hz, 2H).

Example 100

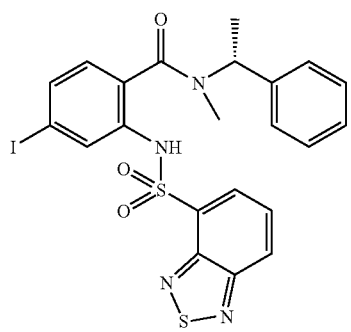

(R)-2-(Benzo[1,2,5]thiadiazole-4-sulfonylamino)-4-iodo-N-methyl-N-(1-phenyl-ethyl)-benzamide This compound was prepared using the general procedure described in EXAMPLE 9. HPLC (reversed-phase): $R_T$=10.19 min (single peak). MS (ESI): m/z 579 [M+H]⁺, 601 [M+Na]⁺. ¹H NMR (400 MHz, CDCl₃): (rotameric broadening) 8.97 (bs, 1H), 8.36 (bd, J=7.0 Hz, 1H), 8.24 (bd, J=8.8 Hz, 1H), 7.94 (d, J=1.4 Hz, 1H), 7.74 (bm, 1H), 7.5-7.35 (bm, 3H), 7.38-7.30 (bm, 2H), 7.32 (dd, J=8.0, 1.4 Hz, 1H), 6.83 (bd, J=8.2 Hz, 1H), 6.08 (bm, 1H), 2.8-2.2 (bs, 3H), 1.7-1.35 (bs, 3H).

Example 101

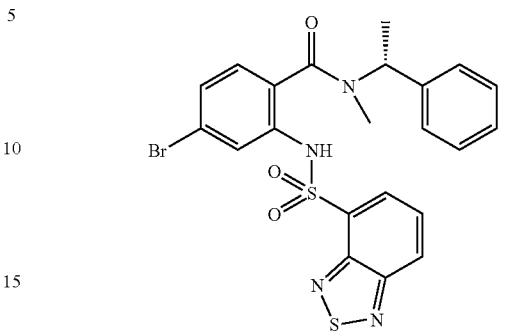

(R)-2-(Benzo[1,2,5]thiadiazole-4-sulfonylamino)-4-bromo-N-methyl-N-(1-phenyl-ethyl)-benzamide This compound was prepared using the general procedure described in EXAMPLE 8. HPLC (reversed-phase): $R_T$=10.14 min (single peak). MS (ESI): m/z ~532 [M+H]⁺, ~554 [M+Na]⁺. ¹H NMR (400 MHz, CDCl₃): (rotameric broadening) 9.08 (bs, 1H), 8.37 (dd, J=7.0, 0.9 Hz, 1H), 8.24 (bd, J=8.8 Hz, 1H), 7.77 (d, J=1.8 Hz, 1H), 7.73 (bm, 1H), 7.5-7.35 (bm, 3H), 7.38-7.30 (bm, 2H), 7.11 (dd, J=8.2, 1.8 Hz, 1H), 6.98 (bm, 1H), 6.05 (bm, 1H), 2.85-2.2 (bs, 3H), 1.8-1.3 (bs, 3H).

Example 102

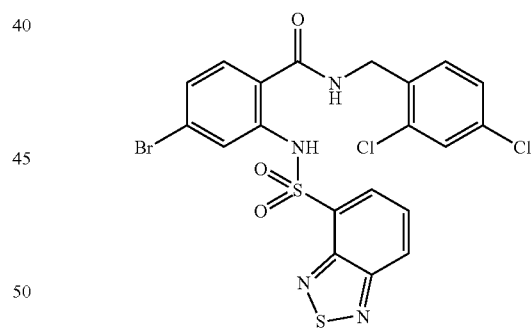

2-(Benzo[1,2,5]thiadiazole-4-sulfonylamino)-4-bromo-N-(2,4-dichloro-benzyl)-benzamide This compound was prepared using the general procedure described in EXAMPLE 8. HPLC (reversed-phase): $R_T$=10.58 min (single peak). MS (ESI): m/z ~572 [M+H]⁺, ~594 [M+Na]⁺. ¹H NMR (400 MHz, CDCl₃): (rotameric broadening) 11.51 (s, 1H), 8.37 (dd, J=7.0, 1.0 Hz, 1H), 8.21 (dd, J=8.8, 1.0 Hz, 1H), 7.90 (d, J=1.8 Hz, 1H), 7.71 (dd, J=8.8, 7.0 Hz, 1H), 7.45 (d, J=7.8 Hz, 1H), 7.44 (d, J=1.8 Hz, 1H), 7.30 (dd, J=8.2, 2.1 Hz, 1H), 7.16 (d, J=8.4 Hz, 1H), 7.09 (dd, J=8.4, 1.8 Hz, 1H), 6.42 (bm, 1H), 4.60 (d, J=6.0 Hz, 2H).

Example 103

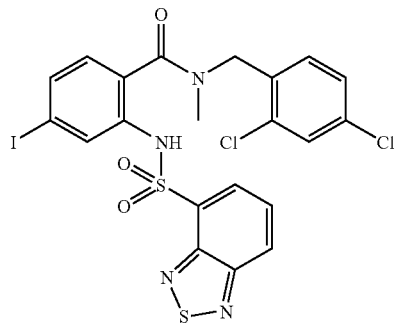

2-(Benzo[1,2,5]thiadiazole-4-sulfonylamino)-N-(2,4-dichloro-benzyl)-4-iodo-N-methyl-benzamide This compound was prepared using the general procedure described in EXAMPLE 8. HPLC (reversed-phase): $R_T$=10.70 min (single peak). MS (ESI): m/z ~633 [M+H]$^+$, ~655 [M+Na]$^+$. $^1$H NMR (400 MHz, CDCl$_3$): (rotameric broadening) 9.00 (bs, 1H), 8.33 (bd, J=6.8 Hz, 1H), 8.26 (bd, J=8.8 Hz, 1H), 7.77 (d, J=1.8 Hz, 1H), 7.74 (bm, 1H), 7.45 (bm, 1H), 7.2-7.1 (bm, 2H), 7.05 (ddd, J=8.4, 8.1, 2.6 Hz, 1H), 6.91 (bm, 1H), 4.7-4.35 (bs, 1.3H), 4.35-4.0 (bs, 0.7H), 3.1-3.25 (bs, 1.1H), 2.7-2.4 (bs, 1.9H).

Example 104

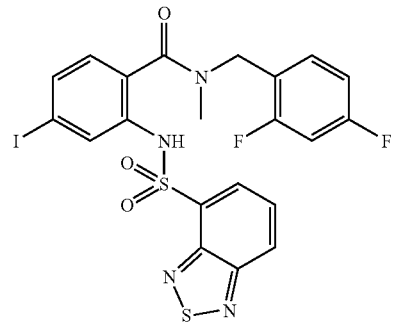

2-(Benzo[1,2,5]thiadiazole-4-sulfonylamino)-N-(2,4-difluoro-benzyl)-4-iodo-N-methyl-benzamide This compound was prepared using the general procedure described in EXAMPLE 9. HPLC (reversed-phase): $R_T$=10.08 min (single peak). MS (ESI): m/z 601 [M+H]$^+$, 623 [M+Na]$^+$. $^1$H NMR (400 MHz, CDCl$_3$): (rotameric broadening) 8.92 (bs, 1H), 8.31 (bd, J=7.0 Hz, 1H), 8.25 (bd, J=8.8 Hz, 1H), 7.96 (d, J=1.5 Hz, 1H), 7.73 (bm, 1H), 7.35 (bd, J=7.6 Hz, 1H), 6.93 (bm, 1H), 6.85 (bm, 1H), 6.78 (bd, J=8.0 Hz, 1H), 4.6-4.35 (bs, 1.3H), 4.35-4.1 (bs, 0.7H), 3.05-2.7 (bs, 1.1H), 2.7-2.45 (bs, 1.9H).

Example 105

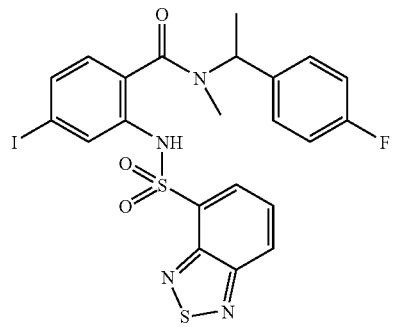

2-(Benzo[1,2,5]thiadiazole-4-sulfonylamino)-N-[1-(4-fluoro-phenyl)-ethyl]-4-iodo-N-methyl-benzamide This compound was prepared using the general procedure described in EXAMPLE 9. HPLC (reversed-phase): $R_T$=10.17 min (single peak). MS (ESI): m/z 597 [M+H]$^+$, 619 [M+Na]$^+$. $^1$H NMR (400 MHz, CDCl$_3$): (rotameric broadening) 8.94 (bs, 1H), 8.37 (bd, J=7.0 Hz, 1H), 8.25 (bd, J=8.8 Hz, 1H), 7.90 (bs, 1H), 7.75 (bm, 1H), 7.5-7.25 (bm, 4H), 7.34 (dd, J=8.1, 1.6, 1H), 7.10 (bm, 1H), 6.82 (bd, J=8.0 Hz, 1H), 6.05 (bm, 1H), 2.8-2.3 (bs, 3H), 1.8-1.4 (bs, 3H).

Example 106

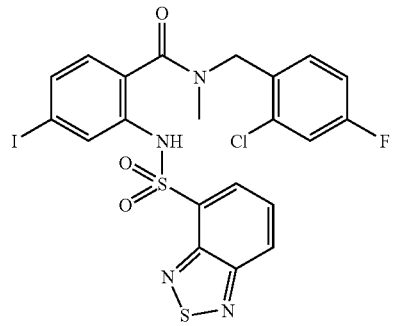

2-(Benzo[1,2,5]thiadiazole-4-sulfonylamino)-N-(2-chloro-4-fluoro-benzyl)-4-iodo-N-methyl-benzamide This compound was prepared using the general procedure described in EXAMPLE 9. HPLC (reversed-phase): $R_T$=10.33 min (single peak). MS (ESI): m/z 617 [M+H]$^+$, 639 [M+Na]$^+$. $^1$H NMR (400 MHz, CDCl$_3$): (rotameric broadening) 8.96 (bs, 1H), 8.32 (bd, J=7.0 Hz, 1H), 8.26 (bd, J=9.0 Hz, 1H), 7.97 (d, J=1.5 Hz, 1H), 7.74 (bm, 1H), 7.5-7.3 (bm, 2H), 7.15 (bm, 1H), 7.04 (ddd, J=8.4, 8.1, 2.5 Hz, 1H), 6.80 (bm, 1H), 4.4-4.0 (bs, 0.7H), 3.1-2.7 (bs, 1.1H), 2.7-2.5 (bs, 1.9H).

Example 107

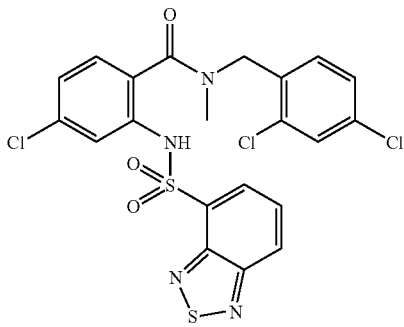

2-(Benzo[1,2,5]thiadiazole-4-sulfonylamino)-4-chloro-N-(2,4-dichloro-benzyl)-N-methyl-benzamide This compound was prepared using the general procedure described in EXAMPLE 7. HPLC (reversed-phase): $R_T$=10.61 min (single peak). MS (ESI): m/z 541 [M+H]$^+$, 563 [M+Na]$^+$. $^1$H NMR (400 MHz, CDCl$_3$): (rotameric broadening) 9.07 (bs, 1H), 8.33 (dd, J=7.0, 0.9 Hz, 1H), 8.26 (bd, J=8.9 Hz, 1H), 7.74 (bm, 1H), 7.63 (d, J=1.8 Hz, 1H), 7.43 (bm, 1H), 7.31 (dd, J=8.2, 2.0, 1H), 7.08-6.8 (bm, 1H), 4.4-4.0 (bs, 0.7H), 3.1-2.7 (bs, 1.1H), 2.7-2.5 (bs, 1.9H).

Example 108

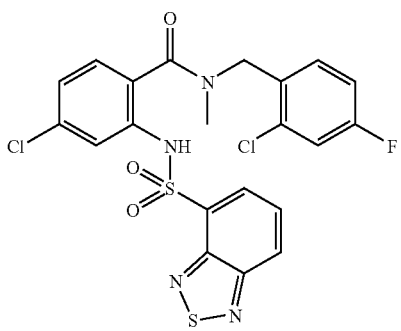

2-(Benzo[1,2,5]thiadiazole-4-sulfonylamino)-4-chloro-N-(2-chloro-4-fluoro-benzyl)-N-methyl-benzamide This compound was prepared using the general procedure described in EXAMPLE 7. HPLC (reversed-phase): $R_T$=10.25 min (single peak). MS (ESI): m/z 525 [M+H]$^+$, 547 [M+Na]$^+$. $^1$H NMR (400 MHz, CDCl$_3$): (rotameric broadening) 9.03 (bs, 1H), 8.33 (bd, J=6.8 Hz, 1H), 8.26 (bd, J=8.9 Hz, 1H), 7.96 (d, J=1.5 Hz, 1H), 7.73 (bm, 1H), 7.61 (d, J=1.8 Hz, 1H), 7.44 (bm, 1H), 7.16 (bm, 1H), 7.1-6.9 (bm, 2H), 7.05 (ddd, J=8.3, 8.1, 2.6 Hz, 1H), 4.8-4.4 (bs, 1.3H), 4.4-4.0 (bs, 0.7H), 3.1-2.7 (bs, 1.9H).

Example 109

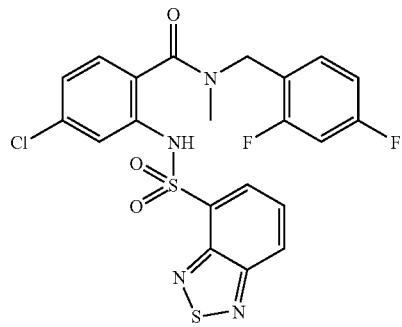

2-(Benzo[1,2,5]thiadiazole-4-sulfonylamino)-4-chloro-N-(2,4-difluoro-benzyl)-N-methyl-benzamide This compound was prepared using the general procedure described in EXAMPLE 7. HPLC (reversed-phase): $R_T$=9.92 min (single peak). MS (ESI): m/z 509 [M+H]$^+$, 531 [M+Na]$^+$. $^1$H NMR (400 MHz, CDCl$_3$): (rotameric broadening) 9.00 (bs, 1H), 8.32 (bd, J=6.9 Hz, 1H), 8.25 (bd, J=8.8 Hz, 1H), 7.73 (bm, 1H), 7.60 (bs, 1H), 7.50 (bm, 1H), 7.01 (bm, 1H), 6.93 (bm, 1H), 6.85 (bm, 1H), 4.7-4.4 (bs, 1.3H), 4.4-4.1 (bs, 0.7H), 3.1-2.7 (bs, 1.1H), 2.7-2.5 (bs, 1.9H).

Example 110

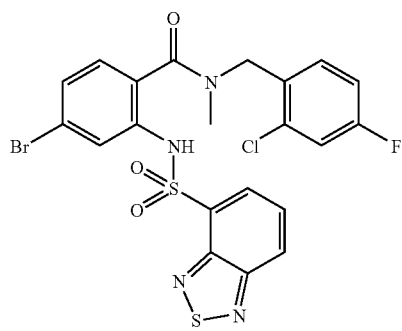

2-(Benzo[1,2,5]thiadiazole-4-sulfonylamino)-4-bromo-N-(2-chloro-4-fluoro-benzyl)-N-methyl-benzamide This compound was prepared using the general procedure described in EXAMPLE 8. HPLC (reversed-phase): $R_T$=10.28 min (single peak). MS (ESI): m/z 569/571 [M+H]$^+$. $^1$H NMR (400 MHz, CDCl$_3$): (rotameric broadening) 9.00 (bs, 1H), 8.33 (bd, J=6.8 Hz, 1H), 8.26 (bd, J=8.8 Hz, 1H), 7.77 (d, J=1.8 Hz, 1H), 7.74 (bm, 1H), 7.44 (bm, 1H), 7.15 (bm, 2H), 7.05 (ddd, J=8.4, 8.1, 2.6 Hz, 1H), 6.96 (bm, 1H), 4.7-4.5 (bs, 1.3H), 4.4-4.0 (bs, 0.7H), 3.1-2.7 (bs, 1.1H), 2.7-2.4 (bs, 1.9H).

Example 111

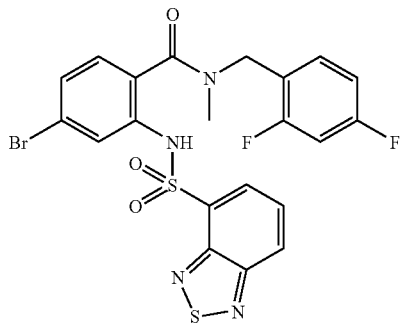

2-(Benzo[1,2,5]thiadiazole-4-sulfonylamino)-4-bromo-N-(2,4-difluoro-benzyl)-N-methyl-benzamide This compound was prepared using the general procedure described in EXAMPLE 8. HPLC (reversed-phase): $R_T$=10.02 min (single peak). MS (ESI): m/z ~555 [M+H]$^+$, ~576 [M+Na]$^+$. $^1$H NMR (400 MHz, CDCl$_3$): (rotameric broadening) 8.95 (bs, 1H), 8.32 (bd, J=6.9 Hz, 1H), 8.25 (bd, J=8.6 Hz, 1H), 7.77 (d, J=1.8 Hz, 1H), 7.72 (bm, 1H), 7.50 (bm, 1H), 7.15 (bd, J=6.8 Hz, 1H), 7.0-6.8 (bm, 3H), 4.7-4.5 (bs, 1.3H), 4.5-4.1 (bs, 0.7H), 3.1-2.7 (bs, 1.1H), 2.7-2.5 (bs, 1.9H).

Example 112

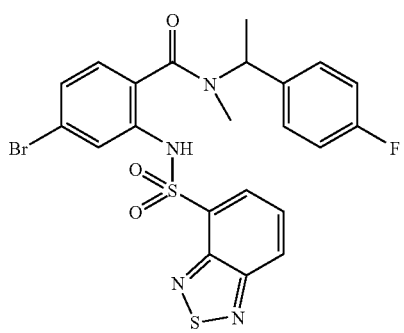

2-(Benzo[1,2,5]thiadiazole-4-sulfonylamino)-4-bromo-N-[1-(4-fluoro-phenyl)-ethyl]-N-methyl-benzamide This compound was prepared using the general procedure described in EXAMPLE 8. HPLC (reversed-phase): $R_T$=10.12 min (single peak). MS (ESI): m/z ~550 [M+H]$^+$, ~573 [M+Na]$^+$. $^1$H NMR (400 MHz, CDCl$_3$): (rotameric broadening) 8.98 (bs, 1H), 8.38 (dd, J=7.0, 0.9 Hz, 1H), 8.25 (bd, J=8.7 Hz, 1H), 7.75 (bm, 1H), 7.72 (d, J=1.8 Hz, 1H), 7.5-7.3 (bm, 2H), 7.17-7.05 (bm, 3H), 6.98 (bd, J=8.1 Hz, 1H), 6.05 (bm, 1H), 2.47 (bs, 3H), 1.55 (bs, 3H).

Example 113

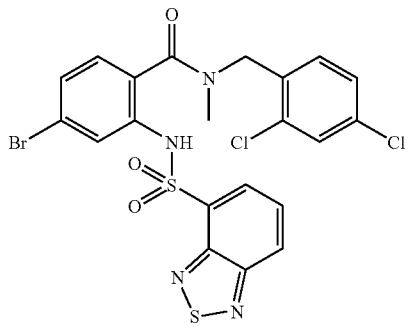

2-(Benzo[1,2,5]thiadiazole-4-sulfonylamino)-4-bromo-N-(2,4-dichloro-benzyl)-N-methyl-benzamide This compound was prepared using the general procedure described in EXAMPLE 8. HPLC (reversed-phase): $R_T$=10.65 min (single peak). MS (ESI): m/z ~587 [M+H]$^+$, ~609 [M+Na]$^+$. $^1$H NMR (400 MHz, CDCl$_3$): (rotameric broadening) 9.02 (bs, 1H), 8.33 (bd, J=7.0, 0.8 Hz, 1H), 8.26 (bd, J=8.8 Hz, 1H), 7.79 (d, J=1.8 Hz, 1H), 7.74 (bm, 1H), 7.45-7.30 (bm, 2H), 7.31 (dd, J=8.2, 1.9 Hz, 1H), 7.15 (bm, 1H), 6.97 (bm, 1H), 4.8-4.4 (bs, 1.3H), 4.4-4.0 (bs, 0.7H), 3.1-2.7 (bs, 1.1H), 2.7-2.5 (bs, 1.9H).

Example 114

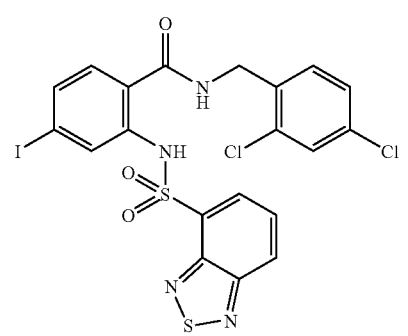

2-(Benzo[1,2,5]thiadiazole-4-sulfonylamino)-N-(2,4-dichloro-benzyl)-4-iodo-benzamide This compound was prepared using the general procedure described in EXAMPLE 9. HPLC (reversed-phase): $R_T$=10.53 min (single peak). MS (ESI): m/z 619 [M+H]$^+$, 641 [M+Na]$^+$. $^1$H NMR (400 MHz, CDCl$_3$): (rotameric broadening) 11.43 (s, 1H), 8.36 (dd, J=7.0, 1.0 Hz, 1H), 8.21 (dd, J=8.8, 1.0 Hz, 1H), 8.08 (d, J=1.6 Hz, 1H), 7.72 (dd, J=8.8, 7.0 Hz, 1H), 7.49-7.40 (m, 2H), 7.33-7.22 (m, 1H), 6.99 (d, J=8.2 Hz, 1H), 6.43 (bm, 1H), 4.59 (d, J=6.0 Hz, 2H).

Example 115

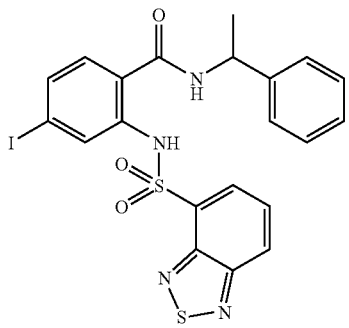

(R)-2-(Benzo[1,2,5]thiadiazole-4-sulfonylamino)-4-iodo-N-(1-phenyl-ethyl)-benzamide This compound was prepared using the general procedure described in EXAMPLE 9. HPLC (reversed-phase): $R_T$=10.07 min (single peak). MS (ESI): m/z 565 [M+H]$^+$, 587 [M+Na]$^+$. $^1$H NMR (400 MHz, CDCl$_3$): (rotameric broadening) 11.55 (s, 1H), 8.36 (dd, J=7.0, 1.1 Hz, 1H), 8.20 (dd, J=8.8, 1.1 Hz, 1H), 8.10 (d, J=1.6 Hz, 1H), 7.71 (dd, J=8.8, 7.0 Hz, 1H), 7.41-7.36 (m, 2H), 7.36-7.26 (m, 4H), 6.98 (d, J=8.3 Hz, 1H), 6.12 (d, J=8.0 Hz, 1H), 5.25 (quint, J=7.3 Hz, 1H), 1.56 (d, J=6.9 Hz, 3H).

Example 116

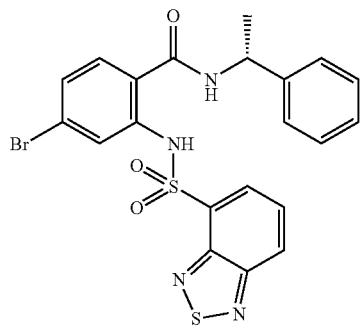

(R)-2-(Benzo[1,2,5]thiadiazole-4-sulfonylamino)-4-bromo-N-(1-phenyl-ethyl)-benzyl)-N-methyl-benzamide This compound was prepared using the general procedure described in EXAMPLE 8. HPLC (reversed-phase): $R_T$=10.00 min (single peak). MS (ESI): m/z 517/519 [M+H]$^+$, 539/541 [M+Na]$^+$. $^1$H NMR (400 MHz, CDCl$_3$): (rotameric broadening) 11.63 (s, 1H), 8.36 (dd, J=7.0, 1.0 Hz, 1H), 8.20 (dd, J=8.8, 1.0 Hz, 1H), 7.91 (d, J=1.8 Hz, 1H), 7.70 (dd, J=8.8, 7.0 Hz, 1H), 7.43-7.30 (m, 5H), 7.15 (d, J=8.4 Hz, 1H), 7.07 (dd, J=8.4, 1.8 Hz, 1H), 6.12 (d, J=7.4 Hz, 1H), 5.29 (quint, J=7.4 Hz, 1H), 1.57 (d, J=6.8 Hz, 2H).

Example 117

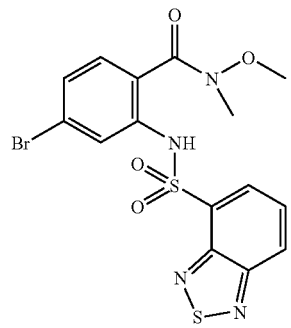

2-(Benzo[1,2,5]thiadiazole-4-sulfonylamino)-4-bromo-N-methoxy-N-methyl-benzamide This compound was prepared using the general procedure described in EXAMPLE 8. HPLC (reversed-phase): $R_T$=9.09 min (single peak). MS (ESI): m/z 457 [M+H]$^+$, 479 [M+Na]$^+$. $^1$H NMR (500 MHz, CDCl$_3$): (rotameric broadening) 9.37 (bs, 1H), 8.27 (dd, J=7.0, 1.0 Hz, 1H), 8.22 (dd, J=8.8, 1.0 Hz, 1H), 7.88 (d, J=1.8 Hz, 1H), 7.68 (dd, J=8.8, 7.0 Hz, 1H), 7.25 (d, J=8.4 Hz, 1H), 7.16 (dd, J=8.4, 1.9 Hz, 1H), 3.16 (s, 3H), 3.10 (s, 3H).

Example 118

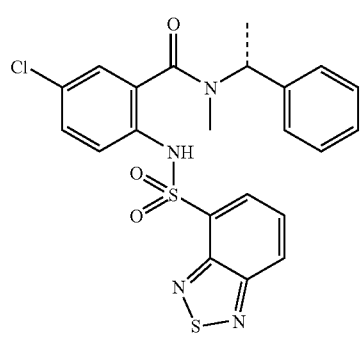

(R)-2-(Benzo[1,2,5]thiadiazole-4-sulfonylamino)-5-chloro-N-methyl-N-(1-phenyl-ethyl)-benzamide This compound was prepared as described using the general procedure of EXAMPLE 43. HPLC (reversed-phase): $R_T$=9.83 min (single peak). MS (ESI): m/z 487 [M+H]$^+$, 509 [M+Na]$^+$. $^1$H NMR (500 MHz, CDCl$_3$): (rotameric broadening) 8.71 (bs, 1H), 8.32 (bd, J=6.7 Hz, 1H), 8.23 (bd, J=7.8 Hz, 1H), 7.69 (bm, 1H), 7.49 (bd, J=8.8 Hz, 1H), 7.49-7.30 (m, 5H), 7.21 (bd, J=8.9 Hz, 1H), 7.08 (bm, 1H), 6.05 (bm, 1H), 2.42 (bs, 3H), 1.58 (bs, 3H).

Example 119

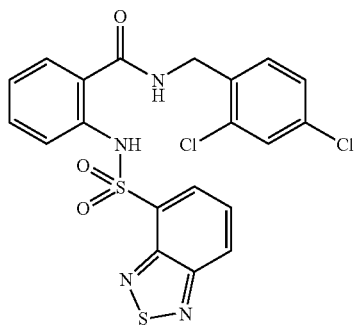

2-(Benzo[1,2,5]thiadiazole-4-sulfonylamino)-N-(2, 4-dichloro-benzyl)-benzamide

This compound was prepared as described in EXAMPLE 41. HPLC (reversed-phase): $R_T$=9.94 min (single peak). MS (ESI): m/z ~494 [M+H]$^+$. $^1$H NMR (500 MHz, CDCl$_3$): (rotameric broadening) 11.36 (s, 1H), 8.32 (bd, J=6.9 Hz, 1H), 8.18 (bd, J=8.7 Hz, 1H), 7.75-7.60 (bm, 2H), 7.46-7.40 (bm, 2H), 7.35-7.26 (bm, 3H), 6.97 (bm, 1H), 6.44 (bm, 1H), 4.59 (d, J=6.0 Hz, 2H).

Example 120

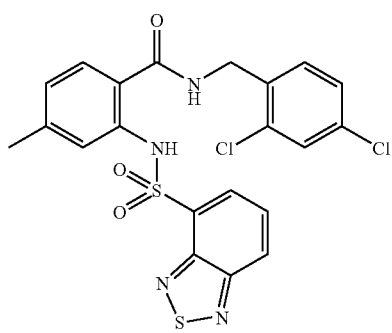

2-(Benzo[1,2,5]thiadiazole-4-sulfonylamino)-N-(2, 4-dichloro-benzyl)-4methyl-benzamide This compound was prepared as described in EXAMPLE 44. HPLC (reversed-phase): $R_T$=10.43 min (single peak). MS (ESI): m/z 507 [M+H]$^+$, 529 [M+Na]$^+$. $^1$H NMR (400 MHz, CDCl$_3$): (rotameric broadening) 11.50 (s, 1H), 8.32 (bd, J=7.0 Hz, 1H), 8.18 (bd, J=8.8 Hz, 1H), 7.66 (dd, J=8.8, 7.0 Hz, 1H), 7.50 (bs, 1H), 7.45-7.40 (m, 2H), 7.30-7.26 (m, 1H), 7.18 (d, J=8.0 Hz, 1H), 6.76 (bd, J=8.1 Hz, 1H), 4.58 (d, J=6.1 Hz, 2H) 2.27 (s, 3H).

Example 121

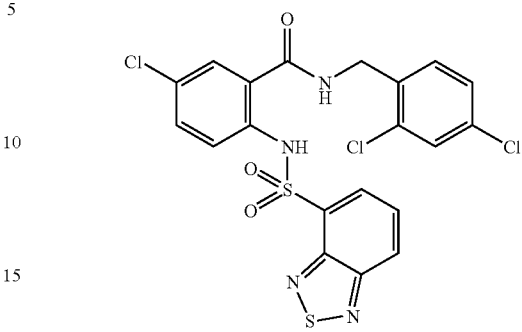

2-(Benzo[1,2,5]thiadiazole-4-sulfonylamino)-5-chloro-N-(2,4-dichloro-benzyl)-benzamide This compound was prepared as described using the general procedure of EXAMPLE 43. HPLC (reversed-phase): $R_T$=10.41 min (single peak). MS (ESI): m/z 527/529 [M+H]$^+$. $^1$H NMR (400 MHz, CDCl$_3$): (rotameric broadening) 11.15 (s, 1H), 8.31 (dd, J=7.0, 0.9 Hz, 1H), 8.20 (dd, J=8.8, 0.9 Hz, 1H), 7.68 (d, J=8.9 Hz, 1H), 7.66 (d, J=8.8 Hz, 1H), 7.44 (s, 1H), 7.43 (d, J=8.2 Hz, 1H), 7.31-7.24 (m, 3H), 6.36 (bm, 1H), 4.57 (d, J=6.0 Hz, 2H).

Example 122

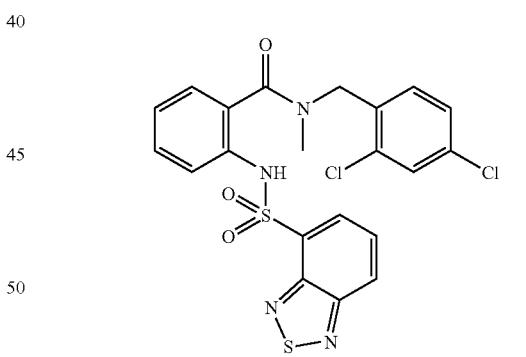

2-(Benzo[1,2,5]thiadiazole-4-sulfonylamino)-N-(2, 4-dichloro-benzyl)-N-methyl-benzamide This compound was prepared as described in EXAMPLE 41. HPLC (reversed-phase): $R_T$=10.08 min (single peak). MS (ESI): m/z 507 [M+H]$^+$, 529 [M+Na]$^+$. $^1$H NMR (400 MHz, CDCl$_3$): (rotameric broadening) 8.86 (bs, 1H), 8.28 (bd, J=7.0 Hz, 1H), 8.24 (bd, J=8.7 Hz, 1H), 7.69 (bm, 1H), 7.57 (d, J=8.2 Hz, 1H), 7.44-7.35 (bm, 2H), 7.35-7.26 (bm, 2H), 7.13-6.95 (bm, 2H), 4.7-4.5 (bs, 1.3H), 4.3-3.9 (bs, 0.7H), 3.0-2.7 (bs, 1.1H), 2.7-2.45 (bs, 1.9H).

Example 123

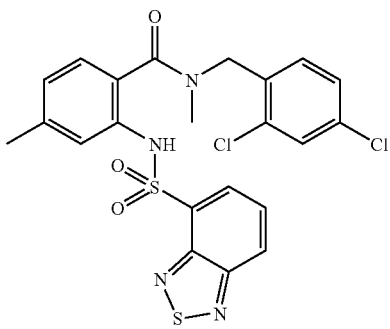

2-(Benzo[1,2,5]thiadiazole-4-sulfonylamino)-N-(2,4-dichloro-benzyl)-4,N-dimethyl-benzamide This compound was prepared as described in EXAMPLE 44. HPLC (reversed-phase): $R_T$=10.39 min (single peak). MS (ESI): m/z 521 [M+H]$^+$. $^1$H NMR (400 MHz, CDCl$_3$): (rotameric broadening) 8.92 (bs, 1H), 8.27 (bd, J=7.0 Hz, 1H), 8.24 (bd, J=9.0 Hz, 1H), 7.70 (bm, 1H), 7.43-7.35 (bm, 3H), 7.30 (bm, 1H), 7.02-6.70 (bm, 2H), 4.7-4.4 (bs, 1.3H), 4.25-3.9 (bs, 0.7H), 3.0-2.7 (bs, 1.1H), 2.7-2.5 (bs, 1.9 H), 2.28 (s, 3H).

Example 124

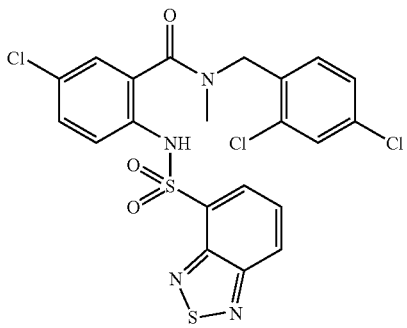

2-(Benzo[1,2,5]thiadiazole-4-sulfonylamino)-5-chloro-N-(2,4-dichloro-benzyl)-N-methyl-benzamide This compound was prepared as described using the general procedure of EXAMPLE 43. HPLC (reversed-phase): $R_T$=10.48 min (single peak). MS (ESI): m/z ~542 [M+H]$^+$. $^1$H NMR (400 MHz, CDCl$_3$): (rotameric broadening) 8.72 (bs, 1H), 8.28-8.23 (bm, 2H), 7.70 (bm, 1H), 7.53 (bd, J=8.8 Hz, 1H), 7.45-7.31 (bm, 2H), 7.31 (dd, J=8.2, 1.9 Hz, 1H), 7.05 (bm, 1H), 4.65-4.4 (bs, 1.3H), 4.4-4.1 (bs, 0.7H), 3.0-2.7 (bs, 1.1H), 2.7-2.45 (bs, 1.9 H).

Example 125

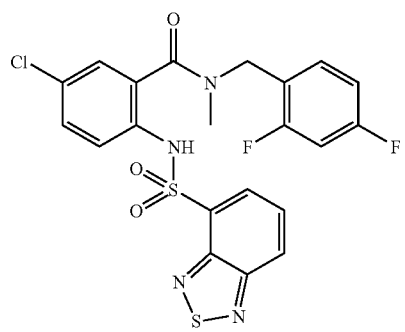

2-(Benzo[1,2,5]thiadiazole-4-sulfonylamino)-5-chloro-N-(2,4-difluoro-benzyl)-N-methyl-benzamide This compound was prepared as described using the general procedure of EXAMPLE 43. HPLC (reversed-phase): $R_T$=9.82 min (single peak). MS (ESI): m/z 509 [M+H]$^+$, 531 [M+Na]$^+$. $^1$H NMR (400 MHz, CDCl$_3$): (rotameric broadening) 8.70 (bs, 1H), 8.32-8.17 (bm, 2H), 7.69 (bm, 1H), 7.54 (d, J=8.8 Hz, 1H), 7.53-7.40 (bm, 1H), 7.24 (d, J=2.4 Hz, 1H), 7.02 (bm, 1H), 6.96-6.80 (bm, 2H), 4.57-4.4 (bs, 1.3H), 4.4-4.1 (bs, 0.7H), 3.0-2.7 (bs, 1.1H), 2.7-2.45 (bs, 1.9 H).

Example 126

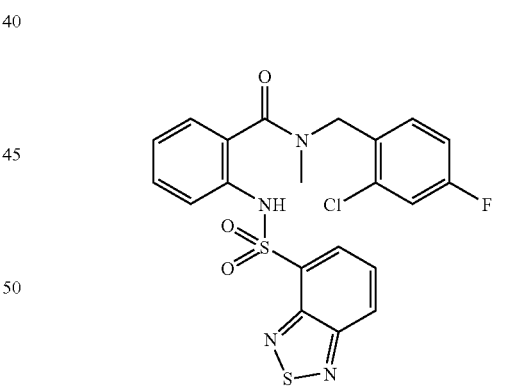

2-(Benzo[1,2,5]thiadiazole-4-sulfonylamino)-N-(2-chloro-4-fluoro-benzyl)-N-methyl-benzamide This compound was prepared as described in EXAMPLE 41. HPLC (reversed-phase): $R_T$=9.65 min (single peak). MS (ESI): m/z 491 [M+H]$^+$, 513 [M+Na]$^+$. $^1$H NMR (400 MHz, CDCl$_3$): (rotameric broadening) 8.81 (bs, 1H), 8.28 (bd, J=7.0 Hz, 1H), 8.24 (bd, J=8.7 Hz, 1H), 7.69 (bm, 1H), 7.53 (bd, J=7.9 Hz, 1H), 7.46 (bm, 1H), 7.31 (bd, J=8.8 Hz, 1H), 7.20-6.97 (bm, 3H), 7.05 (ddd, J=8.2, 8.2, 2.6 Hz, 1H), 4.65-4.4 (bs, 1.3H), 4.4-4.0 (bs, 0.7H), 3.0-2.7 (bs, 1.1H), 2.7-2.4 (bs, 1.9 H).

Example 127

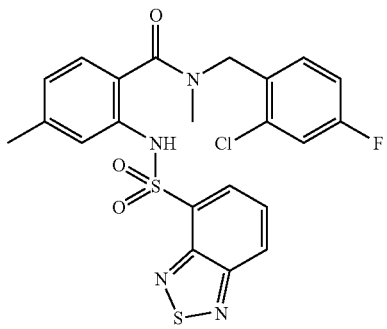

2-(Benzo[1,2,5]thiadiazole-4-sulfonylamino)-N-(2-chloro-4-fluoro-benzyl)-4,N-dimethyl-benzamide This compound was prepared as described in EXAMPLE 44. HPLC (reversed-phase): $R_T$=10.00 min (single peak). MS (ESI): m/z 505 [M+H]$^+$, 527 [M+Na]$^+$. $^1$H NMR (400 MHz, CDCl$_3$): (rotameric broadening) 8.99 (bs, 1H), 8.27 (bd, J=7.0 Hz, 1H), 8.23 (bd, J=8.8 Hz, 1H), 7.69 (bm, 1H), 7.41 (b, 1H), 7.40 (bs, 1H), 7.15 (bm, 1H), 7.04 (ddd, J=8.3, 8.2, 2.5 Hz, 1H), 6.96 (bm, 1H), 7.62 (bm, 1H), 4.65-4.3 (bs, 1.3H), 4.3-3.9 (bs, 0.7H), 2.9-2.65 (bs, 1.1H), 2.65-2.4 (bs, 1.9 H), 2.28 (s, 3H).

Example 128

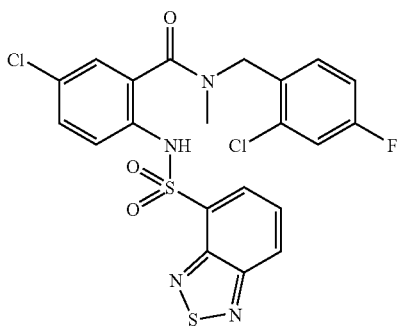

2-(Benzo[1,2,5]thiadiazole-4-sulfonylamino)-5-chloro-N-(2-chloro-4-fluoro-benzyl)-N-methyl-benzamide This compound was prepared as described using the general procedure of EXAMPLE 43. HPLC (reversed-phase): $R_T$=10.10 min (single peak). MS (ESI): m/z ~526 [M+H]$^+$, 547 [M+Na]$^+$. $^1$H NMR (400 MHz, CDCl$_3$): (rotameric broadening) 8.69 (bs, 1H), 8.32-8.23 (bm, 2H), 7.70 (bm, 1H), 7.52 (d, J=8.8 Hz, 1H), 7.43 (bm, 1H), 7.17 (bm, 1H), 7.09-7.01 (bm, 2H), 4.65-4.4 (bs, 1.3H), 4.4-4.05 (bs, 0.7H), 3.0-2.7 (bs, 1.1H), 2.7-2.45 (bs, 1.9 H).

Example 129

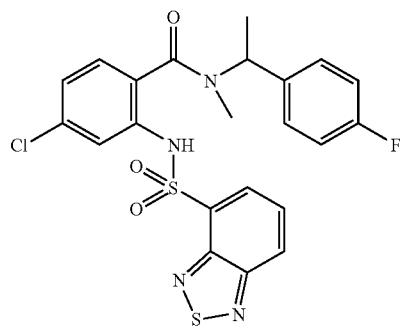

2-(Benzo[1,2,5]thiadiazole-4-sulfonylamino)-4-chloro-N-[1-(4-fluoro-phenyl)-ethyl]-N-methyl-benzamide This compound was prepared using the general procedure described in EXAMPLE 7. HPLC (reversed-phase): $R_T$=10.00 min (single peak). MS (ESI): m/z 505 [M+H]$^+$, 527 [M+Na]$^+$. $^1$H NMR (400 MHz, CDCl$_3$): (rotameric broadening) 9.00 (bs, 1H), 8.38 (bd, J=7.0 Hz, 1H), 8.25 (bd, J=8.8 Hz, 1H), 7.74 (bm, 1H), 7.56 (d, J=1.8 Hz, 1H), 7.5-7.22 (bm, 2H), 7.13-7.02 (bm, 3H), 6.97 (bm, 1H), 6.05 (bm, 1H), 2.7-2.3 (bs, 3H), 2.25-1.8 (bs, 3H).

Example 130

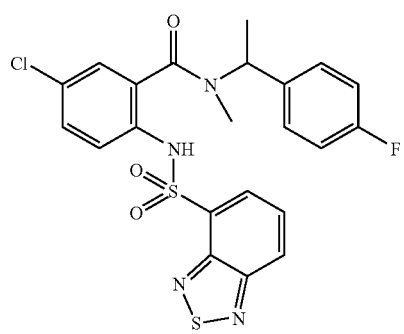

2-(Benzo[1,2,5]thiadiazole-4-sulfonylamino)-5-chloro-N-[1-(4-fluoro-phenyl)-ethyl]-N-methyl-benzamide This compound was prepared as described using the general procedure of EXAMPLE 43. HPLC (reversed-phase): $R_T$=9.93 min (single peak). MS (ESI): m/z 505 [M+H]$^+$, 527 [M+Na]$^+$. $^1$H NMR (400 MHz, CDCl$_3$): (rotameric broadening) 8.68 (bs, 1H), 8.32 (bd, J=7.0 Hz, 1H), 8.24 (bd, J=8.8 Hz, 1H), 7.71 (bm, 1H), 7.5-7.3 (bm, 2H), 7.46 (bd, J=8.8 Hz, 1H), 7.21 (dd, J=8.8, 2.3 Hz, 1H), 7.14-7.07 (bm, 3H), 6.05 (bm, 1H), 2.6-2.3 (bs, 3H), 2.1-1.7 (bs, 3H).

Example 131

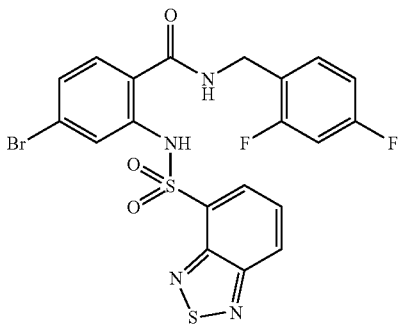

2-(Benzo[1,2,5]thiadiazole-4-sulfonylamino)-4-bromo-N-(2,4-difluoro-benzyl)-benzamide This compound was prepared using the general procedure described in EXAMPLE 8. HPLC (reversed-phase): $R_T$=10.02 min (single peak). MS (ESI): m/z 539/541 [M+H]$^+$. $^1$H NMR (400 MHz, CDCl$_3$): (rotameric broadening) 11.54 (s, 1H), 8.36 (dd, J=7.0, 1.0 Hz, 1H), 8.21 (d, J=8.8 Hz, 1H), 7.90 (d, J=1.8 Hz, 1H), 7.71 (dd, J=8.8, 7.0 Hz, 1H), 7.43 (m, 1H), 7.15 (d, J=8.4 Hz, 1H), 7.08 (dd, J=8.4, 1.8 Hz, 1H), 6.92 (m, 1H), 6.85 (m, 1H), 6.31 (bm, 1H), 4.56 (d, J=5.7 Hz, 2H).

Example 132

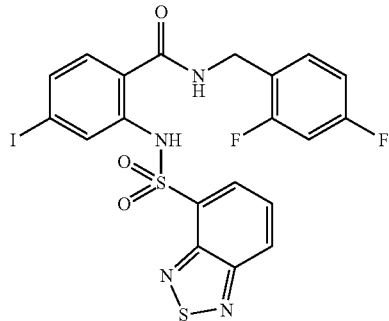

2-(Benzo[1,2,5]thiadiazole-4-sulfonylamino)-N-(2,4-difluoro-benzyl)-4-iodo-benzamide This compound was prepared using the general procedure described in EXAMPLE 9. HPLC (reversed-phase): $R_T$=10.07 min (single peak). MS (ESI): m/z 587 [M+H]$^+$, 609 [M+Na]$^+$. $^1$H NMR (400 MHz, CDCl$_3$): (rotameric broadening) 11.54 (s, 1H), 8.36 (dd, J=7.0, 1.0 Hz, 1H), 8.21 (d, J=8.8 Hz, 1H), 8.09 (d, J=1.6 Hz, 1H), 7.71 (dd, J=8.8, 7.0 Hz, 1H), 7.43 (m, 1H), 7.30 (dd, J=8.3, 1.6 Hz, 1H), 6.98 (d, J=8.3 Hz, 1H), 6.92 (m, 1H), 6.84 (m, 1H), 6.30 (bm, 1H), 4.55 (d, J=5.8 Hz, 2H).

Example 133

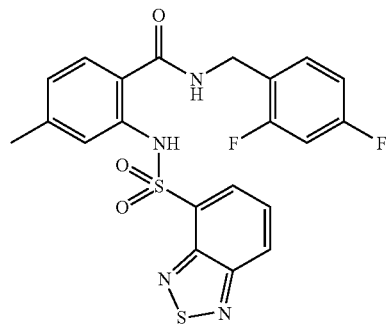

2-(Benzo[1,2,5]thiadiazole-4-sulfonylamino)-N-(2,4-difluoro-benzyl)-4-methyl-benzamide This compound was prepared as described in EXAMPLE 44. HPLC (reversed-phase): $R_T$=9.70 min (single peak). MS (ESI): m/z 475 [M+H]$^+$, 497 [M+Na]$^+$. $^1$H NMR (400 MHz, CDCl$_3$): (rotameric broadening) 11.53 (bs, 1H), 8.32 (dd, J=7.0, 1.0 Hz, 1H), 8.18 (dd, J=8.8, 1.0 Hz, 1H), 7.66 (dd, J=8.8, 7.0 Hz, 1H), 7.51 (bs, 1H), 7.43 (m, 1H), 7.17 (d, J=8.0 Hz, 1H), 6.91 (m, 1H), 6.84 (m, 1H), 6.76 (bd, J=8.4 Hz, 1H), 6.28 (bm, 1H), 4.54 (d, J=5.9 Hz, 2H), 2.26 (s, 3H).

Example 134

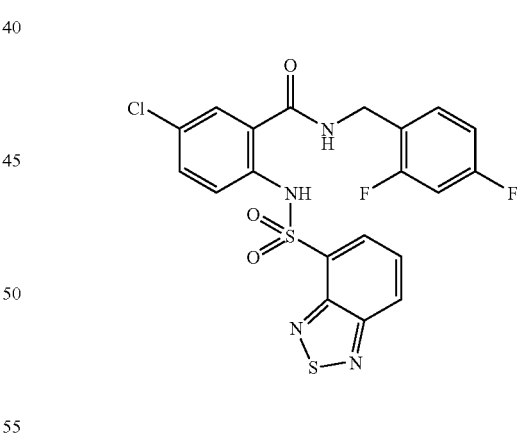

2-(Benzo[1,2,5]thiadiazole-4-sulfonylamino)-5chloro-N-(2,4-difluoro-benzyl)-benzamide This compound was prepared as described in EXAMPLE 43. HPLC (reversed-phase): $R_T$=9.95 min (single peak). MS (ESI): m/z 495 [M+H]$^+$, 517 [M+Na]$^+$. $^1$H NMR (400 MHz, CDCl$_3$): (rotameric broadening) 11.17 (s, 1H), 8.31 (dd, J=7.0, 1.0 Hz, 1H), 8.20 (dd, J=8.8, 1.0 Hz, 1H), 7.68 (d, J=8.9 Hz, 1H), 7.67 (dd, J=8.8, 7.0 Hz, 1H), 7.45 (m, 1H), 7.31-7.23 (m, 2H), 6.92 (m, 1H), 6.87 (m, 1H), 6.26 (bm, 1H), 4.53 (d, J=5.8 Hz, 2H).

Example 135

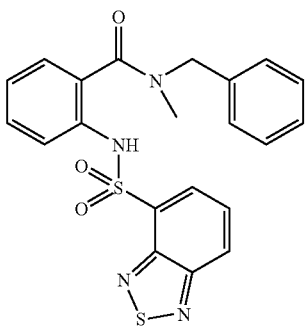

2-(Benzo[1,2,5]thiadiazole-4-sulfonylamino)-N-benzyl-N-methyl-benzamide

This compound was prepared as described in EXAMPLE 41. HPLC (reversed-phase): $R_T$=9.28 min (single peak). MS (ESI): m/z 439 [M+H]$^+$, 461 [M+Na]$^+$. $^1$H NMR (400 MHz, CDCl$_3$): (rotameric broadening) 8.82 (bs, 1H), 8.37-8.17 (bm, 1H), 7.66 (bm, 1H), 7.55 (bm, 1H), 7.45-7.25 (bm, 5H), 7.2-6.9 (bm, 3H), 4.63-4.4 (bs, 1.3H), 4.4-4.1 (bs, 0.7H), 3.1-2.65 (bs, 1.1H), 2.65-2.4 (bs, 1.9H).

Example 136

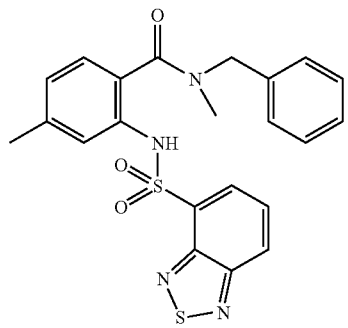

2-(Benzo[1,2,5]thiadiazole-4-sulfonylamino)-N-benzyl-4,N-dimethyl-benzamide

This compound was prepared as described in EXAMPLE 44. HPLC (reversed-phase): $R_T$=9.62 min (single peak). MS (ESI): m/z 453 [M+H]$^+$, 475 [M+Na]$^+$. $^1$H NMR (400 MHz, CDCl$_3$): (rotameric broadening) 8.96 (bs, 1H), 8.29-8.19 (bm, 2H), 7.67 (bm, 1H), 7.42-7.26 (bm, 5H), 7.15-6.95 (bm, 2H), 6.80 (bm, 1H), 4.55-4.3 (bs, 1.3H), 4.3-4.1 (bs, 0.7H), 3.0-2.7 (bs, 1.1H), 2.7-2.35 (bs, 1.9H), 2.27 (s, 3H).

Example 137

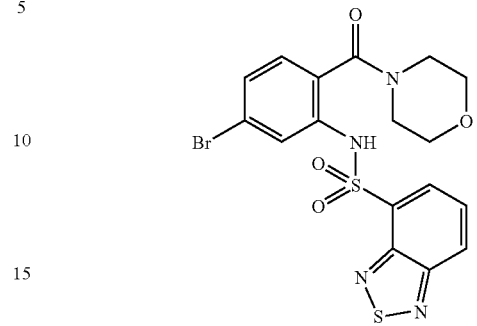

Benzo[1,2,5]thiadiazole-4-sulfonic acid [5-bromo-2-(morpholine-4-carbonyl)-phenyl]-amide This compound was prepared using the general procedure described in EXAMPLE 8. HPLC (reversed-phase): $R_T$=8.43 min (single peak). MS (ESI): m/z ~484 [M+H]$^+$, ~506 [M+Na]$^+$. $^1$H NMR (400 MHz, CDCl$_3$): (rotameric broadening) 8.97 (s, 1H), 8.32 (dd, J=7.0, 1.0 Hz, 1H), 8.27 (dd, J=8.8, 1.0 Hz, 1H), 7.78 (d, J=1.8 Hz, 1H), 7.74 (dd, J=8.8, 7.0 Hz, 1H), 7.18 (dd, J=8.2, 1.8 Hz, 1H), 6.94 (d, J=8.2 Hz, 1H), 3.7-3.18 (bm, 8H).

Example 138

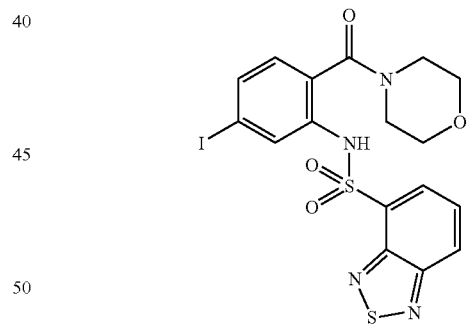

Benzo[1,2,5]thiadiazole-4-sulfonic acid [5-iodo-2-(morpholine-4-carbonyl)-phenyl]-amide This compound was prepared using the general procedure described in EXAMPLE 9. HPLC (reversed-phase): $R_T$=8.50 min (single peak). MS (ESI): m/z 531 [M+H]$^+$, 553 [M+Na]$^+$. $^1$H NMR (400 MHz, CDCl$_3$): (rotameric broadening) 8.91 (s, 1H), 8.31 (dd, J=7.0, 0.9 Hz, 1H), 8.27 (dd, J=8.8, 0.9 Hz, 1H), 7.97 (d, J=1.5 Hz, 1H), 7.74 (dd, J=8.8, 7.0 Hz, 1H), 7.41 (dd, J=8.1, 1.6 Hz, 1H), 6.78 (d, J=8.1 Hz, 1H), 3.75-3.0 (bm, 8H).

Example 139

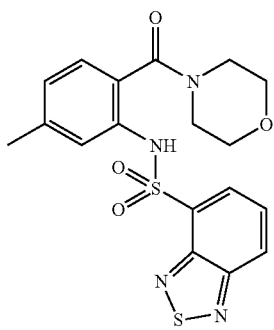

Benzo[1,2,5]thiadiazole-4-sulfonic acid [5-methyl-2-(morpholine-4-carbonyl)-phenyl]-amide This compound was prepared as described in EXAMPLE 44. HPLC (reversed-phase): $R_T$=8.02 min (single peak). MS (ESI): m/z 419 [M+H]$^+$, 441 [M+Na]$^+$. $^1$H NMR (400 MHz, CDCl$_3$): (rotameric broadening) 8.95 (s, 1H), 8.26 (dd, J=7.0, 1.0 Hz, 1H), 8.24 (dd, J=8.8, 1.0 Hz, 1H), 7.69 (dd, J=8.8, 7.0 Hz, 1H), 7.40 (bs, 1H), 6.95 (d, J=7.8 Hz, 1H), 6.85 (bd, J=7.8 Hz, 1H), 3.75-3.1 (bm, 8H), 2.29 (s, 3H).

Example 140

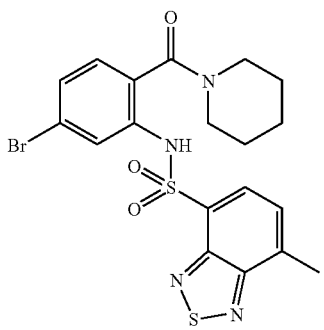

7-Methyl-benzo[1,2,5]thiadiazole-4sulfonic acid [5-bromo-2-(piperidine-1-carbonyl)-phenyl]-amide A. 4-Chlorosulfonyl-7-methyl-2,1,3-benzothiadiazole. A solution of 4-methyl-2,1,3-benzothiadiazole (1.0 g, 6.7 mmol) and chlorosulfonic acid (2 mL) was heated to 140° C. for 2 h, and then was allowed to cool to 23° C. The mixture was carefully poured over crushed ice, and the resulting precipitate was collected by filtration and dried under vacuum to provide the title compound as a tan solid (1.08 g, 65%). This material was sufficiently pure to be used directly. $^1$H NMR (500 MHz, CDCl$_3$): 8.31 (d, J=7.4 Hz, 1H), 7.57 (dd, J=7.4 Hz, 1.1, 1H), 2.91 (d, J=1.1 Hz, 3H).

B. 7-Methyl-benzo[1,2,5]thiadiazole-4sulfonic acid [5-bromo-2-(piperidine-1-carbonyl)-phenyl]-amide. This compound was prepared as described in EXAMPLE 5 substituting 4-chlorosulfonyl-7-methyl-2,1,3-benzothiadiazole for 4-chlorosulfonyl-2,1,3-benzothiadiazole in step D. HPLC (reversed-phase): $R_T$=10.01 min (single peak). MS (ESI): m/z ~496 [M+H]$^+$. $^1$H NMR (500 MHz, CDCl$_3$): (rotameric broadening) 8.92 (s, 1H), 8.18 (d, J=7.2 Hz, 1H), 7.82 (d, J=1.8 Hz, 1H), 7.42 (dd, J=7.2, 1.0 Hz, 1H), 7.14 (dd, J=8.2, 1.8 Hz, 1H), 6.92 (d, J=8.2 Hz, 1H), 3.7-2.8 (bm, 4H), 2.80 (d, J=1.0 Hz, 3H), 1.8-1.2 (bm, 6H).

Example 141

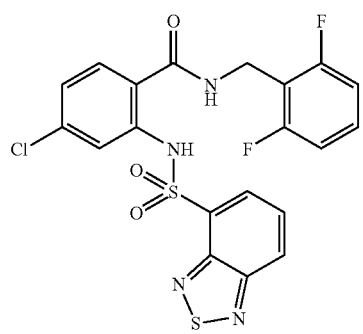

2-(Benzo[1,2,5]thiadiazole-4-sulfonylamino)-4-chloro-N-(2,6-difluoro-benzyl)-benzamide This compound was prepared using the general procedure described in EXAMPLE 7. HPLC (reversed-phase): $R_T$=9.85 min (single peak). MS (ESI): neg. ion m/z 493/495 [M–H]$^-$. $^1$H NMR (400 MHz, CDCl$_3$): (rotameric broadening) 11.52 (s, 1H), 8.35 (dd, J=7.0, 1.0 Hz, 1H), 8.20 (dd, J=8.8, 1.0 Hz, 1H), 7.76 (d, J=2.0 Hz, 1H), 7.70 (dd, J=8.8, 7.0 Hz, 1H), 7.32 (m, 1H), 7.20 (d, J=8.4 Hz, 1H), 7.0-6.89 (m, 3H), 6.22 (bm, 1H), 4.68 (d, J=5.6 Hz, 2H).

Example 142

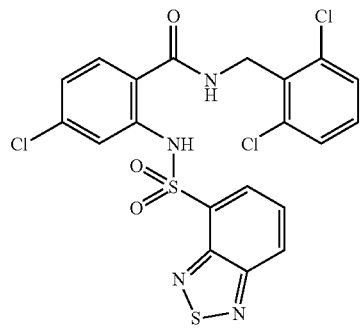

2-(Benzo[1,2,5]thiadiazole-4-sulfonylamino)-4-chloro-N-(2,6-dichloro-benzyl)-benzamide This compound was prepared using the general procedure described in EXAMPLE 7. HPLC (reversed-phase): $R_T$=10.31 min (single peak). MS (ESI): neg. ion m/z 525/527/529 [M–H]$^-$. $^1$H NMR (400 MHz, CDCl$_3$): (rotameric broadening) 11.52 (s, 1H), 8.36 (dd, J=7.0, 1.0 Hz, 1H), 8.20 (dd, J=8.8, 1.0 Hz, 1H), 7.76 (d, J=2.0 Hz, 1H), 7.70 (dd, J=8.8, 7.0 Hz, 1H), 7.37 (d, J=8.0 Hz, 1H), 7.25 (m, 1H), 7.18 (d, J=8.4 Hz, 1H), 6.91 (dd, j=8.4, 2.0 Hz, 1H), 6.16 (bm, 1H), 4.88 (d, J=5.4 Hz, 2H).

Example 143

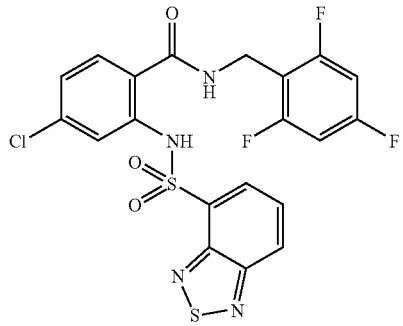

2-(Benzo[1,2,5]thiadiazole-4-sulfonylamino)-4-chloro-N-(2,4,6-trifluoro-benzyl)-benzamide This compound was prepared using the general procedure described in EXAMPLE 7. HPLC (reversed-phase): $R_T$=9.95 min (single peak). MS (ESI): neg. ion m/z 511/513 [M−H]⁻. ¹H NMR (500 MHz, CDCl₃): (rotameric broadening) 11.48 (s, 1H), 8.36 (dd, J=7.0, 1.0 Hz, 1H), 8.21 (dd, J=8.8, 1.0 Hz, 1H), 7.75 (d, J=2.0 Hz, 1H), 7.71 (dd, J=8.8, 7.0 Hz, 1H), 7.19 (d, J=8.4 Hz, 1H), 6.92 (dd, J=8.4, 2.0 Hz, 1H), 6.76-6.69 (m, 2H), 6.18 (bm, 1H), 4.62 (d, J=5.6 Hz, 2H).

Example 144

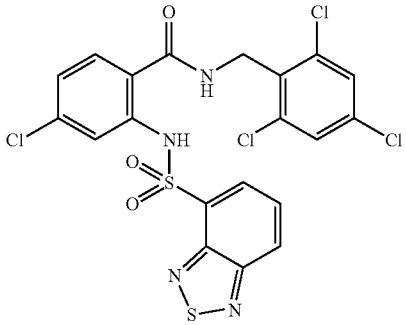

2-(Benzo[1,2,5]thiadiazole-4-sulfonylamino)-4-chloro-N-(2,4,6-trichloro-benzyl)-benzamide This compound was prepared using the general procedure described in EXAMPLE 7. HPLC (reversed-phase): $R_T$=10.74 min (single peak). MS (ESI): neg. ion m/z 559/561/563 [M−H]⁻. ¹H NMR (500 MHz, CDCl₃): (rotameric broadening) 11.47 (s, 1H), 8.36 (dd, J=7.0, 1.0 Hz, 1H), 8.22 (dd, J=8.8, 1.0 Hz, 1H), 7.76 (d, J=2.0 Hz, 1H), 7.71 (dd, J=8.8, 7.0 Hz, 1H), 7.40 (s, 2H), 7.18 (d, J=8.4 Hz, 1H), 6.92 (dd, J=8.4, 2.0 Hz, 1H), 6.13 (bm, 1H), 4.83 (d, J=5.4 Hz, 2H).

Example 145

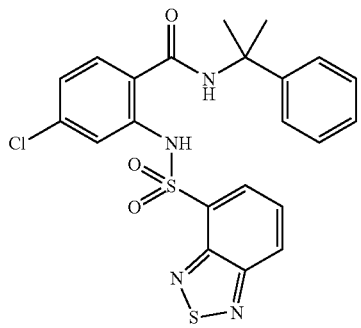

2-(Benzo[1,2,5]thiadiazole-4-sulfonylamino)-4-chloro-N-(1-methyl-1-phenyl-ethyl)-benzamide This compound was prepared using the general procedure described in EXAMPLE 7. HPLC (reversed-phase): $R_T$=10.21 min (single peak). MS (ESI): neg. ion m/z 485/487 [M−H]⁻. ¹H NMR (400 MHz, CDCl₃): (rotameric broadening) 11.59 (s, 1H), 8.35 (dd, J=7.1, 1.0 Hz, 1H), 8.22 (dd, J=8.8, 1.0 Hz, 1H), 7.75 (d, J=2.0 Hz, 1H), 7.71 (dd, J=8.8, 7.1 Hz, 1H), 7.41-7.32 (m, 4H), 7.32-7.26 (m, 2H), 6.94 (dd, J=8.4, 2.0 Hz, 1H), 6.21 (s, 1H), 1.78 (s, 6H).

Example 146

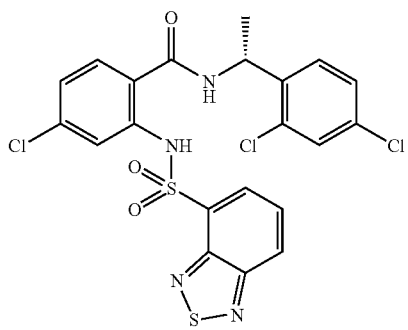

(R)-2-(Benzo[1,2,5]thiadiazole-4-sulfonylamino)-4-chloro-N-[1-(2,4-dichloro-phenyl-ethyl]-benzamide This compound was prepared using the general procedure described in EXAMPLE 7. See EXAMPLE 42 for preparation of (R)-1-(2,4-dichloro-phenyl)-ethylamine. HPLC (reversed-phase): $R_T$=10.63 min (single peak). MS (ESI): neg. ion m/z 539/541/543 [M−H]⁻. ¹H NMR (400 MHz, CDCl₃): (rotameric broadening) 11.53 (s, 1H), 8.35 (dd, J=7.0, 1.0 Hz, 1H), 8.21 (dd, J=8.8, 1.0 Hz, 1H), 7.74 (d, J=2.0 Hz, 1H), 7.70 (dd, J=8.8, 7.0 Hz, 1H), 7.42 (d, J=1.0 Hz, 1H), 7.3-7.25 (m, 2H), 7.28 (d, J=8.4 Hz, 1H), 6.95 (dd, J=8.4, 2.0 Hz, 1H), 6.37 (d, J=7.2 Hz, 1H), 5.42 (quint, J=7.2 Hz, 1H), 1.57 (d, J=7.0 Hz, 3H).

Example 147

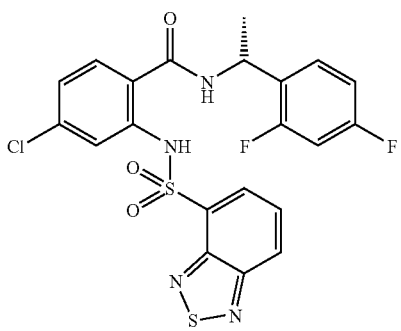

(R)-2-(Benzo[1,2,5]thiadiazole-4-sulfonylamino)-4-chloro-N-[1-(2,4-difluoro-phenyl-ethyl]-benzamide This compound was prepared using the general procedure described in EXAMPLE 7. See EXAMPLE 39 for preparation of (R)-1-(2,4-difluoro-phenyl)-ethylamine. HPLC (reversed-phase): $R_T$=10.10 min (single peak). MS (ESI): neg. ion m/z 507/509 [M−H]$^-$. $^1$H NMR (400 MHz, CDCl$_3$): (rotameric broadening) 11.58 (s, 1H), 8.35 (dd, J=7.0, 1.0 Hz, 1H), 8.20 (dd, J=8.8, 1.0 Hz, 1H), 7.73 (d, J=2.0 Hz, 1H), 7.70 (dd, J=8.8, 7.0 Hz, 1H), 7.32 (dt, J=8.5, 6.3 Hz, 1H), 7.25 (d, J=8.4 Hz, 1H), 6.94 (dd, J=8.4, 2.0 Hz, 1H), 6.93-6.80 (m, 2H), 6.39 (d, J=7.7 Hz, 1H), 5.34 (quint, J=7.4 Hz, 1H), 1.56 (d, J=7.0 Hz, 3H).

Example 148

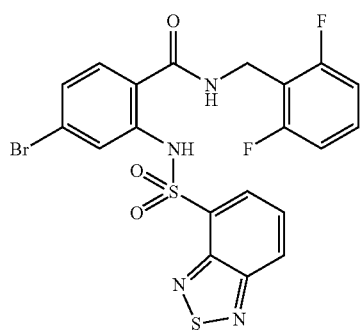

2-(Benzo[1,2,5]thiadiazole-4-sulfonylamino)-4-bromo-N-(2,6-difluoro-benzyl)-benzamide This compound was prepared using the general procedure described in EXAMPLE 8. HPLC (reversed-phase): $R_T$=9.93 min (single peak). MS (ESI): neg. ion m/z 537/539 [M−H]$^-$. $^1$H NMR (500 MHz, CDCl$_3$): (rotameric broadening) 11.46 (s, 1H), 8.35 (dd, J=7.0, 1.0 Hz, 1H), 8.20 (dd, J=8.8, 1.0 Hz, 1H), 7.92 (d, J=1.8 Hz, 1H), 7.70 (dd, J=8.8, 7.0 Hz, 1H), 7.32 (m, 1H), 7.12 (d, J=8.4 Hz, 1H), 7.08 (dd, J=8.4, 1.8 Hz, 1H), 7.00-6.92 (m, 2H), 6.21 (bm, 1H), 4.67 (d, J=5.6 Hz, 2H).

Example 149

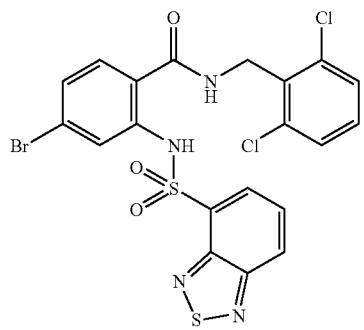

2-(Benzo[1,2,5]thiadiazole-4-sulfonylamino)-4-bromo-N-(2,6-dichloro-benzyl)-benzamide This compound was prepared using the general procedure described in EXAMPLE 8. HPLC (reversed-phase): $R_T$=10.34 min (single peak). MS (ESI): neg. ion m/z 569/571/573 [M−H]$^-$. $^1$H NMR (400 MHz, CDCl$_3$): (rotameric broadening) 11.45 (s, 1H), 8.36 (dd, J=7.0, 0.9 Hz, 1H), 8.21 (dd, J=8.8, 0.9 Hz, 1H), 7.92 (d, J=1.8 Hz, 1H), 7.71 (dd, J=8.8, 7.0 Hz, 1H), 7.37 (d, J=8.0 Hz, 2H), 7.25 (m, 1H), 7.11 (d, J=8.4 Hz, 1H), 7.07 (dd, J=8.4, 1.8 Hz, 1H), 6.15 (bm, 1H), 4.87 (d, J=5.4 Hz, 2H).

Example 150

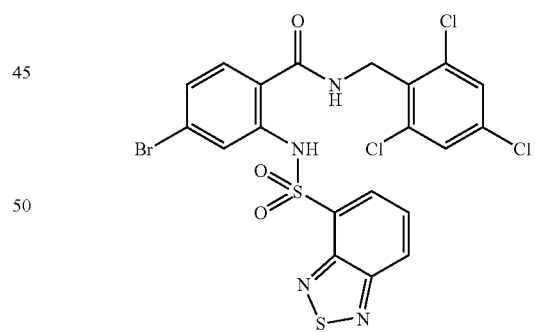

2-(Benzo[1,2,5]thiadiazole-4-sulfonylamino)-4-bromo-N-(2,4,6-trifluoro-benzyl)-benzamide This compound was prepared using the general procedure described in EXAMPLE 8. HPLC (reversed-phase): $R_T$=9.97 min (single peak). MS (ESI): neg. ion m/z 555/557 [M−H]$^-$. $^1$H NMR (400 MHz, CDCl$_3$): (rotameric broadening) 11.44 (s, 1H), 8.35 (dd, J=7.1, 0.8 Hz, 1H), 8.22 (dd, J=8.8, 0.8 Hz, 1H), 7.91 (d, J=1.7 Hz, 1H), 7.71 (dd, J=8.8, 7.1 Hz, 1H), 7.12

(d, J=8.4 Hz, 1H), 7.08 (d, J=8.4, 1.7 Hz, 1H), 6.78-6.67 (m, 2H), 6.19 (bm, 1H), 4.61 (d, J=5.6 Hz, 2H).

Example 151

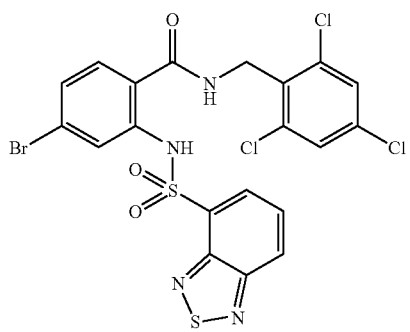

2-(Benzo[1,2,5]thiadiazole-4-sulfonylamino)-4-bromo-N-(2,4,6-trichloro-benzyl)-benzamide This compound was prepared using the general procedure described in EXAMPLE 8. HPLC (reversed-phase): $R_T$=10.78 min (single peak). MS (ESI): neg. ion m/z 603/605/607 [M–H]$^-$. $^1$H NMR (500 MHz, CDCl$_3$): (rotameric broadening) 11.42 (s, 1H), 8.36 (dd, J=7.0, 1.0 Hz, 1H), 8.22 (dd, J=8.8, 1.0 Hz, 1H), 7.92 (d, J=1.6 Hz, 1H), 7.71 (dd, J=8.8, 7.0 Hz, 1H), 7.40 (s, 2H), 7.10 (d, J=8.4 Hz, 1H), 7.07 (dd, J=8.4, 1.6 Hz, 1H), 6.13 (bm, 1H), 4.82 (d, J=5.5 Hz, 2H).

Example 152

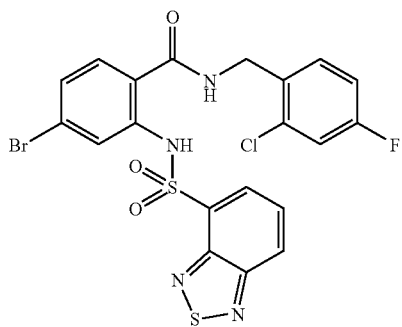

2-(Benzo[1,2,5]thiadiazole-4-sulfonylamino)-4-bromo-N-(2-chloro-4-fluoro-benzyl)-benzamide This compound was prepared using the general procedure described in EXAMPLE 8. HPLC (reversed-phase): $R_T$=10.20 min (single peak). MS (ESI): neg. ion m/z 553/555/557 [M–H]$^-$. $^1$H NMR (500 MHz, CDCl$_3$): (rotameric broadening) 11.51 (s, 1H), 8.36 (dd, J=7.0, 1.0 Hz, 1H), 8.21 (dd, J=8.8, 1.0 Hz, 1H), 7.90 (d, J=1.8 Hz, 1H), 7.71 (dd, J=8.8, 7.0 Hz, 1H), 7.49 (m, 1H), 7.17 (dd, J=8.4, 2.6 Hz, 1H), 7.15

(d, J=8.4 Hz, 1H), 7.10 (dd, J=8.4, 1.9 Hz, 1H), 7.03 (m, 1H), 6.41 (bm, 1H), 4.60 (d, J=6.0 Hz, 2H).

Example 153

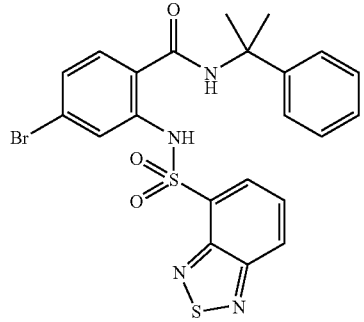

2-(Benzo[1,2,5]thiadiazole-4-sulfonylamino)-4-bromo-N-(1-methyl-1-phenyl-ethyl)-benzamide This compound was prepared using the general procedure described in EXAMPLE 8. HPLC (reversed-phase): $R_T$=10.26 min (single peak). MS (ESI): neg. ion m/z 529/531 [M–H]$^-$. $^1$H NMR (400 MHz, CDCl$_3$): (rotameric broadening) 11.54 (s, 1H), 8.35 (dd, J=7.0, 1.0 Hz, 1H), 8.22 (dd, J=8.8, 1.0 Hz, 1H), 7.91 (d, J=1.9 Hz, 1H), 7.71 (dd, J=8.8, 7.0 Hz, 1H), 7.41-7.33 (m, 4H), 7.31-7.27 (m, 1H), 7.22 (d, J=8.4 Hz, 1H), 7.10 (dd, J=8.4, 1.9 Hz, 1H), 6.21 (bs, 1H), 1.78 (s, 6H).

Example 154

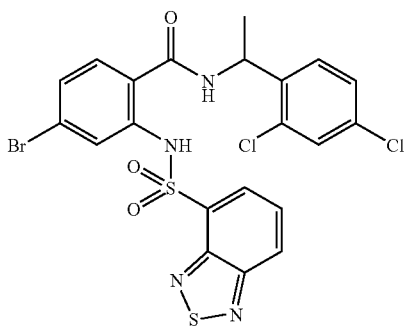

(R)-2-(Benzo[1,2,5]thiadiazole-4-sulfonylamino)-4-bromo-N-[1-(2,4-dichloro-phenyl-ethyl]-benzamide This compound was prepared using the general procedure described in EXAMPLE 8. See EXAMPLE 42 for preparation of (R)-1-(2,4-dichloro-phenyl)-ethylamine. HPLC (reversed-phase): $R_T$=10.70 min (single peak). MS (ESI): neg. ion m/z 583/585/587 [M–H]$^-$. $^1$H NMR (500 MHz, CDCl$_3$): (rotameric broadening) 11.47 (s, 1H), 8.35 (dd, J=7.0, 1.0 Hz, 1H), 8.21 (dd, J=8.8, 1.0 Hz, 1H), 7.91 (d, J=1.8 Hz, 1H), 7.71 (dd, J=8.8, 7.0 Hz, 1H), 7.43 (t, J=1.2 Hz, 1H), 7.20 (d, J=8.4

Hz, 1H), 7.11 (dd, J=8.4, 1.8 Hz, 1H), 6.36 (d, J=7.3 Hz, 1H), 5.41 (quint, J=7.2 Hz, 1H), 1.56 (d, J=7.2 Hz, 3H).

Example 155

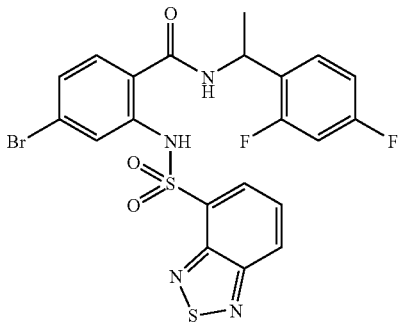

(R)-2-(Benzo[1,2,5]thiadiazole-4-sulfonylamino)-4-bromo-N-[1-(2,4-difluoro-phenyl-ethyl]-benzamide This compound was prepared using the general procedure described in EXAMPLE 8. See EXAMPLE 39 for preparation of (R)-1-(2,4-difluoro-phenyl)-ethylamine. HPLC (reversed-phase): $R_T$=10.17 min (single peak). MS (ESI): neg. ion m/z 551/553 [M–H]$^-$. $^1$H NMR (500 MHz, CDCl$_3$): (rotameric broadening) 11.52 (s, 1H), 8.35 (dd, J=7.0, 1.0 Hz, 1H), 8.20 (dd, J=8.8, 1.0 Hz, 1H), 7.90 (d, J=1.8 Hz, 1H), 7.70 (dd, J=8.8, 7.0 Hz, 1H), 7.31 (dt, J=8.4, 6.2 Hz, 1H), 7.16 (d, J=8.4 Hz, 1H), 7.10 (dd, J=8.4, 1.8 Hz, 1H), 6.89 (m, 1H), 6.85 (m, 1H), 6.37 (d, J=7.6 Hz, 1H), 5.33 (quint, J=7.5 Hz, 1H), 1.56 (d, J=7.0 Hz, 3H).

Example 156

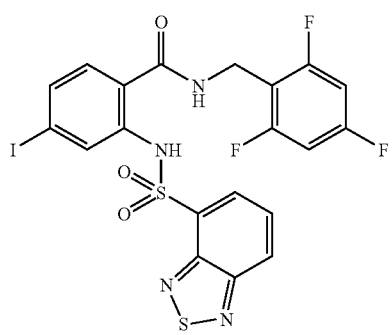

2-(Benzo[1,2,5]thiadiazole-4-sulfonylamino)-4-iodo-N-(2,4,6-trifluoro-benzyl)-benzamide This compound was prepared using the general procedure described in EXAMPLE 6. HPLC (reversed-phase): $R_T$=9.96 min (single peak). MS (ESI): neg. ion m/z 603 [M–H]$^-$. $^1$H NMR (500 MHz, CDCl$_3$): (rotameric broadening) 11.34 (s, 1H), 8.35 (dd, J=7.0, 1.0 Hz, 1H), 8.21 (dd, J=8.8, 1.0 Hz, 1H), 8.10 (d, J=1.6 Hz, 1H), 7.71 (dd, J=8.8, 7.0 Hz, 1H), 7.30 (dd, J=8.3, 1.6 Hz, 1H), 6.95 (d, J=8.3 Hz, 1H), 6.78-6.69 (m, 2H), 6.18 (bm, 1H), 4.60 (d, J=5.6 Hz, 2H).

Example 157

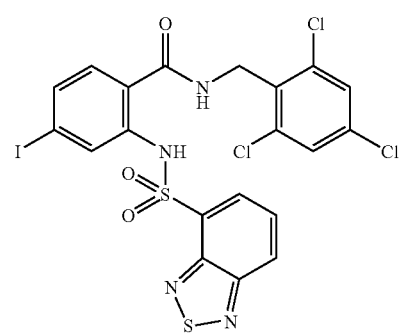

2-(Benzo[1,2,5]thiadiazole-4-sulfonylamino)-4-iodo-N-(2,4,6-trichloro-benzyl)-benzamide This compound was prepared using the general procedure described in EXAMPLE 9. HPLC (reversed-phase): $R_T$=10.83 min (single peak). MS (ESI): neg. ion m/z 651/653/655 [M–H]$^-$. $^1$H NMR (400 MHz, CDCl$_3$): (rotameric broadening) 11.34 (s, 1H), 8.35 (dd, J=7.0, 0.9 Hz, 1H), 8.22 (dd, J=8.8, 0.9 Hz, 1H), 8.10 (d, J=1.5 Hz, 1H), 7.72 (dd, J=8.8, 7.0 Hz, 1H), 7.39 (s, 2H), 7.29 (dd, J=8.2, 1.5 Hz, 1H), 6.93 (d, J=8.2 Hz, 1H), 6.13 (bm, 1H), 4.81 (d, J=5.5 Hz, 2H).

Example 158

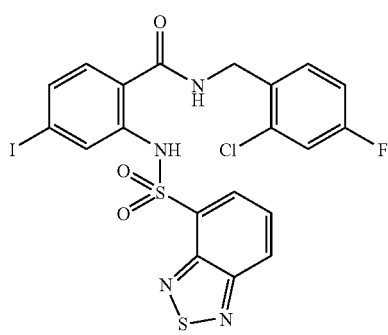

2-(Benzo[1,2,5]thiadiazole-4-sulfonylamino)-N-(2-chloro-4-fluoro-benzyl)-4-iodo-benzamide This compound was prepared using the general procedure described in EXAMPLE 9. HPLC (reversed-phase): $R_T$=10.26 min (single peak). MS (ESI): neg. ion m/z 601/603 [M–H]$^-$. $^1$H NMR (400 MHz, CDCl$_3$): (rotameric broadening) 11.45 (s, 1H), 8.36 (dd, J=7.0, 1.0 Hz, 1H), 8.21 (dd, J=8.8, 1.0 Hz, 1H), 8.08 (d, J=1.6 Hz, 1H), 7.72 (dd, J=8.8, 7.0 Hz, 1H), 7.49 (m, 1H), 7.30 (dd, J=8.2, 1.6 Hz, 1H), 7.17

(dd, J=8.3, 1.6 Hz, 1H), 7.03 (m, 1H), 6.98 (d, J=8.3 Hz, 1H), 6.41 (bm, 1H), 4.60 (d, J=6.0 Hz, 2H).

Example 159

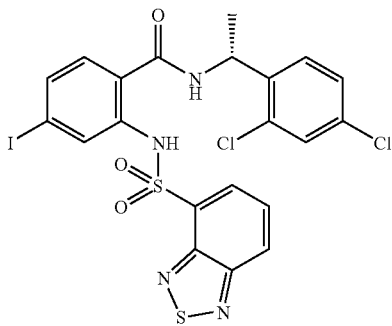

(R)-2-(Benzo[1,2,5]thiadiazole-4-sulfonylamino)-N-[1-(2,4-dichloro-phenyl-ethyl]-4-iodo-benzamide This compound was prepared using the general procedure described in EXAMPLE 9. See EXAMPLE 42 for preparation of (R)-1-(2,4-dichloro-phenyl)-ethylamine. HPLC (reversed-phase): $R_T$=10.75 min (single peak). MS (ESI): neg. ion m/z 631/633 [M–H]−. $^1$H NMR (500 MHz, CDCl$_3$): (rotameric broadening) 11.38 (s, 1H), 8.34 (dd, J=7.0, 1.0 Hz, 1H), 8.22 (dd, J=8.8, 1.0 Hz, 1H), 8.09 (d, J=1.6 Hz, 1H), 7.71 (dd, J=8.8, 7.0 Hz, 1H), 7.42 (t, J=1.2 Hz, 1H), 7.31 (dd, J=8.2, 1.6 Hz, 1H), 7.25 (t, J=0.8 Hz, 1H), 7.03 (d, J=8.3 Hz, 1H), 6.36 (d, J=7.2 Hz, 1H), 5.40 (quint, J=7.2 Hz, 1H), 1.56 (d, J=6.9 Hz, 3H).

Example 160

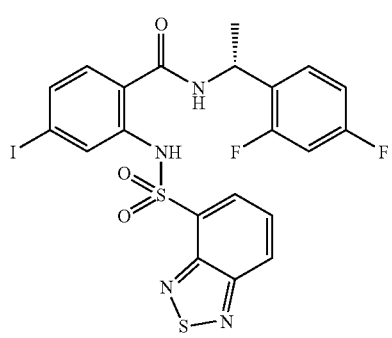

(R)-2-(Benzo[1,2,5]thiadiazole-4-sulfonylamino)-N-[1-(2,4-difluoro-phenyl)-ethyl]--iodo-benzamide This compound was prepared using the general procedure described in EXAMPLE 9. See EXAMPLE 39 for preparation of (R)-1-(2,4-difluoro-phenyl)-ethylamine. HPLC (reversed-phase): $R_T$=10.20 min (single peak). MS (ESI): neg. ion m/z 599 [M–H]−. $^1$H NMR (500 MHz, CDCl$_3$): (rotameric broadening) 11.43 (s, 1H), 8.34 (dd, J=7.0, 1.0 Hz, 1H), 8.20 (dd, J=8.8, 1.0 Hz, 1H), 8.08 (d, J=1.6 Hz, 1H), 7.71 (dd, J=8.8, 7.0 Hz, 1H), 7.35-7.27 (m, 2H), 6.99 (d, J=8.3 Hz, 1H), 6.89 (m, 1H), 6.84 (m, 1H), 6.37 (d, J=7.9 Hz, 1H), 5.32 (quint, J=7.4 Hz, 1H), 1.56 (d, J=7.1 Hz, 3H).

Example 161

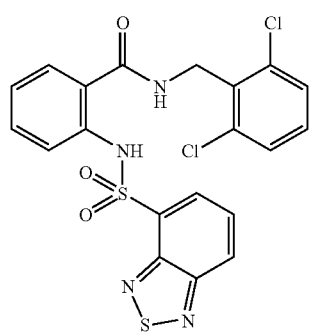

2-(Benzo[1,2,5]thiadiazole-4-sulfonylamino)-N-(2,6-dichloro-benzyl)-benzamide

This compound was prepared as described in EXAMPLE 41. HPLC (reversed-phase): $R_T$=9.78 min (single peak). MS (ESI): neg. ion m/z 491/493 [M–H]−. $^1$H NMR (500 MHz, CDCl$_3$): (rotameric broadening) 11.32 (s, 1H), 8.31 (dd, J=7.0, 0.8 Hz, 1H), 8.18 (d, J=8.8 Hz, 1H), 7.72 (d, J=8.1 Hz, 1H), 7.66 (dd, J=8.8, 7.0 Hz, 1H), 7.37 (d, J=8.0 Hz, 2H), 7.32 (m, 1H), 7.24 (m, 1H), 6.95 (m, 1H), 6.16 (bm, 1H), 4.86 (d, J=5.4 Hz, 2H).

Example 162

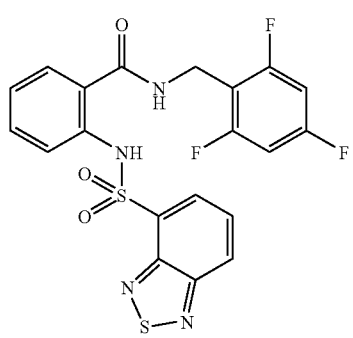

2-(Benzo[1,2,5]thiadiazole-4-sulfonylamino)-N-(2,4,6-trifluoro-benzyl)-benzamide This compound was prepared as described in EXAMPLE 41. HPLC (reversed-phase): $R_T$=9.46 min (single peak). MS (ESI): neg. ion m/z 477 [M–H]−. $^1$H NMR (400 MHz, CDCl$_3$): (rotameric broadening) 11.28 (s, 1H), 8.32 (d, J=7.0 Hz, 1H), 8.18 (d, J=8.8 Hz, 1H), 7.70 (d, J=8.4 Hz, 1H), 7.66 (dd, J=8.8, 7.0 Hz, 1H), 7.33 (m, 1H), 7.25 (m, 1H), 6.96 (m, 1H), 6.73 (m, 1H), 6.21 (bm, 1H), 4.60 (d, J=5.6 Hz, 2H).

Example 163

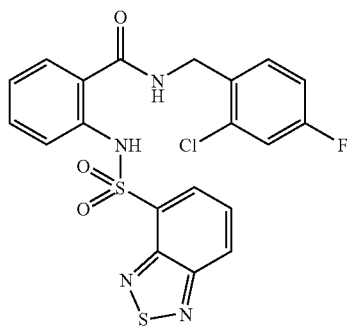

2-(Benzo[1,2,5]thiadiazole-4-sulfonylamino)-N-(2-chloro-4-fluoro-benzyl)-benzamide This compound was prepared as described in EXAMPLE 41. HPLC (reversed-phase): $R_T$=9.68 min (single peak). MS (ESI): neg. ion m/z 475/477 [M–H]⁻. ¹H NMR (400 MHz, CDCl₃): (rotameric broadening) 11.39 (s, 1H), 8.33 (dd, J=7.0, 1.0 Hz, 1H), 8.18 (dd, J=8.8, 1.0 Hz, 1H), 7.69 (m, 1H), 7.66 (dd, J=8.8, 7.0, 1.0 Hz, 1H), 8.18 (dd, J=8.8, 1.0 Hz, 1H), 7.69 (m, 1H), 7.66 (dd, J=8.8, 7.0 Hz, 1H), 7.50 (m, 1H), 7.37-7.26 (m, 2H), 7.17 (dd, J=8.3, 2.6 Hz, 1H), 7.03 (m, 1H), 7.00 (m, 1H), 6.43 (bm, 1H), 4.60 (d, J=6.0 Hz, 2H).

Example 164

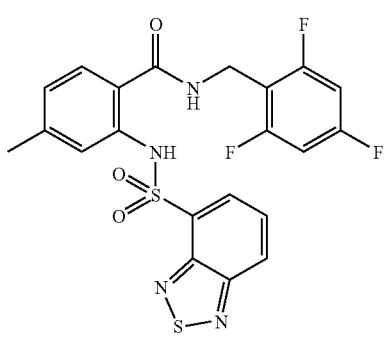

2-(Benzo[1,2,5]thiadiazole-4-sulfonylamino)-4-methyl-N-(2,4,6-trifluoro-benzyl)-benzamide This compound was prepared as described in EXAMPLE 44. HPLC (reversed-phase): $R_T$=9.69 min (single peak). MS (ESI): neg. ion m/z 491 [M–H]⁻. ¹H NMR (400 MHz, CDCl₃): (rotameric broadening) 11.42 (s, 1H), 8.31 (dd, J=7.0, 1.0 Hz, 1H), 8.18 (dd, J=8.8, 1.0 Hz, 1H), 7.66 (dd, J=8.8, 7.0 Hz, 1H), 7.51 (bs, 1H), 7.14 (d, J=8.0 Hz, 1H), 6.77-6.67 (m, 3H), 6.16 (bm, 1H), 4.58 (d, J=5.7 Hz, 2H), 2.27 (s, 3H).

Example 165

2-(Benzo[1,2,5]thiadiazole-4-sulfonylamino)-4-methyl-N-(2,4,6-trichloro-benzyl)-benzamide This compound was prepared as described in EXAMPLE 44. HPLC (reversed-phase): $R_T$=10.47 min (single peak). MS (ESI): neg. ion m/z 539/541/543 [M–H]⁻. ¹H NMR (400 MHz, CDCl₃): (rotameric broadening) 11.40 (s, 1H), 8.31 (d, J=7.0 Hz, 1H), 8.18 (dd, J=8.8, 1H), 7.67 (dd, J=8.8, 7.0 Hz, 1H), 7.52 (s, 1H), 7.39 (s, 2H), 7.11 (d, J=8.0 Hz, 1H), 6.75 (d, J=8.5 Hz, 1H), 6.10 (bm, 1H), 4.79 (d, J=5.5 Hz, 2H), 2.27 (s, 3H).

Example 166

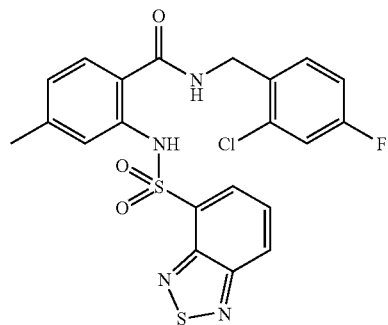

2-(Benzo[1,2,5]thiadiazole-4-sulfonylamino)-N-(2-chloro-4-fluoro-benzyl)-4-methyl-benzamide This compound was prepared as described in EXAMPLE 44. HPLC (reversed-phase): $R_T$=9.89 min (single peak). MS (ESI): neg. ion m/z 489/491 [M–H]⁻. ¹H NMR (400 MHz, CDCl₃): (rotameric broadening) 11.52 (s, 1H), 8.32 (dd, J=7.0, 1.0 Hz, 1H), 8.18 (dd, J=8.8, 1.0 Hz, 1H), 7.66 (dd, J=8.8, 7.0 Hz, 1H), 7.50 (s, 1H), 7.49 (dd, J=8.5, 6.0 Hz, 1H), 7.18 (d, 8.0 Hz, 1H), 7.16 (dd, J=8.3, 2.6 Hz, 1H), 7.02 (m, 1H), 6.76 (dd, J=8.0, 0.8 Hz, 1H), 6.39 (bm, 1H), 4.58 (d, J=6.0 Hz, 2H), 2.27 (s, 3H).

Example 167

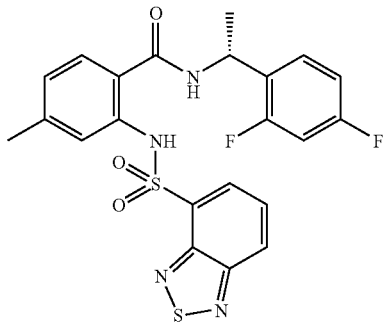

(R)-2-(Benzo[1,2,5]thiadiazole-4-sulfonylamino)-N-[1-(2,4-difluoro-phenyl)-ethyl]-4-methyl-benzamide This compound was prepared as described in EXAMPLE 44. See EXAMPLE 39 for preparation of (R)-1-(2,4-difluoro-phenyl)-ethylamine. HPLC (reversed-phase): $R_T$=9.76 min (single peak). MS (ESI): neg. ion m/z 487 [M–H]$^-$. $^1$H NMR (400 MHz, CDCl$_3$): (rotameric broadening) 11.52 (s, 1H), 8.31 (dd, J=7.1, 1.0 Hz, 1H), 8.16 (dd, J=8.8, 1.0 Hz, 1H), 7.66 (dd, J=8.8, 7.1 Hz, 1H), 7.50 (s, 1H), 7.31 (dt, J=8.8, 6.4 Hz, 1H), 7.19 (d, J=8.0 Hz, 1H), 6.91-6.80 (m, 2H), 6.78 (d, J=7.3 Hz, 1H), 6.35 (d, J=7.0 Hz, 1H), 5.51 (quint, J=7.4 Hz, 1H), 2.28 (s, 3H), 1.54 (d, J=7.0 Hz, 3H).

Example 168

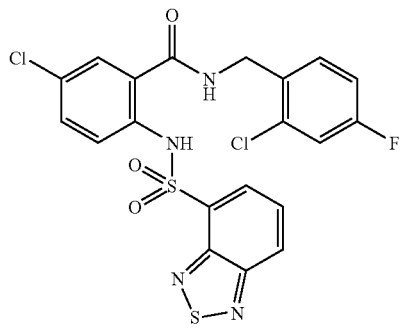

2-(Benzo[1,2,5]thiadiazole-4-sulfonylamino)-5-chloro-N-(2-chloro-4-fluoro-benzyl)-benzamide This compound was prepared as described using the general procedure of EXAMPLE 43. HPLC (reversed-phase): $R_T$=10.15 min (single peak). MS (ESI): neg. ion m/z 509/511 [M–H]$^-$. $^1$H NMR (400 MHz, CDCl$_3$): (rotameric broadening) 11.17 (s, 1H), 8.31 (dd, J=7.0, 1.0 Hz, 1H), 8.20 (dd, J=8.8, 1.0 Hz, 1H), 7.67 (dd, J=8.8, 7.0 Hz, 1H), 7.67 (d, J=8.9 Hz, 1H), 7.48 (m, 1H), 7.29 (m, 1H), 7.25 (m, 1H), 7.18 (dd, J=8.3, 2.6 Hz, 1H), 7.04 (m, 1H), 6.37 (bm, 1H), 4.58 (d, J=6.0 Hz, 2H).

Example 169

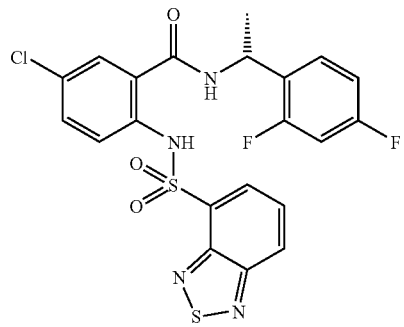

(R)-2-(Benzo[1,2,5]thiadiazole-4-sulfonylamino)-5-chloro-N-[1-(2,4-difluoro-phenyl)-ethyl]-benzamide This compound was prepared as described using the general procedure of EXAMPLE 43. See EXAMPLE 39 for preparation of (R)-1-(2,4-difluoro-phenyl)-ethylamine. HPLC (reversed-phase): $R_T$=10.12 min (single peak). MS (ESI): neg. ion m/z 507/509 [M–H]$^-$. $^1$H NMR (400 MHz, CDCl$_3$): (rotameric broadening) 11.17 (s, 1H), 8.30 (dd, J=7.0, 1.0 Hz, 1H), 8.18 (dd, J=8.8, 1.0 Hz, 1H), 7.67 (d, J=8.8 Hz, 1H), 7.66 (dd, J=8.8, 7.0 Hz, 1H), 7.34-7.25 (m, 3H), 6.92-6.82 (m, 2H), 6.32 (d, J=7.8 Hz, 1H), 5.29 (quint, J=7.4 Hz, 1H), 1.56 (d, J=7.2 Hz, 3H).

Example 170

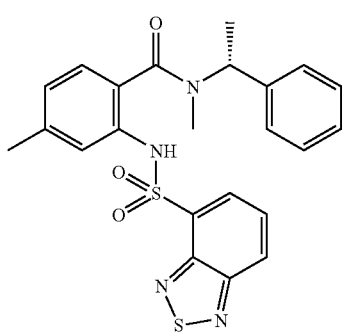

(R)-2-(Benzo[1,2,5]thiadiazole-4-sulfonylamino)-4,N-dimethyl-N-(1-phenyl-ethyl)-benzamide This compound was prepared as described in EXAMPLE 44. HPLC (reversed-phase): $R_T$=9.81 min (single peak). MS (ESI): m/z 467 [M+H]$^+$, 489 [M+Na]$^+$. $^1$H NMR (400 MHz, CDCl$_3$): (rotameric broadening) 9.08 (bs, 1H), 8.34 (dd, J=7.0, 0.7 Hz, 1H), 8.20 (bd, J=8.8 Hz, 1H), 7.69 (bm, 1H), 7.45-7.37 (bm, 4H), 7.37-7.26 (bm, 2H), 7.01 (bd, J=7.6 Hz, 1H), 6.78 (bd, J=7.8 Hz, 1H), 6.05 (bm, 1H), 2.7-2.25 (bs, 3H), 2.25 (s, 3H), 1.7-1.4 (bs, 3H).

Example 171

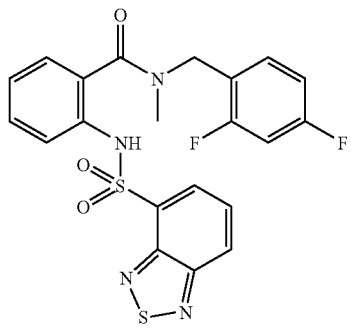

2-(Benzo[1,2,5]thiadiazole-4-sulfonylamino)-N-(2,4-difluoro-benzyl)-N-methyl-benzamide This compound was prepared as described in EXAMPLE 41. HPLC (reversed-phase): $R_T$=9.41 min (single peak). MS (ESI): neg. ion m/z 475 [M+H]⁻, 497 [M+Na]³⁰. ¹H NMR (400 MHz, CDCl₃): (rotameric broadening) 8.83 (bs, 1H), 8.27 (bd, J=6.7 Hz, 1H), 8.22 (bd, J=8.7 Hz, 1H), 7.67 (bm, 1H), 7.55-7.45 (bm, 1H), 7.54 (d, J=8.3 Hz, 1H), 7.30 (bm, 1H), 7.10-7.00 (b, 2H), 6.93 (bm, 1H), 6.84 (bm, 1H), 4.65-4.4 (bs, 1.3H), 4.4-4.1 (bs, 0.7H), 3.0-2.65 (bs, 1.1H), 2.65-2.4 (bs, 1.9H).

Example 172

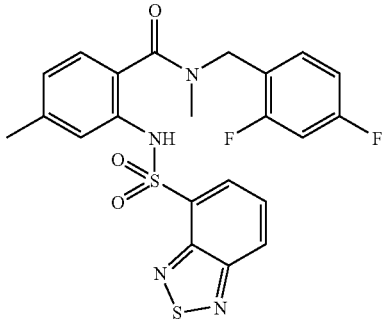

2-(Benzo[1,2,5]thiadiazole-4-sulfonylamino)-N-(2,4-difluoro-benzyl)-4,N-dimethyl-benzamide This compound was prepared as described in EXAMPLE 41. HPLC (reversed-phase): $R_T$=9.80 min (single peak). MS (ESI): neg. ion m/z 489 [M+H]⁺. ¹H NMR (400 MHz, CDCl₃): (rotameric broadening) 9.00 (bs, 1H), 8.27 (bd, J=6.9 Hz, 1H), 8.22 (bd, J=8.8 Hz, 1H), 7.68 (bm, 1H), 7.6-7.4 (bm, 1H), 7.42 (bs, 1H), 6.96-6.85 (bm, 1H), 6.85-

6.75 (bm, 2H), 4.65-4.3 (bs, 1.4H), 4.3-4.0 (bs, 0.6H), 2.9-2.65 (bs, 1H), 2.65-2.45 (bs, 2H), 2.28 (s, 3H).

Example 173

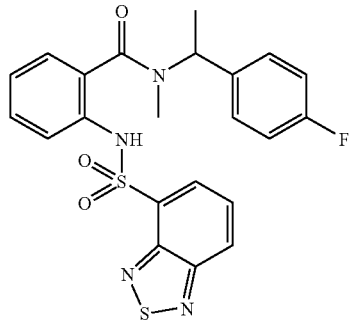

2-(Benzo[1,2,5]thiadiazole-4-sulfonylamino)-N-[1-(4-fluoro-phenyl)-ethyl]-N-methyl-benzamide This compound was prepared as described in EXAMPLE 41. HPLC (reversed-phase): $R_T$=9.48 min (single peak). MS (ESI): m/z 471 [M+H]⁺, 493 [M+Na]⁺. ¹H NMR (400 MHz, CDCl₃): (rotameric broadening) 8.83 (bs, 1H), 8.35 (bd, J=6.9 Hz, 1H), 8.22 (bd, J=8.7 Hz, 1H), 7.70 (bm, 1H), 7.48 (bd, J=8.3 Hz, 1H), 7.48-7.35 (bm, 2H), 7.23 (bm, 1H), 7.19-7.05 (bm, 3H), 7.01 (bm, 1H), 6.05 (bm, 1H), 2.9-2.3 (bs, 3H), 2.2-1.8 (bs, 3H).

Example 174

2-(Benzo[1,2,5]thiadiazole-4-sulfonylamino)-N-[1-(4-fluoro-phenyl)-ethyl]-4,N-dimethyl-benzamide This compound was prepared as described in EXAMPLE 43. HPLC (reversed-phase): $R_T$=9.72 min (single peak). MS (ESI): m/z 485 [M+H]⁺, 507 [M+Na]⁺. ¹H NMR (400 MHz, CDCl₃): (rotameric broadening) 9.03 (bs, 1H), 8.35 (dd, J=7.0, 0.8 Hz, 1H), 8.22 (bd, J=8.8 Hz, 1H), 7.70 (dd, J=8.8, 7.0 Hz, 1H), 7.5-7.25 (bm, 1H), 7.35 (bs, 1H), 7.11-7.05 (bm, 2H), 7.01 (bd, J=7.6 Hz, 1H), 6.79 (dd, J=7.8, 0.6 Hz, 1H), 6.05 (bm, 1H), 2.8-2.2 (bm, 2H), 2.25 (s, 3H), 1.65-1.45 (bm, 6H).

Example 175

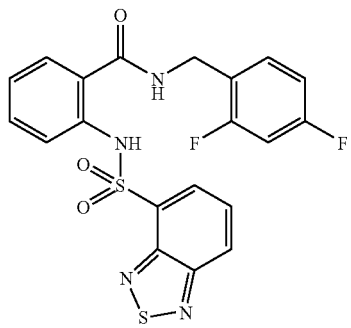

2-(Benzo[1,2,5]thiadiazole-4-sulfonylamino)-N-(2,4-difluoro-benzyl)-benzamide

This compound was prepared as described in EXAMPLE 41. HPLC (reversed-phase): $R_T$=9.47 min (single peak). MS (ESI): m/z 461 [M+H]$^+$, 483 [M+Na]$^+$. $^1$H NMR (400 MHz, CDCl$_3$): (rotameric broadening) 11.39 (s, 1H), 8.32 (d, J=7.0 Hz, 1H), 8.17 (d, J=8.8 Hz, 1H), 7.69 (d, J=8.3 Hz, 1H), 7.66 (dd, J=8.8, 7.0 Hz, 1H), 7.43 (m, 1H), 7.35-7.25 (m, 2H), 6.97 (d, J=7.6 Hz, 1H), 6.91 (m, 1H), 6.84 (m, 1H), 6.35 (bm, 1H), 4.55 (d, J=5.8 Hz, 2H).

Example 176

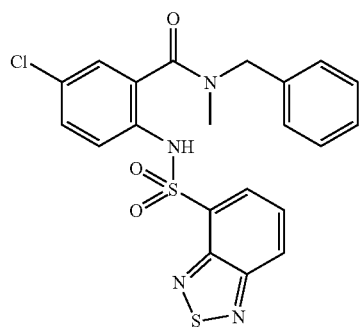

2-(Benzo[1,2,5]thiadiazole-4-sulfonylamino)-N-benzyl-5-chloro-N-methyl-benzamide This compound was prepared as described using the general procedure of EXAMPLE 43. HPLC (reversed-phase): $R_T$=9.75 min (single peak). MS (ESI): m/z 473 [M+H]$^+$, 495 [M+Na]$^+$. $^1$H NMR (400 MHz, CDCl$_3$): (rotameric broadening) 8.82 (bs, 1H), 8.30-8.18 (bm, 2H), 7.75-7.50 (bm, 2H), 7.42-7.29 (bm, 5H), 7.24 (bm, 1H), 7.1-7.0 (bm, 1H), 4.6-4.3 (bs, 1.3H), 4.3-4.1 (bs, 0.7H), 3.0-2.7 (bs, 1.1H), 2.7-2.35 (bs, 1.9H).

The compounds of EXAMPLES 177 and 178 were prepared using the general procedure of EXAMPLE 5.

Example 177

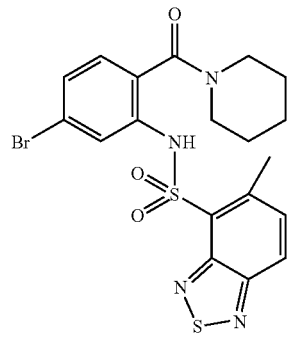

5-Methyl-benzo[1,2,5]thiadiazole-4sulfonic acid [5-bromo-2-(piperidine-1-carbonyl)-phenyl]-amide MS (ESI): m/z 495 [M+H]$^+$.

Example 178

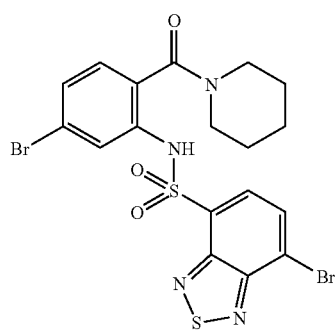

7-Bromo-benzo[1,2,5]thiadiazole-4sulfonic acid [5-bromo-2-(piperidine-1-carbonyl)-phenyl]-amide MS (ESI): m/z 559/561/563 [M+H]$^+$, 581/583/585 [M+Na]$^+$.

The compounds of EXAMPLES 179 through 182 were prepared using the general procedure of EXAMPLE 7.

Example 179

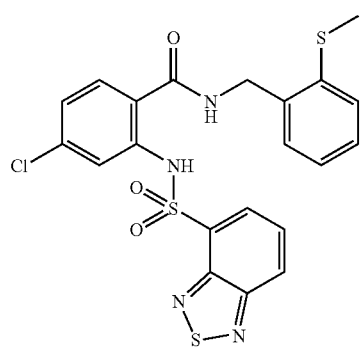

2-(Benzo[1,2,5]thiadiazole-4sulfonylamino)-4-chloro-N-(2-methylsulfanyl-benzyl)-benzamide MS (ESI): neg. ion m/z 503/505 [M−H]$^-$.

Example 180

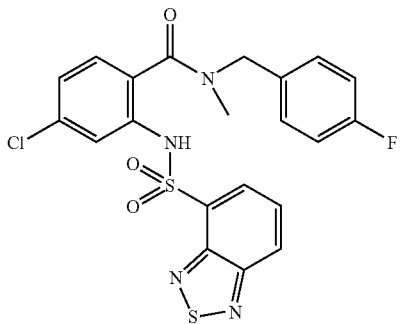

2-(Benzo[1,2,5]thiadiazole-4sulfonylamino)-4-chloro-N-(4-fluoro-benzyl)-N-methyl-benzamide MS (ESI): neg. ion m/z 489/491 [M–H]⁻.

Example 181

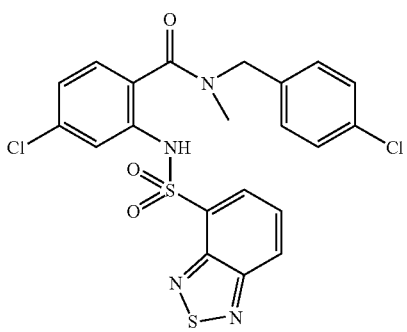

2-(Benzo[1,2,5]thiadiazole-4sulfonylamino)-4-chloro-N-(4-chloro-benzyl)-N-methyl-benzamide MS (ESI): neg. ion m/z 505/507 [M–H]⁻.

Example 182

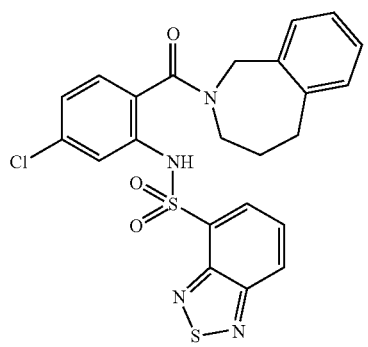

Benzo[1,2,5]thiadiazole-4sulfonic acid [5-chloro-2-(1,3,4,5-tetrahydro-benzo[c]azepine-2-carbonyl)-phenyl]-amide MS (ESI): m/z 499/501 [M+H]⁺, 521/523 [M+Na]⁺.
The compounds of EXAMPLES 183 through 185 were prepared using the general procedure of EXAMPLE 8.

Example 183

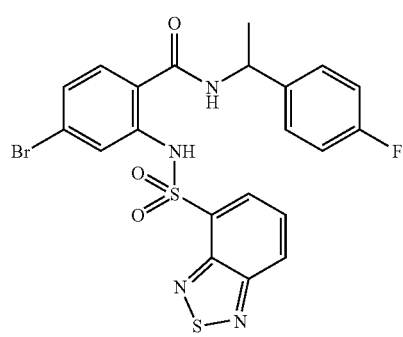

2-(Benzo[1,2,5]thiadiazole-4sulfonylamino)-4-bromo-N-[1-(4-fluoro-phenyl)-ethyl]-benzamide MS (ESI): neg. ion m/z 533/535 [M–H]⁻.

Example 184

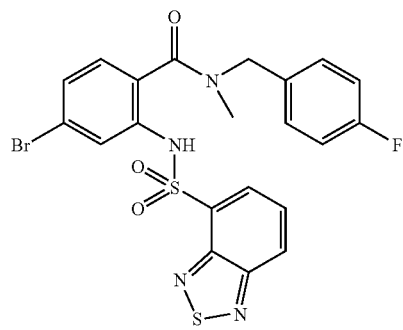

2-(Benzo[1,2,5]thiadiazole-4sulfonylamino)-4-bromo-N-(4-fluoro-benzyl)-N-methyl-benzamide MS (ESI): neg. ion m/z 533/535 [M–H]⁻.

Example 185

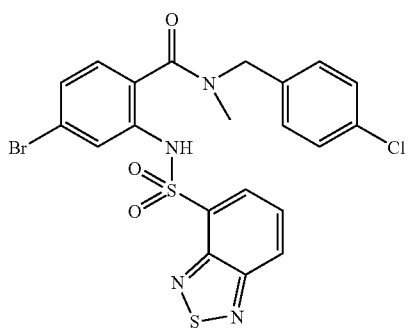

2-(Benzo[1,2,5]thiadiazole-4sulfonylamino)-4-bromo-N-(4-chloro-benzyl)-N-methyl-benzamide MS (ESI): neg. ion m/z 549/551/553 [M–H]⁻.
The compounds of EXAMPLES 186 through 189 were prepared using the general procedure of EXAMPLE 9.

Example 186

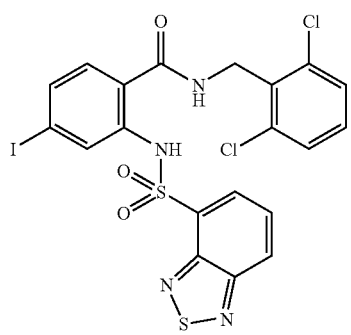

2-(Benzo[1,2,5]thiadiazole-4sulfonylamino)-N-(2,6-dichloro-benzyl)-4-iodo-benzamide MS (ESI): neg. ion m/z 617/619 [M−H]⁻.

Example 187

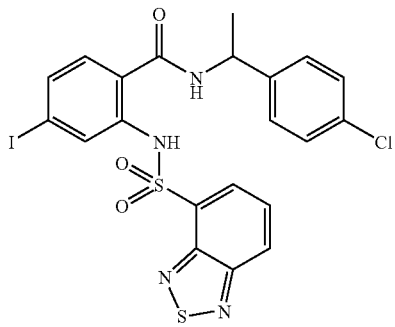

2-(Benzo[1,2,5]thiadiazole-4sulfonylamino)-N-[1-(4-chloro-phenyl)-ethyl]-4-iodo-benzamide MS (ESI): neg. ion m/z 597/599 [M−H]⁻.

Example 188

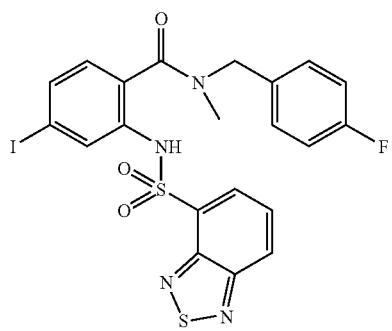

2-(Benzo[1,2,5]thiadiazole-4sulfonylamino)-N-(4-fluoro-benzyl)-4-iodo-N-methyl-benzamide MS (ESI): neg. ion m/z 581 [M−H]⁻.

Example 189

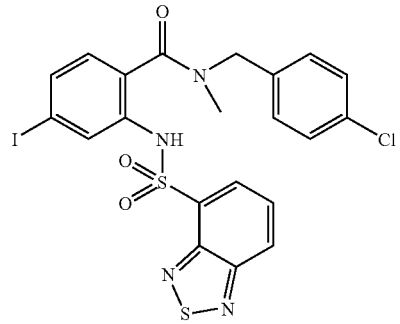

2-(Benzo[1,2,5]thiadiazole-4sulfonylamino)-N-(4-chloro-benzyl)-4-iodo-N-methyl-benzamide MS (ESI): neg. ion m/z 597/599 [M−H]⁻.

The compounds of EXAMPLES 190 through 195 were prepared using the general procedure of EXAMPLE 39.

Example 190

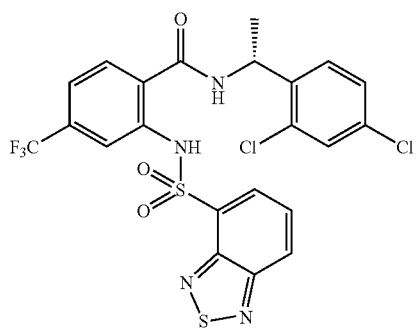

2-(Benzo[1,2,5]thiadiazole-4sulfonylamino)-N-[1-(2,4-dichloro-phenyl)-ethyl]-4-trifluoromethyl-benzamide MS (ESI): m/z 575/577 [M+H]⁺, 597/599 [M+Na]⁺.

Example 191

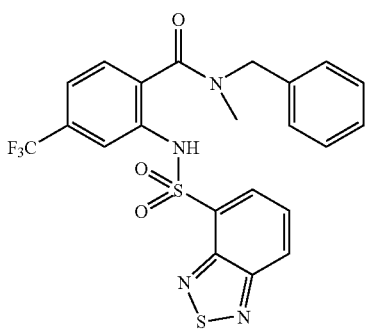

2-(Benzo[1,2,5]thiadiazole-4sulfonylamino)-N-benzyl-N-methyl-4-trifluoromethyl-benzamide MS (ESI): m/z 507 [M+H]⁺, 529 [M+Na]⁺.

Example 192

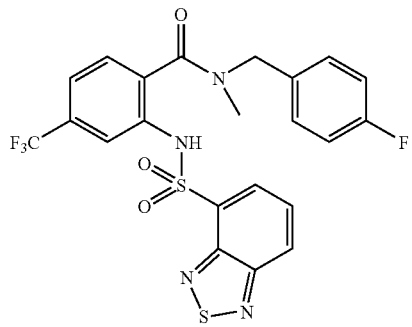

2-(Benzo[1,2,5]thiadiazole-4sulfonylamino)-N-(4-fluoro-benzyl)-N-methyl-4-trifluoromethyl-benzamide MS (ESI): m/z 525 [M+H]$^+$, 547 [M+Na]$^+$.

Example 193

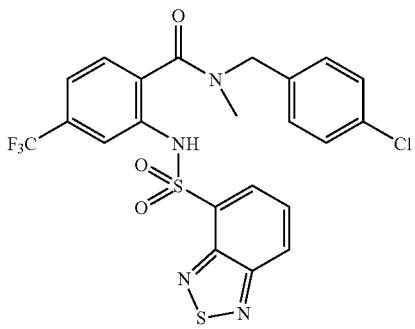

2-(Benzo[1,2,5]thiadiazole-4sulfonylamino)-N-(4-chloro-benzyl)-N-methyl-4-trifluoromethyl-benzamide MS (ESI): m/z 541 [M+H]$^+$, 563 [M+Na]$^+$.

Example 194

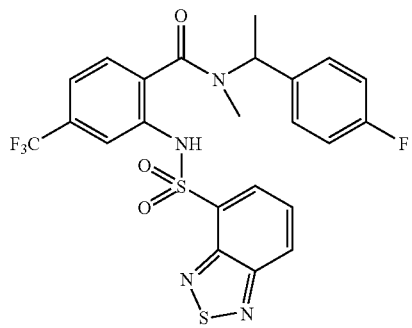

2-(Benzo[1,2,5]thiadiazole-4sulfonylamino)-N-[1-(4-fluoro-phenyl)-ethyl]-N-methyl-4-trifluoromethyl-benzamide MS (ESI): m/z 539 [M+H]$^+$, 561 [M+Na]$^+$.

Example 195

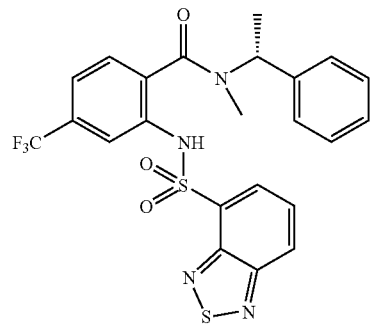

(R)-2-(Benzo[1,2,5]thiadiazole-4sulfonylamino)-N-methyl-N-(1-phenyl-ethyl)-4-trifluoromethyl-benzamide MS (ESI): m/z 521 [M+H]$^+$, 543 [M+Na]$^+$.

The compounds of EXAMPLES 196 through 198 were prepared using the general procedure of EXAMPLE 40.

Example 196

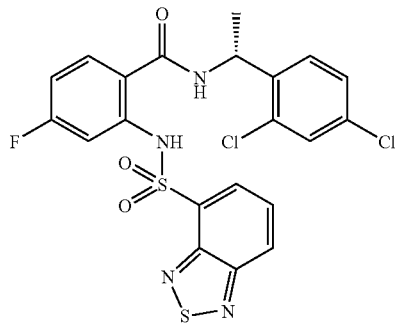

(R)-2-(Benzo[1,2,5]thiadiazole-4sulfonylamino)-N-[1-(2,4-dichloro-phenyl)-ethyl]-4-fluoro-benzamide MS (ESI): m/z 525/527 [M+H]$^+$, 547/549 [M+Na]$^+$.

Example 197

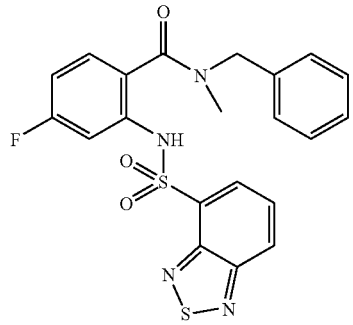

2-(Benzo[1,2,5]thiadiazole-4sulfonylamino)-N-benzyl-4-fluoro-N-methyl-benzamide

MS (ESI): m/z 457 [M+H]$^+$, 479 [M+Na]$^+$.

Example 198

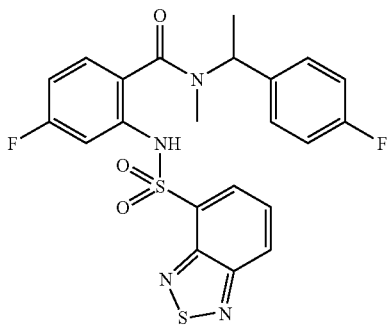

2-(Benzo[1,2,5]thiadiazole-4sulfonylamino)-4-fluoro-N-[1-(4-fluoro-phenyl)-ethyl]-N-methyl-benzamide MS (ESI): m/z 489 [M+H]$^+$, 511 [M+Na]$^+$.

Assay Methods

Binding Assay

Assay Development

Zinc Finger Proteins (ZFP) specific for the CCK2R gene were identified by Sangamo Biosciences. The ZFP domain was fused with the herpes simplex virus VP16 activation domain, and the fusion protein was subsequently cloned into the pcDNA3 mammalian expression vector (Invitrogen, San Diego, Calif.). Tet-inducible cell lines expressing the coding region from the ZFP vector were created using the T-REx-293™ cell line (Invitrogen). After 2 weeks of selection in culture medium containing 400 mg/mL Zeocin (Invitrogen), sixty drug-resistant stable clones were isolated and analyzed for ZFP expression as well as CCK2R induction upon addition of doxycycline to the culture medium. The cell line with the most appropriate CCK2R ZFP construct was used in all further assays and was termed the HEKZFP cell line.

Cell Culture

HEKZFP cells were grown in DMEM supplemented with L-glutamine (2 mM), penicillin (50 units/mL) and streptomycin (50 μg/mL) and 10% FBS (v/v). HEKZFP cells were treated with 2 mM doxycycline (Sigma-Aldrich, MO; USA) for 2 days to de-repress the tet-regulated expression of the CCK2 receptor selective zinc finger proteins and were harvested using a rubber cell scraper.

Membrane Preparation

Membranes were prepared from the HEKZFP cells after induction. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from E. A. Harper et al. (Br. J. Pharmacol. (1996) 118(7):1717-1726). The thawed pellets were homogenized using a Polytron PT-10 (7×1 s). The homogenates were centrifuged for 5 min at 1500 rpm (600×g), and the resulting pellets were discarded. The supernatants were re-centrifuged in order to collect the receptor-membrane pellets (25 min 15,000 rpm; 39,000×g), which were re-suspended in buffer A.

Incubation Conditions

All assays were conducted in 96-well plate (GF/B millipore filter plates) using buffer A. For the optimal cell number determination experiments, cells in concentrations ranging from 2.5×10$^5$ to 12.5×10$^5$ cells/well were incubated with 20 pM [$^{125}$I]-BH-CCK-8S (50 μL 60 pM) solution) in a total volume of 150 μL. Total binding of [$^{125}$I]-BH-CCK-8S was determined in the presence of 15 μL of buffer A. Non-specific binding of [$^{125}$I]-BH-CCK-8S was determined in the presence of 15 μL of 10 μM YF476, a CCK-2 receptor selective antagonist that is structurally unrelated to the radioligand [$^{125}$I]-BH-CCK-8S. The assay preparation was incubated for 1 h at 21±3° C., and then the assay was terminated by rapid filtration of the preparation under reduced pressure. The loaded filters were washed three times using undiluted PBS (100 μL), and then 100 μL of scintillation fluid was added to the filter plate. Bound radioactivity was determined using a Topcount (Packard BioScience, Meriden, Conn.) with a count time of 1 min. From these experiments a cell concentration of 1 pellet in 15 mL of buffer was chosen for use in other assays. To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

Data Analysis

The pKi values were determined using the equation of Y.-C. Cheng and W. H. Prusoff (Biochem. Pharmacol., 1973, 22(23):3099-3108):

$$K_i = \frac{IC_{50}}{1 + \frac{[L]}{K_O}}$$

To circumvent problems associated with computer-assisted data analysis of compounds with low affinity, the data obtained in the current study were weighted according to a method described by Morton. In brief, 100% and 0% specific binding were defined independently using total binding and binding obtained in the presence of a high concentration of the reference antagonist, 2-NAP.

TABLE 1

| EXAMPLE | pK$_i$ |
|---|---|
| 2 | 6.8 |
| 4 | 7.0 |
| 5 | 7.6 |
| 6 | 8.4 |
| 10 | 6.2 |
| 22 | 6.7 |
| 36 | 7.8 |
| 63 | 6.2 |
| 70 | 7.5 |
| 79 | 7.1 |
| 89 | 6.2 |
| 138 | 7.5 |
| 140 | 7.0 |

TABLE 2

| EXAMPLE | pK$_i$ |
|---|---|
| 48 | 6.4 |
| 58 | 6.9 |
| 59 | 6.2 |
| 105 | 8.0 |
| 111 | 7.8 |
| 112 | 8.3 |
| 117 | 6.4 |
| 118 | 6.9 |
| 155 | 7.6 |
| 167 | 7.6 |
| 195 | 8.1 |

Guinea-Pig Gastric Corpeal Muscle Assay

CCK2 receptor-mediated muscle contraction was measured in an isolated muscle-strip assay of guinea-pig gastric corpeal muscle according to the methods described by Roberts et al. (S. P. Roberts, E. A. Harper, G. F. Watt, V. P. Gerskowitch, R. A. Hull, N. P. Shankley, and J. W. Black, Br. J. Pharmacol., 1996, 118(7):1779-1789). In brief, strips of muscle were dissected and suspended in isolated tissue organ baths for isotonic muscle contraction recording. The baths, containing Krebs-Henseleit solution, were maintained at 24° C. and gassed continuously with 95% $O_2$ and 5% $CO_2$. CCK1 receptors known to be present in this assay were blocked using a selective concentration of a suitable CCK1 receptor antagonist (e.g. 2-NAP). The effectiveness of the test compounds was assessed by measuring their effect on contractile concentration-response curves obtained using a well-characterized surrogate for the hormone gastrin (pentagastrin). The title compound of Example 5 behaved as a competitive antagonist in this assay with a pK$_8$ value of 8.8.

What is claimed is:

1. A method for treating pancreatic adenocarcinoma, pain, eating disorders, gastro-esophageal reflux disease, gastroduodenal ulcers, reflux esophagitis, anxiety, colon cancer, peptic ulcers, pancreatic tumors, gastric tumors, Barrett's esophagus, antral G cell hyperplasia, pernicious anaemia and Zollinger-Ellison syndrome comprising administering to a mammal in need of such treatment or prevention an effective dose of a compound of formula (I):

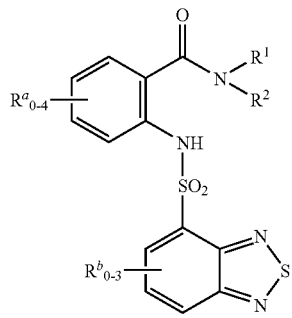

(I)

wherein $R^1$ and $R^2$ are each independently selected from the group consisting of
  a) H, $C_{1-7}$alkyl, $C_{2-7}$alkenyl, $C_{2-7}$alkynyl, $C_{3-7}$cycloalkyl, $C_{3-7}$cycloalkenyl, benzo-fused$C_{4-7}$cycloalkyl where the point of attachment is a carbon atom adjacent to the ring junction, $C_{3-7}$cycloalkyl $C_{1-7}$ alkyl,
  b) naphthyl-$(CR^s_2)$—, benzoyl$C_{0-3}$alkyl-$(CR^s_2)$—, phenyl, said phenyl optionally fused at two adjacent carbon atoms to $R^f$, phenyl-$(CR^s_2)$—, said phenyl optionally fused at two adjacent carbon atoms to $R^f$,
    $R^f$ is a linear 3- to 5-membered hydrocarbon moiety having 0 or 1 unsaturated bonds and having 0, 1 or 2 carbon members which is a carbonyl,
  c) $Ar^6$—$(CR^s_2)$—, where $Ar^6$ is a 6-membered heteroaryl having carbon as a point of attachment, having 1 or 2 heteroatom members which are —N= and optionally benzo fused,
  d) $Ar^5$—$(CR^s_2)$—, where $Ar^5$ is a 5-membered heteroaryl having carbon as a point of attachment, having 1 heteroatom member selected from the group consisting of O, S, >NH or >NC$_{1-4}$alkyl, having 0 or 1 additional heteroatom member which is —N= and optionally benzo fused,
  e) $Ar^{6-6}$—$(CR^s_2)$—, where $Ar^{6-6}$ is phenyl having the point of attachment and fused to a 6-membered heteroaryl having 1 or 2 heteroatom members which are —N=,
  f) $Ar^{6-5}$—$(CR^s_2)$—, where $Ar^{6-5}$ is phenyl having the point of attachment and fused to a 5-membered heteroaryl having 1 heteroatom member selected from the group consisting of O, S, >NH or >NC$_{1-4}$alkyl and having 0 or 1 additional heteroatom member which is —N=,
  g) $C_{1-4}$alkylO— and HSC$_{1-4}$alkyl,
  where $R^1$ and $R^2$ are not simultaneously H and, except in positions where $R^s$ is indicated, each of a) to g) is substituted with 0, 1, 2, or 3 of $R^q$,
  $R^q$ is independently selected from the group consisting of $C_{1-4}$alkyl, hydroxy, fluoro, chloro, bromo, iodo, trifluoromethyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy and $C_{1-4}$alkylS—,
  $R^s$ is independently selected from the group consisting of hydrogen, $C_{1-4}$alkyl, trifluoromethyl, amino$C_{1-4}$alkyl, $C_{1-4}$alkylamino$C_{1-4}$alkyl, di$C_{1-4}$alkylamino$C_{1-4}$ alkyl, HO—$C_{1-4}$alkyl, HS—$C_{1-4}$alkyl, $C_{1-4}$alkylS—$C_{1-4}$alkyl and phenyl;
  or, alternatively,
$R^1$ and $R^2$ may be taken together with the nitrogen to which they are attached and are selected from the group consisting of
  i) 10-Oxa-4-aza-tricyclo[5.2.1.0$^{2,6}$]dec-4-yl, optionally mono- or di-substituted with $R^p$,
    $R^p$ is independently selected from the group consisting of hydroxy, $C_{1-4}$alkyl, hydroxy$C_{1-4}$alkyl, phenyl, mono-, di- or tri-halo substituted phenyl and hydroxyphenyl,
  ii) a 4-7 membered heterocyclic ring said heterocyclic ring having 0 or 1 additional heteroatom members separated from the nitrogen of attachment by at least one carbon member and selected from O, S, —N=, >NH or >NR$^p$, having 0, 1 or 2 unsaturated bonds, having 0, 1 or 2 carbon members which is a carbonyl, optionally having one carbon member which forms a bridge and having 0, 1 or 2 substituents $R^p$,
  iii) a benzo fused 4-7 membered heterocyclic ring said heterocyclic ring having 0 or 1 additional heteroatom members separated from the nitrogen of attachment by at least one carbon member and selected from O, S, —N=, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents $R^p$, iv) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N═, >NH or >NR$^p$, having 0, 1 or 2 unsaturated bonds, having 0, 1 or 2 carbon members which is a carbonyl and having 0, 1 or 2 substituents $R^p$;

v) 8-oxo-1,5,6,8-tetrahydro-2H,4H-1,5-methano-pyrido[1,2-a][1,5]diazocin-3-yl, optionally having 0, 1 or 2 substituents $R^p$;

$R^a$ is, independently, selected from the group consisting of —$C_{1-6}$alkyl, —$C_{2-6}$alkenyl, —$C_{3-6}$cycloalkyl, phenyl, furanyl, thienyl, benzyl, pyrrol-1-yl, —OH, —$OC_{1-6}$alkyl, —$OC_{3-6}$cycloalkyl, —Ophenyl, —Obenzyl, —SH, —$SC_{3-6}$alkyl, —$SC_{3-6}$cycloalkyl, —Sphenyl, —Sbenzyl, —CN, —$NO_2$, —$N(R^y)R^z$ (wherein $R^y$ and $R^z$ are independently selected from H, $C_{1-4}$alkyl or $C_{1-6}$cycloalkyl$C_{1-4}$alkyl), —(C═O)$C_{1-4}$alkyl, —$SCF_3$, halo, —$CF_3$, —$OCF_3$, and —$COOC_{1-4}$alkyl, or, alternatively, two adjacent $R^a$, may be taken together with the carbons of attachment to form a fused ring and selected from the group consisting of phenyl, pryidyl and pyrimidinyl;

$R^b$ is, independently, selected from the group consisting of —$C_{1-4}$alkyl and halogen;

and enantiomers, diastereomers, hydrates, solvates and pharmaceutically acceptable salts, esters and amides thereof.

2. A method for treating pancreatic adenocarcinoma, pain, gastro-esophageal reflux disease, gastroduodenal ulcers, reflux esophagitis, anxiety, colon cancer, peptic ulcers, pancreatic tumors and gastric tumors comprising administering to a mammal in need of such treatment or prevention an effective dose of a compound of formula (I):

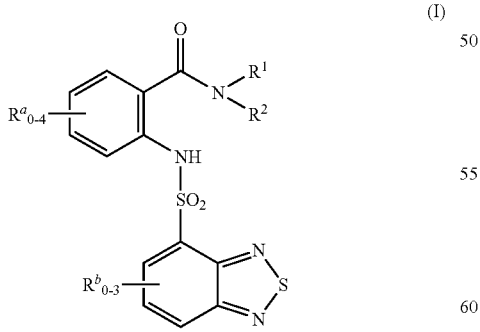

wherein
$R^1$ and $R^2$ are each independently selected from the group consisting of
a) H, $C_{1-7}$alkyl, $C_{2-7}$alkenyl, $C_{2-7}$alkynyl, $C_{3-7}$cycloalkyl, $C_{3-7}$cycloalkenyl, benzo-fused$C_{4-7}$cycloalkyl where the point of attachment is a carbon atom adjacent to the ring junction, $C_{3-7}$cycloalkyl$C_{1-7}$alkyl, b) naphthyl-(CR$^s_2$)—, benzoyl$C_{0-3}$alkyl-(CR$^s_2$)—, phenyl, said phenyl optionally fused at two adjacent carbon atoms to R$^f$, phenyl-(CR$^s_2$)—, said phenyl optionally fused at two adjacent carbon atoms to R$^f$, R$^f$ is a linear 3- to 5-membered hydrocarbon moiety having 0 or 1 unsaturated bonds and having 0, 1 or 2 carbon members which is a carbonyl, c) Ar$^6$—(CR$^s_2$)—, where Ar$^6$ is a 6-membered heteroaryl having carbon as a point of attachment, having 1 or 2 heteroatom members which are —N═ and optionally benzo fused, d) Ar$^5$—(CR$^s_2$)—, where Ar$^5$ is a 5-membered heteroaryl having carbon as a point of attachment, having 1 heteroatom member selected from the group consisting of O, S, >NH or >N$C_{1-4}$alkyl, having 0 or 1 additional heteroatom member which is —N═ and optionally benzo fused, e) Ar$^{6-6}$—(CR$^s_2$)—, where Ar$^{6-6}$ is phenyl having the point of attachment and fused to a 6-membered heteroaryl having 1 or 2 heteroatom members which are —N═, f) Ar$^{6-5}$—(CR$^s_2$)—, where Ar$^{6-5}$ is phenyl having the point of attachment and fused to a 5-membered heteroaryl having 1 heteroatom member selected from the group consisting of O, S, >NH or >N$C_{1-4}$alkyl and having 0 or 1 additional heteroatom member which is —N═, g) $C_{1-4}$alkylO— and HS$C_{1-4}$alkyl, where $R^1$ and $R^2$ are not simultaneously H and, except in positions where $R^s$ is indicated, each of a) to g) is substituted with 0, 1, 2, or 3 of $R^q$, $R^q$ is independently selected from the group consisting of $C_{1-4}$alkyl, hydroxy, fluoro, chloro, bromo, iodo, trifluoromethyl, amino$C_{1-4}$alkyl, $C_{1-4}$alkylamino$C_{1-4}$alkyl, di$C_{1-4}$alkylamino$C_{1-4}$alkyl, HO—$C_{1-4}$alkyl, $C_{1-4}$alkylO—$C_{1-4}$alkyl, HS—$C_{1-4}$alkyl, $C_{1-4}$alkylS—$C_{1-4}$alkyl, $C_{1-4}$alkoxy and $C_{1-4}$alkylS—, $R^s$ is independently selected from the group consisting of hydrogen, $C_{1-4}$alkyl, trifluoromethyl, amino$C_{1-4}$alkyl, $C_{1-4}$alkylamino$C_{1-4}$alkyl, di$C_{1-4}$alkylamino$C_{1-4}$ alkyl, HO—$C_{1-4}$alkyl, HS—$C_{1-4}$alkyl, $C_{1-4}$alkylS—$C_{1-4}$alkyl and phenyl;

or, alternatively, $R^1$ and $R^2$ may be taken together with the nitrogen to which they are attached and are selected from the group consisting of i) 10-Oxa-4-aza-tricyclo[5.2.1.0$^{2,6}$]dec-4-yl, optionally mono- or di-substituted with $R^p$, $R^p$ is independently selected from the group consisting of hydroxy, $C_{1-4}$alkyl, hydroxy$C_{1-4}$alkyl, phenyl, mono-, di- or tri-halo substituted phenyl and hydroxyphenyl, ii) a 4-7 membered heterocyclic ring said heterocyclic ring having 0 or 1 additional heteroatom members separated from the nitrogen of attachment by at least one carbon member and selected from O, S, —N═, >NH or >NR$^p$, having 0, 1 or 2 unsaturated bonds, having 0, 1 or 2 carbon members which is a carbonyl, optionally having one carbon member which forms a bridge and having 0, 1 or 2 substituents $R^p$, iii) a benzo fused 4-7 membered heterocyclic ring said heterocyclic ring having 0 or 1 additional heteroatom members separated from the nitrogen of attachment by at least one carbon member and selected from O, S, —N=, >NH or >NR$^p$, having 0 or 1 additional unsaturated bonds, having 0, 1 or 2 carbon members which is a carbonyl, having 0, 1, 2, or 3 halo substituents on the benzene ring only and having 0, 1 or 2 substituents R$^p$, iv) a 4-7 membered heterocyclic ring said heterocyclic ring having 0 or 1 additional heteroatom members separated from the nitrogen of attachment by at least one carbon member and selected from O, S, —N=, >NH or >NR$^p$, having 0, 1 or 2 unsaturated bonds, having 0, 1 or 2 carbon members which is a carbonyl and optionally having one carbon member which forms a bridge, the heterocyclic ring fused at two adjacent carbon atoms forming a saturated bond or an adjacent carbon and nitrogen atom forming a saturated bond to a 4-7 membered hydrocarbon ring, having 0 or 1 possibly additional heteroatom member, not at the ring junction, selected from O, S, —N=, >NH or >NR$^p$, having 0, 1 or 2 unsaturated bonds, having 0, 1 or 2 carbon members which is a carbonyl and having 0, 1 or 2 substituents R$^p$;

v) 8-oxo-1,5,6,8-tetrahydro-2H,4H-1,5-methano-pyrido[1,2-a][1,5]diazocin-3-yl, optionally having 0, 1 or 2 substituents R$^p$;

R$^a$ is, independently, selected from the group consisting of —C$_{1-6}$alkyl, —C$_{2-6}$alkenyl, —C$_{3-6}$cycloalkyl, phenyl, furanyl, thienyl, benzyl, pyrrol-1-yl, —OH, —OC$_{1-6}$alkyl, —OC$_{3-6}$cycloalkyl, —Ophenyl, —Obenzyl, —SH, —SC$_{1-6}$alkyl, —SC$_{3-6}$cycloalkyl, —Sphenyl, —Sbenzyl, —CN, —NO$_2$, —N(R$^y$)R$^z$ (wherein R$^y$ and R$^z$ are independently selected from H, C$_{1-4}$alkyl or C$_{1-6}$cycloalkylC$_{1-4}$alkyl), —(C=O)C$_{1-4}$alkyl, —SCF$_3$, halo, —CF$_3$, —OCF$_3$, and —COOC$_{1-4}$alkyl, or, alternatively, two adjacent R$^a$, may be taken together with the carbons of attachment to form a fused ring and selected from the group consisting of phenyl, pryidyl and pyrimidinyl;

R$^b$ is, independently, selected from the group consisting of —C$_{1-4}$alkyl and halogen;

and enantiomers, diastereomers, hydrates, solvates and pharmaceutically acceptable salts, esters and amides thereof.

\* \* \* \* \*